(12) United States Patent
Heffernan et al.

(10) Patent No.: US 7,365,095 B2
(45) Date of Patent: Apr. 29, 2008

(54) CHROMANE AND CHROMENE DERIVATIVES AND USES THEREOF

(75) Inventors: Gavin David Heffernan, Florence, NJ (US); Gary Paul Stack, Ambler, PA (US); Jonathan Laird Gross, Cranbury, NJ (US); Dahui Zhou, East Brunswick, NJ (US); Hong Gao, Belle Mead, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/409,467

(22) Filed: Apr. 21, 2006

(65) Prior Publication Data

US 2006/0258714 A1    Nov. 16, 2006

Related U.S. Application Data

(60) Provisional application No. 60/673,820, filed on Apr. 22, 2005.

(51) Int. Cl.
  A61K 31/44    (2006.01)
  A61K 43/40    (2006.01)
  A01N 43/02    (2006.01)
  A01N 43/16    (2006.01)
  A61N 31/335   (2006.01)

(52) U.S. Cl. .................. 514/456; 514/450; 514/337; 549/355; 549/407; 546/282.7; 546/281.7

(58) Field of Classification Search ............... 549/355, 549/407; 546/282.7, 281.7; 514/337, 450, 514/456
See application file for complete search history.

(56) References Cited

U.S. PATENT DOCUMENTS

| | | | |
|---|---|---|---|
| 4,536,518 A | 8/1985 | Welch, Jr. et al. | |
| 4,654,362 A | 3/1987 | Van Lommen et al. | |
| 5,089,637 A | 2/1992 | Urban | |
| RE34,712 E | 8/1994 | Boegesoe et al. | |
| 5,348,976 A | 9/1994 | Shibata et al. | |
| 5,658,796 A | 8/1997 | Rossi, Jr. et al. | |
| 5,731,324 A | 3/1998 | Fisher et al. | |
| 5,767,132 A | 6/1998 | Bottcher et al. | |
| 5,824,682 A | 10/1998 | Van Lommen et al. | |
| 6,083,982 A | 7/2000 | Wechter et al. | |
| 6,294,533 B1 * | 9/2001 | Snutch et al. ............ | 514/231.2 |
| 6,310,107 B1 | 10/2001 | Kato et al. | |
| 6,602,903 B2 | 8/2003 | Guillaumet et al. | |
| 6,700,001 B2 | 3/2004 | Gross | |
| 6,716,998 B2 | 4/2004 | Gross | |
| 6,747,045 B2 | 6/2004 | Wigerinck et al. | |
| 6,812,353 B2 | 11/2004 | Bokel et al. | |
| 7,045,629 B2 | 5/2006 | Bokel et al. | |
| 2004/0029788 A1 | 2/2004 | Bender et al. | |
| 2004/0034004 A1 | 2/2004 | Pfahl et al. | |
| 2004/0077867 A1 | 4/2004 | Kato et al. | |
| 2004/0097433 A1 | 5/2004 | Boddupalli et al. | |
| 2004/0198644 A1 | 10/2004 | Bender et al. | |
| 2005/0014818 A1 | 1/2005 | Mitsuda et al. | |
| 2005/0065099 A1 | 3/2005 | Boddupalli et al. | |
| 2006/0128689 A1 | 6/2006 | Bayburt et al. | |

FOREIGN PATENT DOCUMENTS

| | | |
|---|---|---|
| BR | 1262078 | 5/1968 |
| DE | 4430089 A1 | 2/1996 |
| DE | 10 2004 011 265 | 9/2005 |
| WO | WO00/58301 | 10/2000 |
| WO | WO-03/029238 A1 | 4/2003 |
| WO | WO-03/029239 A1 | 4/2003 |
| WO | WO-03/031439 | 4/2003 |
| WO | WO-05/037817 | 4/2005 |
| WO | WO-05/044812 | 5/2005 |

OTHER PUBLICATIONS

Bishop, et al., *Expert Opinion Ther. Patent*, 13: 1691-1705, 2003.
Cairns, et al., *J. Med. Chem.*, 15: 583, 1972.
Goujon, et al., *Journal of the Chemical Society Perkin Trans*, 1: 496, 2002.
Gross, *Tetrahedron Letters*, 44: 8563, 2003.
Gudi, et al., *Indian J. Chem.*, 7: 971, 1969.
Hassan, et al., *Brit J. Clin. Pharmacol*, 19: 705, 1985.
Ruhemann, *J. Chem. Soc.*, 77: 1121, 1900.
Schaff, et al., *J. Med. Chem.*, 26: 328, 1983.
Snieckus, *Chem. Rev.*, 90: 879, 1990.
Stoermer, et al., *Aust. J. Chem.*, 48:677, 1995.
Witiak, et al., *J. Med. Chem.*, 18: 934, 1975.
Zhang, et al., *Tetrahedron Letters*, 45: 5229, 2004.
International Search Report, PCT/US2006/15208.
Office Action mailed Oct. 17, 2007 in U.S. Appl. No. 10/970,103 filed Oct. 21, 2004.

(Continued)

*Primary Examiner*—Margaret D. Seaman
*Assistant Examiner*—Niloofar Rahmani
(74) *Attorney, Agent, or Firm*—Andrea L.C. Robidoux; Choate Hall & Stewart, LLP

(57) ABSTRACT

Compounds of formula I or pharmaceutically acceptable salts thereof are provided:

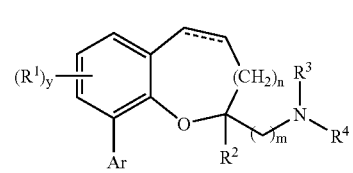

wherein each of $R^1$, $R^2$, $R^3$, $R^4$, y, m, n, and Ar are as defined, and described in classes and subclasses herein, which are agonists or partial agonists of the 2C subtype of brain serotonin receptors. The compounds, and compositions containing the compounds, can be used to treat a variety of central nervous system disorders such as schizophrenia.

19 Claims, No Drawings

OTHER PUBLICATIONS

Office Action mailed Aug. 27, 2007 in U.S. Appl. No. 10/970,714 filed Oct. 21, 2004.
Office Action mailed Sep. 21, 2007 in U.S. Appl. No. 11/113,170 filed Apr. 22, 2005.
Office Action mailed Sep. 25, 2007 in U.S. Appl. No. 11/409,479 filed Apr. 21, 2006.
Office Action mailed Sep. 28, 2007 in U.S. Appl. No. 11/408,319 filed Apr. 21, 2006.
Office Action mailed Oct. 22, 2007 in U.S. Appl. No. 11/409,303 filed Apr. 21, 2006.
Office Action mailed Sep. 19, 2007 in U.S. Appl. No. 11/408,879 filed Apr. 21, 2006.
Office Action mailed Oct. 18, 2007 in U.S. Appl. No. 11/408,909 filed Apr. 21, 2006.
Office Action mailed Jul. 26, 2007 in U.S. Appl. No. 11/409,480 filed Apr. 21, 2006.

* cited by examiner

CHROMANE AND CHROMENE DERIVATIVES AND USES THEREOF

CROSS REFERENCE TO RELATED APPLICATIONS

This application claims priority to U.S. Provisional Patent Application Ser. No. 60/673,820, filed Apr. 22, 2005, the entirety of which is hereby incorporated herein by reference.

FIELD OF THE INVENTION

The present invention relates to 5-$HT_{2C}$ receptor agonists or partial agonists, processes for their preparation, and uses thereof.

BACKGROUND OF THE INVENTION

Schizophrenia affects approximately 5 million people. The most prevalent treatments for schizophrenia are currently the 'atypical' antipsychotics, which combine dopamine ($D_2$) and serotonin (5-$HT_{2A}$) receptor antagonism. Despite the reported improvements in efficacy and side-effect liability of atypical antipsychotics relative to typical antipsychotics, these compounds do not appear to adequately treat all the symptoms of schizophrenia and are accompanied by problematic side effects, such as weight gain (Allison, D. B., et. al., Am. J. Psychiatry, 156: 1686–1696, 1999; Masand, P. S., Exp. Opin. Pharmacother. 1: 377–389, 2000; Whitaker, R., Spectrum Life Sciences. Decision Resources. 2:1–9, 2000).

Atypical antipsychotics also bind with high affinity to 5-$HT_{2C}$ receptors and function as 5-$HT_{2C}$ receptor antagonists or inverse agonists. Weight gain is a problematic side effect associated with atypical antipsychotics such as clozapine and olanzapine, and it has been suggested that 5-$HT_{2C}$ antagonism is responsible for the increased weight gain. Conversely, stimulation of the 5-$HT_{2C}$ receptor is known to result in decreased food intake and body weight (Walsh et. al., Psychopharmacology 124: 57–73, 1996; Cowen, P. J., et. al., Human Psychopharmacology 10: 385–391, 1995; Rosenzweig-Lipson, S., et. al., ASPET abstract, 2000).

Several lines of evidence support a role for 5-$HT_{2C}$ receptor agonism or partial agonism as a treatment for schizophrenia. Studies suggest that 5-$HT_{2C}$ antagonists increase synaptic levels of dopamine and may be effective in animal models of Parkinson's disease (Di Matteo, V., et. al., Neuropharmacology 37: 265–272, 1998; Fox, S. H., et. al., Experimental Neurology 151: 35–49, 1998). Since the positive symptoms of schizophrenia are associated with increased levels of dopamine, compounds with actions opposite to those of 5-$HT_{2C}$ antagonists, such as 5-$HT_{2C}$ agonists and partial agonists, should reduce levels of synaptic dopamine. Recent studies have demonstrated that 5-$HT_{2C}$ agonists decrease levels of dopamine in the prefrontal cortex and nucleus accumbens (Millan, M. J., et. al., Neuropharmacology 37: 953–955, 1998; Di Matteo, V., et. al., Neuropharmacology 38: 1195–1205, 1999; Di Giovanni, G., et. al., Synapse 35: 53–61, 2000), brain regions that are thought to mediate critical antipsychotic effects of drugs like clozapine. However, 5-$HT_{2C}$ agonists do not decrease dopamine levels in the striatum, the brain region most closely associated with extrapyramidal side effects. In addition, a recent study demonstrates that 5-$HT_{2C}$ agonists decrease firing in the ventral tegmental area (VTA), but not in the substantia nigra. The differential effects of 5-$HT_{2C}$ agonists in the mesolimbic pathway relative to the nigrostriatal pathway suggest that 5-$HT_{2C}$ agonists have limbic selectivity, and will be less likely to produce extrapyramidal side effects associated with typical antipsychotics.

SUMMARY OF THE INVENTION

The present invention relates to 5-$HT_{2C}$ receptor agonists or partial agonists and uses thereof. In one aspect, the invention relates to chromane and chromene derivatives that act as agonists or partial agonists of the 5-$HT_{2C}$ receptor. The compounds can be used, for example, to treat schizophrenia and the concomitant mood disorders and cognitive impairments of schizophrenia and depression. In certain embodiments, compounds of the present invention are less likely to produce the body weight increases associated with current atypical antipsychotics. The compounds of the present invention can also be used for the treatment of obesity and its comorbidities. Compounds of the present invention are also useful for treating a variety of psythotic, depression and related disorders, and cognitive disorders as described in detail herein.

In certain embodiments, the invention provides a compound of formula I:

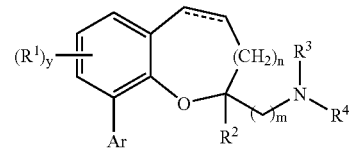

or a pharmaceutically acceptable salt thereof, wherein:
m is 1 or 2;
n is 0 or 1;
----- designates a single or double bond;
Ar is thienyl, furyl, pyridyl, pyrimidinyl or phenyl, wherein Ar is optionally substituted with one or more $R^x$ groups;
each $R^x$ is independently -Ph, halogen, —CN, —R or —OR;
each R is independently hydrogen, $C_{1-6}$ aliphatic or halo-substituted $C_{1-6}$ aliphatic;
y is 0–3;
each $R^1$ is independently —R, —CN, halogen or —OR;
$R^2$ is hydrogen, $C_{1-3}$ alkyl, or —O($C_{1-3}$ alkyl); and
each of $R^3$ and $R^4$ is independently hydrogen, $C_{1-6}$ aliphatic or fluoro-substituted $C_{1-6}$ aliphatic;

In certain other embodiments, the invention relates to methods for treating a patient suffering from schizophrenia, schizophreniform disorder, schizoaffective disorder, delusional disorder, substance-induced psychotic disorder, L-DOPA-induced psychosis, psychosis associated with Alzheimer's dementia, psychosis associated with Parkinson's disease, psychosis associated with Lewy body disease, dementia, memory deficit, intellectual deficit associated with Alzheimer's disease, bipolar disorders, depressive disorders, mood episodes, anxiety disorders, adjustment disorders, eating disorders, epilepsy, sleep disorders, migraines, sexual dysfunction, substance abuse, addiction to alcohol and various other drugs, including cocaine and nicotine, gastrointestinal disorders, obesity, or a central nervous system deficiency associated with trauma, stroke, or spinal cord injury, or other conditions or disorders as described herein, that includes administering to the patient a therapeutically effective amount of a compound of formula I, or a pharmaceutically acceptable salt thereof.

In still other embodiments, the invention relates to compositions comprising a compound of formula I or a pharmaceutically acceptable salt thereof, and one or more pharmaceutically acceptable carriers, excipients, or diluents.

DETAILED DESCRIPTION OF THE INVENTION

1. Compounds and Definitions:

The compounds of the present invention are agonists or partial agonists of the 2C subtype of brain serotonin receptors.

In certain embodiments, the invention provides a compound of formula I:

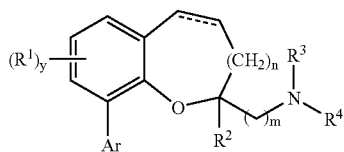

I or a pharmaceutically acceptable salt thereof, wherein:
m is 1 or 2;
n is 0 or 1;
----- designates a single or double bond;
Ar is thienyl, furyl, pyridyl, pyrimidinyl or phenyl wherein
  Ar is optionally substituted with one or more $R^x$ groups;
each $R^x$ is independently -Ph, halogen, —CN, —R or —OR;
each R is independently hydrogen, $C_{1-6}$ aliphatic or halo-substituted $C_{1-6}$ aliphatic;
y is 0–3;
each $R^1$ is independently —R, —CN, halogen or —OR;
$R^2$ is hydrogen, $C_{1-3}$ alkyl, or —O($C_{1-3}$ alkyl); and
each of $R^3$ and $R^4$ is independently hydrogen, $C_{1-6}$ aliphatic or fluoro-substituted $C_{1-6}$ aliphatic;
provided that:
  when ----- designates a single bond and n is 0, then $R^1$ is not —OH in the 6-position; and
  when ----- designates a single bond and n is 0, then $R^1$ is not —OR in the 7-position.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. In certain embodiments, aliphatic groups contain 1–4 aliphatic carbon atoms, and in yet other embodiments, aliphatic groups contain 1–3 aliphatic carbon atoms. In some embodiments, "cycloaliphatic" (or "carbocycle") refers to a monocyclic $C_3$–$C_6$ hydrocarbon that is completely saturated or that contains one or more units of unsaturation, but which is not aromatic, that has a single point of attachment to the rest of the molecule. Such cycloaliphatic groups include cycloalkyl, cycloalkenyl, and cycloalkynyl groups. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "unsaturated," as used herein, means that a moiety has one or more units of unsaturation.

The term "lower alkyl," as used herein, refers to a hydrocarbon chain having up to 4 carbon atoms, preferably 1 to 3 carbon atoms, and more preferably 1 to 2 carbon atoms. The term "alkyl" includes, but is not limited to, straight and branched chains such as methyl, ethyl, n-propyl, isopropyl, n-butyl, isobutyl, sec-butyl, or t-butyl.

The term "alkoxy," as used herein, refers to the group —OR*, wherein R* is a lower alkyl group.

The terms "halogen" or "halo," as used herein, refer to chlorine, bromine, fluorine or iodine.

The term "halo-substituted," as used herein, or as part of a moiety such as "haloalkoxy" refers to an aliphatic group, as defined herein, that has one or more halogen substituents. In certain embodiment, every hydrogen atom on said alkyl group is replaced by a halogen atom. Such halo-substituted aliphatic groups include —$CF_3$. Such haloalkoxy groups include —$OCF_3$.

The term "fluoro-substituted aliphatic," as used herein, an aliphatic group, as defined herein, that has one or more fluorine substituents. In certain embodiment, a fluoro-substituted aliphatic group is a fluoroalkyl group.

The term "fluoroalkyl," as used herein, or as part of a moiety such as "fluoroalkoxy" refers to an alkyl group, as defined herein, that has one or more fluorine substituents. In certain embodiment, every hydrogen atom on said alkyl group is replaced by a fluorine atom.

The term "Ph," as used herein, refers to a phenyl group.

The term "alkenyl," as used herein refers to an aliphatic straight or branched hydrocarbon chain having 2 to 8 carbon atoms that may contain 1 to 3 double bonds. Examples of alkenyl groups include vinyl, prop-1-enyl, allyl, methallyl, but-1-enyl, but-2-enyl, but-3-enyl, or 3,3-dimethylbut-1-enyl. In some embodiments, the alkenyl is preferably a branched alkenyl of 3 to 8 carbon atoms. The term "lower alkenyl" refers to an alkenyl group having 1 to 3 carbon atoms.

The terms "effective amount" and "therapeutically effective amount," as used herein, refer to the amount of a compound of formula I that, when administered to a patient, is effective to at least partially treat a condition from which the patient is suffering. Such conditions include, but are not limited to, schizophrenia, schizoaffective disorder, schizophreniform disorder, L-DOPA-induced psychosis, bipolar disorder, obesity, obsessive compulsive disorder, depression, panic disorder, sleep disorders, eating disorders, epilepsy, pain, or any other disorder as described herein.

The term "pharmaceutically acceptable salts" or "pharmaceutically acceptable salt" includes acid addition salts, that is salts derived from treating a compound of formula I with an organic or inorganic acid such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, or similarly known acceptable acids. Where a compound of formula I contains a substituent with acidic properties, for instance, phenolic hydroxyl as $R^1$ or $R^x$, the term also includes salts derived from bases, for example, sodium salts. In certain embodiments, the present invention provides the hydrochloride salt of a compound of formula I.

The term "patient," as used herein, refers to a mammal. In certain embodiments, the term "patient", as used herein, refers to a human.

The terms "administer," "administering," or "administration," as used herein, refer to either directly administering a compound or composition to a patient, or administering a prodrug derivative or analog of the compound to the patient, which will form an equivalent amount of the active compound or substance within the patient's body.

The terms "treat" or "treating," as used herein, refers to partially or completely alleviating, inhibiting, preventing, ameliorating and/or relieving the condition.

The terms "suffer" or "suffering" as used herein refers to one or more conditions that a patient has been diagnosed with, or is suspected to have.

2. Description of Exemplary Compounds:

In certain embodiments, the invention relates to a compound of formula I:

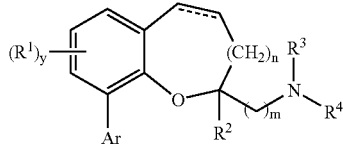

I or a pharmaceutically acceptable salt thereof, wherein:
m is 1 or 2;
n is 0 or 1;
---- designates a single or double bond;
Ar is thienyl, furyl, pyridyl, or phenyl wherein Ar is optionally substituted with one or more $R^x$ groups;
each $R^x$ is independently -Ph, halogen, —CN, —R or —OR;
each R is independently hydrogen, $C_{1-6}$ aliphatic or halo-substituted $C_{1-6}$ aliphatic;
y is 0–3;
each $R^1$ is independently —R, —CN, halogen or —OR;
$R^2$ is hydrogen, $C_{1-3}$ alkyl, or —O($C_{1-3}$ alkyl); and
each of $R^3$ and $R^4$ is independently hydrogen, $C_{1-6}$ aliphatic or fluoro-substituted $C_{1-6}$ aliphatic.

As defined generally above, the n group of formula I is 0 or 1. In certain embodiments, n is 0 thus forming a compound of formula Ia:

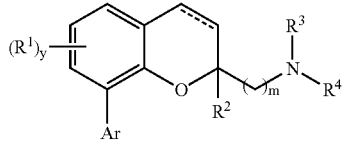

Ia or a pharmaceutically acceptable salt thereof, wherein $R^1$, $R^2$, $R^3$, $R^4$, Ar, y, and m are as defined above for compounds of formula I and in classes and subclasses as described above and herein.

According to another embodiment, the n group of formula I is 1, thus forming a compound of formula Ib:

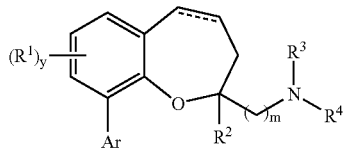

or a pharmaceutically acceptable salt thereof, wherein $R^1$, $R^2$, $R^3$, $R^4$, Ar, y, and m are as defined above for compounds of formula I and in classes and subclasses as described above and herein.

As defined generally above, y is 0–3 and each $R^1$ group of formula I is independently —R, —CN, halogen or —OR. In certain embodiments, each $R^1$ group of formula I is independently hydrogen, $C_{1-3}$ aliphatic, halogen, —OMe or —$CF_3$. In still other embodiments, y is 1, and $R^1$ is halogen.

According to one embodiment, y is 1, n is 1, and $R^1$ is at the 7-position of the bicyclic ring of formula I, thus forming a compound of formula IIa or IIb:

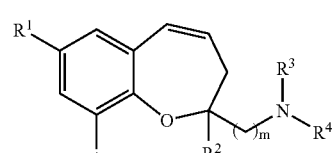

IIa

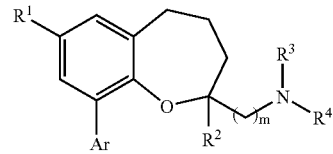

IIb or a pharmaceutically acceptable salt thereof, wherein each $R^1$, $R^2$, $R^3$, $R^4$, Ar, and m are as defined above for compounds of formula I and in classes and subclasses as described above and herein.

According to another embodiment, y is 1, n is 0, and $R^1$ is at the 6- or 7-position of the bicyclic ring of formula I, thus forming a compound of formula IIc, IId, IIe or IIf:

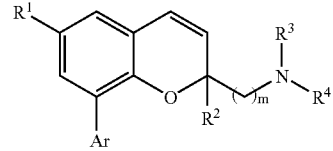

IIc

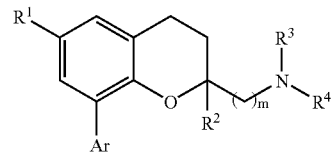

IId

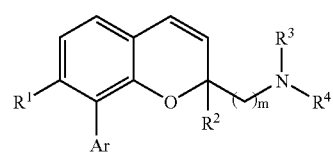

IIe

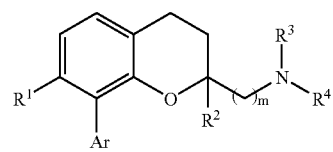

IIf or a pharmaceutically acceptable salt thereof, wherein each $R^1$, $R^2$, $R^3$, $R^4$, Ar, and m are as defined above for compounds of formula I and in classes and subclasses as described above and herein.

As defined generally above, each of the $R^3$ and $R^4$ groups of formula I is independently hydrogen, $C_{1-6}$ aliphatic or fluoro-substituted $C_{1-6}$ aliphatic. In certain embodiments, each of the $R^3$ and $R^4$ groups of formula I is independently hydrogen, methyl, ethyl, 2-fluoroethyl, 2,2-difluoroethyl or cyclopropyl. In other embodiments, one of the $R^3$ and $R^4$ groups of formula I is hydrogen and the other $R^3$ or $R^4$ is hydrogen, methyl, ethyl, 2-fluoroethyl, 2,2-difluoroethyl or cyclopropyl. In other embodiments, neither of the $R^3$ and $R^4$ groups of formula I is hydrogen. In still other embodiments, both of the $R^3$ and $R^4$ groups of formula I are hydrogen.

As defined generally above, each $R^1$ group of formula I is independently —R, —CN, halogen or —OR. In certain embodiments, each $R^1$ group of formula I is hydrogen. In other embodiments, at least one each $R^1$ group of formula I is halogen. According to another aspect of the present invention, one $R^1$ group of formula I is hydrogen and the other $R^1$ groups of formula I are independently halogen, —OH, lower alkyl, lower alkoxy, trifluoromethyl, trifluoromethoxy, or —CN. Yet another aspect of the present invention provides a compound of formula I wherein y is 1 and $R^1$ is halogen. In certain embodiments, y is 1 and $R^1$ is fluoro or chloro.

As defined generally above, the Ar group of formula I is thienyl, furyl, pyridyl, or phenyl, wherein said phenyl is optionally substituted with one or more $R^x$ subsituents independently selected from -Ph, —R, —CN, halogen or —OR. In certain embodiments, the Ar group of formula I is unsubstituted phenyl. In other embodiments, the Ar group of formula I is phenyl with at least one $R^x$ substituent in the ortho position. In other embodiments, the Ar group of formula I is phenyl with at least one $R^x$ substituent in the ortho position selected from -Ph, halogen, lower alkyl, lower alkoxy, or trifluoromethyl. According to one aspect the present invention provides a compound of formula I wherein Ar is phenyl di-substituted in the ortho and meta positions with halogen, lower alkyl or lower alkoxy. Yet another aspect of the present invention provides a compound of formula I wherein Ar is phenyl di-subsituted in the ortho and para positions with halogen, lower alkyl or lower alkoxy. In certain embodidments, Ar is phenyl subsituted at both ortho-positions with independently selected halogen or methyl. Exemplary substituents on the phenyl moiety of the Ar group of formula I include —OMe, fluoro, chloro, methyl, and trifluoromethyl.

According to one embodiment, Ar is phenyl substituted with $R^x$ in the ortho-position thus forming a compound of formula IIIa or IIIb:

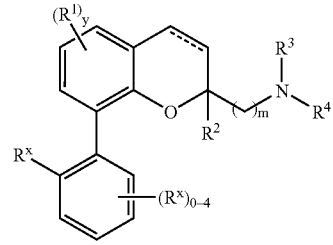

IIIa

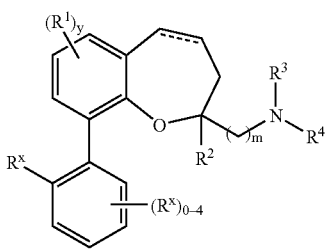

-continued

IIIb or a pharmaceutically acceptable salt thereof, wherein each $R^1$, $R^2$, $R^3$, $R^4$, $R^x$, y and m are as defined above for compounds of formula I and in classes and subclasses as described above and herein.

According to another embodiment, the present invention provides a compound of formula IIIc or IIId:

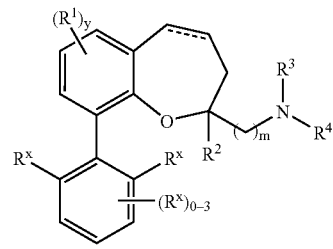

IIIc

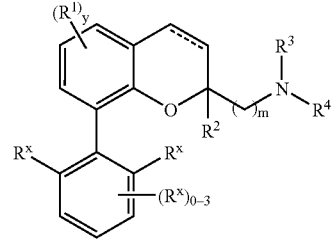

IIId or a pharmaceutically acceptable salt thereof, wherein each $R^1$, $R^2$, $R^3$, $R^4$, $R^x$, y and m are as defined above for compounds of formula I and in classes and subclasses as described above and herein.

In certain embodiments, the Ar group of formula I is selected from the following:

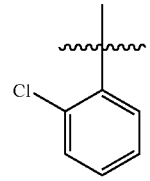

i

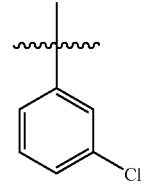

ii

-continued
iii 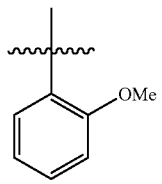
iv 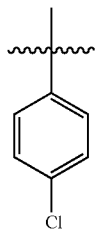
v 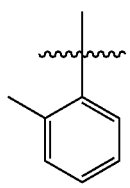
vi 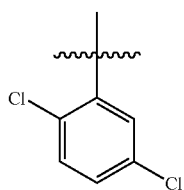
vii 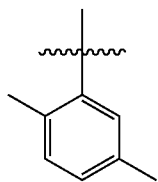
viii 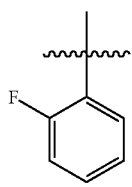
ix 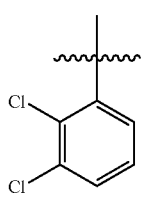
x 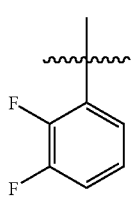
-continued
xi 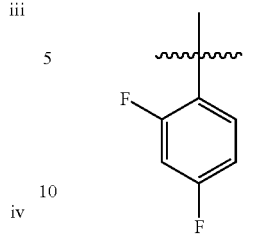
xii 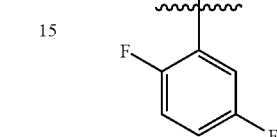
xiii 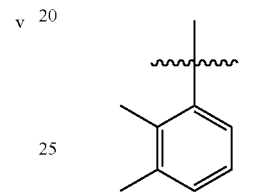
xiv 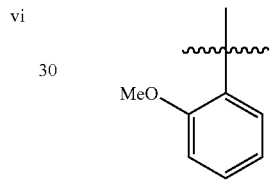
xv 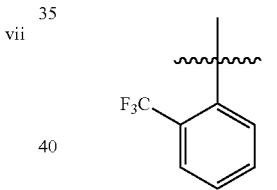
xvi 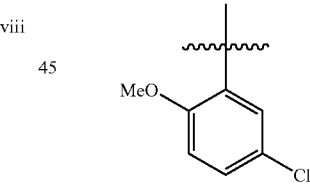
xvii 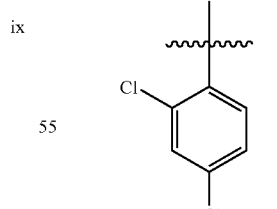
xviii 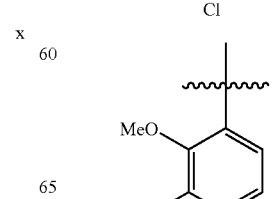

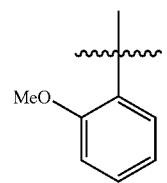 xix
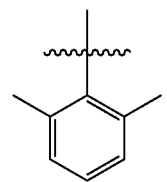 xx
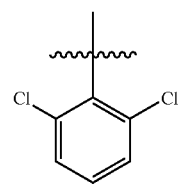 xxi
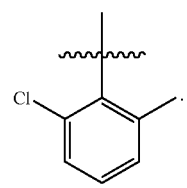 xxii
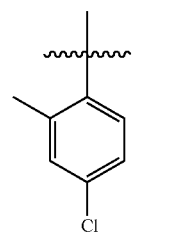 xxiii
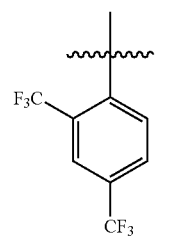 xxiv
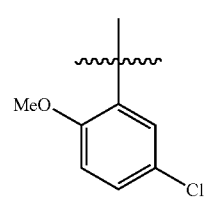 xxv
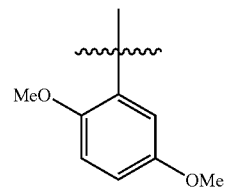 xxvi
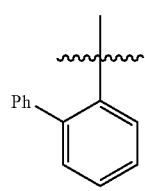 xxvii
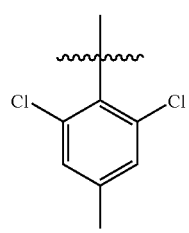 xxviii
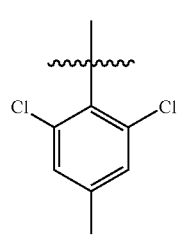 xxix
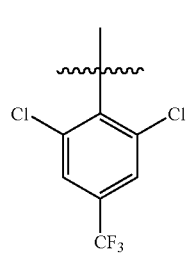 xxx
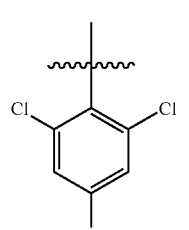 xxxi
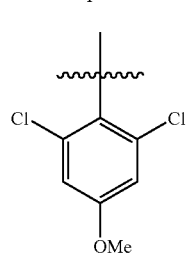 xxxii
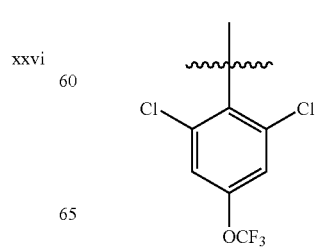 xxxiii -continued
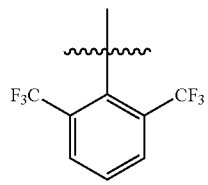
xxxiv
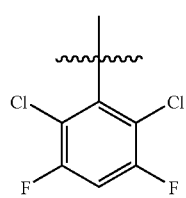
xxxv
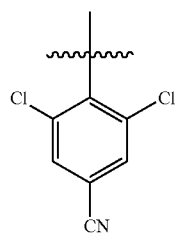
xxxvi
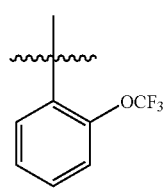
xxxvii
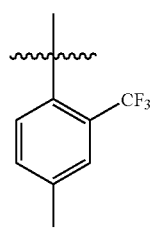
xxxviii
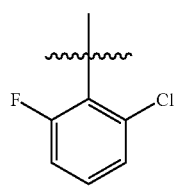
xxxix
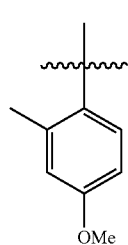
xl
-continued
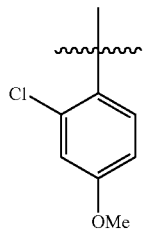
xli
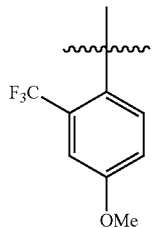
xlii
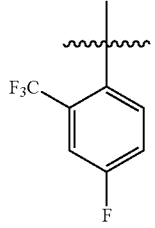
xliii
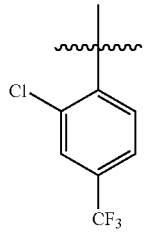
xliv
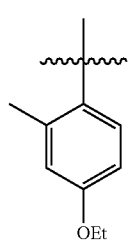
xlv
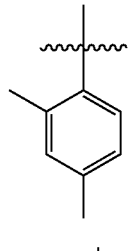
xlvi
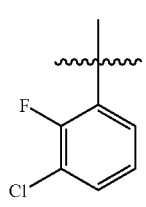
xlvii -continued xlviii
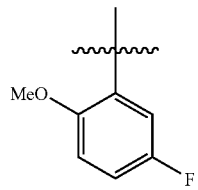

xlix
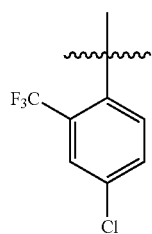

l
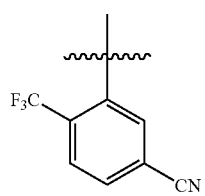

li
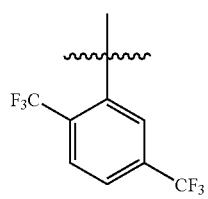

lii
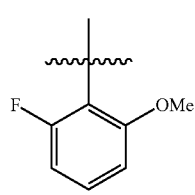

liii
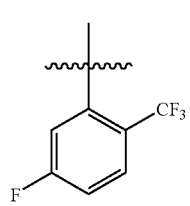

liv
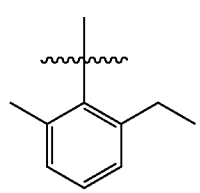

-continued lv
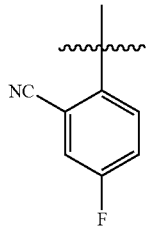

lvi
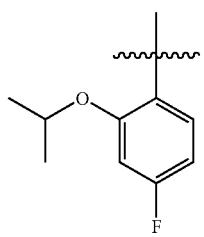

lvii
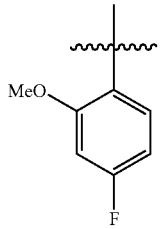

According to another embodiment, the Ar group of formula I is pyridyl.

As defined generally above, the $R^2$ of formula I is hydrogen, $C_{1-3}$ alkyl, or —O($C_{1-3}$ alkyl). In certain embodiments, the $R^2$ of formula I is hydrogen, methyl, or methoxy. In other embodiments, the $R^2$ of formula I is hydrogen or methyl. In still other embodiments, the $R^2$ of formula I is hydrogen.

Compounds of the present invention contain asymmetric carbon atoms and thus give rise to stereoisomers, including enantiomers and diastereomers. Accordingly, it is contemplated that the present invention relates to all of these stereoisomers, as well as to mixtures of the stereoisomers. Throughout this application, the name of the product of this invention, where the absolute configuration of an asymmetric center is not indicated, is intended to embrace the individual stereoisomers as well as mixtures of stereoisomers. In certain embodiments of the invention, compounds having an absolute (R) configuration are preferred.

In certain embodiments, the present invention provides a compound of formula IVa, IVb, IVc, or IVd:

IVa
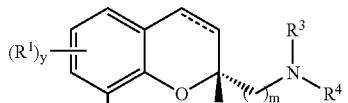

IVb
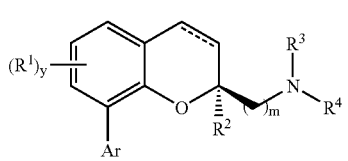

-continued

IVc
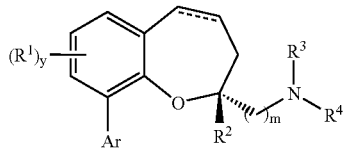

IVd
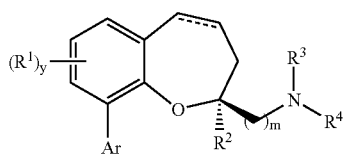

or a pharmaceutically acceptable salt thereof, wherein each R¹, R², R³, R⁴, Ar, y and m are as defined above for compounds of formula I and in classes and subclasses as described above and herein.

According to another embodiment, the present invention provides a compound of any of formula Va, Vb, Vc, Vd, Ve, Vf, Vg, or Vh:

Va
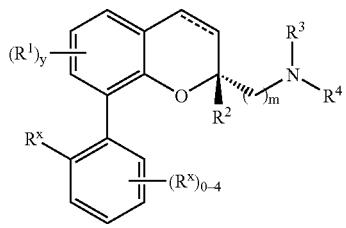

Vb
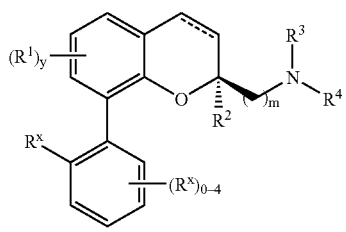

Vc
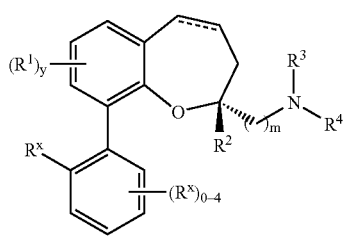

Vd
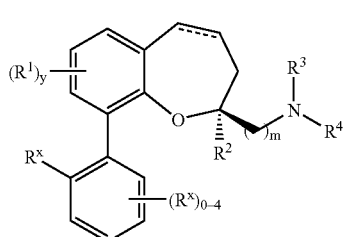

Ve
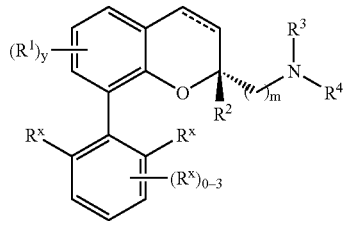

Vf
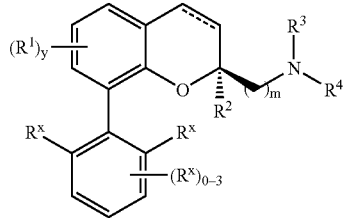

Vg
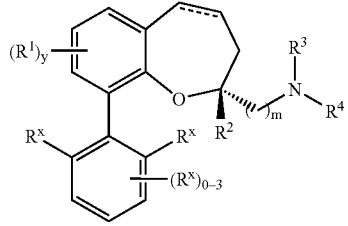

Vh
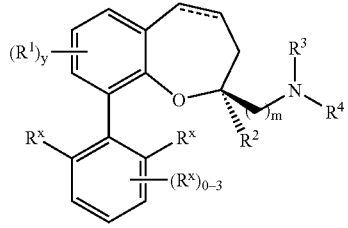

or a pharmaceutically acceptable salt thereof, wherein each R¹, R², R³, R⁴, R$^x$, y and m are as defined above for compounds of formula I and in classes and subclasses as described above and herein.

Where an enantiomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. "Substantially free," as used herein, means that the compound is made up of a significantly greater proportion of one enantiomer. In certain embodiments the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H.

*Tables of Resolving Agents and Optical Resolutions* p. 268 (E. L. Eliel, Ed., Univ. of Notre Dame Press, Notre Dame, Ind. 1972).

It is further recognized that atropisomers of the present compounds may exit. The present invention thus encompasses atropisomeric forms of compounds of formula I as defined above, and in classes and subclasses described above and herein.

Exemplary compounds of formula I are set forth in Table 1, below.

TABLE 1

Exemplary Compounds of Formula I:

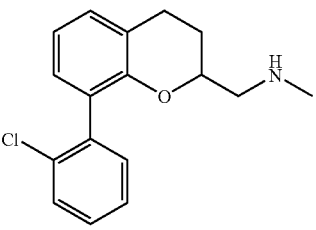

I-1

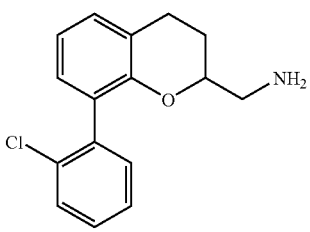

I-2

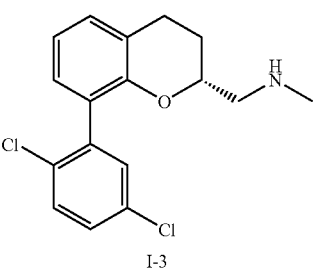

I-3

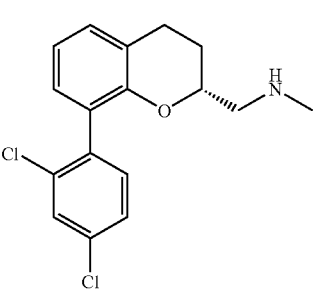

I-4

TABLE 1-continued

Exemplary Compounds of Formula I:

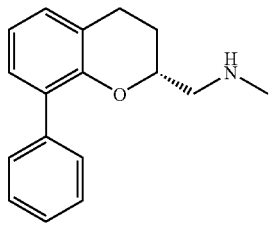

I-5

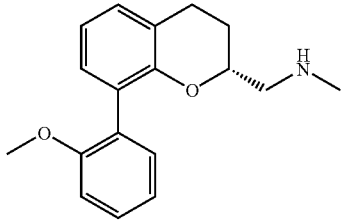

I-6

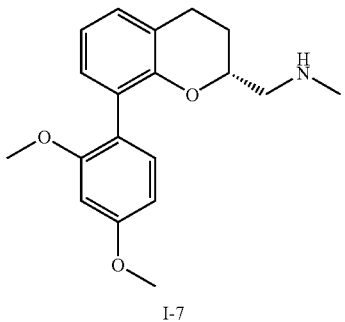

I-7

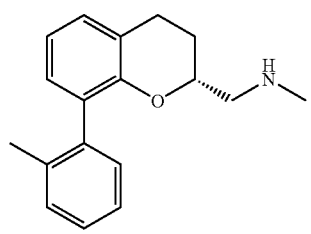

I-8

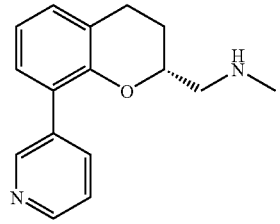

I-9

TABLE 1-continued
Exemplary Compounds of Formula I:
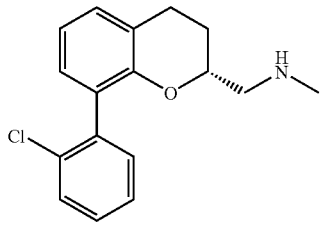
I-10
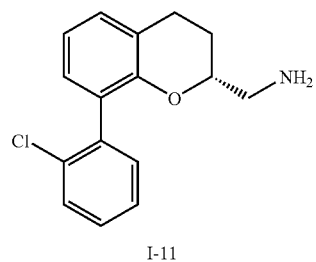
I-11
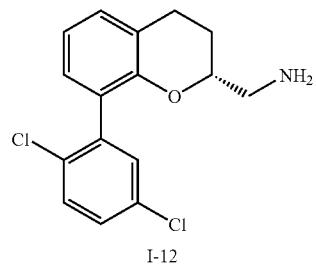
I-12
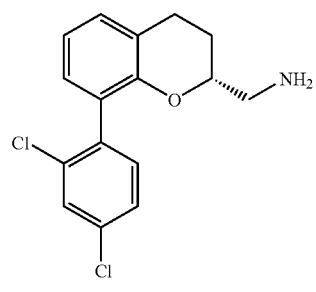
I-13
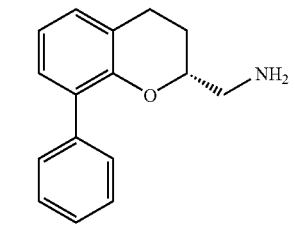
I-14
TABLE 1-continued
Exemplary Compounds of Formula I:
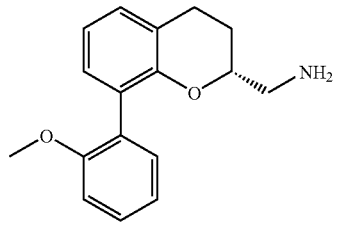
I-15
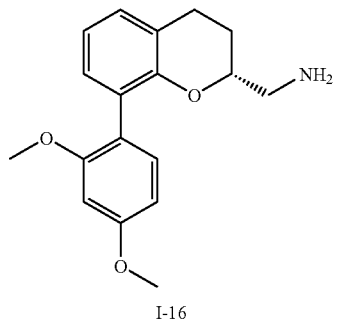
I-16
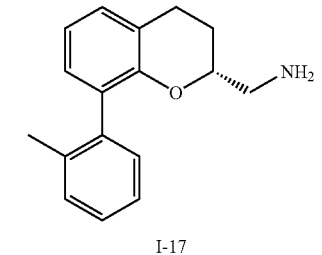
I-17
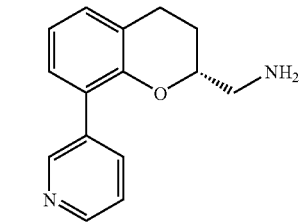
I-18
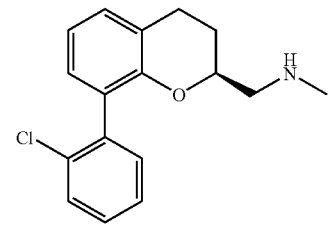
I-19

TABLE 1-continued
Exemplary Compounds of Formula I:
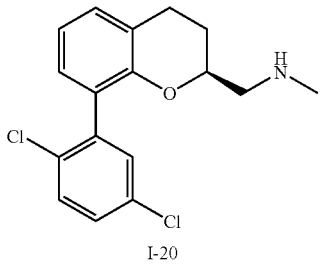
I-20
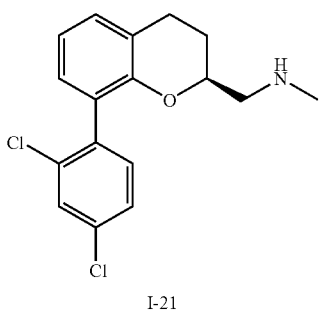
I-21
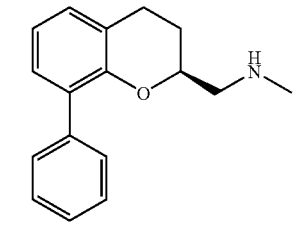
I-22
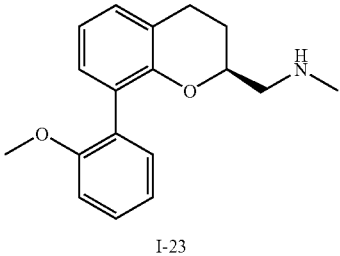
I-23
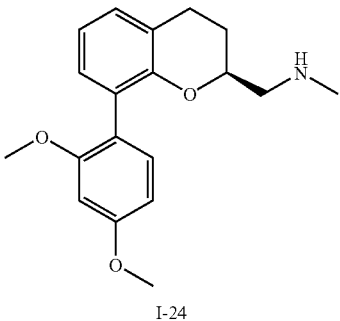
I-24
TABLE 1-continued
Exemplary Compounds of Formula I:
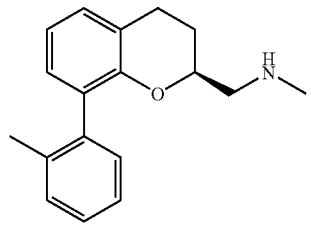
I-25
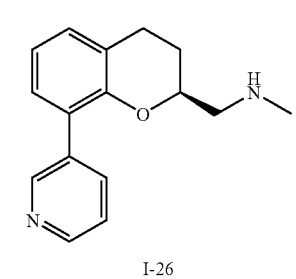
I-26
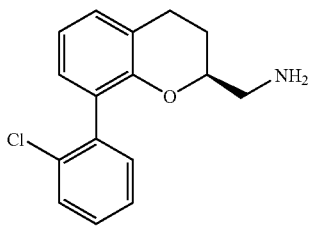
I-27
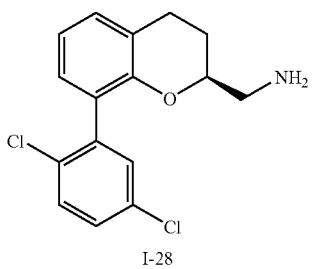
I-28
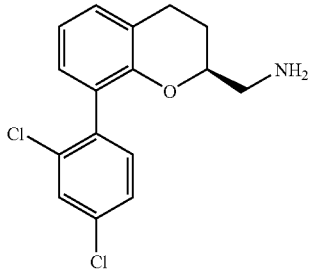
I-29

TABLE 1-continued
Exemplary Compounds of Formula I:
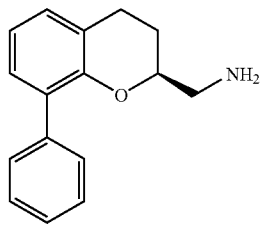
I-30
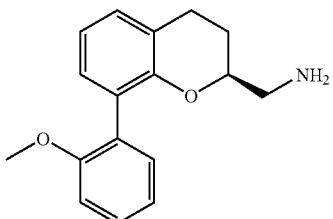
I-31
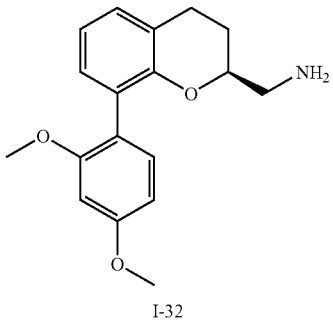
I-32
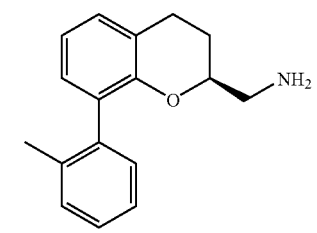
I-33
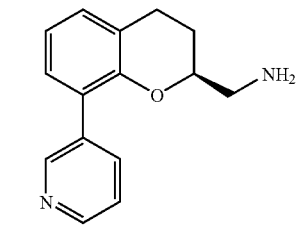
I-34
TABLE 1-continued
Exemplary Compounds of Formula I:
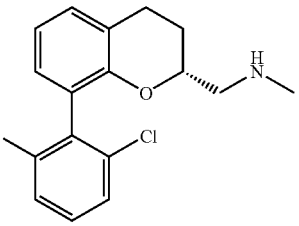
I-35
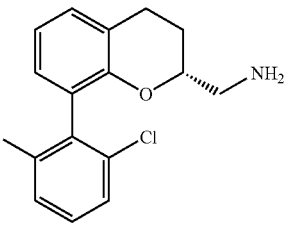
I-36
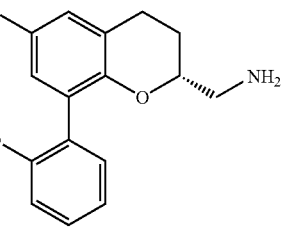
I-37
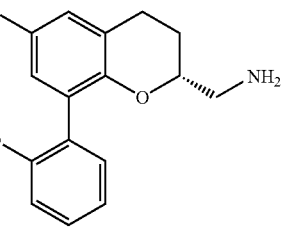
I-38
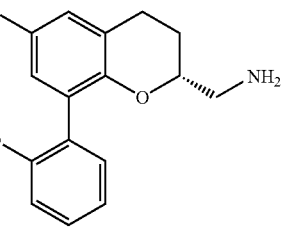
I-39

TABLE 1-continued
Exemplary Compounds of Formula I:
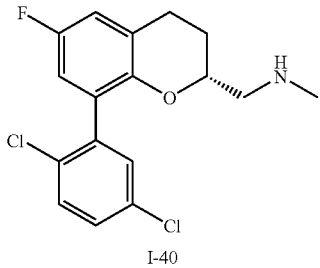
I-40
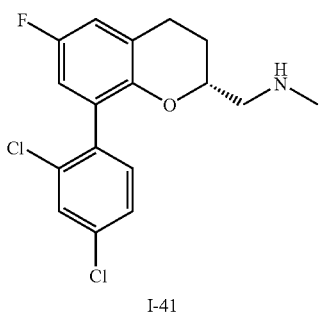
I-41
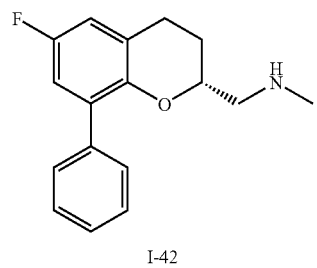
I-42
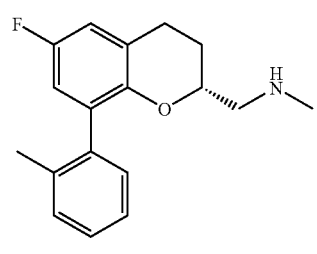
I-43
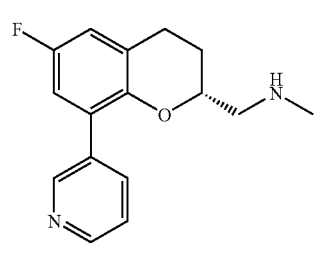
I-44
TABLE 1-continued
Exemplary Compounds of Formula I:
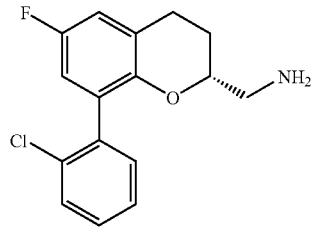
I-45
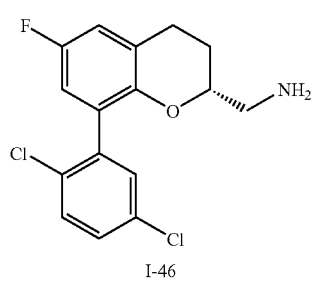
I-46
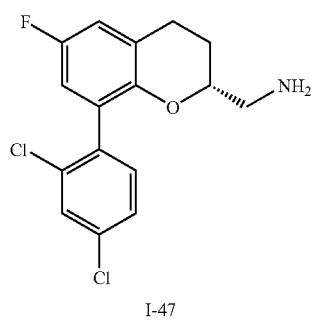
I-47
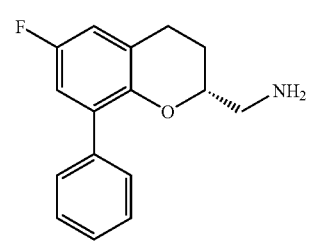
I-48
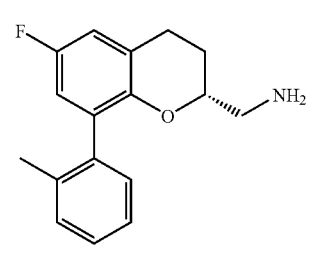
I-49

TABLE 1-continued
Exemplary Compounds of Formula I:
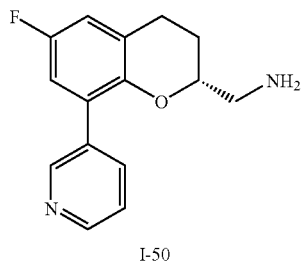
I-50
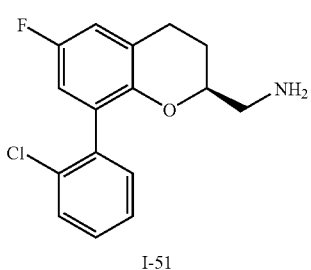
I-51
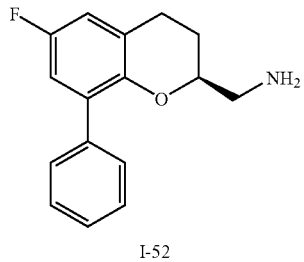
I-52
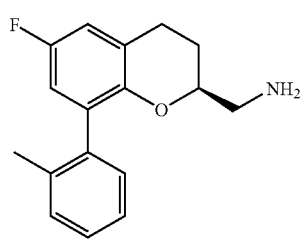
I-53
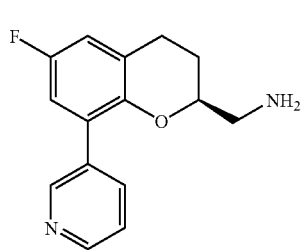
I-54
TABLE 1-continued
Exemplary Compounds of Formula I:
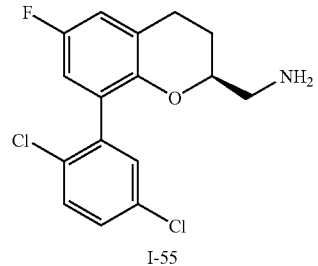
I-55
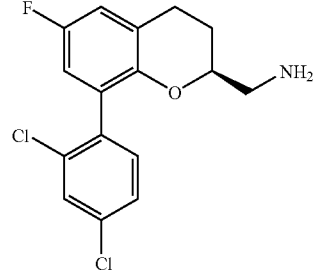
I-56
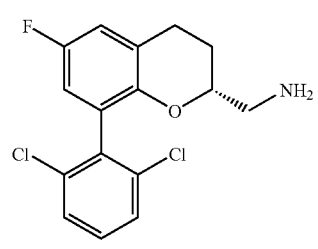
I-57
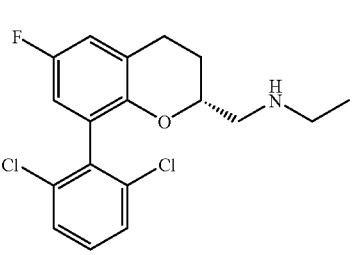
I-58
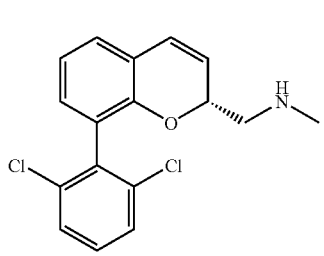
I-59

TABLE 1-continued
Exemplary Compounds of Formula I:
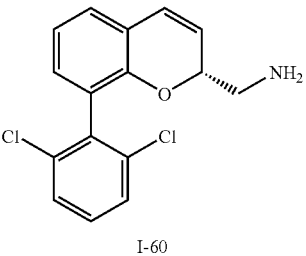
I-60
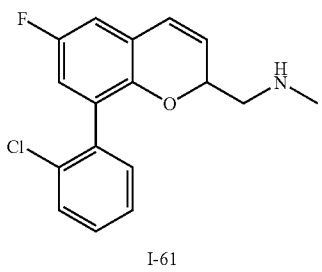
I-61
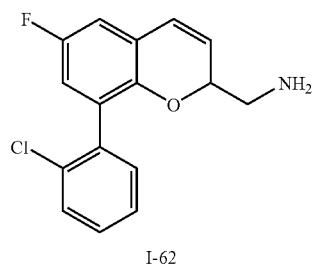
I-62
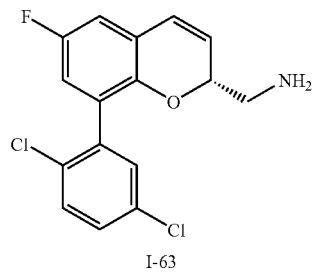
I-63
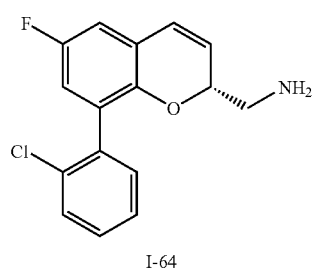
I-64
TABLE 1-continued
Exemplary Compounds of Formula I:
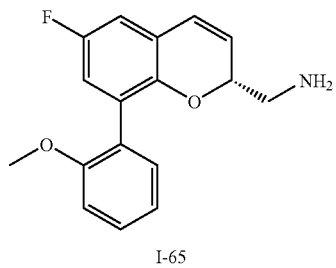
I-65
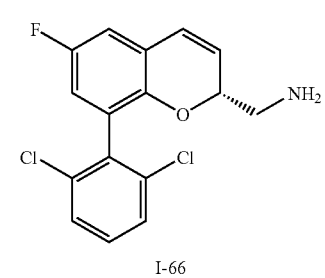
I-66
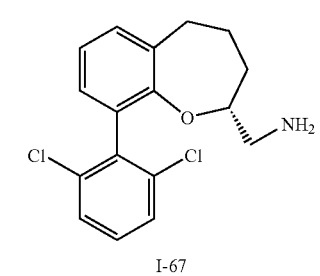
I-67
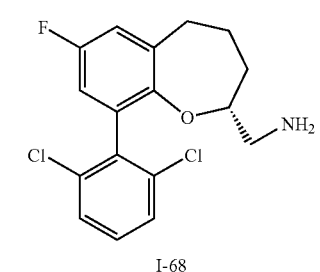
I-68
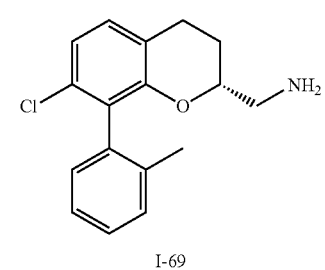
I-69

TABLE 1-continued
Exemplary Compounds of Formula I:
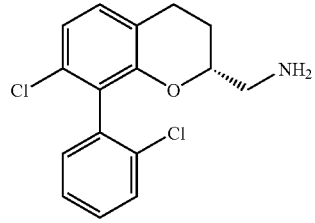
I-70
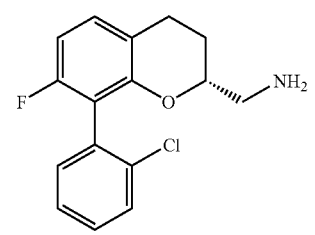
I-71
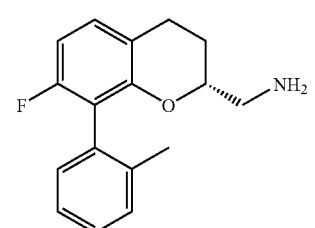
I-72
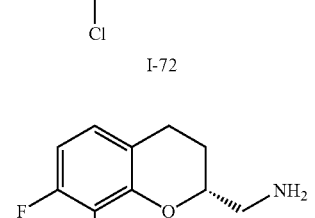
I-73
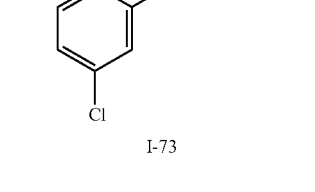
I-74
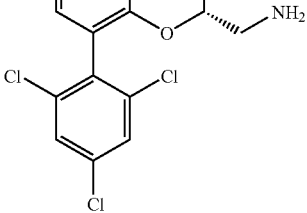
I-75
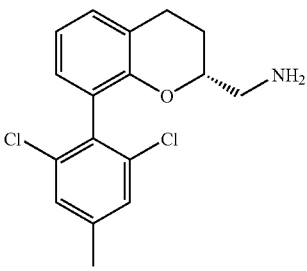
I-76
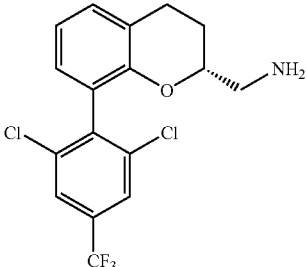
I-77
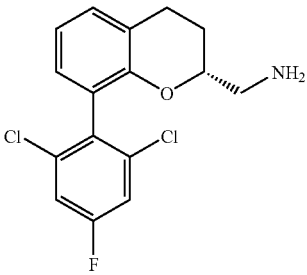
I-78
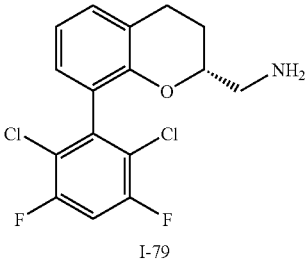
I-79

TABLE 1-continued
Exemplary Compounds of Formula I:
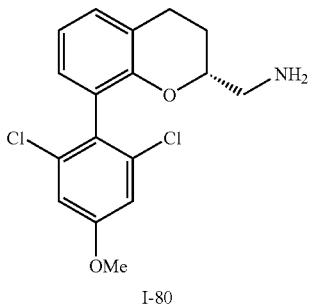
I-80
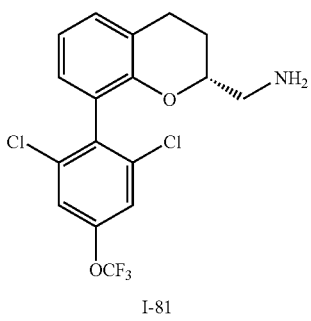
I-81
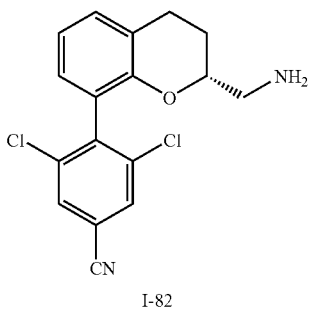
I-82
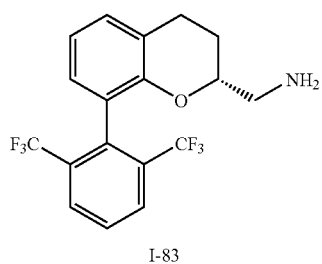
I-83
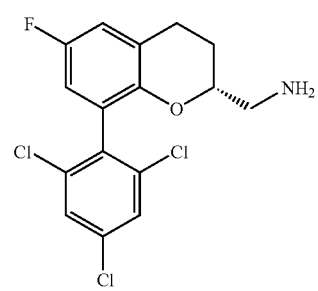
I-84
TABLE 1-continued
Exemplary Compounds of Formula I:
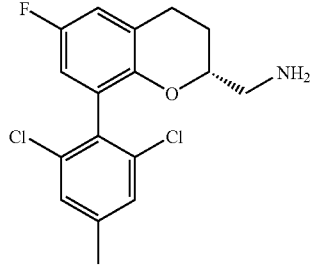
I-85
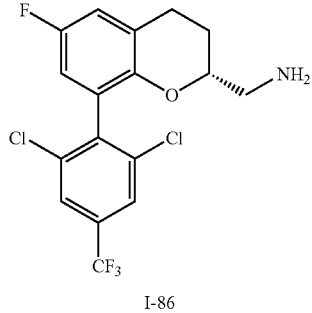
I-86
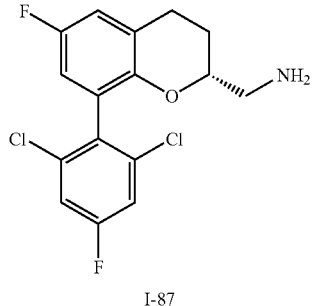
I-87
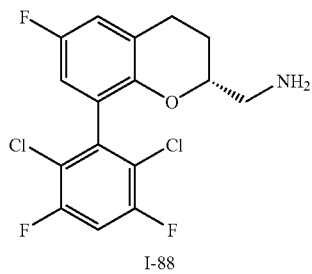
I-88
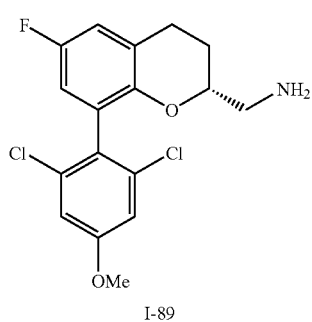
I-89

TABLE 1-continued
Exemplary Compounds of Formula I:
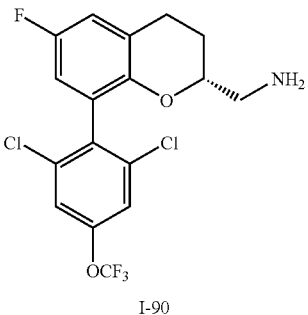
I-90
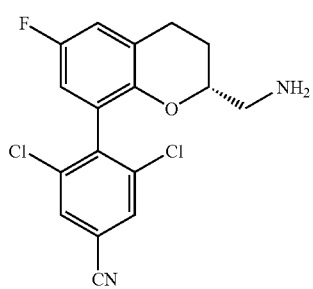
I-91
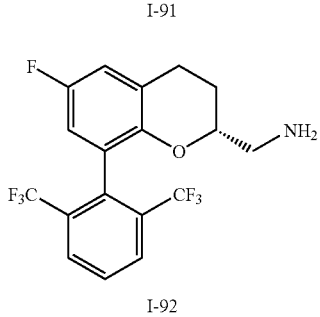
I-92
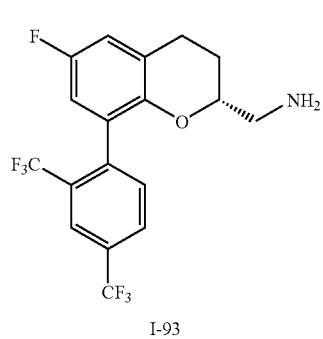
I-93
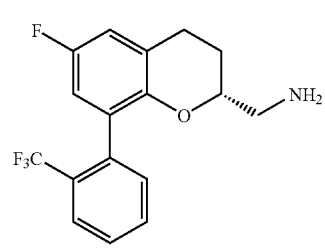
I-94
TABLE 1-continued
Exemplary Compounds of Formula I:
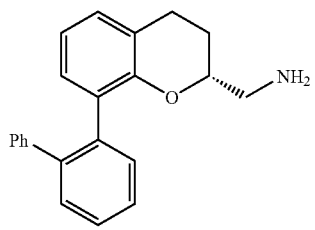
I-95
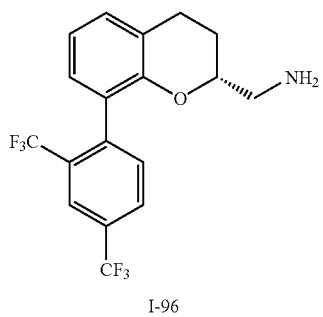
I-96
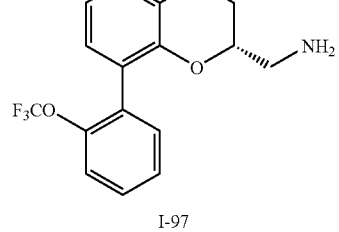
I-97
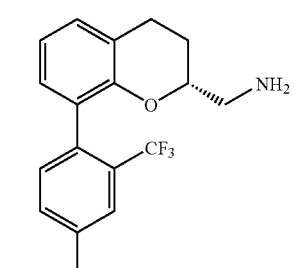
I-98
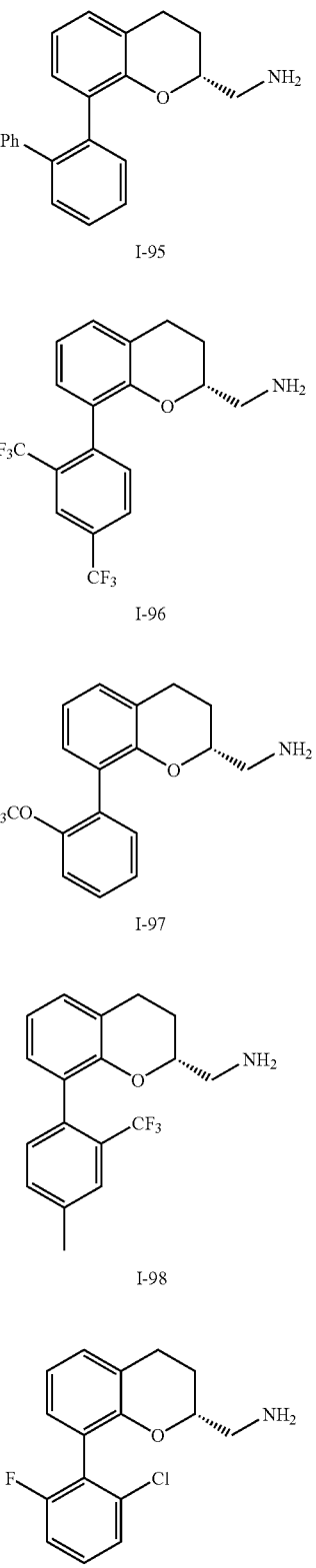
I-99

TABLE 1-continued
Exemplary Compounds of Formula I:
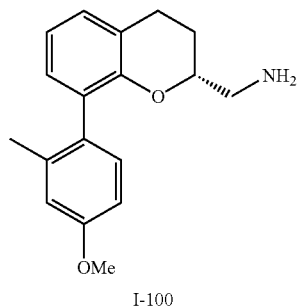
I-100
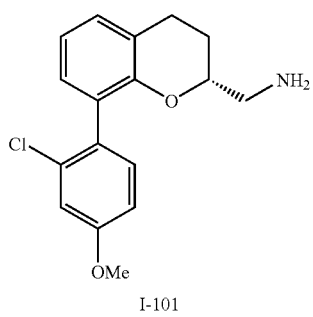
I-101
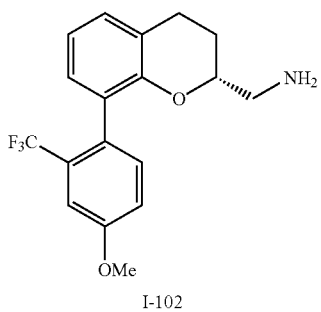
I-102
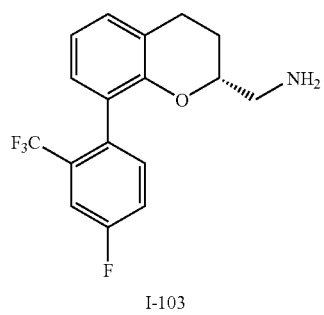
I-103
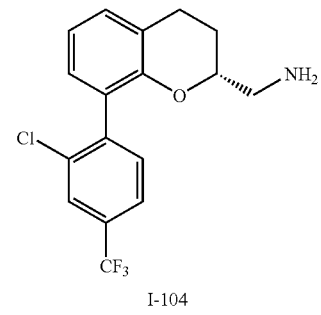
I-104
TABLE 1-continued
Exemplary Compounds of Formula I:
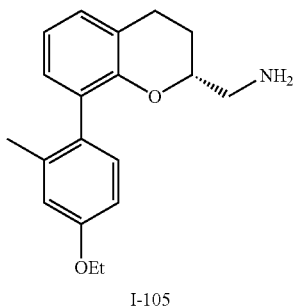
I-105
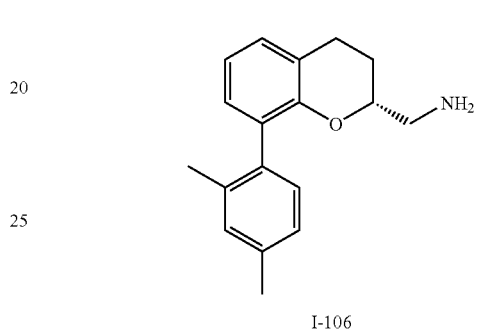
I-106
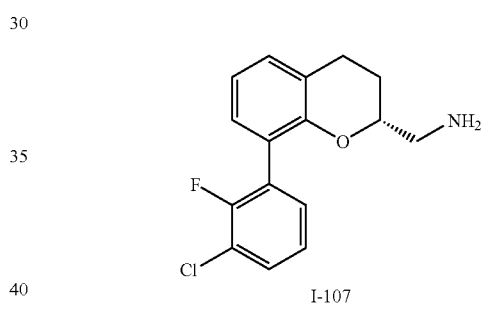
I-107
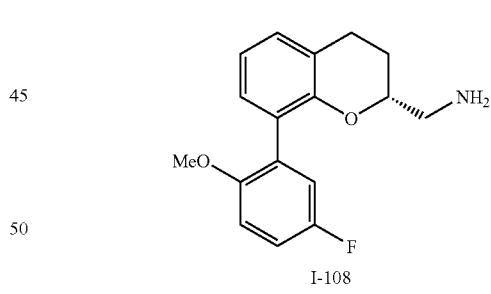
I-108
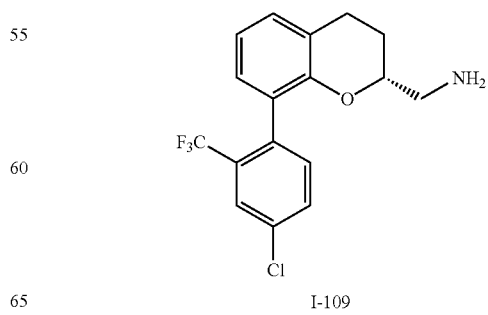
I-109

TABLE 1-continued
Exemplary Compounds of Formula I:
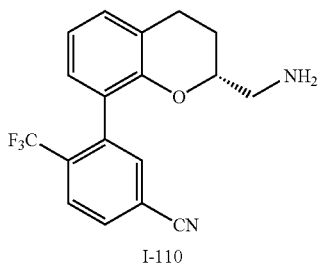
I-110
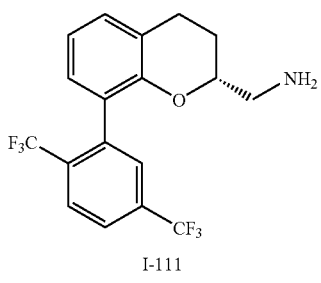
I-111
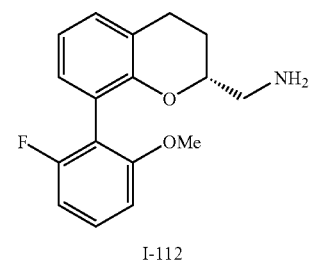
I-112
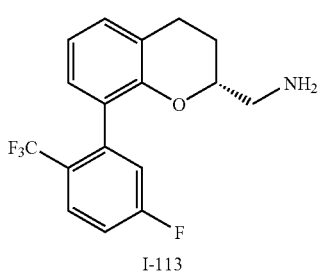
I-113
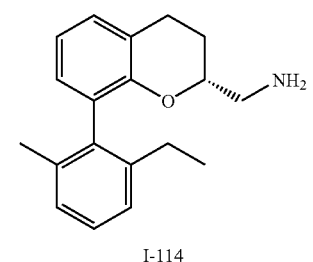
I-114
TABLE 1-continued
Exemplary Compounds of Formula I:
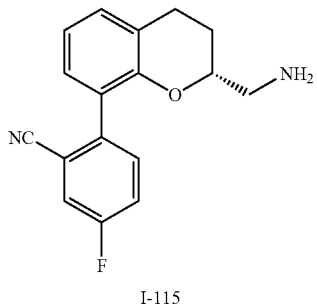
I-115
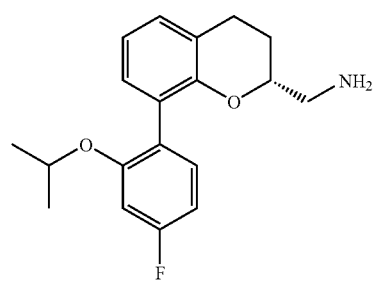
I-116
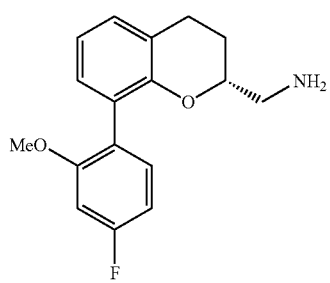
I-117
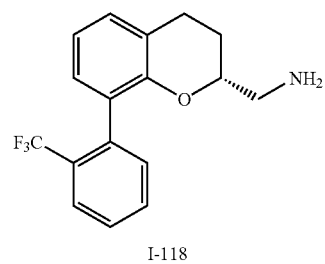
I-118
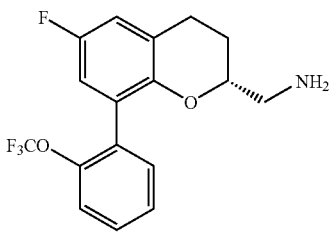
I-119

TABLE 1-continued

Exemplary Compounds of Formula I:

I-120

I-121

I-122

I-123

I-124

I-125

I-126

I-127

I-128

I-129

TABLE 1-continued

Exemplary Compounds of Formula I:

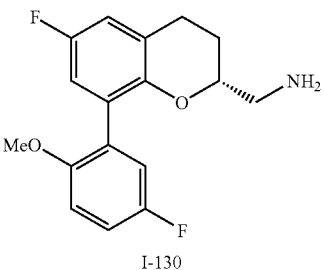
I-130

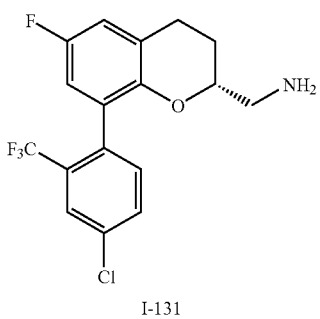
I-131

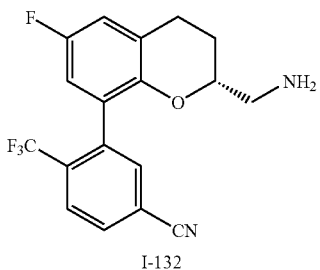
I-132

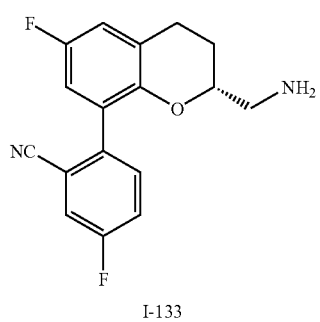
I-133

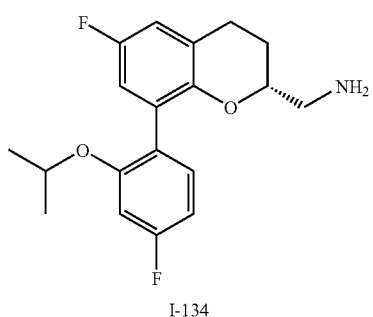
I-134

TABLE 1-continued

Exemplary Compounds of Formula I:

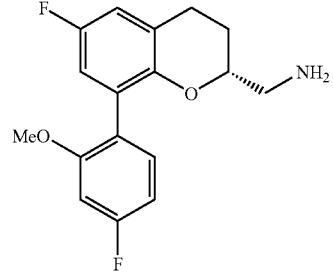
I-135

It will be appreciated that for each racemic compound disclosed in Table 1, above, both enantiomers are separately contemplated and included herein. For example, for compound I-1 depicted above as a racemate, each of its enantiomers of structures I-1a and I-1b:

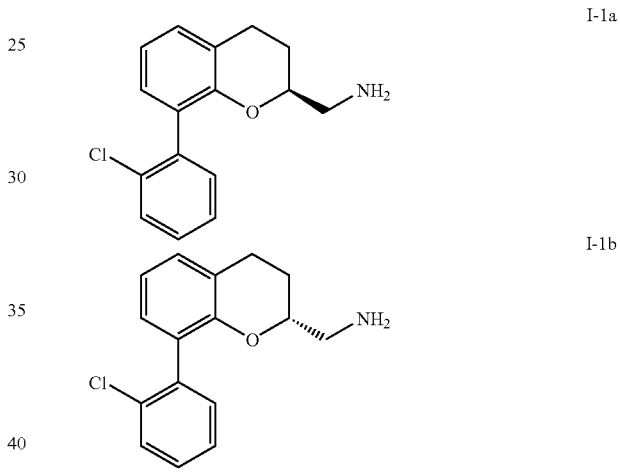

are contemplated and included herein.

It will be appreciated that for each enantiomer disclosed in Table 1, above, the opposite enantiomer is contemplated and included herein. For example, for compounds I-36 and I-57 depicted above as a single enantiomer, their opposite enantiomers of structures I-36a and I-57a:

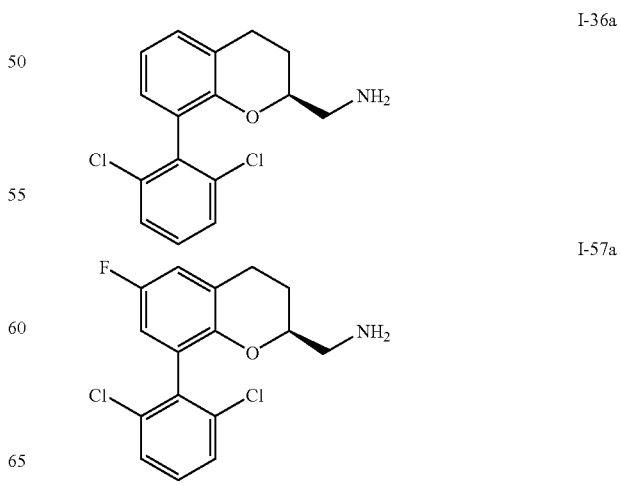

are also contemplated and included herein.

In addition, for each enantiomer disclosed in Table 1, above, the racemate of that compound is also contemplated and included herein. For example, for compounds I-36 and I-57 depicted above as a single enantiomer, their racemates of structures I-36b and I-57b:

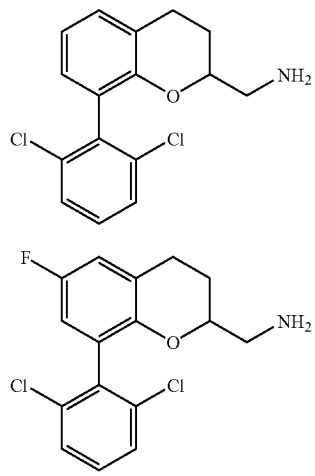

I-36b

I-57b are also contemplated and included herein.

3. General Methods of Providing the Present Compounds:

Compounds of the present invention are prepared by methods known to one of ordinary skill in the art and by methods illustrated in Scheme 1–17, below. Unless otherwise noted, all variables are as defined above and in classes and subclasses described above and herein.

The chroman and 2H-chromene derivatives of formula Ia of the present invention are prepared as illustrated in Scheme 1, below. Unless otherwise noted the variables are as defined above. Specifically, Suzuki coupling of the appropriately substituted bromide or triflate (1) with a suitable coupling partner, such as arylboronic acids, using a palladium catalyst under basic conditions affords the biaryl derivative (2). The source of palladium is normally tetrakis(triphenylphosphine)palladium (0) or another suitable source such as trans-dichlorobis(tri-o-tolylphosphine)palladium (II). The normal choices for the reaction base are sodium or potassium carbonate, cesium or potassium fluoride or potassium phosphate, and the solvent choices include tetrahydrofuran, dioxane, ethylene glycol dimethyl ether, water and toluene. Displacement of the tosylate leaving group in (2) with a monoalkylamine or dialkylamine affords a compound of formula Ia. The reaction can be executed in a suitable aprotic solvent including but not limited to tetrahydrofuran or dimethyl sulfoxide at temperatures ranging from room temperature to 100° C.

Scheme 1

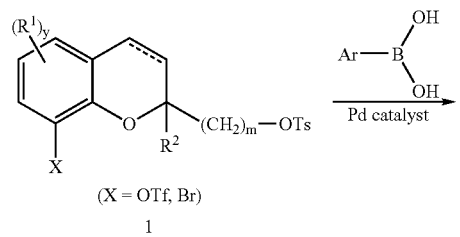

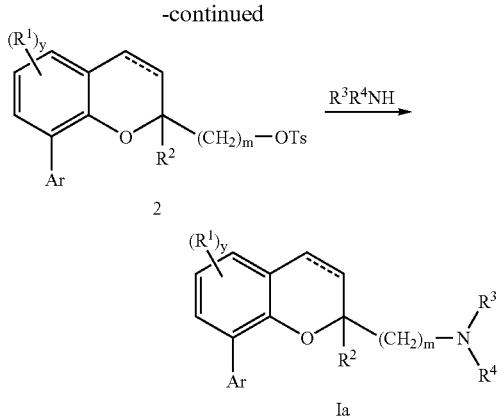

Alternatively, the tosylate (2) can be converted to the azide (3), on treatment with sodium azide, and the azide reduced to amine with a suitable reducing agent such as triphenylphosphine in tetrahydrofuran and water to afford compounds of formula Ia, wherein $R^3$ and $R^4$ are hydrogen, Scheme 2.

Scheme 2

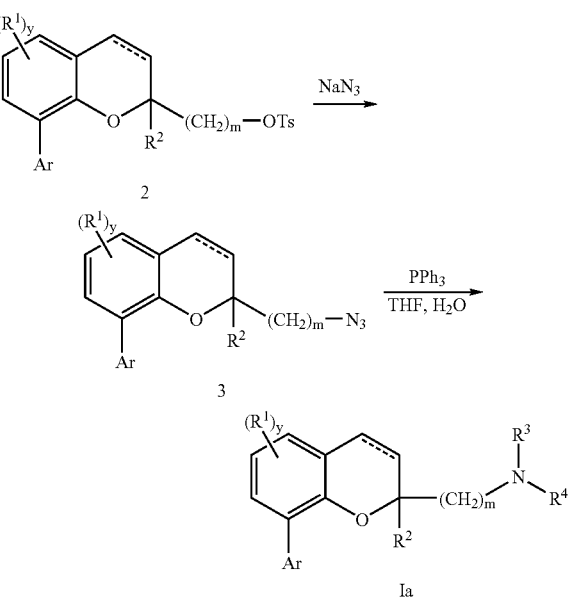

The intermediate tosylates (1), wherein X is OTf, can be prepared as illustrated in Scheme 3. Wittig reaction of an appropriately substituted 2-hydroxy-3-methoxybenzaldehyde (4) with a phosphorus ylid gives an alkene (5). Mitsunobu etherification of (5) on treatment with a substituted allylic alcohol (6), diethyl azodicarboxylate and triphenylphosphine affords diene (7). The diene (7) is then subjected to a ring closing metathesis reaction on treatment with bis(tricyclohexylphosphine)benzylidine ruthenium (IV) dichloride (Schwab, P. et al. Journal of the American Chemical Society 1996, 118, 100) to give 2H-chromene derivative (8). Hydrogenation of the double bond of the 2H-chromene derivative (8) in the presence of a metal catalyst gives the chroman derivative (9). Suitable metal catalysts include palladium on activated carbon, platinum (IV) oxide or sulfided platinum on carbon and the choice of catalyst is dependent on the substituents on the aromatic ring. The methyl ether present on (9) is cleaved on treatment with iodotrimethylsilane in a halogenated solvent such as 1,2-dichloroethane to give phenol (10). The phenol (10) is reacted with trifluoromethanesulfonic anhydride in the presence of a base such as pyridine or N,N-diisopropylethylamine to give the triflate (1), wherein $R^2$ is hydrogen, X is ---- and represents a single bond.

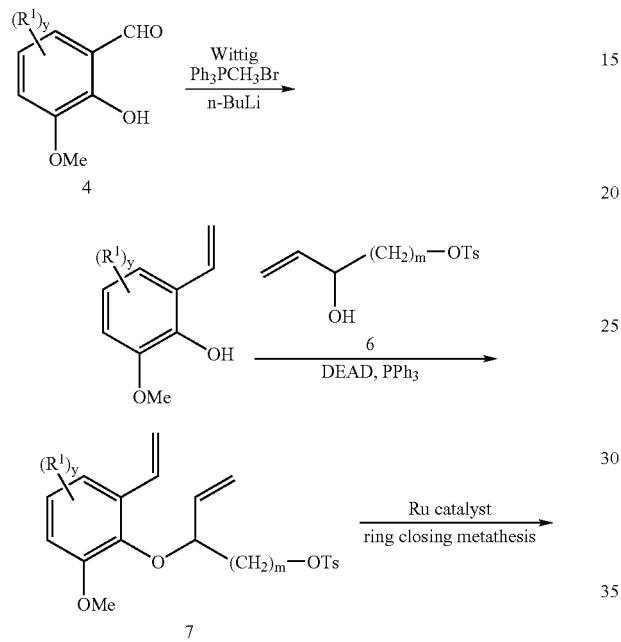

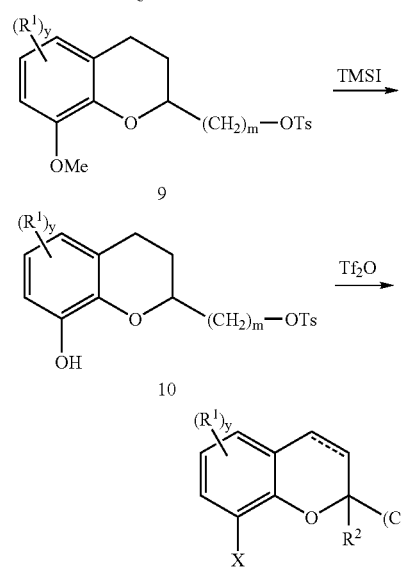

Alternatively, the intermediate tosylate (1), wherein X is bromide, can be prepared as illustrated in Scheme 4 and Scheme 5.

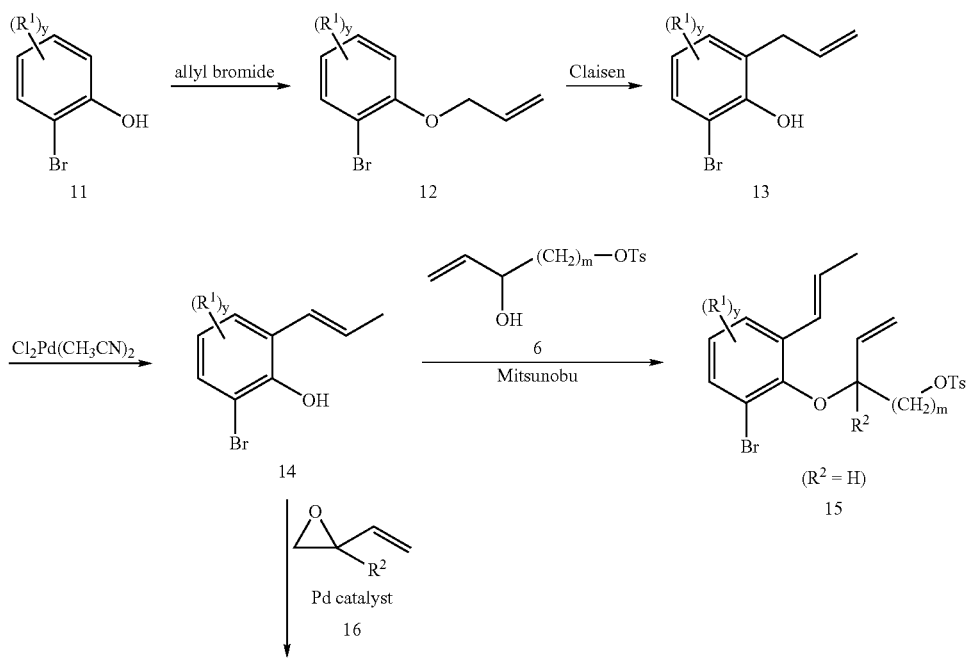

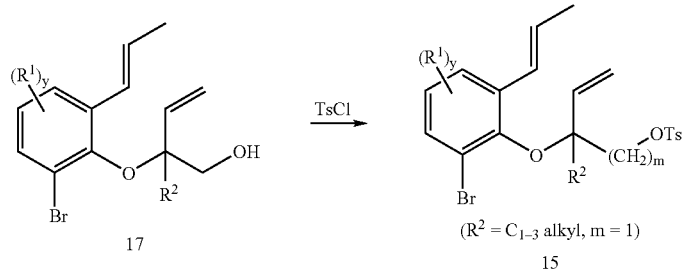

The substituted 2-bromophenol (11) is alkylated with allyl bromide in the presence of a suitable base such as sodium hydride or potassium carbonate to give (12). Claisen rearrangement of (12) in a refluxing high-boiling point solvent such as 1-methyl-2-pyrrolidinone or ethylene glycol gives phenol derivative (13). The double bond in (13) is isomerized to give (14), in which the double bond is in conjugation with the aromatic ring, on treatment with a suitable palladium catalyst such as bis(acetonitrile)palladium (II) dichloride. Mitsunobu etherification of (14) on treatment with a substituted allylic alcohol (6), diethyl azodicarboxylate and triphenylphosphine affords diene (15), wherein $R^2$ is hydrogen. Alternatively, treatment of phenol (14) with a substituted vinyloxirane (16) in the presence of a suitable palladium catalyst, such as tetrakis(triphenylphosphine) palladium (0), will give the diene (17) (Goujon, J-Y. et al. Journal of the Chemical Society Perkin Trans 1 2002, 496). Treatment of the alcohol (17) with p-toluenesulfonyl chloride in the presence of a suitable base such as pyridine or N,N-diisopropylethylamine gives the tosylate (15), wherein $R^2$ is $C_{1-3}$ alkyl and m is 1.

As illustrated in Scheme 5, subjecting diene (15) to a ring closing metathesis reaction on treatment with bis(tricyclohexylphosphine)benzylidine ruthenium (IV) dichloride gives 2H-chromene derivative (18). Hydrogenation of the double bond of the 2H-chromene derivative (18) without reduction of the aryl bromide can be achieved using a suitable catalyst such as platinum (IV) oxide or sulfided platinum to give a chroman derivative of formula 1, wherein ---- represents a single bond and X is bromide.

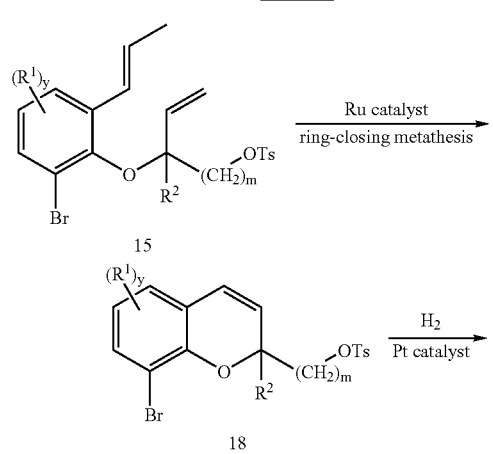

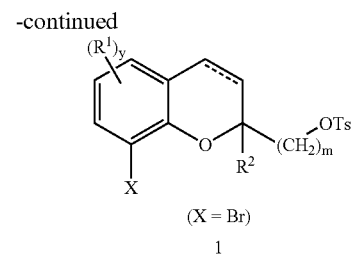

Alternatively, the intermediate 8-arylchroman or 8-aryl-2H-chromene intermediates (2) can be prepared as illustrated in Scheme 6.

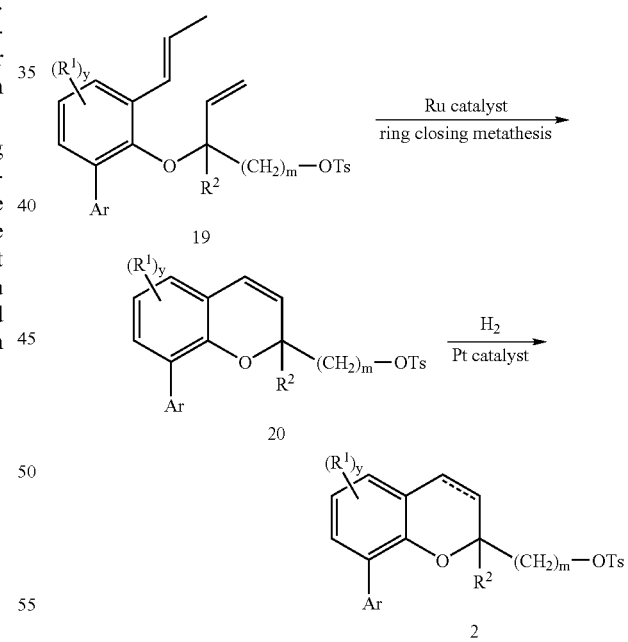

Diene (19) is subjected to a ring closing metathesis reaction on treatment with bis(tricyclohexylphosphine)benzylidine ruthenium (IV) dichloride to give 2H-chromene derivative (20). Hydrogenation of the double bond of the 2H-chromene derivative (20) can be achieved using a suitable catalyst such as platinum (IV) oxide or sulfided platinum to give the chroman derivative (2), wherein ---- represents a single bond, Scheme 6.

Synthesis of an intermediate diene of formula 19 is illustrated in Scheme 7.

Scheme 7

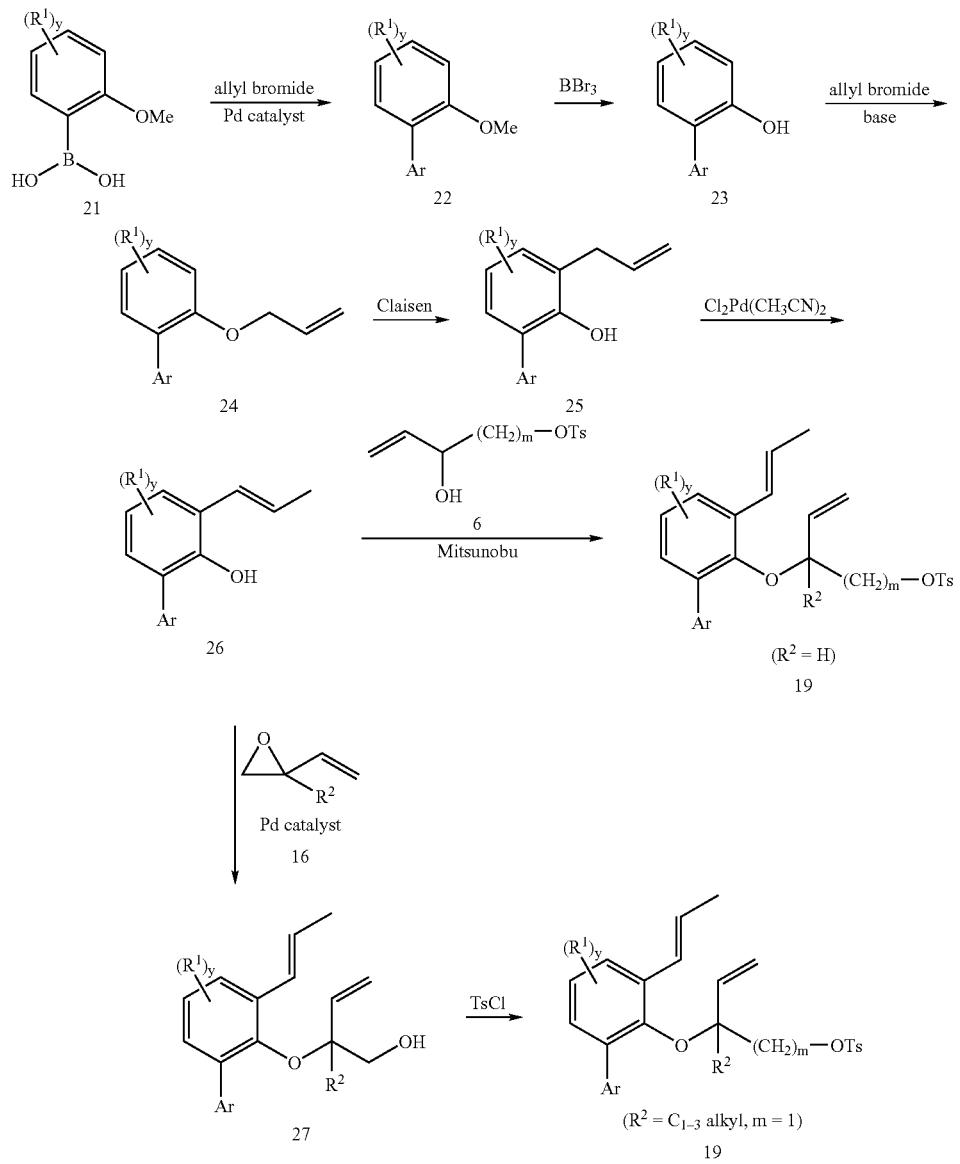

Suzuki coupling of 2-methoxyphenylboronic acids (21) with different aryl halides using a palladium catalyst under basic conditions affords anisole derivatives (22). The source of palladium is normally tetrakis(triphenylphosphine)palladium (0) or another suitable source such as trans-dichlorobis(tri-o-tolylphosphine)palladium (II). Typically, the reaction base is sodium or potassium carbonate, cesium or potassium fluoride or potassium phosphate, and the solvent includes tetrahydrofuran, dioxane, ethylene glycol dimethyl ether, water, toluene and mixtures thereof. Cleavage of the methyl ether in (22) with boron tribromide gives phenol (23) that can be alkylated with allyl bromide in the presence of a suitable base to give allyl ether derivatives (24). Claisen rearrangement of (24) in a refluxing high-boiling point solvent such as 1-methyl-2-pyrrolidinone or ethylene glycol gives phenol derivative (25). The double bond in (25) is isomerized to give (26), in which the double bond is in conjugation with the aromatic ring, on treatment with bis(acetonitrile)palladium (II) dichloride in refluxing dichloromethane. Mitsunobu etherification of (26) on treatment with a substituted allylic alcohol (6), diethyl azodicarboxylate and triphenylphosphine affords diene (19), wherein $R^2$ is hydrogen. Alternatively, treatment of phenol (26) with a substituted vinyloxirane (16) in the presence of a suitable palladium catalyst, such as tetrakis(triphenylphosphine)palladium (0), will give the diene (27) (Goujon, J-Y. et al. Journal of the Chemical Society Perkin Trans 1 2002, 496). Treatment of the alcohol (27) with p-toluenesulfonyl chloride in the presence of a suitable base such as pyridine or N,N-diisopropylethylamine gives the tosylate (19), wherein $R^2=C_{1-3}$ alkyl and m is 1, Scheme 7.

An alternative synthesis of compounds of formula (Ia) is illustrated in Scheme 8 and Scheme 9.

Scheme 8

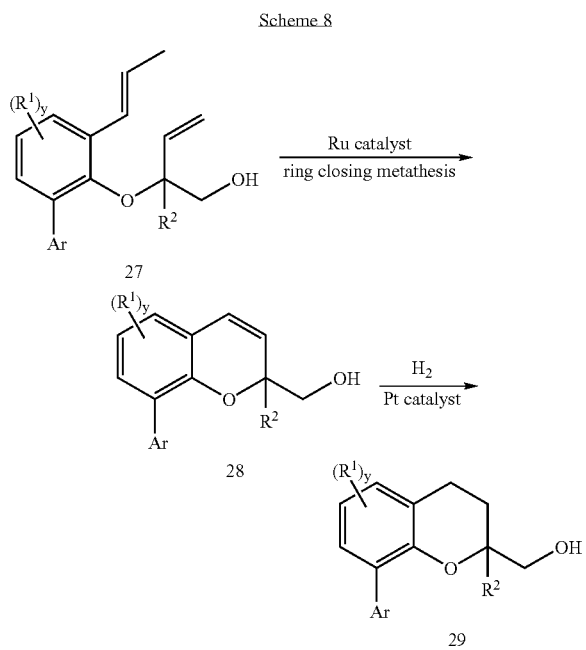

Diene (27) is subjected to a ring closing metathesis reaction on treatment with bis(tricyclohexylphosphine)benzylidine ruthenium (IV) dichloride to give 2H-chromene derivative (28). Hydrogenation of the double bond of the 2H-chromene derivative (28) can be achieved using a suitable catalyst such as platinum (IV) oxide or sulfided platinum to give the chroman derivative (29), Scheme 8.

Scheme 9

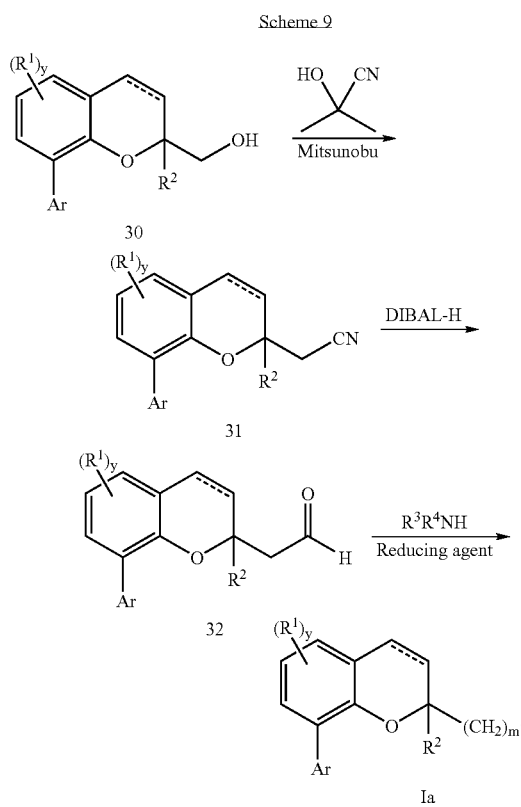

Mitsunobu homologation of the chroman or 2H-chromene alcohol (30) with acetone cyanohydrin in the presence of N,N,N',N'-tetramethylazodicarboxamide and tributylphosphine (Tsunoda, T. et al. Tetrahedron Letters 1999, 40, 7355) gives nitrile (31). The nitrile (31) may be reduced to give the corresponding aldehyde (32) on treatment with a suitable metal hydride reducing agent, such as diisobutylaluminium hydride. Reductive amination then gives the compounds of formula 1a, wherein m is 2.

The 2,3,4,5-tetrahydro-benzo[b]oxepine derivatives (Ib) of the present invention are prepared as illustrated in Scheme 10.

Scheme 10

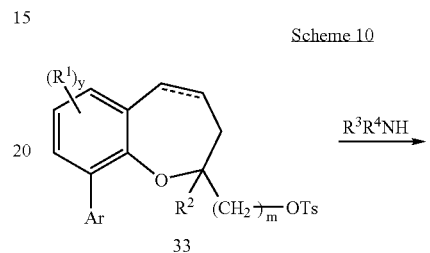

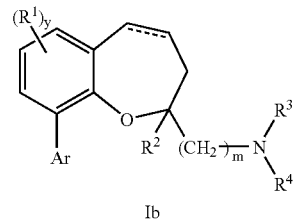

Displacement of the tosylate leaving group in (33) with a monoalkylamine or dialkylamine affords a compound of formula Ib. The reaction can be executed in a suitable aprotic solvent including but not limited to tetrahydrofuran or dimethyl sulfoxide at temperatures ranging from room temperature to 100° C.

Scheme 11

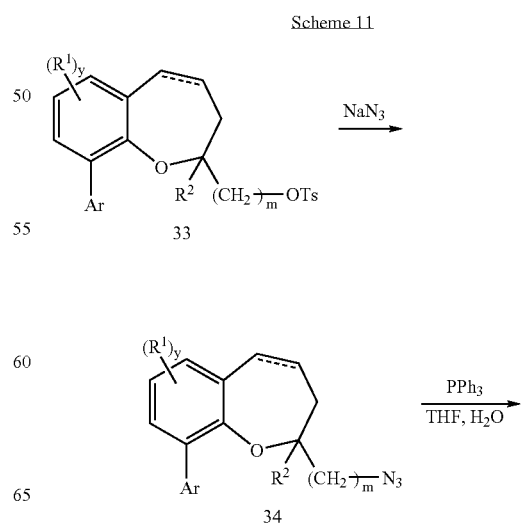

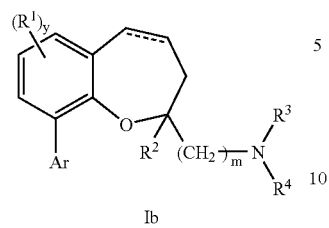

Ib

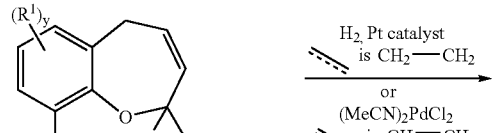

36

Alternatively, a tosylate (33) can be converted to azide (34), on treatment with sodium azide, and the azide reduced to amine with a suitable reducing agent such as triphenylphosphine in tetrahydrofuran and water to give the compounds of formula Ib, wherein $R^3$ and $R^4$ are hydrogen, Scheme 11.

Synthesis of the intermediate tosylate (33) is illustrated in Scheme 12.

Scheme 12

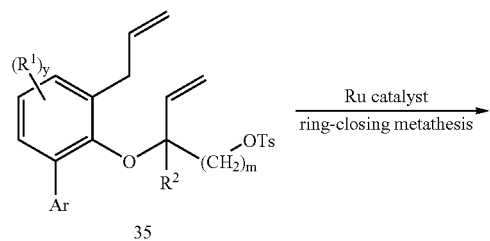

35

33

Diene (35) is subjected to a ring closing metathesis reaction on treatment with bis(tricyclohexylphosphine)benzylidine ruthenium (IV) dichloride to give 2H-chromene derivative (36). Hydrogenation of the double bond of the 2H-chromene derivative (36) can be achieved using a suitable catalyst such as platinum (IV) oxide or sulfided platinum to give the chroman derivative (33), wherein ---- represents a single bond, Scheme 12. Isomerization of the double bond can be achieved by treatment of 36 with dichlorobis(acetonitrile)palladium (II) in refluxing methylene chloride to give the chroman derivative (33), wherein ---- represents a double bond, Scheme 12.

Synthesis of the diene (35) is illustrated in Scheme 13.

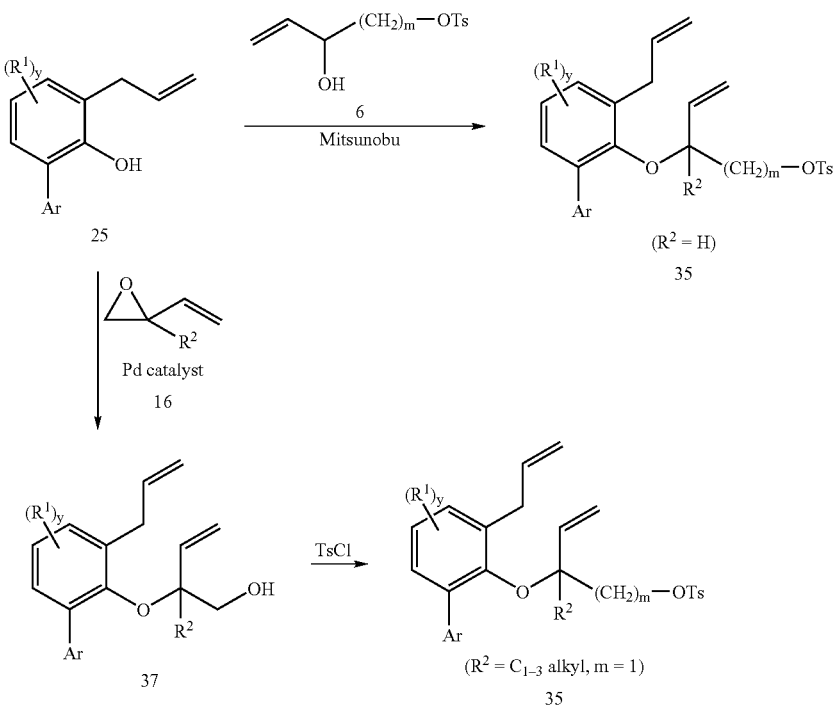

Mitsunobu etherification of (25) on treatment with a substituted allylic alcohol (6), diethyl azodicarboxylate and triphenylphosphine affords diene (35), wherein $R^2$ is hydrogen. Alternatively, treatment of phenol (25) with a substituted vinyloxirane (16) in the presence of a suitable palladium catalyst, such as tetrakis(triphenylphosphine)palladium (0), will give the diene (37) (Goujon, J.-Y. et al. Journal of the Chemical Society Perkin Trans 1 2002, 496). Treatment of the alcohol (37) with p-toluenesulfonyl chloride in the presence of a suitable base such as pyridine or N,N-diisopropylethylamine gives the tosylate (35), wherein $R^2=C_{1-3}$ alkyl and m is 1, Scheme 13.

Scheme 14, below, depicts an alternative method for preparing compounds of the present invention.

the conjugate addition step may be run in the presence or absence of a base, and with or without heating. In certain embodiments, the conjugate addition is run in the presence of potassium carbonate, potassium hydroxide, sodium hydroxide, tetrabutylammonium hydroxide, benzyltrimethylammonium hydroxide, triethylbenzylammonium hydroxide, 1,1,3,3-tetramethylguanidine, 1,8-diazabicyclo[5.4.0]undec-7-ene, N-methylmorpholine, diisopropylethylamine, tetramethylethylenediamine, pyridine, or triethylamine. In certain embodiments, the reaction is carried out in a suitable medium. A suitable medium is a solvent or a solvent mixture that, in combination with the combined reacting partners and reagents, facilitates the progress of the reaction therebetween. The suitable solvent may solubilize one or more of

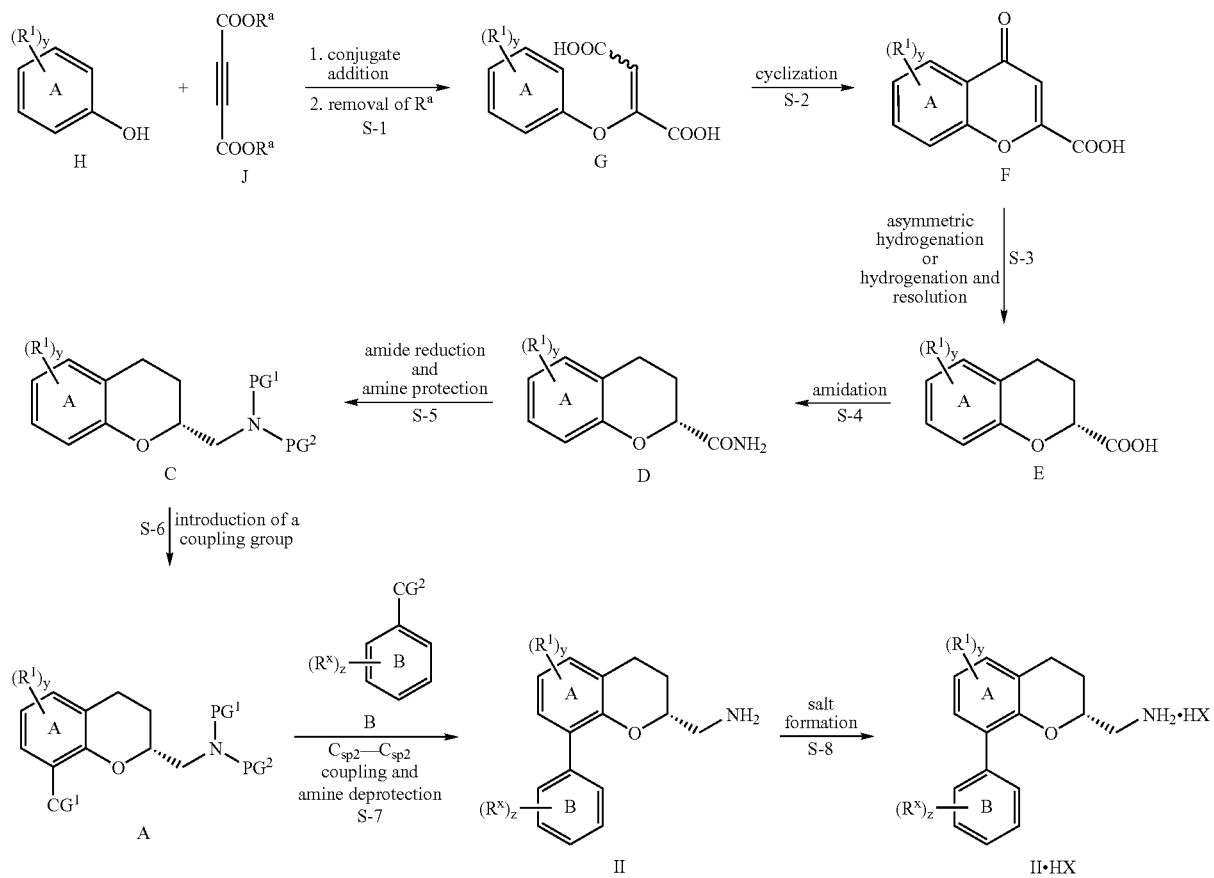

Scheme 14 wherein each z is 0–5.

In step S-1 a compound of formula H is allowed to react via conjugate addition with a compound of formula J, following which the $R^a$ groups are removed to afford the product of formula G, as depicted in Scheme 15, below. One of ordinary skill in the art will appreciate that a wide variety of reaction conditions may be employed to promote this transformation, therefore a wide variety of reaction conditions are envisioned; see, generally, *March's Advanced Organic Chemistry: Reactions, Mechanisms, and Structure*, M. B. Smith and J. March, 5th Edition, John Wiley & Sons, 2001 and *Comprehensive Organic Transformaions*, R. C. Larock, 2nd Edition, John Wiley & Sons, 1999. For example, the reaction components, or, alternatively, the suitable solvent may facilitate the suspension of one or more of the reaction components; see, generally, March (2001). In certain embodiments the present transformation is run in excess of the phenol reagent (corresponding to formula H), diphenyl ether, dioxane, anisole, acetone, tetrahydrofuran, ethyl acetate, isopropyl acetate, dimethylformamide, ethylene glycol, toluene, water, diisopropylethylamine, triethylamine, pyridine, N-methylmorpholine, acetonitrile, N-methylpyrrolidine, or mixtures thereof. In other embodiments the reaction is conducted at temperatures between around 25° C. and about 110° C. In yet other embodiments, the reaction is conducted at around 25° C. In other embodiments, the conjugate addition is carried out according to the procedures outlined in Ruhemann, S. J *Chem. Soc.* 1900, 77, 1121, Gudi, M. N. et al. *Indian J. Chem.* 1969, 7, 971, Cairns, H. et al. *J. Med. Chem.* 1972, 15, 583, Stoermer, M. J. and Fairlie, D. P. *Aust. J. Chem.* 1995, 48, 677, and Fitzmaurice, C. et al. British Patent No. 1262078, (filed 24 May 1968).

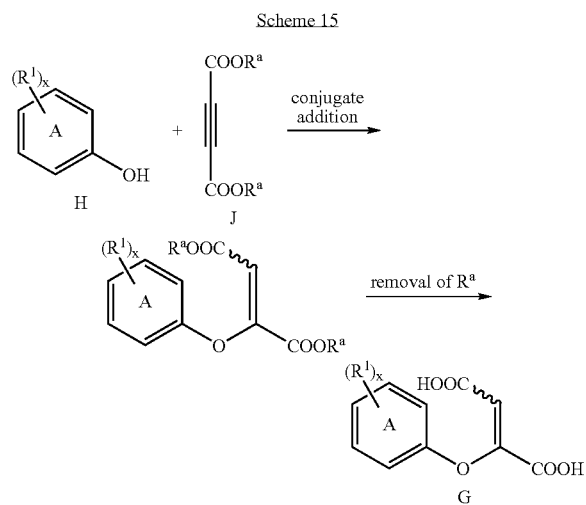

Scheme 15

At step S-2, a compound of formula G is cyclized to afford a compound of formula F. One of ordinary skill in the art will recognize that there are a wide variety of reaction conditions that can be employed to cyclize compounds of formula G, therefore, a wide variety of conditions are envisioned; see generally, March, (2001) and Larock (1999). In certain embodiments, the cyclization is promoted by treating a compound of fomula G with a suitable Bronsted acid. Exemplary acids include hydrochloric, sulfuric, phosphoric, polyphosphoric, methanesulfonic, Eaton's reagent ($P_2O_5MeSO_3H$), chlorosulfonic, camphorsulfonic, and p-toluenesulfonic. In other embodiments, additional reagents are employed, including, for example, phosphorus pentoxide, phosphorus trichloride, phosphorus pentachloride, acetyl chloride, or acetic anhydride. One of ordinary skill in the art will recognize that some of the conditions described will promote formation of an intermediate acyl-chloride prior to undergoing cyclization. In yet another embodiment, the reaction is conducted with acetyl chloride or water as solvent. In still other embodiments, the cyclization is conducted as described in Ruhemann (1900), Gudi (1969), Cairns (1972), Stoermer (1995), or Fitzmaurice, C. et al. British Patent No. 1262078, (filed 24 May 1968).

In step S-3, a compound of formula F is reduced to afford a compound of formula E. One of ordinary skill in the art will recognize that compounds of formulae E, D, C, A, II, and II-HX contain a stereogenic carbon. Accordingly, this invention encompasses each individual enantiomer of compounds of formulae E, D, C, A, II, and II-HX as well as mixtures thereof. While a single stereochemical isomer is depicted for formulae E, D, C, A, II, and II-HX in Scheme 14, it will be appreciated that mixtures of enantiomers of these formulae are accessible enriched in either enantiomer via the present invention. As used herein, the terms "enantiomerically enriched" and "enantioenriched" denote that one enantiomer makes up at least 75% of the preparation. In certain embodiments, the terms denote that one enantiomer makes up at least 80% of the preparation. In other embodiments, the terms denote that at least 90% of the preparation is one of the enantiomers. In other embodiments, the terms denote that at least 95% of the preparation is one of the enantiomers. In still other embodiments, the terms denote that at least 97.5% of the preparation is one of the enantiomers. In yet another embodiment, the terms denote that the preparation consists of a single enantiomer to the limits of detection (also referred to as "enantiopure"). As used herein, when "enantioenriched" or "enantiomerically enriched" are used to describe a singular noun (e.g., "an enantioenriched compound of formula II" or "an enantioenriched chiral amine"), it should be understood that the "compound" or "acid" may be enantiopure, or may in fact be an enantioenriched mixture of enantiomers. Similarly, when "racemic" is used to describe a singular noun (e.g., "a racemic compound of formula E"), it should be understood that the term is in fact describing a 1:1 mixture of enantiomers.

In one aspect of the present invention, step S-3 is carried out by (a) first subjecting the compound of formula F to hydrogenation conditions, (b) forming diastereomeric salts by combining the racemic mixture of the hydrogenation product with an enantioenriched chiral amine, (c) selectively crystallizing one of the diastereomeric salts to afford a diastereomerically enriched mixture of salts, and (d) recovering the acid in enantioenriched form from the diastereomerically enriched salt, as depicted in Scheme 16, below. In certain embodiments, the hydrogenation in (a) is conducted in the presence of a palladium catalyst. In other embodiments, the palladium catalyst is palladium on carbon. In still other embodiments, the hydrogenation is run in methanol, ethanol, or acetic acid. According to one aspect of the present invention, the hydrogenation is run in methanol. In yet other embodiments, the hydrogenation is conducted in the presence of sulfuric acid, acetic acid, or both. In some embodiments, the hydrogenation is conducted in the presence of sulfuric acid. In still other embodiments, the hydrogenation is conducted as described in Witiak, D. T. et al. *J. Med. Chem.* 1975, 18, 934. In another aspect of the present invention, the enantioenriched chiral amine is (R)-1-phenylpropylamine. In certain embodiments, the crystallization in step (c) is conducted in acetonitrile, methanol, ethanol, isopropanol, ethyl acetate, isopropyl acetate, diethyl ether, tert-butyl methyl ether, benzene, toluene, dichloromethane or the like. In certain embodiments, the free acid is liberated in step (d) by treating the salt with hydrochloric acid or sulfuric acid. In other embodiments, step (d) is conducted in toluene, water, or mixtures thereof. In other embodiments, the resolution step is conducted as described in Wigerinck, P. T. B. P. et al., International patent application number WO 9929687 A1 (1999); Van Lommen, G. R. E. et al., European patent application publication number EP 145067 A2 (1985); or Schaff, T. K. et al. *J. Med. Chem.* 1983, 26, 328.

Scheme 16

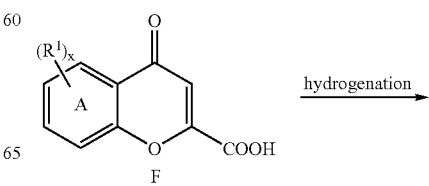

-continued

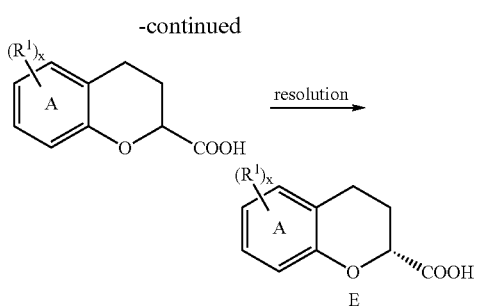

In another aspect of the present invention, step S-3 is carried out by (a) first subjecting the compound of formula F to hydrogenation conditions, (b) resolving the racemic reduced product by enzymatic means. In certain embodiments, the enzymatic resolution is carried out according to Schutt, H., German patent application publication number DE 4430089 A1 (1996); Urban, F. J., European patent application publication number EP 0448254 A2 (1991); and Rossi, R. F., Jr., international patent application publication number WO 9640975 A1 (1996).

In yet another aspect of the present invention, step S-3 is carried out by (a) hydrogenating a compound of formula F in an asymmetric fashion to afford an intermediate ketone-containing compound in enantiomerically enriched form, and (b) hydrogenating said intermediate to reduce the keto moiety and afford a compound of formula E in enantiomerically enriched form, as shown in Scheme 17, below. In certain embodiments, the asymmetric hydrogenation in step (a) is catalyzed by a suitable chiral catalyst. In certain embodiments, the chiral catalyst is a complex comprising a transition metal species and a suitable chiral ligand. In certain embodiments, the transition metal species is a late transition metal species (e.g., a Ru, Rh, Pd, Ir, or Pt species). In other embodiments the transition metal species is a rhodium or ruthenium species. In certain embodiments, the chiral ligand contains a phosphorus moiety that is capable of binding a transition metal species (e.g., a phosphine or phosphite moiety). In other embodiments the chiral ligand contains an olefinic moiety that is capable of binding a transition metal species. In yet other embodiments, the chiral ligand contains a carbene moiety that is capable of binding to a transition metal species. Suitable chiral ligands for asymmetric hydrogenation are well known in the art; see, e.g., *Stereochemistry of Organic Compounds*, E. L. Eliel and S. H. Silen, 1994, John Wiley and Sons; *Asymmetric Catalysis in Organic Synthesis*, R. Noyori, 1994, John Wiley and Sons; X. Cui and K. Burgess, *Chem. Rev.* 2005, 105, 3272; and W. Tang and X. Zhang, *Chem. Rev.* 2003, 103, 3029. Additional exemplary chiral ligands include, but are not limited to, JosiPhos-type, MandyPho™-type, WalPhos-type, TaniaPhos™-type, RoPhos-type, DIPAMP-type, Butiphane-type, BPE-type, QUINAP-type, BINAP-type, NorPhos-type, MonoPhos™-type, TunePhos-type, MalPhos-type, DuPhos-type, PHOX-type, KetalPhos-type, f-KetalPhos-type, TangPhos-type, BIPHEP-type, ferrotane-type, Binaphane-type, f-Binaphane-type, Binapine-type, FAP-type, MOP-type, DIOP-type, ChiraPhos-type, BPPM-type, and BICP-type. The term "asymmetric hydrogenation," as used herein refers to the hydrogenation of an achiral or chiral substrate which results in an enantiomerically enriched chiral product. In certain embodiments the asymmetric hydrogenation is catalyzed by a chiral transition metal-containing species. In certain embodiments, the hydrogenation in step (b) is is conducted in the presence of a palladium catalyst. In other embodiments, the palladium catalyst is palladium on carbon. In still other embodiments, the hydrogenation is run in methanol. In yet other embodiments, the hydrogenation is conducted in the presence of sulfuric acid and acetic acid.

Scheme 17

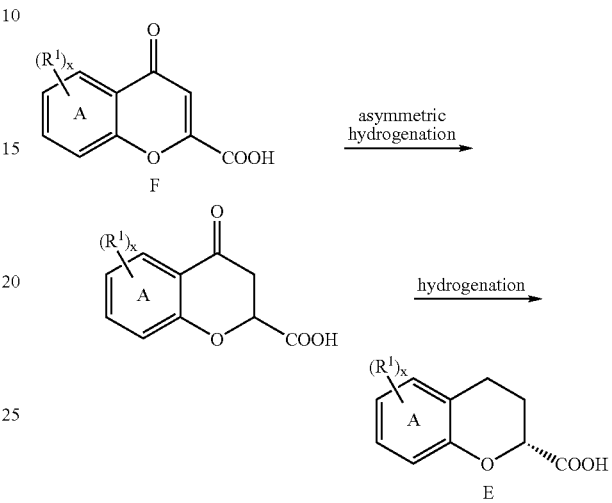

In step S-4, a compound of formula E is amidated to afford a compound of formula D. One of ordinary skill in the art will recognize that there are a wide variety of reaction conditions that can be employed to amidate compounds of formula G, therefore, a wide variety of conditions are envisioned; see generally, March (2001); Larock (1999); Benz, G. "Synthesis of Amides and Related Compounds." in Comprehensive Organic Synthesis, Trost, B. M., Editor, Pergamon Press: New York, N.Y., Vol. 6; and Bailey, P. D. et al. "Amides" in Comprehensive Organic Functional Group Transformation, Katritzky, et. al. Editors, Pergamon: New York, N.Y., Vol. 5. In certain embodiments, the amidation is conducted by first activating the carboxylic acid to facilitate acylation (e.g., by reaction with $SOCl_2$ or similar reagents), and subsequently treating the activated species with a source of ammonia [e.g., ammonia gas or solution in tetrahydrofuran toluene, heptane, tert-butyl methyl ether, diethyl ether, ethyl acetate, isopropyl acetate, dichloromethane, chloroform, dichloroethan, or water (e.g., $NH_4OH$)]. In other embodiments, this reaction is conducted by first activating the carboxylic acid to facilitate acylation by reaction with $SOCl_2$ and subsequently treating the activated species with $NH_4OH$. In still other embodiments, the reaction is run in toluene, benzene, ethyl acetate, dichloromethane, chloroform, dichloroethane, combinations thereof. In some embodiments, the cyclization is run in the absence of solvent. In other embodiments, the reaction is run at a temperature between about 25° C. and 150° C. In still other embodiments, the reaction is run at a temperature between about 50° C. and about 100° C. In yet other embodiments, the reaction is conducted according to Zhang, M. et al. *Tetrahedron Lett.* 2004, 45, 5229 or Devant, R. International patent application publication number WO05037817 (2005).

In step S-5, the amide moiety in compounds of formula D is reduced to an amine, and the resulting amine is protected to afford compounds of formula C. In compounds of formulae C and A, $PG^1$ and $PG^2$ are amino protecting groups. Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NIHFmoc), formamido, acetamido, chloroacetamido, dichloroacetamido, trichloroacetamido, phenylacetamido, trifluoroacetamido, benzamido, t-butyidiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, and 2,2,5,5-tetramethyl-[1,2,5]azadisilolidine and the like. Notwithstanding the definition above, one of either $PG^1$ or $PG^2$ in compounds of formulae C and A may be hydrogen. According to one aspect of the invention, the —$N(PG^1)(PG^2)$ moiety of formulae C and A, is t-butyloxycarbonylamino (—NHBOC).

One of ordinary skill in the art will recognize that there are a wide variety of reaction conditions that can be employed to reduce an amide, therefore, a wide variety of conditions are envisioned; see generally, March, (2001) and Larock (1999). In certain embodiments, the reduction step is performed by treating a compound of formula D with Red-Al [sodium bis(2-methoxyethoxy)aluminumhydride] or lithium aluminum hydride. In other embodiments, the reduction step is run in toluene, benzene, tetrahydrofuran, diethyl ether, tert-butyl methyl ether, or a mixture thereof. In certain embodiments, the reduction step is run at a temperature between about −40° C. and about 100° C. In other embodiments, the reduction step is run at a temperature between about 0° C. and 40° C. In still other embodiments the reduction is conducted as described in Gross, J. L. *Tetrahetron Lett.* 2003, 44, 8563; Mayweg, A. et al., U.S. patent application publication No. US 05250769 (2005); Devant, R. et al., International patent application publication number WO 05037817 (2005); Mitsuda, M. et al., International patent application publication number WO 03040382 (2003); Bokel, H. et al., International patent application publication number WO 02020507 (2002); or Bokel, H. et al., German patent application publication number DE 10120619 (2002).

Similarly, one of ordinary skill in the art will recognize that there are a wide variety of methods that can be employed to protect an amine, therefore, a wide variety of conditions are contemplated; see generally, Green (1999).

In step S-6, a $CG^1$ group is introduced at the open ortho position relative to the sp2-hybridized carbon bearing the chromane oxygen in formula C. The $CG^1$ group of formula A is a coupling group that facilitates transition metal-mediated $C_{sp2}$—$C_{sp2}$ coupling between the attached $C_{sp2}$ carbon and the $C_{sp2}$ carbon bearing a $CG^2$ coupling group in compounds of formula B, as shown in step S-7. Suitable coupling reactions are well known to one of ordinary skill in the art and typically involve one of the coupling groups being an electron-withdrawing group (e.g., Cl, Br, I, OTf, etc.), such that the resulting polar carbon-CG bond is susceptible to oxidative addition by an electron-rich metal (e.g., a low-valent palladium or nickel species), and the complementary coupling group being an electropositive group (e.g., boronic acids, boronic esters, boranes, stannanes, silyl species, zinc species, aluminum species, magnesium species, zirconium species, etc.), such that the carbon which bears the electropositive coupling group is susceptible to transfer to other electropositive species (e.g., a $Pd^{II-IV}$ species or a $N^{II-IV}$ species). Exemplary reactions and coupling groups include those described in *Metal-Catalyzed Cross-Coupling Reactions*. A. de Meijere and F. Diederich, Eds., $2^{nd}$ Edition, John Wiley & Sons, 2004; and *Handbook of Organopalladium Chemistry for Organic Synthesis*, Negishi, E., de Meijere, A. Editors, Wiley: New York, N.Y., 2002. In certain embodiments, $CG^1$ in compounds of formula A is a boronic acid, a boronic ester, or a borane. In other embodiments, $CG^1$ in compounds of formula A is a boronic ester. According to one aspect of the present invention, $CG^1$ in compounds of formula A is a boronic acid.

Reactions and reaction sequences that are used to promote the transformation depicted in step S-6 include initial directed orthometallation followed by treatment with suitable reagent to afford a compound of formula A. In certain embodiments, directed orthometallation is succeeded with treatment with a borate ester, which is optionally subsequently hydrolyzed to afford a boronic acid; see, e.g., Snieckus, V. *Chem. Rev.* 1990, 90, 879 and Schlosser, M. *Angew. Chem. Int. Ed.* 2005, 44, 376. Another exemplary sequence involves halogenation followed by a metallation/transmetallation sequence to afford a compound of formula A. In certain embodiments, halogenation and transmetallation is succeeded with treatment with a borate ester, which is optionally subsequently hydrolyzed to afford a boronic acid; see, generally, de Meijere (2004) and Snieckus (1990). According to one aspect of the present invention, a compound of formula C is first subjected to orthometallation to afford an intermediate arylmetal compound that is allowed to react with a borate ester to afford, following aqueous workup, a compound of formula A. In certain embodiments, the orthometallation is accomplished by treating a compound of formula C with an alkyl lithium reagent. In other embodiments the alkyllithium reagent employed is selected from tert-butyllithium, n-butyllithium, s-butyllithium, hexyllithium, and the like. In other embodiments the alkyllithium reagent employed is tert-butyllithium. In yet other embodiments, the reaction is run in tetrahydrofuran, diethyl ether, dimethoxyethane, tert-butyl methyl ether, or combinations thereof. In other embodiments, the lithiation reaction is run in tetrahydrofuran. In still other embodiments the reaction is run at a temperature between about 0° C. and about −90° C. In still other embodiments the reaction is run at a temperature between about −30° C. and about −50° C. In cetain embodiments, the lithiation is run in the presence of one or more of N,N,N',N'-tetramethylethylenediamine, or hexamethylphosphoric triamide. In other embodiments, the borate ester is triisopropylborate $[B(OiPr)_3]$. According to another aspect of the present invention, a compound of formula C is first brominated, then is subjected to halogen-metal exchange to afford an intermediate arylmetal compound that is allowed to react with a borate ester to afford, optionally following hydrolysis (by, e.g., treatment with aqueous hydrochloric acid, aqueous sulfuric acid, or the like) to the boronic acid, a compound of formula A.

In step S-7, a compound of formula A is coupled to a compound of formula B, via a $C_{sp2}$—$C_{sp2}$ coupling reaction between the carbon centers bearing complementary coupling groups $CG^1$ and $CG^2$ to provide a compound of formula II. Suitable coupling reactions and suitable coupling groups are as described above (see the description of embodiments for $CG^1$, above). In certain embodiments, $CG^2$ in compounds of formula B is Br, I, or OTf. According to one aspect of the present invention, $CG^2$ in compounds of formula B is Br. In certain embodiments, the transformation is catalyzed by a palladium species. According to one aspect of the invention, the transformation is catalyzed by palladium tetrakis triphenylphosphine. In certain embodiments, the coupling reaction is run with dimethylacetamide, tetrahydrofuran, dimethoxyethane, toluene, dimethylformamide, N-methylpyrrolidine, or mixtures thereof, as solvent. In certain embodiements the coupling reaction is run with dimethylacetamide as solvent. According to another aspect of the present invention, the reaction is run in the presence of potassium phosphate or potassium carbonate. In other embodiments, the reaction is heated. According to one aspect of the invention, the reaction is heated to a temperature of about 100° C.

One of ordinary skill in the art will appreciate that a compound of formula II, as prepared by the methods of the present invention, may be treated with a suitable Bronsted acid, HX, as depicted in step S-8, to form a salt thereof (represented by formula II-HX). Exemplary acids include hydrogen halides, carboxylic acids, sulfonic acids, sulfuric acid, and phosphoric acid. According to one aspect of the present invention, a compound of formula II is treated with HCl to form a compound of formula II-HX wherein X is Cl. In certain embodiments, where the acid is HCl, it is introduced into the medium containing the compound of formula II in gaseous form. In other embodiments, the acid is introduced into the medium containing the compound of formula II as a solution in methanol, ethanol, isopropanol, or water. In yet other embodiments, the acid is introduced into the medium containing the compound of formula II as a solution in isopropanol. In certain embodiments, the medium containing the compound of formula II is isopropanol. According to one aspect of the present invention, the deprotection step of step S-7 and the salt formation of step S-8 are conducted in a single step by employing the acid HX in the deprotection step.

Although certain exemplary embodiments are depicted and described above and herein, it will be appreciated that compounds of the invention can be prepared according to the methods described generally above using appropriate starting materials by methods generally available to one of ordinary skill in the art. Additional embodiments are exemplified in more detail herein.

4. Uses, Formulation and Administration

Compounds of the present invention have affinity for and agonist or partial agonist activity at the 2C subtype of brain serotonin receptors and are thus of interest for the treatment of a variety of disorders and/or the alleviation of one or more associated symptoms. Such disorders associated with modulations of the 2C subtype of brain serotonin receptors are described in detail below. The present invention contemplates that compounds of the present invention are associated with a rapid onset of action. In addition, compounds of the present invention lack the side-effect of sexual dysfunction.

Compounds of the present invention are useful for treating one or more psychotic disorders, as described herein, without causing diabetogenesis. Diabetogenesis is a side-effect associated with atypical antipsychotic agents. Without wishing to be bound by any particular theory, it is believed that the diabetogenesis associated with atypical antipsychotic agents results from the fact that those agents are $5\text{-HT}_{2C}$ antagonists. As described herein, the present compounds are $5\text{-HT}_{2C}$ agonists, or partial agonists, and therefore are not associated with diabetogenesis.

Compounds of the present invention are useful for treating one or more psychotic disorders such as schizophrenia including paranoid type, disorganized type, catatonic type, and undifferentiated type, schizophreniform disorder, schizoaffective disorder, delusional disorder, substance-induced psychotic disorder, and psychotic disorder not otherwise specified; L-DOPA-induced psychosis; psychosis associated with Alzheimer's dementia; psychosis associated with Parkinson's disease; and psychosis associated with Lewy body disease.

Compounds of the present invention are also useful for treating symptoms related to psychotic disorders of the schizophrenic types, including the so called "positive" and "negative" symptoms of schizophrenia. These symptoms include for example hallucinations, delusions, paranoia, anxiety, agitation, excessive aggression, tension, thought disorder, blunted affect, and social or emotional withdrawal in psychotic patients. Other symptoms often associated with psychotic disorders include cognition disorders or deficits such as poor attention and impaired function, depression, suicide, metabolic syndrome, and substance abuse. Thus, another embodiment of the present invention provides a method for treating one or more symptoms associated with a psychotic disorder.

In other embodiments, the present compounds are useful for treating anxiety disorders such as panic attack, agoraphobia, panic disorder, specific phobia, social phobia, social anxiety disorder, obsessive compulsive disorder, posttraumatic stress disorder, acute stress disorder, generalized anxiety disorder, separation anxiety disorder, substance-induced anxiety disorder, and anxiety disorder not otherwise specified.

According to another embodiment, the present compounds are useful for treating bipolar disorders. Such bipolar disorders include bipolar I disorder, bipolar II disorder, and cyclothymic disorder; bipolar mania, dementia, and depression with psychotic features. The present compounds are also useful for treating (including the preventing) of cycling that may occur between bipolar depression and bipolar mania.

A more complete description of the aforementioned mental disorders can be found in the Diagnostic and Statistical Manual of Mental Disorders, 4th edition, Washington, D.C., American Psychiatric Association (1994), incorporated herein by reference in its entirety.

In certain embodiments, compounds of the present invention are administered in combination with one or more anti-psychotic agents. Such anti-psychotic agents are well known in the art and include clozapine (e.g., Clozaril®), risperidone (e.g., Risperidal®), olanzapine (e.g., Zyprexa®), quetiapine (e.g., Seroquel®), ziprasidone (e.g., Geodon®), aripiprazole, amisulpiride, chlorpromazine, fluphenazine, haloperidol (e.g., Haldol®), loxapine, mesoridazine, molindone, perphenazine, pimozide, seroquel, sulpiride, thioridazine, thiothixene, trifluoperazine, and bifeprunox to name a few.

The combination of a compound of the present invention with one or more anti-psychotic agents is useful for treating schizophrenia including paranoid type, disorganized type, catatonic type, and undifferentiated type, schizophreniform disorder, schizoaffective disorder, delusional disorder, substance-induced psychotic disorder, and psychotic disorder not otherwise specified; L-DOPA-induced psychosis; psychosis associated with Alzheimer's dementia; psychosis associated with Parkinson's disease; psychosis associated with Lewy body disease; bipolar disorders such as bipolar I disorder, bipolar II disorder, and cyclothymic disorder; bipolar mania, dementia, and depression with psychotic features. In some embodiments, these combinations are useful in the treatment of bipolar disorder, including for example treating the cycling between bipolar depression and bipolar mania.

In other embodiments, administration of a compound of the present invention with an anti-psychotic agent provide anti-psychotic benefits while eliminating or minimizing certain side affects (e.g., akathisia, dystonia, Parkinsonism dyskinesia and late dyskinesia and the like) typically observed when the anti-psychotic agent(s) is/are taken alone.

In other embodiments, compounds of the present invention are useful for treating one or more depressive disorders such as major depressive disorder, seasonal affective disorder, dysthymic disorder, substance-induced mood disorder, depressive disorder not otherwise specified, and treatment resistant depression.

Another aspect of the present invention provides a method for treating one or more mood episodes such as major depressive episode, manic episode, mixed episode, and hypomanic episode; and adjustment disorders such as adjustment disorders with anxiety and/or depressed mood.

Compounds of the present invention are also useful for treating symptoms related to depressive disorders including somatic symptoms such as neuropathic pain and sexual dysfunction. Other somatic symptoms include hopelessness, helplessness, anxiety and worries, memory complaints with or without objective signs of cognitive impairment, loss of feeling of pleasure (anhedonia), slowed movement, irritability, and lack of interest in personal care, such as poor adherence to medical or dietary regimens.

In certain embodiments, the present invention provides a method of treating sexual dysfunction related to depression. In other embodiments, the present invention provides a method of treating sexual dysfunction associated with administering a serotonin reuptake inhibitor (SRI) for treating a depressive or other disorder. Such methods of treating sexual dysfunction are described in detail below.

In certain embodiments, compounds of the present invention are administered in combination with one or more antidepressive agents. Suitable antidepressant agents include, for example, serotonin reuptake inhibitors (SRIs), norepinephrine reuptake inhibitors (NRIs), combined serotonin-norepinephrine reuptake inhibitors (SNRIs), monoamine oxidase inhibitors (MAOs), reversible inhibitors of monoamine oxidase (RIMAs), phosphodiesterase-4 (PDE4) inhibitors, corticotropin releasing factor (CRF) antagonists, alpha.-adrenoreceptor antagonists or other compounds including atypical antidepressants. Additional antidepressants for administering in combination with compounds of the present invention include triple uptake inhibitors such as DOV 216303 and DOV 21947 . . . ; melatonin agonists such as agomelotine, super neurotransmitter uptake blockers (SNUBs; e.g., NS-2389 from GlaxoSmithKline and Neurosearch; (R)-DDMA from Sepracor), and/or substance P/neurokinin receptor antagonists (e.g., aprepitant/MK-869 from Merck; NKP-608 from Novartis; CPI-122721 from Pfizer; R673 from Roche; TAK637 from Takeda; and GW-97599 from GlaxoSmithKline).

Another class of antidepressant agents for administering in combination with compounds of the present invention are noradrenergic and specific serotonergic antidepressants (NaSSAs). A suitable example of a NaSSA is mirtazepine.

Suitable NRIs for administering in combination with compounds of the present invention include tertiary amine tricyclics and secondary amine tricyclics. Suitable examples of tertiary amine tricyclics include: amitriptyline, clomipramine, doxepin, imipramine (See U.S. Pat. No. 2,554,736, incorporated herein by reference in its entirety) and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Another NRI for administering in combination with compounds of the present invention is reboxetine (Edronax™; 2-[.alpha.-(2-ethoxy)phenoxy-benzyl]morpholine, usually administered as the racemate; See U.S. Pat. No. 4,229,449, incorporated herein by reference in its entirety).

Suitable SSRIs for administering in combination with compounds of the present invention include: citalopram (1-[3-(dimethylamino)propyl]-(4-fluorophenyl)-1,3-dihydro-5-isobenzofurancarbonitrile; See U.S. Pat. No. 4,136,193; Christensen et al., *Eur. J. Pharmacol.* 41:153, 1977; Dufour et al., *Int. Clin. Psychopharmacol.* 2:225, 1987; Timmerman et al., ibid., 239, each of which is incorporated herein by reference in its entirety); fluoxetine (N-methyl-3-(p-trifluoromethylphenoxy)-3-phenylpropylamine, marketed in the hydrochloride salt form and as the racemic mixture of its two isoforms; see, for example, U.S. Pat. No. 4,314,081; Robertson et al., *J. Med. Chem.* 31:1412, 1988, each of which is incorporated herein by reference); fluoxetine/olanzapine in combination; fluvoxamine (5-methoxy-1-[4-(trifluoromethyl)phenyl]-1-pentanone O-(2-aminoethyl)oxime; See U.S. Pat. No. 4,085,225; Claassen et al., *Brit. J. Pharmacol.* 60:505, 1977; De Wilde et al., *J. Affective Disord.* 4:249, 1982; Benfield et al., *Drugs* 32:313, 1986, each of which is incorporated herein by reference in its entirety); paroxetine (trans-(−)-3-[(1,3-benzodioxol-5-yloxy)methyl]-4-(4-fluorophenyl)piperidine; See U.S. Pat. No. 3,912,743; U.S. Pat. No. 4,007,196; Lassen, *Eur. J. Pharmacol.* 47:351, 1978; Hassan et al., *Brit. J. Clin. Pharmacol.* 19:705, 1985; Laursen et al., *Acta Psychiat. Scand.* 71:249, 1985; Battegay et al., *Neuropsychobiology* 13:31, 1985, each of which is incorporated herein by reference in its entirety); sertraline, (1S-cis)-4-(3,4-dichlorophenyl)-1,2,3,4-tetrahydro-N-methyl-1-naphthylamine hydrochloride; See U.S. Pat. No. 4,536,518, incorporated herein by reference in its entirety); escitalopram (see U.S. Pat. No. RE 34,712); and pharmaceutically acceptable salts thereof.

Suitable MAOIs for administering in combination with compounds of the present invention include: isocarboxazid, pheneizine, selegiline and tranylcypromine, and pharmaceutically acceptable salts thereof.

Suitable reversible MAOIs for administering in combination with compounds of the present invention include: moclobemide (4-chloro-N-[2-(4-morpholinyl)-ethyl]benzamide; See U.S. Pat. No. 4,210,754, incorporated herein by reference in its entirety), selegiline, and pharmaceutically acceptable salts thereof.

Suitable SNRIs for administering in combination with compounds of the present invention include venlafaxine (see U.S. Pat. No. 4,535,186, incorporated herein by reference in its entirety; see also U.S. Pat. Nos. 5,916,923, 6,274,171, 6,403,120, 6,419,958, 6,444,708, each of which is incorporated herein by reference in its entirety), and pharmaceutically acceptable salts and analogs, including the O-desmethylvenlafaxine succinate salt; milnacipran (N,N-diethyl-2-aminomethyl-1-phenylcyclopropanecarboxamide; see U.S. Pat. No. 4,478,836; Moret et al., *Neuropharmacology* 24:1211–19, 1985, each of which is incorporated herein by reference in its entirety); nefazodone (available from Bristol Myers Squibb and Dr. Reddy Labs Inc.); duloxetine; and pharmaceutically acceptable salts thereof.

Suitable CRF antagonists for administering in combination with compounds of the present invention include those compounds described in International Patent Specification Nos. WO 94/13643, WO 94/13644, WO 94/13661, WO 94/13676 and WO 94/13677.

Suitable atypical antidepressants for administering in combination with compounds of the present invention include: bupropion (Wellbutrin™; (.+-.)-1-(3-chlorophenyl)-2-[(1,1-dim-ethylethyl)amino]-1-propanone), lithium, nefazodone, trazodone and viloxazine, and pharmaceutically acceptable salts thereof. Another suitable atypical antidepressant is sibutramine.

Particular antidepressants for administering in combination with compounds of the present invention include, but are not limited to, adinazolam, alaproclate, alnespirone, amineptine, amitriptyline, amitriptyline/chlordiazepoxide combination, amoxapine, aprepitant, atipamezole, azamianserin, bazinaprine, befuraline, bifemelane, binodaline, bipenamol, brofaromine, buproprion, caroxazone, cericlamine, cianopramine, cimoxatone, citalopram, clemeprol, clomipramine, clovoxamine, dazepinil, deanol, demexiptiline, desipramine, O-desmethylvenlafaxine, dibenzepin, dothiepin, doxepin, droxidopa, duloxetine, elzasonan, enefexine, eptapirone, escitalopram, estazolam, etoperidone, femoxetine, fengabine, fezolamine, fluotracen, fluoxetine, fluvoxamine, gepirone, idazoxan, imipramine, indalpine, indeloxazine, iprindole, isocarboxazid, levoprotiline, litoxetine, lofepramine, maprotiline, medifoxamine, metapramine, metralindole, mianserin, milnacipran, minaprine, mirtazapine, moclobemide, montirelin, nebracetam, nefopam, nefozodine, nemititide, nialamide, nomifensine, norfluoxetine, nortriptyline, orotirelin, oxaflozane, paroxetine, pheneizine, pinazepam, pirlindone, pizotyline, protryptiline, reboxetine, ritanserin, robalzotan, rolipram, selegiline, sercloremine, sertraline, setiptiline, sibutramine, sulbutiamine, sulpiride, sunepitron, teniloxazine, thozalinone, thymoliberin, tianeptine, tiflucarbine, tofenacin, tofisopam, toloxatone, tomoxetine, tranylcypromine, trazodone, trimiprimine, venlafaxine, veralipride, vilazodone, viloxazine, viqualine, zimelidine and zometrapine, and pharmaceutically acceptable salts thereof, and St. John's wort herb, or Hypencuin perforatum, or extracts thereof.

Suitable classes of anti-anxiety agents for administering in combination with compounds of the present invention include 5-HT$_{1A}$ agonists or antagonists, especially 5-HT$_{1A}$ partial agonists, neurokinin recepter (NK) antagonists (e.g., saredutant and osanetant) and corticotropin releasing factor (CRF) antagonists. Suitable 5-HT$_{1A}$ receptor agonists or antagonists that may be used in the present invention include, in particular, the 5-HT$_{1A}$ receptor partial agonists buspirone, flesinoxan, gepirone and ipsapirone, and pharmaceutically acceptable salts thereof. An example of a compound with 5-HT$_{1A}$ receptor antagonist/partial agonist activity is pindolol. new 5HT$_{1A}$ agonists variza, alnespirone, gepirone, sunepitron, MKC242, vilazodone, eptapirone, and ORG12962 from Organon; new 5HT$_{1A}$ antagonists such as robalzotan; new 5-HT$_{1B}$ agonists such as elzasonan; new 5HT$_2$ antagonists such as YM-992 (from Yamanouchi Pharmaceuticals) and nemifitide.

According to the present invention, the inventive combinations may be administered in conjunction with one or more other agents that is useful in treating depression or other mood disorders. Alternatively or additionally, inventive combinations may be administered with one or more other pharmaceutical agents active in treating any other symptom or medical condition present in the mammal that is related or unrelated to the depression or mood disorder being experienced by the mammal. Examples of such pharmaceutical agents include, for example, anti-angiogenic agents, anti-neoplastic agents, anti-diabetic agents, anti-infective agents, pain-relieving agents, anti-psychotic agents, gastrointestinal agents, etc., or combinations thereof. Other pharmaceutical agents useful in the practice of the present invention include, for example, adjunctive therapies typically used to enhance the effects of an antidepressant. Such adjunctive agents may include, for instance, mood stabilizers (e.g., lithium, valproic acid, carbamazepine, etc.); pindolol, stimulants (e.g., methylphenidate, dextroamphetamine, etc.); or thyroid augmenting agents (e.g., T$_3$); antipsychotics, anti-anxiety agents (e.g., benzodiazepines), and/or agents that relieve sexual dysfunction (e.g., buspirone, which also has anti-anxiety effects; dopaminergic agents such as amantadine, pramipexole, bupropion, etc.).

As 5-HT$_{2C}$ modulators, compounds of the present invention are useful for treating a variety of disorders. Such disorders include premenstrual syndrome (PMS), premenstrual dysphoric disorder (PMDD), motion or motor disorders such as Parkinson's disease; chronic fatigue syndrome, anorexia nervosa, disorders of sleep (e.g., sleep apnea), and mutism.

Premenstrual dysphoric disorder, or PMDD, is a severe form of PMS. Like PMS, PMDD typically occurs the week before the onset of menstruation and disappears a few days after. PMDD is characterized by severe monthly mood swings and physical symptoms that interfere with everyday life, especially a woman's relationships with her family and friends. PMDD symptoms go far beyond what are considered manageable or normal premenstrual symptoms.

PMDD is a combination of symptoms that may include irritability, depressed mood, anxiety, sleep disturbance, difficulty concentrating, angry outbursts, breast tenderness and bloating. The diagnostic criteria emphasize symptoms of depressed mood, anxiety, mood swings or irritability. The condition affects up to one in 20 American women who have regular menstrual periods. According to another embodiment, the present invention provides a method for treating one or more symptoms associated with PMDD.

Selective serotonin reuptake inhibitors (SSRIs) are the current preferred method for treating symptoms associated with PMDD. According to another aspect, the present invention provides a method for treating PMDD, or one or more symptoms associated with PMDD, by administering a compound of formula I in combination with an SSRI. In certain embodiments, the SSRI is fluoxetine, venlafaxine, paroxetine, duloxetine, or sertraline.

According to another embodiment, compounds of the present invention are useful for treating a variety of eating disorders. In certain embodiments, the eating disorder is hyperphagia, bulimia or anorexia nervosa. In certain embodiments, compounds of the present invention are useful for treating gastrointestinal disorders, such as malfunction of gastrointestinal motility or intestinal propulsion. Compounds of the present invention are also useful in connection with weight loss or control (e.g., reduction in calorie or food intake, and/or appetite suppression). Such methods are particularly useful for treating obesity with its consequent comorbidities including diabetes insipidus, Type II diabetes, cardiovascular disease, hypertension, hyperlipidemia, stroke, osteoarthritis, sleep apnea, gall bladder disease, gout, some cancers, some infertility, and early mortality.

In certain embodiments, compounds of the present invention are administered in combination with one or more anti-obesity agents. Such anti-obesity agents are known in the art and include apolipoprotein-B secretion/microsomal triglyceride transfer protein (apo-B/MTP) inhibitors, 11β-hydroxy steroid dehydrogenase-1 (11(β-HSD type 1) inhibitors, $PYY_{3.36}$ and analogs thereof, MCR-4 agonists, cholecystokinin-A (CCK-A) agonists, monoamine reuptake inhibitors (such as sibutramine), sympathomimetic agents, R3 adrenergic receptor agonists, dopamine agonists (such as bromocriptine), melanocyte-stimulating hormone receptor analogs, cannabinoid 1 receptor antagonists (e.g., rimonabant), melanin concentrating hormone antagonists, leptins (the OB protein), leptin analogs, leptin receptor agonists, galanin antagonists, lipase inhibitors (such as tetrahydrolipstatin, i.e. orlistat), anorectic agents (such as a bombesin agonist), Neuropeptide-Y receptor antagonists, thyromimetic agents, dehydroepiandrosterone or an analog thereof, glucocorticoid receptor agonists or antagonists, orexin receptor antagonists, urocortin binding protein antagonists, glucagon-like peptide-1 receptor agonists, ciliary neurotrophic factors (such as Axokine$^{TA}$), human agouti-related proteins (AGRP), ghrelin receptor antagonists, histamine 3 receptor antagonists or inverse agonists, and neuromedin U receptor agonists.

In other embodiments, a compound of the present invention is administered in combination with an anti-obesity agent selected from orlistat, sibutramine, bromocriptine, ephedrine, leptin, rimonabant, pseudoephedrine, PYY3.36 or an analog thereof, and 2-oxo-N-(5-phenyipyrazinyl) spiro-[isobenzofuran-1(3H),4-piperidine]-1-carboxamide. According to another aspect of the invention, a compound of the present invention is administered in combination with an anti-obesity agent in conjunction with typical treatments for obesity such as exercise and a sensible diet.

According to another embodiment, a compound of the present invention is administered in combination with one or more agents for treating diabetes and associated conditions. In certain embodiments, a compound of the present invention is administered in combination with one or more such agents including insulin and insulin analogs (e.g., LysPro Insulin); GLP-1 (7–37) (insulinotropin) and GLP-1 (7–36)-$NH_2$; sulfonylureas and analogs thereof: chlorpropamide, glibenclamide, tolbutamide, tolazamide, acetohexamide, Glypizide®, glimepiride, repaglinide, meglitinide; biguanides: metformin, phenformin, buformin; "2-antagonists and imidazolines: midaglizole, isaglidole, deriglidole, idazoxan, efaroxan, fluparoxan; other insulin secretagogues: linogliride, A-4166; glitazones: ciglitazone, Actos® (pioglitazone), englitazone, troglitazone, darglitazone, Avandia® (BRL49653); fatty acid oxidation inhibitors: clomoxir, etomoxir; glucosidase inhibitors: acarbose, miglitol, emiglitate, voglibose, MDL-25,637, camiglibose, MDL-73,945; 13-agonists: BRL 35135, BRL 37344, RO 16-8714, ICI D7114, CL 316,243; or phosphodiesterase inhibitors: L-386, 398.

In other embodiments, a compound of the present invention is administered in combination with one or more lipid-lowering agents: benfluorex: vanadate and vanadium complexes (e.g., Nagiivan®) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin"), AC 2993, nateglinide, aldose reductase inhibitors (e.g., zopolrestat), glycogen phosphorylase inhibitors, sorbitol dehydrogenase inhibitors, sodium-hydrogen exchanger type 1 (NNE-1) inhibitors and/or cholesterol biosynthesis inhibitors or cholesterol absorption inhibitors, especially a HMG-CoA reductase inhibitor, or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, or an anti-oxidant. In other embodiments, a compound of the present invention is administered in combination with one or more naturally occurring compounds that acts to lower plasma cholesterol levels. Such naturally occurring compounds are commonly referred to as nutraceuticals and include, for example, garlic extract, Hoodia plant extracts, and niacin.

In certain embodiments, compounds of the present invention are useful for inducing, assisting or maintaining desirable bladder control in a mammal. The methods are particularly useful for treating a mammal that is experiencing or susceptible to bladder instability or urinary incontinence. Inventive methods include prevention, treatment or inhibition of bladder-related urinary conditions and bladder instability, including idiopathic bladder instability, nocturnal enuresis, nocturia, voiding dysfunction and urinary incontinence (including, for example, stress incontinence, urge incontinence, and/or mixed incontinence). Also treatable or preventable by administration of a compound of this invention is bladder instability secondary to prostate hypertrophy, as is a method for enhancing urethral tone and reducing undesirable urine leakage even in an otherwise healthy person. For example, the inventive methods are applicable to alleviating urine leakage often occurring in women during the first year after childbirth.

In other embodiments, the present compounds are useful for treating urine retention or detrusor sphincter dyssynergia. Patients suffering from urine retention include those suffering from spinal cord injuries or male patients with benign prostatic hyperplasia.

According to the present invention, a compounds of the present invention is also useful in promoting the temporary delay of urination whenever desirable. Such compounds may be utilized in accordance with the present invention to stabilize the bladder in any applicable context. Inventive methods therefore may be utilized to allow a recipient to control the urgency and frequency of urination.

In some embodiments of the invention, compounds of the present invention are administered to a mammal in need thereof for the treatment, prevention, inhibition and/or amelioration of urge urinary incontinence (also known as bladder instability, neurogenic bladder, voiding dysfunction, hyperactive bladder, detrusor overactivity, detrusor hyperreflexia or uninhibited bladder) or mixed urinary incontinence. Inventive uses include, but are not limited to, those for bladder activities and instabilities in which the urinary urgency is associated with prostatitis, prostatic hypertrophy, interstitial cystitis, urinary tract infections or vaginitis. The methods of this invention may also be used to assist in inhibition or correction of the conditions of Frequency-Urgency Syndrome, and lazy bladder, also known as infrequent voiding syndrome.

Compounds of the present invention may also be used to treat, prevent, inhibit, or limit the urinary incontinence, urinary instability or urinary urgency associated with or resulting from administrations of other medications, including diuretics, vasopressin antagonists, anticholinergic agents, sedatives or hypnotic agents, narcotics, alpha-adrenergic agonists, alpha-adrenergic antagonists, or calcium channel blockers.

Compounds of the present invention are useful for inducing or assisting in urinary bladder control or preventing or treating the maladies described herein in humans in need of such relief, including adult and pediatric uses. They may also be utilized for veterinary applications, particularly including canine and feline bladder control methods. If desired, the methods herein may also be used with farm animals, such as ovine, bovine, porcine and equine breeds.

According to the present invention, compounds of the present invention may be administered alone to modulate bladder activity, or alternatively may be administered in combination with (whether simultaneously or sequentially) one or more other pharmaceutical agents useful in the modulation of bladder activity. Alternatively or additionally, the compounds of the present invention may be administered in combination with one or more other pharmaceutical agents useful in the treatment or prevention of one or more other symptoms, disorders, or diseases suffered by the individual in need of bladder activity modulation.

Other pharmaceutical agents useful in the modulation of bladder activity, and particularly for treatment, prevention, inhibition, and/or amelioration of urinary incontinence, include, for example, desmopressin acetate (available as DDAVP® Nasal Spray and DDAVP® tablets from Aventis Pharmaceuticals), as well as a desmopressin acetate rhinal tube (available from Ferring Pharmaceuticals Inc.). Other products include, for example, tolterodine tartrate (available as Detrol™ tablets from Pharmacia & Upjohn), oxybutinin chloride (available in the form of Ditropang tablets and syrup and Ditropan XL® extended release tablets from ALZA Pharmaceuticals), propanthaline bromide (available in tablet form from Roxane Laboratories, Inc.), hyoscyamine and hyoscyamine sulfate (available, respectively, as Cystopaz® tablets and Cystopaz-M® timed release capsules from PolyMedica Pharmaceuticals (U.S.A.), Inc.), hyoscyamine hydrobromide, flavoxate HCl (available in Urispas® 100 mg tablets from ALZA Pharmaceuticals), imipramine HCl (available in 10 mg, 25 mg and 50 mg tablets from Geneva Pharmaceuticals, Inc.), phenylpropanolamine, midodrine HCl (available in 2.5 mg and 5 mg Proamatine® tablets from Shire US Inc.), phenoxybenzamine HCl (available as Dibenzyline® capsules from WellSpring Pharmaceuticals Corporation), and prazosin HCl (available in Minipress® capsules from Pfizer Inc.). Each of these medicaments may be administered in the pharmaceutically effective amounts and regimens known in the art, including those listed in the Physicians' Desk Reference, 55 Edition, 2001, published by Medical Economics Company, Inc. at Monvale, N.J. 07645-1742, the relevant portions of which are incorporated herein by reference.

Yet other pharmaceutical agents that can act to modulate bladder activity include, for example, other regulators of the $5HT_{2C}$ receptor. For example, U.S. Patent Application 2004/0235856 (previously incorporated herein by reference in its entirety) describes a variety of $5HT_{2C}$ receptor modulators that are useful in accordance with the practice of the present invention. Additional $5HT_{2C}$ agonists are exemplified in Bishop et al., *Expert Opin. Ther. Patent* 13:1691–1705, 2003, the entire contents of which are incorporated herein by reference.

Still other pharmaceutical agents that can act to modulate bladder activity include, for example, modulators of one or more KCNQ potassium channels. In some embodiments of the present invention, compounds of the present invention are administered in conjunction with one or more agonists of KCNQ 2/3 or KCNQ3/5. Such KCNQ modulators include, for example, compounds described in U.S. Pat. No. 5,384,330 and those described in U.S. Pat. No. 5,565,483, as well as those described in U.S. Patent Application No. 2002/0183395; and U.S. Patent Application No. 2004/0029949. The entire contents of each of these patents and patent applications is incorporated herein by reference. In some embodiments of the present invention, compounds of the present invention are administered with retigabine.

In some embodiments of the present invention, compounds of the present invention are administered in conjunction with one or more compounds which act as vasopressin agonists including, but not limited to those described in U.S. Pat. No. 6,194,407 (Failli et al.), U.S. Pat. No. 6,090,803 (Failli et al.), U.S. Pat. No. 6,096,736 (Ogawa et al.), and U.S. Pat. No. 6,096,735 (Ogawa et al.).

In general, it will often be desirable in accordance with the present invention to administer one or more compounds of the present invention in conjunction with one or more alpha-adrenergic receptor agonists and/or one or more other sympathomimetic drugs.

According to the present invention, compounds of formula I may be used to treat, prevent, or alleviate dependence, withdrawal, or symptoms thereof for any of a variety of substances including, for example, recreational substances (e.g., alcohol, tobacco [for example, nicotine]), pharmacologic agents (e.g., pain relievers [for example, Vicodin® Lortab®, Lorcet®, Percocet®, Percodan®, Tylox®, Hydrocodone, OxyContin®, methadone, Tramadol, etc], tranquilizers, stimulants, or sedatives), and illicit drugs (e.g., marijuana, heroine, cocaine, ecstasy, LSD, PCP, methamphetamine, etc.).

The term "substance abuse", as used herein, may be defined with reference to criteria set form in the *Diagnostic and Statistical Manual of Mental Disorders*, $4^{th}$ Ed. (1994) ("DSM-IV"), which was prepared by the Task Force on Nomenclature and Statistics of the American Psychiatric Association. A feature of substance abuse is a maladaptive pattern of substance use manifested by recurrent and significant adverse consequences related to the repeated use of substances. As recited in the DSM-IV, substance abuse is defined as maladaptive pattern of substance abuse leading to clinicalyl significant impairment or distress, as manifested by one(or more) of the following, occurring within a 12-month period: (1) recurrent substance use resulting in a failure to fulfill major role obligations at work, school, or home; (2) recurrent substance use in situations in which it is physically hazardous; (3) recurrent substance-related legal problems; and (4) continued substance use despite having persistent or recurrent social or interpersonal problems cause or exacerbated by the effects of the substance. In addition, the DMS-IV requires that the symptoms of substance abuse do not meet the criteria for substance dependence.

The term "substance dependence", as used herein, may be defined with reference to criteria set form in the Diagnostic and Statistical Manual of Mental Disorders, $4^{th}$ Ed. (1994) ("DSM-IV"), which was prepared by the Task Force on Nomenclature and Statistics of the American Psychiatric Association. The criteria for substance dependence set forth in DSM-IV is a pattern of substance use, leading to clinically significant impairment or distress as manifested by at least three selected from the following group, occurring at any time within the same twelve month period: (1) tolerance as defined by either (a) a need for substantially increased amounts of the substance to achieve the desired effect; or (b) substantially diminished effect with continued use of the same amount of the substance; (2) withdrawal, as demonstrated by either (a) the characteristic withdrawal syndrome for the specific substance; or (b) the same, or a closely related substance is taken to relieve or avoid withdrawal symptoms; (3) the substance is often taken in larger amounts or over a longer period then was intended; (4) there is a persistent desire or unsuccessful efforts to cut down or control substance use; (5) a great deal of time is spent in activities to obtain the substance, use the substance, or recover from its effects; (6) important social, occupational or recreational activities are given up or reduced because of substance use; and (7) the substance use is continued despite knowledge of having a persistent or recurrent physical or psychological problem that is likely to have been caused or exacerbated by the substance. Substance dependence can be with physiological dependence; that is evidence of tolerance or withdrawal is present, or without physiological dependence, where no evidence of tolerance or withdrawal is present. Four of the conditions set forth in DSM-IV include remission. These types of remission are based on the interval of time that has elapsed since the cessation of dependencies and whether there is continued presence of one or more of the symptoms included in the criteria for dependencies.

In certain embodiments, compounds of the present invention are useful for treating alcoholism (e.g., alcohol abuse, addiction and/or dependence including treatment for abstinence, craving reduction and relapse prevention of alcohol intake) and/or tobacco abuse (e.g., smoking addiction, cessation and/or dependence including treatment for craving reduction and relapse prevention of tobacco smoking).

In evaluating substance abuse in accordance with the present invention, reference may be made, for example, to the National Survey on Drug Use and Health (NSDUH), which obtains information on nine different categories of illicit drug use: marijuana, cocaine, heroin, hallucinogens, inhalants, and nonmedical use of prescription-type pain relievers, tranquilizers, stimulants, and sedatives. In these categories, hashish is included with marijuana, and crack is considered a form of cocaine. Several drugs are grouped under the hallucinogens category, including LSD, PCP, peyote, mescaline, mushrooms, and "Ecstasy" (MDMA). Inhalants include a variety of substances, such as amyl nitrite, cleaning fluids, gasoline, paint, and glue. The four categories of prescription-type drugs (pain relievers, tranquilizers, stimulants, and sedatives) cover numerous drugs available through prescriptions and sometimes illegally "on the street." Methamphetamine is considered a type of stimulant. Respondents are asked to report only uses of drugs that were not prescribed for them or drugs they took only for the experience or feeling they caused. Over-the-counter drugs and legitimate uses of prescription drugs are not included. NSDUH reports combine the four prescription-type drug groups into a category referred to as "any psychotherapeutics."

The NSDUH categorizes alcohol abuse through use of questions about the frequency of the consumption of alcoholic beverages, such as beer, wine, whiskey, brandy, and mixed drinks. An extensive list of examples of the kinds of beverages covered is given to respondents prior to the question administration. A "drink" is defined as a can or bottle of beer, a glass of wine or a wine cooler, a shot of liquor, or a mixed drink with liquor in it. Times when the respondent only had a sip or two from a drink are not considered as consumption. For this report, estimates for the prevalence of alcohol use are reported primarily at three levels defined for both males and females and for all ages as follows:

Current use—At least one drink in the past 30 days (includes binge and heavy use).

Binge use—Five or more drinks on the same occasion at least once in the past 30 days (includes heavy use).

Heavy use—Five or more drinks on the same occasion on at least 5 different days in the past 30 days The NSDUH also characterizes the use of tobacco products, including cigarettes, chewing tobacco, snuff, cigars, and pipe tobacco. For analytic purposes, data for chewing tobacco and snuff are combined as "smokeless tobacco." Cigarette use is defined as smoking "part or all of a cigarette." Questions to determine nicotine dependence among current cigarette smokers also are included in NSDUH. Nicotine dependence is based on criteria from the Nicotine Dependence Syndrome Scale (NDSS) or the Fagerstrom Test of Nicotine Dependence (FTND).

In other embodiments, compounds of the present invention are useful for treating withdrawal from drug addiction including addiction to nicotine, alcohol, and other substances of abuse. Individuals often suffer the symptoms of nicotine withdrawal as a consequence of the discontinued use of tobacco in any form, including, but not limited to smoking of cigarette, cigar, or pipe tobacco, or the oral or intranasal ingestion of tobacco or chewing tobacco. Such oral or intranasal tobacco includes, but is not limited to snuff and chewing tobacco. The cessation of nicotine use or reduction in the amount of nicotine use, is often followed within 24 hours by symptoms including dysphoric, depressed mood; light-headedness; insomnia; irritability, frustration or anger; anxiety; nervous tremor; difficulty concentrating; restlessness; decreased heart rate; increased appetite or weight gain; and the craving for tobacco or nicotine. These symptoms often cause clinically significant distress or impairment in social, occupational, or other important areas of functioning.

The discontinued or reduction in administration of an opioid, typically self-administration, through injection or orally, through smoking or intranasal ingestion, often results in the presence of a characteristic opioid withdrawal condition. This withdrawal condition can also be precipitated by administration of an opioid antagonist such as naloxone or naltrexone after opioid use. Opioid withdrawal is characterized by symptoms that are generally opposite to the opioid agonist effects. These withdrawal symptoms may include anxiety; restlessness; muscle aches, often in the back and legs; craving for opioids; irritability and increased sensitivity to pain; dysphoric mood; nausea or vomiting; lacrimation; rhinorrhoea; papillary dilation; piloerection; sweating; diarrhea; yawning; fever; and insomnia. When dependence is on short-acting opioids, such as heroin, withdrawal symptoms usually occur within 6–24 hours after the last dose, while with longer-acting opioids, such as methadone, symptoms may take 2–4 days to emerge. These symptoms often cause clinically significant distress or impairment in social, occupational or other important areas of functioning. The present invention is most preferably used to alleviate one or more symptoms attributed to opioid withdrawal when such symptoms are not due to a general medical condition and are not better accounted for by another medical disorder.

The discontinued or reduction in use of ethanol (ethanol containing beverages) results in the onset of ethanol withdrawal conditions. Ethanol withdrawal conditions are characterized by symptoms that begin when blood concentrations of ethanol decline sharply, within 4 to 12 hours after ethanol use has been stopped or reduced. These ethanol withdrawal symptoms include craving for ethanol; autonomic hyperactivity (such as sweating or pulse rate greater than 100); hand tremor; insomnia; nausea; vomiting; transient visual, tactile, or auditory hallucinations or illusions; psychomotor agitation; anxiety; and grand mal seizures. These symptoms often cause clinically significant distress or impairment in social, occupational, or other important areas of functioning. The present invention is most preferably used to alleviate one or more symptoms attributed to ethanol withdrawal when such symptoms are not due to a general medical condition and are not better accounted for by another medical disorder.

According to another embodiment, a compound of the present invention is administered in combination with one or more agents useful for treating substance abuse. In certain embodiments, a compound of the present invention is administered in combination with one or more agents to treat tobacco abuse. Such agents include nicotine receptor partial agonists bupropion hypochloride (Zyban™) and nicotine replacement therapies.

According to yet another embodiment, a compound of the present invention is administered in combination with one or more agents to treat alcoholism, such as opioid antagonists (e.g., naltrexone, ReVia™), nalmefene, disulfiram (Antabuse™), and acamprosate (Campral™).

In certain embodiments, a compound is administered in combination with one or more agents for reducing alcohol withdrawal symptoms such as benzodiazepines, beta-blockers, clonidine, carbamazepine, pregabalin, and gabapentin (Neurontin™). In other embodiments of the invention, therapy utilizing compounds of the present invention is administered concomitantly with, in connection with, and/or subsequent to an educational and/or behavioral modification program to enhance continued abstinence from substance dependence or abuse. The method of the present invention may be particularly useful in treating symptoms of withdrawal often observed in rehabilitation or other treatment programs. Therefore, the programs can be more effective by focusing on educational and behavioral modification goals, further reducing the incidence of program non-completion.

In certain embodiments, compounds of the present invention are useful for treating one or more intellectual deficit disorders comprising administering a compound of the present invention. In other embodiments, such intellectual deficit disorders include dementia, such as dementia of aging, vascular dementia, mild cognitive impairment, age-related cognitive decline, and mild neurocognitive disorder; Alzheimer's disease, and memory deficit, attention deficit disorders (ADD, also known as Attention Deficit Hyperactivity Disorder or ADHD) in both children and adults. In certain embodiments, the present invention provides a method of treating ADD and/or ADHD in a pediatric patient comprising administering to said patient a compound of formula I or pharmaceutical composition thereof.

In other embodiments, the present invention provides a method of treating one or more cognition disorders. According to another aspect, the cognition disorder is a learning disorder. Such learning disorders are known in the art and include autism, dyslexia, Asperger's syndrome, a neurobiological disorder similar to autism and characterized by serious deficits in social and communication skills; specific learning disability, a disorder in one or more of the basic psychological processes involved in understanding or in using spoken or written language, which may manifest itself in an imperfect ability to listen, think, speak, read, write, spell or to do mathematical calculations; dysgraphia, a disorder that causes difficulty with forming letters or writing within a defined space; dyscalculia, a disorder that causes people to have problems doing arithmetic and grasping mathematical concepts; dyspraxia, a problem with the body's system of motion that interferes with a person's ability to make a controlled or coordinated physical response in a given situation; visual perceptual deficit, difficulty receiving and/or processing accurate information from the sense of sight, although there is nothing wrong with vision; and auditory perceptual deficit, difficulty receiving accurate information through auditory means, even though there is no problem with hearing.

In certain embodiments, the present invention provides a method for treating one or more impulsivity disorders (e.g. borderline personality disorder), disruptive behavior disorders, or impulse control disorders. In certain embodiments, the present invention provides a method for treating Tourette's syndrome (TS), an inherited, neurological disorder characterized by repeated and involuntary body movements (tics) and/or uncontrollable vocal sounds.

According to another aspect, the present invention provides a method for treating one or more behavioral addictions and addictive disorders. Behavioral addictions and addictive disorders result from the intoxication one senses from the release of brain chemicals (e.g., serotonin, adrenaline, epinepherine, etc.) during certain activities. Such disorders are known in the art and include gambling, sex addiction, eating disorders, spending addiction, rage/anger, workaholism, exercise addiction, risk taking addictions, and perfectionism to name a few.

In certain embodiments, a compound of the present invention is administered in combination with one or more cognitive improvement agents. Such agents are well known in the art and include donepezil hydrochloride (Aircept™) and other acetylcholinesterase inhibitors; galantamine, neuroprotective agents (e.g., memantine); ADD/ADHD agents (e.g., methylphenidate (Ritalin$^{Tm}$), atomoxetine (Strattera™), methylphenidate, sustained release (Concerta™) and amphetamine/dextroamphetamine (Adderall™).

According to another aspect, the present invention provides a method for treating sexual dysfunction comprising administering a compound of the present invention. In certain embodiments, the sexual dysfunction is associated with a depressive disorder. In other embodiments, the sexual dysfunction is associated with treatment of a disorder by administration of a serotonin reuptake inhibitor. Compounds of the present invention are useful for treating sexual dysfunction in the male and in the female. Such disorders include male erectile dysfunction (MED) and female sexual dysfunction (FSD), e.g. female sexual arousal disorder (FSAD).

In other embodiments, the present invention provides a method for treating one or more disorders associated with sexual dysfunction including: HSDD, characterized by a deficiency, or absence of, sexual fantasies and desire for sexual activity; FSAD, characterized by a persistent or recurrent inability to attain, or to maintain until completion of the sexual activity, an adequate lubrication-swelling response of sexual excitement; FOD characterized by persistent or recurrent delay in, or absence of, orgasm following a normal sexual excitement phase; Sexual Pain Disorders such as dyspareunia and vaginismus; and/or HSDD characterized by a woman who has no or little desire to be sexual, and has no or few sexual thoughts or fantasies.

According to another embodiment, a compound of the present invention is administered in combination with one or more agents for treating male sexual dysfunction (e.g., male erectile dysfunction). Such agents are known in the art and include a dopaminergic agent (e.g. D2, D3 or D4 agonists and apomorphine); an NPY (neuropeptide Y) (preferably an NPY-1 and/or NPY-5 inhibitor); a melanocortin receptor agonist or modulator or melanocortin enhancer; an NEP inhibitor; a PDE inhibitor (preferably, a cGMP PDE-5 inhibitor); a bombesin receptor antagonist or modulator, and a soluble secreted endopeptidase inhibitor (SEPi). In certain embodiments, a compound of the present invention is administered in combination with one or more agents for treating male sexual dysfunction such as alprostadil or sildenafil.

According to yet another embodiment, a compound of the present invention is administered in combination with one or more agents for treating female sexual dysfunction. Such agents are known in the art and include estrogen receptor modulators (e.g., estrogen agonists and/or estrogen antagonists); testosterone replacement agents, testosternone (Tostrelle), dihydrotestosterone, dehydroepiandrosterone (DHEA), a testosterone implant; eg dehydroandrostendione, estrogen, estrogen, medroxyprogesterone, medroxyprogesterone acetate (MPA), a combination of estrogen and a methyl testosterone hormone replacement therapy agent; Premarin, Cenestin, Oestrofeminal, Equin, Estrace, Estrofem, Elleste Solo, Estring, Eastraderm TTS, Eastraderm Matrix, Dermestril, Premphase, Preempro, Prempak, Premique, Estratest, Estratest HS, Tibolone, a dopaminergic agent; eg apomorphine or a selective D2, D3 or $D2/D_3$ agonist such as, pramipexole and ropirinol, a NPY (neuropeptide Y) inhibito; eg a NPY (neuropeptide Y) inhibitor such as a NPY1 or NPY5 inhibitor, preferably NPY1 inhibitor, a melanocortin receptor modulator or a melanocortin enhancer; eg melanotan II, PT-14, PT-141, a NEP (neutral endopeptidase) inhibitor; a PDE (phosphodiesterase) inhibitor; eg sildenafil, and/or a bombesin receptor modulator.

According to the present invention, compounds of the present invention are useful for treating any of a variety of different types of pain experienced by mammals, such as humans. For example, the compounds of the present invention may be used to treat treating acute pain (short duration) or chronic pain (regularly reoccurring or persistent), whether centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery such as burn pain, or headaches such as migraines or tension headaches, or combinations of these pains. One skilled in the art will recognize that these pains may overlap one another. For example, a pain caused by inflammation may also be visceral or musculoskeletal in nature.

In one embodiment of the present invention, one or more compounds of the present invention is/are administered in mammals to treat chronic pain such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromyalgia, temporomandibular joint, or myofascial pain syndrome; bony pain associated with for example bone or joint degenerating disorders such as osteoarthritis, rheumatoid arthritis, or spinal stenosis; headaches such migraine or tension headaches; or pain associated with infections such as HIV, sickle cell anemia, autoimmune disorders, multiple sclerosis, or inflammation such as osteoarthritis or rheumatoid arthritis.

In some embodiments, the compounds of the present invention are used to treat chronic pain that is neuropathic pain, visceral pain, musculoskeletal pain, bony pain, headache, cancer pain or inflammatory pain or combinations thereof, in accordance with the methods described herein. Inflammatory pain can be associated with a variety of medical conditions such as osteoarthritis, rheumatoid arthritis, surgery, or injury. Neuropathic pain may be associated with for example diabetic neuropathy, peripheral neuropathy, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, or nerve damage cause by injury resulting in peripheral and/or central sensitization such as phantom limb pain, reflex sympathetic dystrophy or postthoracotomy pain, cancer, chemical injury, toxins, nutritional deficiencies, or viral or bacterial infections such as shingles or HIV, or combinations thereof. Inventive treatment methods further include treatments in which the neuropathic pain is a condition secondary to metastatic infiltration, adiposis dolorosa, burns or central pain conditions related to thalamic conditions.

Neuropathic pains described above may also be, in some circumstances, classified as "painful small fiber neuropathies" such as idiopathic small-fiber painful sensory neuropathy, or "painful large fiber neuropathies" such as demylinating neuropathy or axonal neuropathy, or combinations thereof. Such neuropathies are described in more detail, for example, in the J. Mendell et al., *N. Engl. J. Med.* 2003, 348:1243–1255, which is hereby incorporated by reference in its entirety.

In another embodiment, the compounds useful in the present invention may be administered to totally or partially inhibit a neuropathic pain condition from developing. For example, compounds of the present invention may be administered to a mammal who is at risk for developing a neuropathic pain condition such as a mammal who has contracted shingles or a mammal who is being treated for cancer.

In one embodiment, the compounds useful in the present invention may be administered prior to or during a surgical procedure to partially or totally inhibit development of pain associated with the surgical procedure.

As mentioned previously, the methods of the present invention may be used to treat pain that is somatic and/or visceral in nature. For example, somatic pain that can be treated in accordance with the methods of the present invention includes pain associated with structural or soft tissue injury experienced during surgery, dental procedures, burns, or traumatic body injuries. Examples of visceral pain that can be treated in accordance with the methods of the present invention include those types of pain associated with or resulting from maladies of the internal organs such as ulcerative colitis, irritable bowel syndrome, irritable bladder, Crohn's disease, rheumatologic (arthralgias), tumors, gastritis, pancreatitis, infections of the organs, or biliary tract disorders, or combinations thereof. One skilled in the art will also recognize that the pain treated according to the methods of the present invention may also be related to conditions of hyperalgesia, allodynia, or both. Additionally, chronic pain to be treated in accordance with the present invention may be with or without peripheral or central sensitization.

The present invention also provides use of the compounds of the present invention to treat acute and/or chronic pains associated with female conditions, which may also be referred to as female-specific pain. Such types of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes.

In certain embodiments, a compound of the present invention is administered in combination with a pain relieving agent. Examples of pain relieving agents that may be administered with compounds of the present invention include, but are not limited to, analgesics such as non-narcotic analgesics or narcotic analgesics; anti-inflammatory agents such as non-steroidal anti-inflammatory agents (NSAIDs), steroids or anti-rheumatic agents; migraine preparations such as beta adrenergic blocking agents, ergot derivatives, or isometheptene; tricyclic antidepressants such as amitryptyline, desipramine, or imipramine; anti-epileptics such as gabapentin, carbamazepine, topiramate, sodium valproate or phenytoin; $\alpha_2$ agonists; or selective serotonin reuptake inhibitors/selective norepinepherine uptake inhibitors, or combinations thereof.

One skilled in the art will recognize that some agents described herein act to relieve multiple conditions such as pain and inflammation, while other agents may just relieve one symptom such as pain. A specific example of an agent having multiple properties is aspirin, where aspirin is anti-inflammatory when given in high doses, but at lower doses is just an analgesic. The pain relieving agent may include any combination of the aforementioned agents, for example, the pain relieving agent may be a non-narcotic analgesic in combination with a narcotic analgesic.

Non-narcotic analgesics useful in the practice of the present invention include, for example, salicylates such as aspirin, ibuprofen (Motrin®, Advil®), ketoprofen (Orudis®), naproxen (Naprosyn®), acetaminophen, indomethacin or combinations thereof. Examples of narcotic analgesic agents that may be used in combination with compounds of the present invention include opioid analgesics such as fentenyl, sufentanil, morphine, hydromorphone, codeine, oxycodone, buprenorphine or pharmaceutically acceptable salts thereof or combinations thereof. Examples of anti-inflammatory agents that may be used in combination with compounds of the present invention include but are not limited to aspirin; ibuprofen; ketoprofen; naproxen; etodolac (Lodine®); COX-2 inhibitors such as celecoxib (Celebrex®), rofecoxib (Vioxx®), valdecoxib (Bextra®), parecoxib, etoricoxib (MK663), deracoxib, 2-(4-ethoxy-phenyl)-3-(4-methanesulfonyl-phenyl)-pyrazolo[1,5-b]pyridazine, 4-(2-oxo-3-phenyl-2,3-dihydrooxazol-4-yl)benzenesulfonamide, darbufelone, flosulide, 4-(4-cyclohexyl-2-methyl-5-oxazolyl)-2-fluorobenzenesulfonamide), meloxicam, nimesulide, 1-Methylsulfonyl-4-(1,1-dimethyl-4-(4-fluorophenyl)cyclopenta-2,4-dien-3-yl)benzene, 4-(1,5-Dihydro-6-fluoro-7-methoxy-3-(trifluoromethyl)-(2)-benzothiopyrano(4,3-c) pyrazol-1-yl)benzenesulfonamide, 4,4-dimethyl-2-phenyl-3-(4-methylsulfonyl)phenyl)cyclo-butenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropyl butan-1-one, or their physiologically acceptable salts, esters or solvates; sulindac (Clinoril®); diclofenac (Voltaren®); piroxicam (Feldene®); diflunisal (Dolobid®), nabumetone (Relefen®), oxaprozin (Daypro®), indomethacin (Indocin®); or steroids such as Pediaped® prednisolone sodium phosphate oral solution, Solu-Medrole methylprednisolone sodium succinate for injection, Prelone® brand prednisolone syrup.

Further examples of anti-inflammatory agents that may be used for treating pain, for example associated with rheumatoid arthritis, in accordance with the present invention include naproxen, which is commercially available in the form of EC-Naprosyn® delayed release tablets, Naprosyn®, Anaprox® and Anaprox® DS tablets and Naprosyn® suspension from Roche Labs, Celebrex® brand of celecoxib tablets, Vioxx® brand of rofecoxib, Celestone® brand of betamethasone, Cupramine® brand penicillamine capsules, Depen® brand titratable penicillamine tablets, Depo-Medrol® brand of methylprednisolone acetate injectable suspension, Arava™ leflunomide tablets, Azulfidine EN-tabs® brand of sulfasalazine delayed release tablets, Feldene® brand piroxicam capsules, Cataflam® diclofenac potassium tablets, Voltaren® diclofenac sodium delayed release ta blets, Voltaren®-XR diclofenac sodium extended release tablets, or Enbrel® etanerecept products.

Examples of yet other agents used to treat inflammations, especially rheumatoid arthritis, include immunosuppressants such as Gengraf™ brand cyclosporine capsules, Neoral® brand cyclosporine capsules or oral solution, or Imuran® brand azathioprine tablets or IV injection; Indocin® brand indomethacin capsules, oral suspension or suppositories; Plaquenil® brand hydroxychloroquine sulfate; or Remicade® infliximab recombinant for IV injection; or gold compounds such as auranofin or Myochrisyine® gold sodium thiomalate injection.

As 5-$HT_{2C}$ modulators, compounds of the present invention are useful for treating a variety of disorders. Such disorders include premenstrual syndrome, motion or motor disorders such as Parkinson's disease and epilepsy; migraines, chronic fatigue syndrome, anorexia nervosa, disorders of sleep (e.g., sleep apnea), and mutism.

In other embodiments, compounds of the present invention are useful for treating one or more central nervous system deficiencies associated, for example, with trauma, stroke, and spinal cord injuries, neurodegenerative diseases or toxic or infective CNS diseases (e.g., encephalitis or meningitis), or Parkinson's disease. The compounds of the present invention can therefore be used to improve or inhibit further degradation of central nervous system activity during or following the malady or trauma in question. Included in these improvements are maintenance or improvement in motor and motility skills, control, coordination and strength.

5. Pharmaceutically Acceptable Compositions

In other embodiments, the invention relates to compositions comprising at least one compound of formula I, or a pharmaceutically acceptable salt thereof, and one or more pharmaceutically acceptable carriers, excipients, or diluents. Such compositions include pharmaceutical compositions for treating or controlling disease states or conditions of the central nervous system. In certain embodiments, the compositions comprise mixtures of one or more compounds of formula I.

In certain embodiments, the invention relates to compositions comprising at least one compound of formula I, or a pharmaceutically acceptable salt thereof, and one or more pharmaceutically acceptable carriers, excipients, or diluents. Such compositions are prepared in accordance with acceptable pharmaceutical procedures, such as, for example, those described in *Remingtons Pharmaceutical Sciences,* 17th edition, ed. Alfonoso R. Gennaro, Mack Publishing Company, Easton, Pa. (1985), which is incorporated herein by reference in its entirety. Pharmaceutically acceptable carriers are those carriers that are compatible with the other ingredients in the formulation and are biologically acceptable.

The compounds of formula I can be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The compounds of formula I can be administered rectally or vaginally in the form of a conventional suppository. For administration by intranasal or intrabronchial inhalation or insufflation, the compounds of formula I can be formulated into an aqueous or partially aqueous solution, which can then be utilized in the form of an aerosol. The compounds of Formula I can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The amount of compound of formula I provided to a patient will vary depending upon what is being administered, the purpose of the administration, such as prophylaxis or therapy, the state of the patient, the manner of administration, and the like. In therapeutic applications, compounds of formula I are provided to a patient suffering from a condition in an amount sufficient to treat or at least partially treat the symptoms of the condition and its complications. An amount adequate to accomplish this is a "therapeutically effective amount" as described previously herein. The dosage to be used in the treatment of a specific case must be subjectively determined by the attending physician. The variables involved include the specific condition and the size, age, and response pattern of the patient. The treatment of substance abuse follows the same method of subjective drug administration under the guidance of the attending physician. Generally, a starting dose is about 5 mg per day with gradual increase in the daily dose to about 1000 mg per day, to provide the desired dosage level in the patient.

6. Combination with Other Agents

Compounds of formula I may be administered alone in order to treat various disorders in accordance with the present invention, or may be combined with one or more other pharmaceutical agents as described herein. Where the present invention involves administration of two or more pharmaceutical agents, the two or more agents may be administered simultaneously (such as individually at the same time, or together in a pharmaceutical composition), and/or successively with one another. In general, a compound of formula I and the other pharmaceutical agent(s) are administered in a manner so that both are present in the mammal body for a certain period of time to treat the disorder.

Also, the two or more pharmaceutical agents may be delivered via the same route of administration or by different routes. Desirable routes of administration may well depend upon the particular agent(s) chosen, many of which have recommended administration route(s) known to those skilled in the art. For example, opioids are generally administered by oral, intravenous, or intramuscular administration routes. Similarly, as is known in the art, doses of pharmaceutical agents in a composition may be affected by administration route. In general, pharmaceutical agents may be dosed and administered according to practices known to those skilled in the art such as those disclosed in references such as the Physicians' Desk Reference, 55 Edition, 2001, published by Medical Economics Co., Inc., Montvale, N.J.

A more complete list of pharmaceutically active agents, including pain relieving agents, can be found in the Physicians' Desk Reference, 55 Edition, 2001, published by Medical Economics Co., Inc., Montvale, N.J. Each of these agents may be administered in conjunction with one or more comopunds of formula I according to the present invention.

For most or all of these agents, recommended effective dosages and regimes are known in the art; many can be found in the above-referenced Physicians' Desk Reference, 55 Edition, 2001, published by Medical Economics Co., Inc., Montvale, N.J.

In certain embodiments, the present invention is directed to prodrugs of compounds of formula I. The term "prodrug," as used herein, means a compound that is convertible in vivo by metabolic means (e.g. by hydrolysis) to a compound of formula I. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Delivery Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is hereby incorporated by reference in its entirety.

EXAMPLES

As depicted in the Examples below, in certain exemplary embodiments, compounds are prepared according to the following general procedures. It will be appreciated that although the general methods depict the synthesis of certain compounds of the present invention, the following general methods, in addition to the Schemes set forth above and other methods known to one of ordinary skill in the art, can be applied to all compounds and subclasses and species of each of these compounds, as described herein.

Example 1

N-{[8-(2-chlorophenyl)-3,4-dihydro-2H-chromen-2-yl]methyl}-N-methylamine hydrochloride Step 1: A suspension of methyltriphenylphosphonium bromide (19.7 g, 55.0 mmol) in anhydrous tetrahydrofuran (200 mL) was cooled to 0° C. and n-butyllithium (2.5 M in hexanes, 24.0 mL, 60.0 mmol) was added during 5–10 minutes with stirring. The resulting clear, orange solution was stirred at 0° C. for an additional 30 minutes and then was added via cannula to a solution of o-vanillin (3.80 g, 25.0 mmol) in tetrahydrofuran (100 mL) at 23° C. After 3 hours, the reaction was quenched with saturated aqueous ammonium chloride solution (100 mL), diluted with water (300 mL), and the aqueous phase was extracted with ether (3×200 mL). The organic phase was washed with water (300 mL) and brine (300 mL), dried over magnesium sulfate and filtered through a plug of silica gel (10 cm diam×5–6 cm H). Concentration under reduced pressure provided crude 2-methoxy-6-vinyl-phenol as a clear, colorless oil (4.20 g) that was used without further purification. $^1$H NMR (DMSO): δ3.79 (s, 3 H, OC$\underline{H}$3), 5.19 (dd, 1H, CH=C$\underline{H}$H), 5.74 (dd, 1$\underline{H}$, C$\underline{H}$=CHH), 6.74 (t, 1H, Ar$\underline{H}$), δ6.86 (dd, 1H, Ar$\underline{H}$), 6.96 (dd, 1H, C$\underline{H}$=CHH), 7.04 (dd, 1H, Ar$\underline{H}$), and 8.74 (s, 1H, ArO$\underline{H}$).

Step 2: A solution of crude 2-methoxy-6-vinyl-phenol (4.20 g, 25.0 mmol), 2-hydroxy-3-buten-1-yl p-tosylate (7.27 g, 30.0 mmol) and triphenylphosphine (7.87 g, 30.0 mmol) in tetrahydrofuran (ca. 200 mL) was treated with diethylazodicarboxylate (5.22 g, 30.0 mmol) via syringe at 23° C. with stirring. After 18 hours, the reaction was quenched with water (200 mL) and the organic phase was separated. The aqueous phase was extracted with ethyl acetate (2×250 mL) and the combined organic phases were washed with water (200 mL) and brine (300 mL), dried over magnesium sulfate and concentrated under reduced pressure to yield an oily yellow residue (21.3 g) which was pre-adsorbed on silica gel (50 g in dichloromethane). Purification by flash chromatography using a solvent gradient of 5 to 20% ethyl acetate in hexane provided 2-(2-methoxy-6-vinylphenoxy)but-3-enyl 4-methylbenzenesulfonate (4.4 g, 47% overall) as a clear, colorless oil. HRMS: calcd for $C_{20}H_{22}O_5S+H^+$, 375.12607. found (ESI, [M+H]$^+$), 375.1273.

Step 3: A solution of 2-(2-methoxy-6-vinylphenoxy)but-3-enyl 4-methylbenzenesulfonate (4.4 g, 12 mmol) in dichloromethane (100 mL) was treated with benzylidene-bis(tricyclohexylphosphine)dichlororuthenium (0.9 g) at 23° C. with stirring. After 4 hours, the solvent volume was reduced under reduced pressure (to ca. 10 mL) and the solution was pre-adsorbed on silica gel (5 g). Purification by flash chromatography using a solvent gradient of 10 to 20% ethyl acetate in hexane provided 8-methoxy-2H-1-benzopyran-2-methanol 4-methylbenzenesulfonate (4.0 g, 98%) as a dark oil. MS (ESI) m/z 345.0 ([M−H]$^−$).

Step 4: A solution of 8-methoxy-2H-1-benzopyran-2-methanol 4-methylbenzenesulfonate (13.8 g, 39.8 mmol) in ethyl acetate (280 mL) was hydrogenated over 10% palladium-on-carbon (2.8 g) at 55 psi in a 2 L Parr flask. After 6 hours, the catalyst was filtered (Celite) and washed with ethyl acetate (3×100 mL). Concentration of the filtrate provided toluene-4-sulfonic acid 8-methoxy-chroman-2-yl methyl ester (13.9 g, 100%) as a tan solid. MS (ESI) m/z 349.0 ([M+H]$^+$).

Step 5: A solution of toluene-4-sulfonic acid 8-methoxy-chroman-2-yl methyl ester (10.5 g, 30.1 mmol) in 1,2-dichloroethane (ca. 300 mL) was treated with iodotrimethylsilane (9.4 mL, d 1.406, 66 mmol) at 23° C. with stirring and the solution was heated at 80° C. (oil bath). After 5 hours, the cooled solution was quenched with 1 N aqueous hydrochloric acid (250 mL) and stirred for 5–10 minutes. The organic phase was separated and the aqueous phase was extracted with dichloromethane (2×250 mL). The combined organic phases were washed with saturated aqueous sodium bicarbonate solution (400 mL) and brine (400 mL), dried over magnesium sulfate and concentrated under reduced pressure to yield a dark oil (10.6 g) which was pre-adsorbed on silica gel (20 g in dichloromethane). Purification by flash chromatography using a solvent gradient of 10 to 20% ethyl acetate in hexane provided toluene-4-sulfonic acid 8-hydroxy-chroman-2-yl methyl ester (7.6 g, 75%) as an off-white solid.

HRMS: calcd for $C_{17}H_{18}O_5S+H$, 335.09532. found (ESI, [M+H]$^+$), 335.0942.

Step 6: A solution of toluene-4-sulfonic acid 8-hydroxy-chroman-2-yl methyl ester (14.0 g, 41.9 mmol) and pyridine (10.2 mL, 126 mmol) in dichloromethane (ca. 300 mL) was treated with trifluoromethanesulfonic anhydride (14.1 mL, 83.8 mmol) at 0° C. with stirring. After ca. 5 minutes, the cooling bath was removed and the solution was warmed to 23° C. After 1 additional hour, the reaction solution was diluted with dichloromethane (300 mL) and washed with 1 N aqueous hydrochloric acid (500 mL), water (3×500 mL) and saturated brine (500 mL). The organic phase was dried over magnesium sulfate and concentrated under reduced pressure to provide (8-{[(trifluoromethyl)sulfonyl]oxy}-3,4-dihydro-2H-chromen-2-yl)methyl 4-methylbenzenesulfonate (19.0 g, 97%) as a light tan solid. HRMS: calcd for $C_{18}H_{17}F_3O_7S_2$+H, 467.04460. found (ESI, [M+H]$^+$), 467.0438.

Step 7: A mixture of (8-{[(trifluoromethyl)sulfonyl]oxy}-3,4-dihydro-2H-chromen-2-yl)methyl 4-methylbenzenesulfonate (0.49 g, 1.05 mmol), 2-chlorophenylboronic acid (0.33 g, 2.1 mmol), potassium carbonate (0.44 g, 3.2 mmol) and lithium chloride (0.13 g, 3.1 mmol) in dioxane (3.75 ml) and water (1.25 mL) was purged with nitrogen for 20 minutes. Tetrakis(triphenylphosphine)palladium(0) (60 mg, 0.052 mmol) was added and the reaction mixture heated at 100° C. for 1 hour. The cooled reaction mixture was then partitioned between ethyl acetate (50 mL) and 1 M aqueous sodium hydroxide (50 mL). The organic layer was separated, washed with water (50 mL) dried over magnesium sulfate, filtered and concentrated under reduced pressure to afford an orange oil. Purification by flash chromatography using a solvent gradient of 5 to 10% ethyl acetate in hexane gave 400 mg (89%) of [8-(2-chlorophenyl)-3,4-dihydro-2H-chromen-2-yl]methyl 4-methylbenzenesulfonate as a white solid. HRMS: calcd for $C_{23}H_{21}ClO_4S+NH_4^+$, 446.11873. found (ESI, [M+NH$_4$]$^+$), 446.1179.

Step 8: To a suspension of [8-(2-chlorophenyl)-3,4-dihydro-2H-chromen-2-yl]methyl 4-methylbenzenesulfonate (0.13 g, 0.30 mmol) in dimethylsulfoxide (0.5 mL) was added a solution of methylamine (2.0 M in tetrahydrofuran, 1.5 mL, 3.0 mmol) and the mixture heated to 60° C. in a sealed vial for 24 hours. The cooled reaction mixture was then diluted with diethyl ether (10 mL), washed with water (5×5 mL) and saturated brine (5 mL), dried over magnesium sulfate, filtered and concentrated under reduced pressure to afford a yellow oil. Purification by flash chromatography using a solvent gradient of 0.5 to 5% ammonia saturated methanol solution in dichloromethane gave 69 mg (79%) of N-{[8-(2-chlorophenyl)-3,4-dihydro-2H-chromen-2-yl]methyl}-N-methylamine. The product was dissolved in diethyl ether (1 mL) and a solution of hydrogen chloride (1.0 M in diethyl ether, 0.25 mL, 0.25 mmol) was added followed by 2-propanol (3 drops). The resulting white precipitate was filtered to afford 74 mg (76%) of N-{[8-(2-chlorophenyl)-3,4-dihydro-2H-chromen-2-yl]methyl}-N-methylamine hydrochloride as a white solid. HRMS: calcd for $C_{17}H_{18}ClNO+H^+$, 288.11497. found (ESI, [M+H]$^+$), 288.1143.

Example 2

{[8-(2-chlorophenyl)-3,4-dihydro-2H-chromen-2-yl]methyl}amine trifluoroacetate

Step 1: A solution of [8-(2-chlorophenyl)-3,4-dihydro-2H-chromen-2-yl]methyl 4-methylbenzenesulfonate, prepared in Example 1, step 7 (0.25 g, 0.58 mmol) and sodium azide (0.15 g, 2.3 mmol) in anhydrous dimethyl sulfoxide (9.5 mL) was heated to 70° C. under nitrogen for 16 hours. The cooled reaction mixture was then diluted with diethyl ether (50 mL), washed with water (5×25 mL) and saturated brine (25 mL), dried over magnesium sulfate, filtered and concentrated under reduced pressure to afford 0.14 g (82%) of 2-azidomethyl-8-(2-chloro-phenyl)-chroman as a colorless oil that was used without further purification.

MS (ESI) m/z 272.0 ([M+H−N$_2$]$^+$).

Step 2: To a solution of 2-azidomethyl-8-(2-chloro-phenyl)-chroman (0.14 g, 0.47 mmol) in tetrahydrofuran (7.8 mL) was added polymer-bound triphenylphosphine (~3mmol/g, 0.31 g, 0.93 mmol) followed by water (0.8 mL) and the mixture gently shaken for 22 hours. The brown suspension was then filtered through celite, the filter cake washed with diethyl ether (50 mL) and the combined filtrates dried over magnesium sulfate, filtered and concentrated under reduced pressure to afford a yellow oil. Purification by reverse phase HPLC using a solvent gradient of 5 to 95% acetonitrile in water containing 0.1% trifluoroacetic acid followed by trituration of the product with diethyl ether (3×2 mL) gave 77 mg (45%) of {[8-(2-chlorophenyl)-3,4-dihydro-2H-chromen-2-yl]methyl}amine trifluoroacetate as a tan solid.

HRMS: calcd for $C_{16}H_{16}ClNO+H^+$, 274.09932. found (ESI, [M+H]$^+$), 274.0992.

Example 3

{[(2R)-8-(2,5-dichlorophenyl)-3,4-dihydro-2H-chromen-2-yl]methyl}methylamine hydrochloride Step 1: Racemic (8-{[(trifluoromethyl)sulfonyl]oxy}-3,4-dihydro-2H-chromen-2-yl)methyl 4-methylbenzenesulfonate, was dissolved in acetonitrile and the resulting solution injected onto a Supercritical Fluid Chromatography instrument. The baseline resolved enantiomers were collected using the conditions described below.

Column: Whelk-O-1 (4.6×250 mm)
Mobile Phase: 8% 2-propanol/92% CO$_2$
Column Temperature: 35° C.
Flow Rate: 2 mL/minute
Wavelength: 222 nm ((2S)-8-{[(trifluoromethyl)sulfonyl]oxy}-3,4-dihydro-2H-chromen-2-yl)methyl 4-methylbenzene sulfonate (98.2% enantiomeric excess) was isolated as peak 1.

HRMS: calcd for $C_{18}H_{17}F_3O_7S_2+H^+$, 467.04406. found (ESI, [M+H]$^+$), 467.0468.

((2R)-8-{[(trifluoromethyl)sulfonyl]oxy}-3,4-dihydro-2H-chromen-2-yl)methyl4-methylbenzene sulfonate (>99.8% enantiomeric excess) was isolated as peak 2.

$[\alpha]_D^{25}$=−30° (c=0.0114 g/mL, DMSO);

HRMS: calcd for $C_{18}H_{17}F_3O_7S_2+H^+$, 467.04406. found (ESI, [M+H]$^+$), 467.0453.

Step 2: A mixture of ((2R)-8-{[(trifluoromethyl)sulfonyl]oxy}-3,4-dihydro-2H-chromen-2-yl)methyl 4-methylbenzenesulfonate (0.50 g, 1.1 mmol), 2,5-dichlorophenylboronic acid (0.42 g, 2.2 mmol), potassium carbonate (0.46 g, 3.3 mmol) and lithium chloride (0.14 g, 3.3 mmol) in dioxane (3.75 ml) and water (1.25 mL) was purged with nitrogen for 30 minutes. Tetrakis(triphenylphosphine)palladium (0) (60 mg, 0.052 mmol) was added and the reaction mixture heated at 100° C. for 4 hours. The cooled reaction mixture was then partitioned between ethyl acetate (15 mL) and 1 M aqueous sodium hydroxide (15 mL). The organic layer was separated, washed with saturated brine (15 mL) dried over magnesium sulfate, filtered and concentrated under reduced pressure to afford an orange oil. Purification by flash chromatography using a solvent gradient of 5 to 20% ethyl acetate in hexane gave 0.46 g (90%) of [(2R)-8-(2,5-dichlorophenyl)-3,4-dihydro-2H-chromen-2-yl]methyl 4-methylbenzenesulfonate as an off-white solid. HRMS: calcd for $C_{23}H_{20}Cl_2O_4S+H^+$, 463.05321. found (ESI, [M+H]$^+$), 463.0553.

Step 3: To a suspension of [(2R)-8-(2,5-dichlorophenyl)-3,4-dihydro-2H-chromen-2-yl]methyl 4-methylbenzenesulfonate (0.15 g, 0.324 mmol) in dimethylsulfoxide (0.5 mL) was added a solution of methylamine (2.0 M in tetrahydrofuran, 1.62 mL, 3.24 mmol) and the mixture heated to 60° C. in a sealed vial for 24 hours. The cooled reaction mixture was then diluted with diethyl ether (10 mL), washed with 1.0 M aqueous sodium hydroxide solution (5 mL) and water (5×5 mL), dried over magnesium sulfate, filtered and concentrated under reduced pressure to afford a yellow oil. Purification by flash chromatography using a solvent gradient of 0.5 to 5% ammonia saturated methanol solution in dichloromethane gave {[(2R)-8-(2,5-dichlorophenyl)-3,4-dihydro-2H-chromen-2-yl]methyl}methylamine as a colorless syrup. The product was dissolved in diethyl ether (1 mL) and a solution of hydrogen chloride (1.0 M in diethyl ether, 0.25 mL, 0.25 mmol) was added followed by 2-propanol (3 drops). The resulting white precipitate was filtered and the solid product triturated with diethyl ether (3×3 mL) to afford 56 mg (48%) of {[(2R)-8-(2,5-dichlorophenyl)-3,4-dihydro-2H-chromen-2-yl]methyl}methylamine hydrochloride as a white solid. MS (ESI) m/z 322.0 ([M+H]$^+$).

Example 4

{[(2R)-8-(2,4-dichlorophenyl)-3,4-dihydro-2H-chromen-2-yl]methyl}methylamine hydrochloride Prepared according to Example 3, replacing 2,5-dichlorophenylboronic acid with 2,4-dichlorophenylboronic acid in step 2. MS (ESI) m/z 322.0 ([M+H]$^+$).

Example 5

N-methyl-N-{[(2R)-8-phenyl-3,4-dihydro-2H-chromen-2-yl]methyl}amine hydrochloride Prepared according to Example 3, replacing 2,5-dichlorophenylboronic acid with phenylboronic acid in step 2. HRMS: calcd for $C_{17}H_{19}NO+H^+$, 254.15394. found (ESI, [M+H]$^+$), 254.1546.

Example 6

N-{[(2R)-8-(2-methoxyphenyl)-3,4-dihydro-2H-chromen-2-yl]methyl}-N-methylamine hydrochloride Prepared according to Example 3, replacing 2,5-dichlorophenylboronic acid with 2-methoxyphenylboronic acid in step 2. HRMS: calcd for $C_{18}H_{21}NO_2+H^+$, 284.16450. found (ESI, [M+H]$^+$), 284.1661.

Example 7

N-{[(2R)-8-(2,4-dimethoxyphenyl)-3,4-dihydro-2H-chromen-2-yl]methyl}-N-methylamine hydrochloride Prepared according to Example 3, replacing 2,5-dichlorophenylboronic acid with 2,4-dimethoxyphenylboronic acid in step 2. HRMS: calcd for $C_{19}H_{23}NO_3+H^+$, 314.17507. found (ESI, [M+H]$^+$), 314.1743.

Example 8

N-methyl-N-{[(2R)-8-(2-methylphenyl)-3,4-dihydro-2H-chromen-2-yl]methyl}amine hydrochloride Prepared according to Example 3, replacing 2,5-dichlorophenylboronic acid with 2-methylphenylboronic acid in step 2. HRMS: calcd for $C_{18}H_{21}NO+H^+$, 268.16959. found (ESI, [M+H]$^+$), 268.1699.

Example 9

N-methyl-N-{[(2R)-8-pyridin-3-yl-3,4-dihydro-2H-chromen-2-yl]methyl}amine hydrochloride Prepared according to Example 3, replacing 2,5-dichlorophenylboronic acid with 3-pyridineboronic acid in step 2. HRMS: calcd for $C_{16}H_{18}N_2O+H^+$, 255.14919. found (ESI, [M+H]$^+$), 255.1508.

Example 10

N-{[(2R)-8-(2-chlorophenyl)-3,4-dihydro-2H-chromen-2-yl]methyl}-N-methylamine hydrochloride Prepared according to Example 3, replacing 2,5-dichlorophenylboronic acid with 2-chlorophenylboronic acid in step 2. HRMS: calcd for $C_{17}H_{18}ClNO+H^+$, 288.11497. found (ESI, [M+H]$^+$), 288.1146.

Example 11

{[(2R)-8-(2-chlorophenyl)-3,4-dihydro-2H-chromen-2-yl]methyl}amine hydrochloride Step 1: A mixture of ((2R)-8-{[(trifluoromethyl)sulfonyl]oxy}-3,4-dihydro-2H-chromen-2-yl)methyl 4-methylbenzenesulfonate, prepared in Example 3, step 1 (0.50 g, 1.1 mmol), 2-chlorophenylboronic acid (0.34 g, 2.2 mmol), potassium carbonate (0.46 g, 3.3 mmol) and lithium chloride (0.14 g, 3.3 mmol) in dioxane (3.75 mL) and water (1.25 mL) was purged with nitrogen for 30 minutes. Tetrakis (triphenylphosphine)palladium (0) (60 mg, 0.052 mmol) was added and the reaction mixture heated to 100° C. for 4 hours. The cooled reaction mixture was then partitioned between ethyl acetate (15 mL) and 1 M aqueous sodium hydroxide (15 mL). The organic layer was separated, washed with saturated brine (15 mL) dried over magnesium sulfate, filtered and concentrated under reduced pressure to afford an orange oil. Purification by flash chromatography using a solvent gradient of 5 to 20% ethyl acetate in hexane gave 0.38 g (81%) of [(2R)-8-(2-chlorophenyl)-3,4-dihydro-2H-chromen-2-yl]methyl 4-methylbenzene sulfonate as a white solid. HRMS: calcd for $C_{23}H_{21}ClO_4S+H^+$, 429.09218. found (ESI, [M+H]$^+$), 429.0924.

Step 2: A solution of [(2R)-8-(2-chlorophenyl)-3,4-dihydro-2H-chromen-2-yl]methyl 4-methylbenzenesulfonate (0.24 g, 0.56 mmol) and sodium azide (0.15 g, 2.24 mmol) in anhydrous dimethyl sulfoxide (10 mL) was heated to 70° C. under nitrogen for 15 hours. The cooled reaction mixture was then diluted with diethyl ether (50 mL), washed with water (5×25 mL) and saturated brine (25 mL), dried over magnesium sulfate, filtered and concentrated under reduced pressure to afford 0.14 g (82%) of {[(2R)-8-(2-chlorophenyl)-3,4-dihydro-2H-chromen-2-yl]methyl}azide as a colorless oil that was used without further purification.

Step 3: To a solution of {[(2R)-8-(2-chlorophenyl)-3,4-dihydro-2H-chromen-2-yl]methyl}azide (0.14 g, 0.47 mmol) in tetrahydrofuran (7.8 mL) and water (0.8 mL) was added polymer-bound triphenylphosphine (~3 mmol/g, 0.36 g, 1.08 mmol) and the mixture gently shaken for 3 days. The brown suspension was then filtered through celite, the filter cake washed with diethyl ether (10 mL) and the combined filtrates dried over magnesium sulfate, filtered and concentrated under reduced pressure to afford a yellow oil. The crude product was purified by reverse phase HPLC using a solvent gradient of 5 to 95% acetonitrile in water containing 0.1% trifluoroacetic acid. The fractions containing product were concentrated under reduced pressure to remove acetonitrile and the aqueous phase basified by the addition of sodium carbonate and then extracted with ethyl acetate (100 mL). The separated organic phase was dried over magnesium sulfate and concentrated under reduced pressure to afford {[(2R)-8-(2-chlorophenyl)-3,4-dihydro-2H-chromen-2-yl]methyl}amine as a yellow syrup. The product was dissolved in diethyl ether (1 mL) and a solution of hydrogen chloride (1.0 M in diethyl ether, 0.25 mL, 0.25 mmol) was added followed by 2-propanol (2 drops). The resulting white precipitate was filtered and the solid product triturated with diethyl ether (3×3 mL) to afford 36 mg (25%) of {[(2R)-8-(2-chlorophenyl)-3,4-dihydro-2H-chromen-2-yl]methyl}amine hydrochloride as a white solid.

HRMS: calcd for $C_{16}H_{16}ClNO+H^+$, 274.09932. found (ESI, $[M+H]^+$), 274.1016.

Example 12

{[(2R)-8-(2,5-dichlorophenyl)-3,4-dihydro-2H-chromen-2-yl]methyl}amine hydrochloride Prepared according to Example 11, replacing 2-chlorophenylboronic acid with 2,5-dichlorophenylboronic acid in step 1. HRMS: calcd for $C_{16}H_{15}Cl_2NO+H^+$, 308.06034. found (ESI, $[M+H]^+$), 308.0602.

Example 13

{[(2R)-8-(2,4-dichlorophenyl)-3,4-dihydro-2H-chromen-2-yl]methyl}amine hydrochloride Prepared according to Example 11, replacing 2-chlorophenylboronic acid with 2,4-dichlorophenylboronic acid in step 1. HRMS: calcd for $C_{16}H_{15}Cl_2NO+H^+$, 308.06034. found (ESI, $[M+H]^+$), 308.0616.

Example 14

{[(2R)-8-phenyl-3,4-dihydro-2H-chromen-2-yl]methyl}amine hydrochloride

Prepared according to Example 11, replacing 2-chlorophenylboronic acid with phenylboronic acid in step 1. HRMS: calcd for $C_{16}H_{17}NO+H^+$, 240.13829. found (ESI, [M+H]+), 240.1398.

Example 15

{[(2R)-8-(2-methoxyphenyl)-3,4-dihydro-2H-chromen-2-yl]methyl}amine hydrochloride Prepared according to Example 11, replacing 2-chlorophenylboronic acid with 2-methoxyphenylboronic acid in step 1. HRMS: calcd for $C_{17}H_{19}NO_2+H^+$, 270.14885. found (ESI, $[M+H]^+$), 270.1502.

Example 16

{[(2R)-8-(2,4-dimethoxyphenyl)-3,4-dihydro-2H-chromen-2-yl]methyl}amine hydrochloride Prepared according to Example 11, replacing 2-chlorophenylboronic acid with 2,4-dimethoxyphenylboronic acid in step 1. HRMS: calcd for $C_{18}H_{21}NO_3+H^+$, 300.15942. found (ESI, $[M+H]^+$), 300.1589.

Example 17

{[(2R)-8-(2-methylphenyl)-3,4-dihydro-2H-chromen-2-yl]methyl}amine hydrochloride Prepared according to Example 11, replacing 2-chlorophenylboronic acid with 2-methylphenylboronic acid in step 1. HRMS: calcd for $C_{17}H_{19}NO+H^+$, 254.15394. found (ESI, $[M+H]^+$), 254.1538.

Example 18

{[(2R)-8-pyridin-3-yl-3,4-dihydro-2H-chromen-2-yl]methyl}amine hydrochloride

Prepared according to Example 11, replacing 2-chlorophenylboronic acid with 3-pyridineboronic acid in step 1. HRMS: calcd for $C_{15}H_{16}N_2O+H^+$, 241.13354. found (ESI, $[M+H]^+$), 241.1329.

Example 19

{[(2S)-8-(2-chlorophenyl)-3,4-dihydro-2H-chromen-2-yl]methyl}methylamine hydrochloride Prepared according to Example 3, replacing ((2R)-8-{[(trifluoromethyl)sulfonyl]oxy}-3,4-dihydro-2H-chromen-2-yl)methyl4-methylbenzene sulfonate with ((2S)-8-{[(trifluoromethyl)sulfonyl]oxy}-3,4-dihydro-2H-chromen-2-yl)methyl 4-methylbenzenesulfonate and 2,5-dichlorophenylboronic acid with 2-chlorophenylboronic acid in step 2. HRMS: calcd for $C_{17}H_{18}ClNO+H^+$, 288.11497. found (ESI, $[M+H]^+$), 288.1161.

Example 20

{[(2S)-8-(2,5-dichlorophenyl)-3,4-dihydro-2H-chromen-2-yl]methyl}methylamine hydrochloride Prepared according to Example 3, replacing ((2R)-8-{[(trifluoromethyl)sulfonyl]oxy}-3,4-dihydro-2H-chromen-2-yl)methyl 4-methylbenzene sulfonate with ((2S)-8-{[(trifluoromethyl)sulfonyl]oxy}-3,4-dihydro-2H-chromen-2-yl (methyl 4-methylbenzenesulfonate in step 2. HRMS: calcd for $C_{17}H_{17}Cl_2NO+H^+$, 322.07599. found (ESI, $[M+H]^+$), 322.0782.

Example 21

{[(2S)-8-(2,4-dichlorophenyl)-3,4-dihydro-2H-chromen-2-yl]methyl}methylamine hydrochloride Prepared according to Example 3, replacing ((2R)-8-{[(trifluoromethyl)sulfonyl]oxy}-3,4-dihydro-2H-chromen-2-yl)methyl 4-methylbenzene sulfonate with ((2S)-8-{[(trifluoromethyl)sulfonyl]oxy}-3,4-dihydro-2H-chromen-2-yl) methyl 4-methylbenzenesulfonate and 2,5-dichlorophenylboronic acid with 2,4-dichlorophenylboronic acid in step 2. HRMS: calcd for $C_{17}H_{17}Cl_2NO+H^+$, 322.07599. found (ESI, $[M+H]^+$), 322.0775.

Example 22

N-methyl-1-[(2S)-8-phenyl-3,4-dihydro-2H-chromen-2-yl]methanamine hydrochloride Prepared according to Example 3, replacing ((2R)-8-{[(trifluoromethyl)sulfonyl]oxy}-3,4-dihydro-2H-chromen-2-yl)methyl 4-methylbenzenesulfonate with ((2S)-8-{[(trifluoromethyl)sulfonyl]oxy}-3,4-dihydro-2H-chromen-2-yl)methyl 4-methylbenzene sulfonate and 2,5-dichlorophenylboronic acid with phenylboronic acid in step 2. HRMS: calcd for $C_{17}H_{19}NO+H^+$, 254.15394. found (ESI, $[M+H]^+$), 254.1565.

Example 23

{[(2S)-8-(2-methoxyphenyl)-3,4-dihydro-2H-chromen-2-yl]methyl}methylamine hydrochloride Prepared according to Example 3, replacing ((2R)-8-{[(trifluoromethyl)sulfonyl]oxy}-3,4-dihydro-2H-chromen-2-yl)methyl 4-methylbenzene sulfonate with ((2S)-8-{[(trifluoromethyl)sulfonyl]oxy}-3,4-dihydro-2H-chromen-2-yl)methyl 4-methylbenzenesulfonate and 2,5-dichlorophenylboronic acid with 2-methoxyphenylboronic acid in step 2. HRMS: calcd for $C_{18}H_{21}NO_2+H^+$, 284.16450. found (ESI, $[M+H]^+$), 284.1635.

Example 24

{[(2S)-8-(2,4-dimethoxyphenyl)-3,4-dihydro-2H-chromen-2-yl]methyl}methylamine hydrochloride Prepared according to Example 3, replacing ((2R)-8-{[(trifluoromethyl)sulfonyl]oxy}-3,4-dihydro-2H-chromen-2-yl)methyl 4-methylbenzene sulfonate with ((2S)-8-{[(trifluoromethyl)sulfonyl]oxy}-3,4-dihydro-2H-chromen-2-yl)methyl 4-methylbenzenesulfonate and 2,5-dichlorophenylboronic acid with 2,4-dimethoxyphenylboronic acid in step 2. HRMS: calcd for $C_{19}H_{23}NO_3+H^+$, 314.17507. found (ESI, $[M+H]^+$), 314.1766.

Example 25

N-methyl-1-[(2S)-8-(2-methylphenyl)-3,4-dihydro-2H-chromen-2-yl]methanamine hydrochloride Prepared according to Example 3, replacing ((2R)-8-{[(trifluoromethyl)sulfonyl]oxy}-3,4-dihydro-2H-chromen-2-yl)methyl 4-methylbenzene sulfonate with ((2S)-8-{[(trifluoromethyl)sulfonyl]oxy}-3,4-dihydro-2H-chromen-2-yl)methyl 4-methylbenzenesulfonate and 2,5-dichlorophenylboronic acid with 2-methylphenylboronic acid in step 2. HRMS: calcd for $C_{18}H_{21}NO+H^+$, 268.16959. found (ESI, $[M+H]^+$), 268.1712.

Example 26

N-methyl-1-[(2S)-8-pyridin-3-yl-3,4-dihydro-2H-chromen-2-yl]methanamine hydrochloride Prepared according to Example 3, replacing ((2R)-8-{[(trifluoromethyl)sulfonyl]oxy}-3,4-dihydro-2H-chromen-2-yl)methyl 4-methylbenzene sulfonate with ((2S)-8-{[(trifluoromethyl)sulfonyl]oxy}-3,4-dihydro-2H-chromen-2-yl)methyl 4-methylbenzenesulfonate and 2,5-dichlorophenylboronic acid with 3-pyridineboronic acid in step 2. HRMS: calcd for $C_{16}H_{18}N_2O+H^+$, 255.14919. found (ESI, $[M+H]^+$), 255.1495.

Example 27

{[(2S)-8-(2-chlorophenyl)-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzenesulfonate with ((2S)-8-{[(trifluoromethyl)sulfonyl]oxy}-3,4-dihydro-2H-chromen-2-yl)methyl 4-methylbenzenesulfonate in step 1. HRMS: calcd for $C_{16}H_{16}ClNO+H^+$, 274.09932. found (ESI, $[M+H]^+$), 274.0986.

Example 28

{[(2S)-8-(2,5-dichlorophenyl)-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzenesulfonate with ((2S)-8-{[(trifluoromethyl)sulfonyl]oxy}-3,4-dihydro-2H-chromen-2-yl)methyl 4-methylbenzene sulfonate and 2-chlorophenylboronic acid with 2,5-dichlorophenylboronic acid in step 1. HRMS: calcd for $C_{16}H_{15}Cl_2NO+H^+$, 308.06034. found (ESI, $[M+H]^+$), 308.0623.

Example 29

{[(2S)-8-(2,4-dichlorophenyl)-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzene sulfonate with ((2S)-8-{[(trifluoromethyl)sulfonyl]oxy}-3,4-dihydro-2H-chromen-2-yl)methyl 4-methylbenzene sulfonate and 2-chlorophenylboronic acid with 2,4-dichlorophenylboronic acid in step 1. HRMS: calcd for $C_{16}H_{15}Cl_2NO+H^+$, 308.06034. found (ESI, $[M+H]^+$), 308.06.

Example 30

{[(2S)-8-phenyl-3,4-dihydro-2H-chromen-2-yl]methyl}amine hydrochloride

Prepared according to Example 11, replacing ((2R)-8-{[(trifluoromethyl)sulfonyl]oxy}-3,4-dihydro-2H-chromen-2-yl)methyl 4-methylbenzenesulfonate with ((2S)-8-{[(trifluoromethyl)sulfonyl]oxy}-3,4-dihydro-2H-chromen-2-yl)methyl 4-methylbenzene sulfonate and 2-chlorophenylboronic acid with phenylboronic acid in step 1. HRMS: calcd for $C_{16}H_{17}NO+H^+$, 240.13829. found (ESI, $[M+H]^+$), 240.1381.

Example 31

{[(2S)-8-(2-methoxyphenyl)-3,4-dihydro-2H-chromen-2-yl]methyl}amine hydrochloride:

Prepared according to Example 11, replacing ((2R)-8-{[(trifluoromethyl)sulfonyl]oxy}-3,4-dihydro-2H-chromen-2-yl)methyl 4-methylbenzene sulfonate with ((2S)-8-{[(trifluoromethyl)sulfonyl]oxy}-3,4-dihydro-2H-chromen-2-yl) methyl 4-methylbenzene sulfonate and 2-chlorophenylboronic acid with 2-methoxyphenylboronic acid in step 1. HRMS: calcd for $C_{17}H_{19}NO_2+H^+$, 270.14885. found (ESI, [M+H]$^+$), 270.1485.

Example 32

{[(2S)-8-(2,4-dimethoxyphenyl)-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzene sulfonate with ((2S)-8-{[(trifluoromethyl)sulfonyl]oxy}-3,4-dihydro-2H-chromen-2-yl) methyl 4-methylbenzenesulfonate and 2-chlorophenylboronic acid with 2,4-dimethoxyphenylboronic acid in step 1. HRMS: calcd for $C_{18}H_{21}NO_3+H^+$, 300.15942. found (ESI, [M+H]$^+$), 300.1585.

Example 33

{[(2S)-8-(2-methylphenyl)-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzenesulfonate with ((2S)-8-{[(trifluoromethyl)sulfonyl]oxy}-3,4-dihydro-2H-chromen-2-yl) methyl 4-methylbenzene sulfonate and 2-chlorophenylboronic acid with 2-methylphenylboronic acid in step 1. HRMS: calcd for $C_{17}H_{19}NO+H^+$, 254.15394. found (ESI, [M+H]$^+$), 254.155.

Example 34

{[(2S)-8-pyridin-3-yl-3,4-dihydro-2H-chromen-2-yl]methyl}amine hydrochloride

Prepared according to Example 11, replacing ((2R)-8-{[(trifluoromethyl)sulfonyl]oxy}-3,4-dihydro-2H-chromen-2-yl)methyl 4-methylbenzene sulfonate with ((2S)-8-{[(trifluoromethyl)sulfonyl]oxy}-3,4-dihydro-2H-chromen-2-yl) methyl 4-methylbenzenesulfonate and 2-chlorophenylboronic acid with 3-pyridineboronic acid in step 1. HRMS: calcd for $C_{15}H_{16}N_2O+H^+$, 241.13354. found (ESI, [M+H]$^+$), 241.1346.

Example 35

{[(2R)-8-(2,6-dichlorophenyl)-3,4-dihydro-2H-chromen-2-yl]methyl}methylamine hydrochloride Step 1: A mixture of 1-bromo-2,6-dichlorobenzene (5.0 g, 0.022 mol), 2-methoxyphenylboronic acid (5.045 g, 0.033 mol) and potassium carbonate (7.65 g, 0.055 mol) in dioxane (130 mL) and water (13 mL) was purged with nitrogen for 20 minutes. Trans-dichlorobis(tri-o-tolylphosphine)palladium (II) (0.87 g, 0.0011 mol) was added and the reaction mixture heated to 100° C. for 36 hours. The cooled reaction mixture was then filtered through celite washing the filter cake with ethyl acetate. The combined organic filtrates were diluted to 500 mL by the addition of ethyl acetate, then washed with 2.0 M aqueous sodium hydroxide (2×350 mL), water (350 mL) and saturated brine (350 mL), dried over magnesium sulfate, filtered and concentrated under reduced pressure to afford a yellow oil. Purification by flash chromatography using a solvent gradient of 0.5 to 2% ethyl acetate in hexane gave 2.74 g (49%) of 2',6'-dichloro-1,1'-biphenyl-2-yl methyl ether as a white solid. MS (EI) m/z 252 (M$^+$).

Step 2: To a solution of 2',6'-dichloro-1,1'-biphenyl-2-yl methyl ether (5.83 g, 0.023 mol) in anhydrous dichloromethane (100 mL) at 0° C. under nitrogen was added a solution of boron tribromide (1.0 M in dichloromethane, 27.6 mL, 0.0276 mol) dropwise over 40 minutes via a syringe pump. The reaction mixture was then stirred at room temperature for 17 hours, then quenched by the addition of absolute ethanol (50 mL). The mixture was stirred at room temperature for 1.5 hours then concentrated under reduced pressure to afford a dark oil. The oil was dissolved in 2.0 M aqueous sodium hydroxide solution (200 mL) and the resulting milky suspension extracted with diethyl ether (200 mL). The separated aqueous phase was then cooled to 0° C. and acidified to pH 1 by the addition of concentrated hydrochloric acid. The resulting milky suspension was extracted with ethyl acetate (300 mL), the separated organic phase washed with water (200 mL) and saturated brine (200 mL), dried over magnesium sulfate and concentrated under reduced pressure to afford a yellow oil. Purification by flash chromatography using a solvent gradient of 3 to 15% ethyl acetate in hexane gave 4.99 g (91%) of 2',6'-dichloro-1,1'-biphenyl-2-ol as a white solid. MS (EI) m/z 238 (M$^+$).

Step 3: To a solution of 2',6'-dichloro-1,1'-biphenyl-2-ol (5.4 g, 0.0226 mol) in acetone (100 mL) was added potassium carbonate (3.75 g, 0.0271 mol) followed by allyl bromide (2.58 mL, 0.0298 mol) and the reaction mixture heated to reflux for 24 hours. The cooled reaction mixture was poured into water (300 mL), the mixture stirred vigorously for 1 hour then extracted with ethyl acetate (300 mL). The separated organic extract was washed with water (200 mL) and saturated brine (200 mL), dried over magnesium sulfate and concentrated under reduced pressure to afford a yellow syrup. Purification by flash chromatography using a solvent gradient of 1 to 2% ethyl acetate in hexane gave 5.84 g (93%) of 2'-(allyloxy)-2,6-dichloro-1,1'-biphenyl as a colorless oil. MS (EI) m/z 278 (M$^+$).

Step 4: A solution of 2'-(allyloxy)-2,6-dichloro-1,1'-biphenyl (5.7 g, 0.0204 mol) in anhydrous 1-methyl-2-pyrrolidinone (50 mL) was heated to 180° C. for 42 hours then at 190° C. for 5 days. The cooled reaction mixture was poured into water (300 mL), the mixture stirred vigorously for 15 minutes then the resulting oily suspension extracted with ethyl acetate (400 mL). The organic extract was washed with water (300 mL) and saturated brine (300 mL), dried over magnesium sulfate and concentrated under reduced pressure to afford a brown oil. Purification by flash chromatography using a solvent gradient of 2 to 4% ethyl acetate in hexane gave 4.71 g (83%) of 3-allyl-2',6'-dichloro-1,1'-biphenyl-2-ol as a colorless oil. MS (ES) m/z 278.9 ([M+H]$^+$).

Step 5: A mixture of 3-allyl-2',6'-dichloro-1,1'-biphenyl-2-ol (2.922 g, 10.47 mmol) and bis(acetonitrile)dichloropalladium (II) (136 mg, 0.523 mmol) in anhydrous dichloromethane was heated to reflux under nitrogen for 1 hour. The cooled reaction mixture was then concentrated to a small volume under reduced pressure and directly preadsorbed onto silica gel. Purification by flash chromatography using a solvent gradient of 2 to 7.5% ethyl acetate in hexane gave 2.81 g (96%) of 2',6'-dichloro-3-[(1E)-prop-1-enyl]-1,1'-biphenyl-2-ol as a colorless syrup. HRMS: calcd for $C_{15}H_{12}Cl_2O$, 278.02652. found (EI, M+), 278.0262.

Step 6: To a solution of 2',6'-dichloro-3-[(1E)-prop-1-enyl]-1,1'-biphenyl-2-ol (1.35 g, 4.84 mmol), (S)-2-hydroxy-3-buten-1-yl p-tosylate (1.64 g, 6.77 mmol) and triphenylphosphine (1.78 g, 6.77 mmol) in anhydrous toluene (50 mL) was added dropwise diethylazodicarboxylate (1.07 mL, 6.77 mmol) and the reaction mixture stirred at room temperature for 19 hours. The reaction was quenched by the addition of water (40 mL) and the biphasic mixture stirred vigorously for 5 minutes. The mixture was then partitioned between diethyl ether (200 mL) and water (200 mL), the organic phase separated, washed with water (200 mL) and saturated brine (100 mL), dried over magnesium sulfate, filtered and concentrated under reduced pressure to afford a yellow syrup. Purification by flash chromatography using a solvent gradient of 2 to 10% ethyl acetate in hexane afforded 2.06 g (85%) of (2R)-2-({2',6'-dichloro-3-[(1E)-prop-1-enyl]-1,1'-biphenyl-2-yl}oxy)but-3-enyl 4-methylbenzenesulfonate as a colorless syrup. MS (ESI) m/z 520 ([M+NH$_4$]$^+$).

Step 7: To a solution of (2R)-2-({2',6'-dichloro-3-[(1E)-prop-1-enyl]-1,1'-biphenyl-2-yl}oxy)but-3-enyl 4-methylbenzenesulfonate (2.02 g, 4.01 mmol) in anhydrous dichloroethane (50 mL) at room temperature under nitrogen was added benzylidene-bis(tricyclohexylphosphine)dichlororuthenium (0.33 g, 0.401 mmol) and the reaction mixture stirred at room temperature for 20 hours and then heated to 50° C. for 45 hours. The cooled reaction mixture was concentrated to a small volume under reduced pressure and then directly pre-adsorbed onto silica gel. Purification by flash chromatography using a solvent gradient of 5 to 15% ethyl acetate in hexane afforded 1.52 g (82%) of [(2R)-8-(2,6-dichlorophenyl)-2H-chromen-2-yl]methyl 4-methylbenzenesulfonate as a brown foam. MS (ESI) m/z 478 ([M+NH$_4$]$^+$).

Step 8: A solution of [(2R)-8-(2,6-dichlorophenyl)-2H-chromen-2-yl]methyl 4-methylbenzenesulfonate (0.846 g, 1.83 mmol) in ethyl acetate (10 mL) was added to a suspension of platinum (IV) oxide (45 mg, 0.198 mmol) in absolute ethanol (30 mL) and the mixture hydrogenated at 10 psi of hydrogen for 100 minutes. The reaction mixture was then filtered through celite and the filtrate concentrated under reduced pressure to afford a brown syrup. Purification by flash chromatography using a solvent gradient of 5 to 20% ethyl acetate in hexane afforded 0.548 g (64%) of [(2R)-8-(2,6-dichlorophenyl)-3,4-dihydro-2H-chromen-2-yl]methyl 4-methylbenzenesulfonate as a yellow solid. HRMS: calcd for $C_{23}H_{20}Cl_2O_4S+H^+$, 463.0532 1. found (ESI, [M+H]$^+$), 463.0555.

Step 9: To a solution of [(2R)-8-(2,6-dichlorophenyl)-3,4-dihydro-2H-chromen-2-yl]methyl 4-methylbenzenesulfonate (239 mg, 0.54 mmol) in anhydrous dimethyl sulfoxide (1 mL) was added a solution of methylamine (2.0 M in tetrahydrofuran, 2.7 mL, 5.4 mmol) and the mixture heated to 60° C. in a sealed vial for 42 hours. The cooled reaction mixture was then poured into 1:1 v/v 2.0 M aqueous sodium hydroxide and saturated brine (50 mL) and the mixture extracted with ethyl acetate (50 mL). The separated organic phase was washed with 1:1 v/v 2.0 M aqueous sodium hydroxide and saturated brine (50 mL), and half saturated brine (50 mL), dried over magnesium sulfate, filtered and concentrated under reduced pressure to afford a yellow syrup. Purification by flash chromatography using a solvent gradient of 0.5 to 5% ammonia saturated methanol solution in dichloromethane gave 125 mg (75%) of {[(2R)-8-(2,6-dichlorophenyl)-3,4-dihydro-2H-chromen-2-yl]methyl}methylamine as a white solid. The product was dissolved in 2-propanol (1 mL) and diethyl ether (2.5 mL) and a solution of hydrogen chloride (1.0 M in diethyl ether, 0.39 mL, 0.39 mmol) was added followed by hexane (3 mL). The resulting white precipitate was filtered to afford 118 mg (64%) of {[(2R)-8-(2,6-dichlorophenyl)-3,4-dihydro-2H-chromen-2-yl]methyl}methylamine hydrochloride as a white crystalline solid. HRMS: calcd for $C_{17}H_{17}Cl_2NO+H^+$, 322.07599; found (ESI, [M+H]$^+$), 322.0757.

Example 36

{[(2R)-8-(2,6-dichlorophenyl)-3,4-dihydro-2H-chromen-2-yl]methyl}amine hydrochloride Step 1: A solution of [(2R)-8-(2,6-dichlorophenyl)-3,4-dihydro-2H-chromen-2-yl]methyl 4-methylbenzenesulfonate, prepared in Example 35, step 8 (308 mg, 0.664 mmol) and sodium azide (173 mg, 2.66 mmol) in anhydrous dimethyl sulfoxide (10 mL) was heated to 75° C. under nitrogen for 22 hours. The cooled reaction mixture was quenched by the addition of water (20 mL) and the resulting suspension stirred vigorously for 5 minutes. The mixture was then partitioned between ethyl acetate (100 mL) and water (100 mL), the organic phase separated, washed with water (100 mL) and saturated brine (100 mL), dried over magnesium sulfate, filtered and concentrated under reduced pressure to afford a cream solid. Purification by flash chromatography using a solvent gradient of 5% ethyl acetate in hexane gave 210 mg (95%) of {[(2R)-8-(2,6-dichlorolphenyl)-3,4-dihydro-2H-chromen-2-yl]methyl}azide as a white solid. MS (APPI) m/z 333.1 (M$^+$).

Step 2: To a solution of {[(2R)-8-(2,6-dichlorophenyl)-3,4-dihydro-2H-chromen-2-yl]methyl}azide (0.21 g, 0.628 mmol) in tetrahydrofuran (10 mL) and water (1 mL) was added polymer-bound triphenylphosphine (~3 mmol/g, 0.628 g, 1.885 mmol) and the reaction mixture stirred at room temperature for 4 days. The brown suspension was then filtered through celite, the filter cake washed with ethyl acetate (50 mL) and the combined filtrates concentrated under reduced pressure to afford a yellow syrup. Purification by flash chromatography using a solvent gradient of 0.5 to 5% ammonia saturated methanol solution in dichloromethane gave 159 mg (82%) of {[(2R)-8-(2,6-dichlorophenyl)-3,4-dihydro-2H-chromen-2-yl]methyl}amine as a colorless syrup. The product was dissolved in 2-propanol (1 mL) and diethyl ether (2.5 mL) and a solution of hydrogen chloride (1.0 M in diethyl ether, 0.517 mL, 0.517 mmol) was added followed by hexane (2 mL). The resulting white precipitate was filtered to afford 155 mg (72%) of {[(2R)-8-(2,6-dichlorophenyl)-3,4-dihydro-2H-chromen-2-yl]methyl}amine hydrochloride as a white crystalline solid, mp 188–190° C.; $[\alpha]_D^{25}$=–6.74° (c=5.4 mg/0.7 mL MeOH). HRMS: calcd for $C_{16}H_{15}Cl_2NO+H^+$, 308.06034. found (ESI, [M+H]$^+$), 308.0603.

Example 37

{[8-(2-chlorophenyl)-6-fluoro-3,4-dihydro-2H-chromen-2-yl]methyl}amine hydrochloride Step 1: To a mixture of 2-bromo-4-fluorophenol (9.75 g, 0.051 mol) and potassium carbonate (7.76 g, 0.056 mol) in acetone (125 mL) was added allyl bromide (4.64 mL, 0.054 mol) and the reaction mixture heated to reflux for 3.5 hours. The cooled reaction mixture was then poured into water and the resulting oily suspension extracted with dichloromethane (2×500 mL). The combined organic extracts were dried over magnesium sulfate, filtered and concentrated under reduced pressure to afford 11.79 g (100%) of 1-(allyloxy)-2-bromo-4-fluorobenzene as a yellow oil. MS (ESI) m/z 229.9 (M$^+$).

Step 2: A mixture of 1-(allyloxy)-2-bromo-4-fluorobenzene (3 g, 0.013 mol) and ethylene glycol (17 mL) was heated at 220° C. in a sealed vial under microwave irradiation for 20 minutes. The cooled reaction mixture was then poured into 2 M aqueous sodium hydroxide solution (150 mL) and the resulting milky suspension washed with diethyl ether (150 mL). The aqueous phase was then acidified to pH 1 by the addition of concentrated hydrochloric acid and the resulting oily suspension extracted with diethyl ether (150 mL). The organic extract was washed with water (2×100 mL) and saturated brine (100 mL), dried over magnesium sulfate, filtered and concentrated under reduced pressure to afford a yellow oil. Purification by flash chromatography using a solvent gradient of 0 to 1% ethyl acetate in hexane gave 2.07 g (69%) of 2-allyl-6-bromo-4-fluorophenol as a colorless oil. MS (ESI) m/z 229.0 ([M−H]⁻).

Step 3: To a solution of 2-allyl-6-bromo-4-fluorophenol (7.14 g, 0.0309 mol) in anhydrous dichloromethane (100 mL) at room temperature under nitrogen was added bis(acetonitrile)dichloropalladium (II) (0.4 g, 1.54 mmol) and the reaction mixture heated to reflux for 1 hour. Additional bis(acetonitrile)dichloropalladium (II) (0.1 g, 0.39 mmol) was added and heating to reflux continued for 1 additional hour. The cooled reaction mixture was then concentrated under reduced pressure to afford a brown semi-solid. Purification by flash chromatography using a solvent gradient of 0 to 2% ethyl acetate in hexane gave 6.44 g (90%) of 2-bromo-4-fluoro-6-[(1E)-prop-1-enyl]phenol as a white solid. MS (ESI) m/z 229 ([M−H]⁻).

Step 4: To a solution of 2-bromo-4-fluoro-6-[(1E)-prop-1-enyl]phenol (6.37 g, 0.0276 mol), toluene-4-sulfonic acid 2-hydroxy-but-3-enyl ester (8.8 g, 0.0363 mol) and triphenylphosphine (10.12 g, 0.0386 mol) in anhydrous toluene (200 mL) at 0° C. under nitrogen was added a solution of diethyl azodicarboxylate (6.72 g, 0.0386 mol) in anhydrous toluene (100 mL) over 10 minutes then the reaction mixture stirred at room temperature for 19 hours. The reaction was quenched by the addition of water (400 mL), stirred vigorously for 5 minutes and the resulting oily suspension extracted with diethyl ether (300 mL). The organic phase was separated, washed with water (2×500 mL), and saturated brine (400 mL), dried over magnesium sulfate, filtered and concentrated under reduced pressure to afford a yellow oil. Purification by flash chromatography using a solvent gradient of 2 to 10% ethyl acetate in hexane gave 12.11 g (96%) of 2-{2-bromo-4-fluoro-6-[(1E)-prop-1-enyl]phenoxy}but-3-enyl 4-methylbenzenesulfonate as a colorless oil. HRMS: calcd for $C_{20}H_{20}BrFO_4S+NH_4^+$, 472.05879. found (ESI, [M+NH$_4$]⁺), 472.0581.

Step 5: To a solution of 2-{2-bromo-4-fluoro-6-[(1E)-prop-1-enyl]phenoxy}but-3-enyl 4-methylbenzenesulfonate (10.95 g, 0.024 mol) in dry dichloromethane (300 mL) at room temperature under nitrogen was added benzylidenebis(tricyclohexylphosphine)dichlororuthenium (1.97 g, 2.4 mmol) and the reaction mixture stirred at room temperature for 5 days. The reaction mixture was then concentrated under reduced pressure to a small volume and directly pre-adsorbed onto silica gel. Purification by flash chromatography using a solvent gradient of 5 to 30% ethyl acetate in hexane gave 9.5 g (96%) of (8-bromo-6-fluoro-2H-chromen-2-yl)methyl 4-methylbenzenesulfonate as a grey solid.

HRMS: calcd for $C_{17}H_{14}BrFO_4S+NH_4^+$, 430.01184. found (ESI, [M+NH$_4$]⁺), 430.0116.

Step 6: A solution of (8-bromo-6-fluoro-2H-chromen-2-yl)methyl 4-methylbenzenesulfonate (300 mg, 0.73 mmol) in absolute ethanol was added to 5% sulfided platinum on carbon (50 mg) and the mixture hydrogenated at 55 psi of hydrogen for 1 hour. The mixture was then filtered through celite and the filtrate concentrated under reduced pressure to afford a white semi-solid. Purification by flash chromatography using a solvent gradient of 5 to 25% ethyl acetate in hexane gave 148 mg (49%) of (8-bromo-6-fluoro-3,4-dihydro-2H-chromen-2-yl)methyl 4-methylbenzenesulfonate as a white solid.

HRMS: calcd for $C_{17}H_{16}BrFO_4S+H^+$, 415.00095. found (ESI, [M+H]⁺), 415.0004.

Step 7: To a solution of (8-bromo-6-fluoro-3,4-dihydro-2H-chromen-2-yl)methyl 4-methylbenzenesulfonate (0.33 g, 0.795 mmol) and 2-chlorophenylboronic acid (249 mg, 1.589 mmol) in dioxane (9 mL) was added a solution of potassium carbonate (329 mg, 2.38 mmol) in water (3 mL) and the mixture purged with nitrogen for 20 minutes. Trans-dichlorobis(tri-o-tolylphosphine)palladium (II) (31.2 mg, 0.0397 mmol) was added and the reaction mixture heated to reflux for 18 hours. The cooled reaction mixture was then partitioned between ethyl acetate (100 mL) and 2.0 M aqueous sodium hydroxide (100 mL). The organic layer was separated, washed with water (100 mL) and saturated brine (100 mL), dried over magnesium sulfate, filtered and concentrated under reduced pressure to afford a yellow syrup. Purification by flash chromatography using a solvent gradient of 5 to 20% ethyl acetate in hexane gave 253 mg (71%) of toluene-4-sulfonic acid 8-(2-chloro-phenyl)-6-fluoro-chroman-2-ylmethyl ester as a colorless syrup. MS (ESI) m/z 464 ([M+NH$_4$]⁺).

Step 8: A solution of toluene-4-sulfonic acid 8-(2-chlorophenyl)-6-fluoro-chroman-2-ylmethyl ester (253 mg, 0.566 mmol) and sodium azide (147 mg, 2.264 mmol) in anhydrous dimethyl sulfoxide (8 mL) was heated to 70° C. under nitrogen for 20 hours. The cooled reaction mixture was quenched by the addition of water (30 mL) and the resulting suspension stirred vigorously for 10 minutes. The mixture was then partitioned between ethyl acetate (100 mL) and water (100 mL), the organic phase separated, washed with water (100 mL) and saturated brine (100 mL), dried over magnesium sulfate, filtered and concentrated under reduced pressure to afford 170 mg (95%) of 2-azidomethyl-8-(2-chloro-phenyl)-6-fluoro-chroman a colorless syrup.

Step 9: To a solution of 2-azidomethyl-8-(2-chloro-phenyl)-6-fluoro-chroman (170 mg, 0.535 mmol) in tetrahydrofuran (5 mL) and water (0.5 mL) was added polymer-bound triphenylphosphine (~3 mmol/g, 0.535 g, 1.605 mmol) and the reaction mixture stirred at room temperature for 24 hours. The brown suspension was then filtered through celite, the filter cake washed with ethyl acetate (50 mL) and the combined filtrates concentrated under reduced pressure to afford a yellow syrup. The product was dissolved in 2-propanol (1 mL) and diethyl ether (2 mL) and a solution of hydrogen chloride (1.0 M in diethyl ether, 0.51 mL, 0.51 mmol) added followed hexane (4 mL). The resulting white precipitate was filtered to afford 118 mg (67%) of {[8-(2-chlorophenyl)-6-fluoro-3,4-dihydro-2H-chromen-2-yl]methyl}amine hydrochloride as a white solid. HRMS: calcd for $C_{16}H_{15}ClFNO+H^+$, 292.08990. found (ESI, [M+H]⁺), 292.0903.

Example 38

1-[(2R)-6-fluoro-8-(2-methoxyphenyl)-3,4-dihydro-2H-chromen-2-yl]methanamine hydrochloride Step 1: To a solution of 2-bromo-4-fluoro-6-(prop-1-enyl)phenol, prepared in Example 37, step 4 (4.5 g, 0.019 mol)

and (S)-toluene-4-sulfonic acid 2-hydroxy-but-3-enyl ester (7.07 g, 0.028 mol) and triphenylphosphine (11.22 g, 0.043 mol) in anhydrous THF (200 mL) at room temperature was added diethyl azodicarboxylate (7.7 mL, 0.047 mol) then the reaction mixture stirred at room temperature for 19 hours. The reaction was quenched by the addition of water (100 mL), stirred vigorously for 5 minutes and the resulting oily suspension extracted with methylene chloride (300 mL). The organic phase was separated, washed with water (2×100 mL), and saturated brine (100 mL), dried over anhydrous sodium sulfate, filtered and concentrated under reduced pressure to afford a yellow oil. Purification by flash chromatography using a solvent gradient of 0 to 20% ethyl acetate in hexane gave 7.26 g (82%) of (R)-2-[2-bromo-4-fluoro-6-(prop-1-enyl)phenoxy]but-3-enyl 4-methylbenzenesulfonate as a colorless oil. MS (ES) m/z 472.1 ([M+NH$_4$]$^+$).

Step 2: To a solution of (R)-2-[2-bromo-4-fluoro-6-(prop-1-enyl)phenoxy]but-3-enyl 4-methylbenzenesulfonate (7.26 g, 0.016 mol) in dry dichloromethane (300 mL) at room temperature under nitrogen was added benzylidene-bis(tricyclohexylphosphine)-dichlororuthenium (2.6 g, 3.2 mmol) and the reaction mixture stirred at room temperature for 18 hours. The reaction mixture was then concentrated under reduced pressure to a small volume and directly pre-adsorbed onto silica gel. Purification by flash chromatography using a solvent gradient of 5 to 30% ethyl acetate in hexane gave 6.7 g (100%) of (R)-(8-bromo-6-fluoro-2H-chromen-2-yl)methyl-4-methylbenzenesulfonate as a grey solid. $[\alpha]_D^{25}$=+206.6° (c 1% solution in MeOH); MS (ES) m/z 430.0 ([M+NH$_4$]$^+$).

Step 3: To a solution of (R)-(8-bromo-6-fluoro-2H-chromen-2-yl)methyl-4-methylbenzenesulfonate (0.40 g, 0.97 mmol) and 2-methoxyphenylboronic acid (0.44 g, 2.9 mmol) in dioxane (10 mL) was added potassium carbonate (0.33 g, 2.4 mmol), dichlorobis(tri-o-tolylphosphine)palladium (II) (23 mg, 0.029 mmol) and water (2 mL). The reaction mixture was heated to reflux for 2 hours. The cooled reaction mixture was then partitioned between ethyl acetate (100 mL) and 2.0 M aqueous sodium hydroxide (100 mL). The organic layer was separated, washed with water (100 mL) and saturated brine (100 mL), dried over anhydrous sodium sulfate, filtered and concentrated under reduced pressure. Purification by flash chromatography using a solvent gradient of 0 to 20% ethyl acetate in hexane gave 0.46 g (100%) of(R)-6-fluoro-8-(2-methoxyphenyl)-2H-chromen-2-yl)methyl 4-methylbenzenesulfonate as a colorless oil. MS (ES) m/z 441.0 ([M+H]$^+$).

Step 4: A solution of (R)-6-fluoro-8-(2-methoxyphenyl)-2H-chromen-2-yl)methyl 4-methylbenzenesulfonate (0.46 g, 1.04 mmol) in absolute ethanol was added to platinum (IV) oxide (50 mg) and the mixture hydrogenated at 45 psi of hydrogen for 18 hour. The mixture was then filtered through celite and the filtrate concentrated under reduced pressure to afford a white semi-solid. Purification by flash chromatography using a solvent gradient of 5 to 25% ethyl acetate in hexane gave 0.40 g (86%) of (R)-6-fluoro-8-(2-methoxyphenyl)chroman-2-yl)methyl 4-methylbenzenesulfonate as a colorless oil. MS (APPI) m/z 443 ([M+H]$^+$).

Step 5: A solution of (R)-6-fluoro-8-(2-methoxyphenyl) chroman-2-yl)methyl 4-methylbenzenesulfonate (400 mg, 0.90 mmol) and sodium azide (290 mg, 4.5 mmol) in anhydrous DMF (20 mL) was heated to 70° C. under nitrogen for 20 hours. The cooled reaction mixture was quenched by the addition of water (30 mL) and the resulting suspension stirred vigorously for 10 minutes. The mixture was then partitioned between ethyl acetate (100 mL) and water (100 mL), the organic phase separated, washed with water (100 mL) and saturated brine (100 mL), dried over anhydrous sodium sulfate, filtered and concentrated under reduced pressure. Chromatography with 0–20% ethyl acetate in hexanes afforded 0.21 g (74%) of (R)-2-(azidomethyl)-6-fluoro-8-(2-methoxyphenyl)-chroman as a colorless oil.

MS (APPI) m/z 313 ([M+H]$^+$).

Step 6: To a solution of (R)-2-(azidomethyl)-6-fluoro-8-(2-methoxyphenyl)-chroman (210 mg, 0.67 mmol) in tetrahydrofuran (15 mL) and water (0.5 mL) was added triphenylphosphine (0.21 g, 0.80 mmol) and the reaction mixture stirred at room temperature for 24 hours. Chromatography with 0–10% methanol in ethyl methylene chloride plus 1% NH$_4$OH afforded [(R)-6-fluoro-8-(2-methoxyphenyl)-3,4-dihydro-2H-chromen-2-yl]methanamine as a colorless oil. The oil was dissolved in ethyl acetate and made into its hydrochloride salt (0.95 g, 69%) as a white solid using excess ethereal hydrochloric acid, mp 100° C. decomposed; MS (ES) m/z 288.1 ([M+H]$^+$); $[\alpha]_D^{25}$=−34.64° (c=5.7 mg/0.7 mL MeOH).

Elemental analysis for $C_{17}H_{18}FNO_2 \cdot HCl \cdot 0.3\ H_2O$: Theory: C, 62.03; H, 6.00; N, 4.25. Found: C, 62.24; H, 6.47; N, 4.01.

Example 39

{[(2R)-8-(2-chlorophenyl)-6-fluoro-3,4-dihydro-2H-chromen-2-yl]methyl}methylamine hydrochloride Step 1: Racemic (8-bromo-6-fluoro-3,4-dihydro-2H-chromen-2-yl)methyl 4-methylbenzenesulfonate, prepared in Example 37, step 6 was dissolved in acetonitrile and the resulting solution injected onto a Supercritical Fluid Chromatography instrument. The baseline resolved enantiomers were collected using the conditions described below.

Column: OJ-H (4.6×250 mm) Mobile Phase: 20% ethanol/80% CO$_2$ Column Temperature: 35° C. Flow Rate: 2 mL/minute Wavelength: 222 nm

[(2R)-8-bromo-6-fluoro-3,4-dihydro-2H-chromen-2-yl] methyl 4-methylbenzenesulfonate (98.2% enantiomeric excess) was isolated as peak 1.

MS (ESI) m/z 415 ([M+H]$^+$).

[(2S)-8-bromo-6-fluoro-3,4-dihydro-2H-chromen-2-yl] methyl 4-methylbenzenesulfonate (98.6% enantiomeric excess) was isolated as peak 2.

$[\alpha]_D^{25}$=+25° (c=0.0107 g/mL, DMSO); MS (ESI) m/z 415 ([M+H]$^+$).

Step 2: {[(2R)-8-(2-chlorophenyl)-6-fluoro-3,4-dihydro-2H-chromen-2-yl]methyl}methylamine hydrochloride was prepared according to Example 3, replacing ((2R)-8-{[(trifluoromethyl)sulfonyl]oxy}-3,4-dihydro-2H-chromen-2-yl) methyl 4-methylbenzene sulfonate with [(2R)-8-bromo-6-fluoro-3,4-dihydro-2H-chromen-2-yl]methyl 4-methylbenzenesulfonate and 2,5-dichlorophenylboronic acid with 2-chlorophenylboronic acid in step 2. MS (ESI) m/z 306 ([M+H]$^+$).

Example 40

{[(2R)-8-(2,5-dichlorophenyl)-6-fluoro-3,4-dihydro-2H-chromen-2-yl]methyl}methylamine hydrochloride Prepared according to Example 3, replacing ((2R)-8-{[(trifluoromethyl)sulfonyl]oxy}-3,4-dihydro-2H-chromen-2-yl)methyl 4-methylbenzenesulfonate with [(2R)-8-bromo- 6-fluoro-3,4-dihydro-2H-chromen-2-yl]methyl 4-methylbenzenesulfonate in step 2. MS (ESI) m/z 340 ([M+H]+).

Example 41

{[(2R)-8-(2,4-dichlorophenyl)-6-fluoro-3,4-dihydro-2H-chromen-2-yl]methyl}methylamine hydrochloride Prepared according to Example 3, replacing ((2R)-8-{[(trifluoromethyl)sulfonyl]oxy}-3,4-dihydro-2H-chromen-2-yl)methyl 4-methylbenzenesulfonate with [(2R)-8-bromo-6-fluoro-3,4-dihydro-2H-chromen-2-yl]methyl 4-methylbenzenesulfonate and 2,5-dichlorophenylboronic acid with 2,4-dichlorophenylboronic acid in step 2. MS (ESI) m/z 340 ([M+H]+).

Example 42

{[(2R)-6-fluoro-8-phenyl-3,4-dihydro-2H-chromen-2-yl]methyl}methylamine hydrochloride Prepared according to Example 3, replacing ((2R)-8-{[(trifluoromethyl)sulfonyl]oxy}-3,4-dihydro-2H-chromen-2-yl)methyl 4-methylbenzene sulfonate with [(2R)-8-bromo-6-fluoro-3,4-dihydro-2H-chromen-2-yl]methyl 4-methylbenzenesulfonate and 2,5-dichlorophenylboronic acid with phenylboronic acid in step 2. MS (ESI) m/z 272 ([M+H]+).

Example 43

{[(2R)-6-fluoro-8-(2-methylphenyl)-3,4-dihydro-2H-chromen-2-yl]methyl}methylamine hydrochloride Prepared according to Example 3, replacing ((2R)-8-{[(trifluoromethyl)sulfonyl]oxy}-3,4-dihydro-2H-chromen-2-yl)methyl 4-methylbenzene sulfonate with [(2R)-8-bromo-6-fluoro-3,4-dihydro-2H-chromen-2-yl]methyl 4-methylbenzenesulfonate and 2,5-dichlorophenylboronic acid with 2-methylphenylboronic acid in step 2. MS (ESI) m/z 286 ([M+H]+).

Example 44

{[(2R)-6-fluoro-8-pyridin-3-yl-3,4-dihydro-2H-chromen-2-yl]methyl}methylamine hydrochloride Prepared according to Example 3, replacing ((2R)-8-{[(trifluoromethyl)sulfonyl]oxy}-3,4-dihydro-2H-chromen-2-yl)methyl 4-methylbenzene sulfonate with [(2R)-8-bromo-6-fluoro-3,4-dihydro-2H-chromen-2-yl]methyl 4-methylbenzenesulfonate and 2,5-dichlorophenylboronic acid with 3-pyridineboronic acid in step 2. MS (ESI) m/z 273 ([M+H]+).

Example 45

{[(2R)-8-(2-chlorophenyl)-6-fluoro-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzene sulfonate with [(2R)-8-bromo-6-fluoro-3,4-dihydro-2H-chromen-2-yl]methyl 4-methylbenzenesulfonate in step 1. MS (ESI) m/z 292 ([M+H]+).

Example 46

{[(2R)-8-(2,5-dichlorophenyl)-6-fluoro-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzene sulfonate with [(2R)-8-bromo-6-fluoro-3,4-dihydro-2H-chromen-2-yl]methyl 4-methylbenzenesulfonate and 2-chlorophenylboronic acid with 2,5-dichlorophenylboronic acid in step 1. MS (ESI) m/z 326 ([M+H]+).

Example 47

{[(2R)-8-(2,4-dichlorophenyl)-6-fluoro-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzene sulfonate with [(2R)-8-bromo-6-fluoro-3,4-dihydro-2H-chromen-2-yl]methyl 4-methylbenzenesulfonate and 2-chlorophenylboronic acid with 2,4-dichlorophenylboronic acid in step 1. MS (ESI) m/z 326 ([M+H]+).

Example 48

{[(2R)-6-fluoro-8-phenyl-3,4-dihydro-2H-chromen-2-yl]methyl}amine hydrochloride

Prepared according to Example 11, replacing ((2R)-8-{[(trifluoromethyl)sulfonyl]oxy}-3,4-dihydro-2H-chromen-2-yl)methyl 4-methylbenzenesulfonate with [(2R)-8-bromo-6-fluoro-3,4-dihydro-2H-chromen-2-yl]methyl 4-methylbenzenesulfonate and 2-chlorophenylboronic acid with phenylboronic acid in step 1.

MS (ESI) m/z 258 ([M+H]+).

Example 49

{[(2R)-6-fluoro-8-(2-methylphenyl)-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzene sulfonate with [(2R)-8-bromo-6-fluoro-3,4-dihydro-2H-chromen-2-yl]methyl 4-methylbenzenesulfonate and 2-chlorophenylboronic acid with 2-methylphenylboronic acid in step 1. MS (ESI) m/z 272 ([M+H]+).

Example 50

{[(2R)-6-fluoro-8-pyridin-3-yl-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzenesulfonate with [(2R)-8-bromo-6-fluoro-3,4-dihydro-2H-chromen-2-yl]methyl 4-methylbenzenesulfonate and 2-chlorophenylboronic acid with 3-pyridineboronic acid in step 1.

MS (ESI) m/z 259 ([M+H]+).

Example 51

{[(2S)-8-(2-chlorophenyl)-6-fluoro-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzene sulfonate with [(2S)-8-bromo-6-fluoro-3,4-dihydro-2H-chromen-2-yl]methyl 4-methylbenzenesulfonate in step 1. MS (ESI) m/z 292 ([M+H]$^+$).

Example 52

{[(2S)-6-fluoro-8-phenyl-3,4-dihydro-2H-chromen-2-yl]methyl}amine hydrochloride

Prepared according to Example 11, replacing ((2R)-8-{[(trifluoromethyl)sulfonyl]oxy}-3,4-dihydro-2H-chromen-2-yl)methyl 4-methylbenzenesulfonate with [(2S)-8-bromo-6-fluoro-3,4-dihydro-2H-chromen-2-yl]methyl 4-methylbenzenesulfonate and 2-chlorophenylboronic acid with phenylboronic acid in step 1.

MS (ES) m/z 258.1 ([M+H]$^+$).

Example 53

{[(2S)-6-fluoro-8-(2-methylphenyl)-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzene sulfonate with [(2S)-8-bromo-6-fluoro-3,4-dihydro-2H-chromen-2-yl]methyl 4-methylbenzenesulfonate and 2-chlorophenylboronic acid with 2-methylphenylboronic acid in step 1. MS (ES) m/z 272.1 ([M+H]$^+$).

Example 54

{[(2S)-6-fluoro-8-pyridin-3-yl-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzenesulfonate with [(2S)-8-bromo-6-fluoro-3,4-dihydro-2H-chromen-2-yl]methyl 4-methylbenzenesulfonate and 2-chlorophenylboronic acid with 3-pyridineboronic acid in step 1.

MS (ESI) m/z 259 ([M+H]$^+$).

Example 55

{[(2S)-8-(2,5-dichlorophenyl)-6-fluoro-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzene sulfonate with [(2S)-8-bromo-6-fluoro-3,4-dihydro-2H-chromen-2-yl]methyl 4-methylbenzenesulfonate and 2-chlorophenylboronic acid with 2,5-dichlorophenylboronic acid in step 1. MS (ES) m/z 326.0 ([M+H]$^+$).

Example 56

{[(2S)-8-(2,4-dichlorophenyl)-6-fluoro-3,4-dihydro-2H-chromen-2-yl]methyl}amine hydrochloride Prepared according to Example 11, replacing ((2R)-8-{[(trifluoromethyl)sulfonyl]oxy}-3,4-dihydro-2H-chromen-2-yl)methyl 4-methylbenzene sulfonate with [(2S)-8-bromo-6-fluoro-3,4-dihydro-2H-chromen-2-yl]methyl 4-methylbenzenesulfonate and 2-chlorophenylboronic acid with 2,4-dichlorophenylboronic acid in step 1. MS (ES) m/z 326.1 ([M+H]$^+$).

Example 57

{[(2R)-8-(2,6-dichlorophenyl)-6-fluoro-3,4-dihydro-2H-chromen-2-yl]methyl}amine hydrochloride Step 1: To a solution of 2,6-dichlorobromobenzene (3.5 g, 15.7 mmol) and sodium hydroxide (3.14 g, 78.5 mmol) in DME-water (2:1) was added 5-fluoro-2-methoxybenzene boronic acid (4.0 g, 23.5 mmol) at 90° C., followed by tetrakis(triphenylphosphine)palladium (0) (0.9 g, 0.78 mmol). The reaction mixture was heated at 90° C. overnight and cooled to room temperature. The mixture was extracted with methylene chloride and washed with water. The organic solvent was removed under vacuum. Chromatography with 5% ethyl acetate in hexanes afforded 2.62 g (87%) of 2',6'-dichloro-5-fluoro-2-methoxybiphenyl as a colorless oil. MS (EI) m/z 270 (M$^+$).

Step 2: To a solution of 2',6'-dichloro-5-fluoro-2-methoxybiphenyl (12.44 g, 46 mmol) in methylene chloride (200 mL) was added boron tribromide (10.8 mL, 92 mol) at −78° C. The resulting mixture was stirred at −78° C. to room temperature overnight. The reaction mixture was poured into the ice-NH$_4$OH and extracted with methylene chloride. The organic layer was washed with water and dried over anhydrous sodium sulfate and filtered. The solvent was removed under vacuum. Chromatography with 10–40% ethyl acetate in hexanes afforded 11.63 g (98%) of 2',6'-dichloro-5-fluorobiphenyl-2-ol as a colorless oil. MS (ES) m/z 255.1([M−H]$^-$).

Step 3: To a solution of 2',6'-dichloro-5-fluorobiphenyl-2-ol (11.63 g, 45 mmol) in DMF (150 mL) was added allyl bromide (5.8 mL, 67.5 mmol) and potassium carbonate (18.6 g, 135 mmol) at room temperature. The resulting mixture was stirred at room temperature overnight and poured into water. The mixture was extracted with methylene chloride and washed with water. The solvent was removed under vacuum. Chromatography with 0–30% ethyl acetate in hexanes afforded 12.7 g (94%) of 2-allyloxy-2',6'-dichloro-5-fluorobiphenyl as a light yellow oil. MS (EI) m/z 296 (M$^+$).

Step 4: A solution of 2-allyloxy-2',6'-dichloro-5-fluorobiphenyl (11.02 g, 37 mmol) in decahydronaphthalene (100 mL) was refluxed for 38 h. The solvent was removed under vacuum. Chromatography with 0–20% ethyl acetate in hexanes afforded 9.26 g (84%) of 3-ally-2',6'-dichloro-5-fluorobiphenyl-2-ol as a light yellow oil. MS (ES) m/z 295.0 ([M−H]$^-$).

Step 5: A solution of 3-allyl-',6'-dichloro-5-fluorobiphenyl-2-ol (6.0 g, 20 mmol) and bis(acetonitrile)dichloropalladium (II) (0.53 g, 2.1 mmol) in methylene chloride was refluxed for 24 h. The solvent was removed under vacuum. Chromatography with 0–30% ethyl acetate in hexanes afforded 3.0 g (50%) of 2',6'-dichloro-5-fluoro-3-(prop-1-enyl)-biphenyl-2-ol as a colorless oil. MS (ES) m/z 295.0 ([M−H]⁻).

Step 6: To a solution of 2',6'-dichloro-5-fluoro-3-(prop-1-enyl)-biphenyl-2-ol (2.98 g, 10.0 mmol), (S)-2-hydroxy-3-buten-1-yl p-tosylate (3.64 g, 15.0 mmol) and triphenylphosphine (5.3 g, 20.0 mmol) in anhydrous tetrahydrofuran (50 mL) was added dropwise diethylazodicarboxylate (4.0 mL, 25.0 mmol) and the reaction mixture stirred at room temperature for 16 hours. The mixture was extracted with methylene chloride and washed with water. The solvent was removed under vacuum. Chromatography with 0–30% ethyl acetate in hexanes afforded 3.0 g (57%) of (R)-2-(2',6'-dichloro-5-fluoro-3-(Rrop-1-enyl)biphenyl-2-yloxy)but-3-enyl 4-methyl benzenesulfonate as a light yellow oil. $[\alpha]_D^{25}=-4°$ (0.9% solution in MeOH); MS (ES) m/z 538.1 (M+NH$_4^+$]⁺).

Step 7: To a solution of (R)-2-(2',6'-dichloro-5-fluoro-3-(prop-1-enyl)biphenyl-2-yloxy)but-3-enyl 4-methyl benzenesulfonate (3.0 g, 5.7 mmol) in anhydrous methylene chloride (50 mL) at room temperature under nitrogen was added benzylidene-bis(tricyclohexylphosphine)-dichlororuthenium (0.94 g, 1.14 mmol) and the reaction mixture stirred at room temperature overnight. The cooled reaction mixture was concentrated to a small volume under reduced pressure. Chromatography with 0–15% ethyl acetate in hexanes afforded 1.80 g (65%) of [(R)-(8-(2,6-dichlorophenyl)-6-fluoro-2H-chromen-2-yl]methyl 4-methylbenzenesulfonate as a brown foam. $[\alpha]_2^D=+185.2°$ (c 1% solution in MeOH); MS (ESI) m/z 496.0 ([M+NH$_4$]⁺).

Step 8: A solution of [(R)-(8-(2,6-dichlorophenyl)-6-fluoro-2H-chromen-2-yl]methyl 4-methylbenzenesulfonate (0.6 g, 1.25 mmol) in ethyl acetate/ethanol (10/10 mL) was added platinum(IV) oxide (45 mg, 0.198 mmol) and the mixture hydrogenated at 45 psi of hydrogen for 2 hours. The reaction mixture was then filtered through celite and the filtrate concentrated under reduced pressure. Chromatography with 0–15% ethyl acetate in hexanes afforded 0.48 g (80%) of [(R)-8-(2,6-dichlorophenyl)-6-fluorochroman-2-yl]methyl 4-methylbenzenesulfonate as a colorless oil. $[\alpha]_{25}^D=+9.51°$ (c 5.3 mg/0.7 mL MeOH); MS (ES) m/z 498.0 ([M+NH$_4$]⁺).

Step 9: A solution of (R)-8-(2,6-dichlorophenyl)-6-fluorochroman-2-yl]methyl 4-methylbenzenesulfonate (460 mg, 0.96 mmol) and sodium azide (0.31 g, 4.8 mmol) in anhydrous DMF (20 mL) was heated to 90° C. under nitrogen overnight. The cooled reaction mixture was quenched by the addition of water (20 mL). The mixture was then partitioned between ethyl acetate (100 mL) and water (100 mL), the organic phase separated, washed with water (100 mL) and saturated brine (100 mL), dried over anhydrous sodium sulfate, filtered and concentrated under reduced pressure to afford a cream solid. Chromatography with 0–15% ethyl acetate in hexanes gave 270 mg (83%) of (R)-2-(azidomethyl)-8-(2,6-dichlorophenyl)-6-fluorochroman as a light yellow oil. $[\alpha]_D^{25}=+19.82°$ (c 5.3 mg/0.7 mL MeOH); MS (EI) m/z 351 (M⁺).

Step 10: To a solution of (R)-2-(azidomethyl)-8-(2,6-dichlorophenyl)-6-fluorochroman (0.26 g, 0.73 mmol) in tetrahydrofuran (10 mL) and water (1 mL) was added polymer-bound triphenylphosphine (~3 mmol/g, 0.74 g, 2.2 mmol) and the reaction mixture stirred at room temperature for 2 days. The brown suspension was then filtered through celite, the filter cake washed with ethyl acetate (50 mL) and the combined filtrates concentrated under vacuum. The solvent was removed under vacuum. Chromatography with 0–10% methanol in methylene chloride plus 1% NH$_4$OH afforded {[(R)-8-(2,6-dichlorophenyl)-6-fluoro-3,4-dihydro-2H-chromen-2-yl]methyl}amine as a colorless oil. The colorless oil was dissolved in ethyl acetate and made into its hydrochloride salt (0.18 g, 67%) as a white crystalline solid using excess ethereal hydrochloric acid, mp 190–192° C.; MS (ES) m/z 326.0 ([M+H]⁺); $[\alpha]_D^{25}=-4.39°$ (c 1% solution in MeOH).

Elemental Analysis for C$_{16}$H$_{14}$Cl$_2$NFO.HCl: Theory: C, 52.99; H, 4.17; N, 3.86. Found: C, 52.99; H, 3.72; N, 3.75

Example 58

N-{[(2R)-8-(2,6-dichlorophenyl)-6-fluoro-3,4-dihydro-2H-chromen-2-yl]methyl}ethanamine hydrochloride Step 1: A solution of (R)-8-(2,6-dichlorophenyl)-6-fluorochroman-2-yl]methyl 4-methylbenzenesulfonate, prepared in Example 57, step 8 (100 mg, 0.21 mmol) and ethylamine (2.0 M in THF, 1.0 mL, 2.1 mmol) in anhydrous DMSO was heated at 45° C. for 18 hours. The mixture was then partitioned between ethyl acetate (100 mL) and water (100 mL), the organic phase separated, washed with water (100 mL) and saturated brine (100 mL), dried over anhydrous sodium sulfate, filtered and concentrated under reduced pressure. Column chromatography on silica gel with 0–10% methanol in methylene chloride plus 1% NH$_4$OH afforded N-{[(2R)-8-(2,6-dichlorophenyl)-6-fluoro-3,4-dihydro-2H-chromen-2-yl]methyl}ethanamine as a yellow oil. The yellow oil was dissolved in ethyl acetate and made into its hydrochloride salt (52 mg, 69%) as a white crystalline solid using excess ethereal hydrochloric acid, mp>225° C.; MS (EI) m/z 349 (M⁺); $[\alpha]_D^{25}=50.0°$ (c=1% SOLUTION, MeOH); MS (ES) m/z 354.1;

Elemental analysis for C$_{18}$H$_{18}$Cl$_2$FNO.HCl: Theory: C, 55.33; H, 4.90; N, 3.58. Found: C, 55.01; H, 4.95; N, 3.50.

Example 59

{[(2R)-8-(2,6-dichlorophenyl)-2H-chromen-2-yl]methyl}methylamine hydrochloride:

To a solution of [(2R)-8-(2,6-dichlorophenyl)-2H-chromen-2-yl]methyl 4-methylbenzenesulfonate, prepared in Example 35, step 7 (0.33 g, 0.715 mmol) in anhydrous dimethyl sulfoxide (1.2 mL) was added a solution of methylamine (2.0 M in tetrahydrofuran, 3.58 mL, 7.15 mmol) and the mixture heated at 60° C. in a sealed vial for 26 hours. The cooled reaction mixture was then poured into 1:1 v/v 2.0 M aqueous sodium hydroxide solution:saturated brine (50 mL) and the product extracted with ethyl acetate (50 mL). The separated organic extract was washed with 1:1 v/v 2.0 M aqueous sodium hydroxide solution:saturated brine (50 mL), and half saturated brine (50 mL), dried over magnesium sulfate, filtered and concentrated under reduced pressure to afford a brown syrup. Purification by flash chromatography using a solvent gradient of 0 to 5% ammonia saturated methanol solution in dichloromethane gave 160 mg (70%) of {[(2R)-8-(2,6-dichlorophenyl)-2H-chromen-2-yl]methyl}methylamine as a yellow syrup. The product was dissolved 2-propanol (1.5 mL) and diethyl ether (3 mL) and a solution of hydrogen chloride (1.0 M in diethyl ether, 0.36 mL, 0.36 mmol) was added followed by hexane (4 mL). The resulting white precipitate was filtered to afford 121 mg (47%) of {[(2R)-8-(2,6-dichlorophenyl)-2H-chromen-2-yl]methyl}methylamine hydrochloride as a tan solid. HRMS: calcd for C$_{17}$H$_{15}$Cl$_2$NO+H⁺, 320.06034. found (ESI, [M+H]⁺), 320.0619.

Example 60

{[(2R)-8-(2,6-dichlorophenyl)-2H-chromen-2-yl]methyl}amine hydrochloride

Step 1: A solution of [(2R)-8-(2,6-dichlorophenyl)-2H-chromen-2-yl]methyl 4-methylbenzenesulfonate prepared in Example 35, step 7 (250 mg, 0.542 mmol) and sodium azide (141 mg, 2.17 mmol) in anhydrous dimethyl sulfoxide (10 mL) was heated at 70° C. under nitrogen for 20 hours. The cooled reaction mixture was quenched by the addition of water (20 mL) and the resulting suspension stirred vigorously for 5 minutes. The mixture was then partitioned between ethyl acetate (100 mL) and water (100 mL), the organic phase separated, washed with water (100 mL) and saturated brine (100 mL), dried over magnesium sulfate, filtered and concentrated under reduced pressure to afford 120 mg (67%) of (2R)-2-azidomethyl-8-(2,6-dichloro-phenyl)-2H-chromene as a colorless syrup that was used without further purification.

Step 2: To a solution of (2R)-2-azidomethyl-8-(2,6-dichloro-phenyl)-2H-chromene (120 mg, 0.361 mmol) in tetrahydrofuran (5 mL) and water (0.5 mL) was added polymer-bound triphenylphosphine (~3 mmol/g, 0.361 g, 1.084 mmol) and the reaction mixture stirred at room temperature for 43 hours. The brown suspension was then filtered through celite, the filter cake washed with ethyl acetate (50 mL) and the combined filtrates concentrated under reduced pressure to afford a yellow syrup. Purification by flash chromatography using a solvent gradient of 0 to 5% ammonia saturated methanol solution in dichloromethane gave 100 mg (90%) of {[(2R)-8-(2,6-dichlorophenyl)-2H-chromen-2-yl]methyl}amine as a colorless syrup. The product was dissolved in 2-propanol (1 mL) and diethyl ether (2 mL), a solution of hydrogen chloride (1.0 M in diethyl ether, 0.326 mL, 0.326 mmol) was added followed hexane (7 mL). The resulting white precipitate was filtered to afford 100 mg (80%) of {[(2R)-8-(2,6-dichlorophenyl)-2H-chromen-2-yl]methyl}amine hydrochloride as an off-white solid.

MS (ESI) m/z 306 ([M+H]$^+$).

Example 61

{[8-(2-chlorophenyl)-6-fluoro-2H-chromen-2-yl]methyl}methylamine hydrochloride

Step 1: A solution of (8-bromo-6-fluoro-2H-chromen-2-yl)methyl 4-methylbenzenesulfonate, prepared in Example 37, step 5 (1.0 g, 2.42 mmol) and 2-chlorophenylboronic acid (1.14 g, 7.26 mmol) in dioxane (18 mL) was added a solution of potassium carbonate (1.0 g, 7.26 mmol) in water (6 mL) and the mixture purged with nitrogen for 20 minutes. Trans-dichlorobis(tri-o-tolylphosphine)palladium (II) (95 mg, 0.12 mmol) was added and the reaction mixture heated at 100° C. for 2 hours. The cooled reaction mixture was then partitioned between ethyl acetate (100 mL) and 2.0 M aqueous sodium hydroxide (100 mL). The organic layer was separated, washed with water (100 mL) and saturated brine (100 mL), dried over magnesium sulfate, filtered and concentrated under reduced pressure to afford a yellow oil. Purification by flash chromatography using a solvent gradient of 5 to 20% ethyl acetate in hexane gave 0.57 g (53%) of [8-(2-chlorophenyl)-6-fluoro-2H-chromen-2-yl]methyl 4-methylbenzenesulfonate as a white solid. HRMS: calcd for $C_{23}H_{18}ClFO_4S+NH_4^+$, 462.09366. found (ESI, [M+NH$_4$]$^+$), 462.0916.

Step 2: To a solution of [8-(2-chlorophenyl)-6-fluoro-2H-chromen-2-yl]methyl 4-methylbenzenesulfonate (0.33 g, 0.748 mmol) in anhydrous dimethyl sulfoxide (1.2 mL) was added a solution of methylamine (2.0 M in tetrahydrofuran, 3.74 mL, 7.48 mmol) and the mixture heated to 60° C. in a sealed vial for 2 days. The cooled reaction mixture was then poured into 2.0 M aqueous sodium hydroxide solution (40 mL) and the product extracted with ethyl acetate (50 mL). The separated organic extract was washed with water (50 mL), and saturated brine (50 mL), dried over magnesium sulfate, filtered and concentrated under reduced pressure to afford a brown syrup. Purification by flash chromatography using a solvent gradient of 0 to 5% ammonia saturated methanol solution in dichloromethane gave 101 mg (45%) of {[8-(2-chlorophenyl)-6-fluoro-2H-chromen-2-yl]methyl}methylamine as a yellow syrup. The product was dissolved 2-propanol (1 mL) and diethyl ether (2 mL), a solution of hydrogen chloride (1.0 M in diethyl ether, 0.33 mL, 0.33 mmol) was added followed by hexane (3 mL). The resulting precipitate was filtered to afford 100 mg (39%) of {[8-(2-chlorophenyl)-6-fluoro-2H-chromen-2-yl]methyl}methylamine hydrochloride as a tan crystalline solid. HRMS: calcd for $C_{17}H_{15}ClFNO+H^+$, 304.08990. found (ESI, [M+H]$^+$), 304.0891.

Example 62

{[8-(2-chlorophenyl)-6-fluoro-2H-chromen-2-yl]methyl}amine hydrochloride

Step 1: A solution of [8-(2-chlorophenyl)-6-fluoro-2H-chromen-2-yl]methyl 4-methylbenzenesulfonate prepared in Example 61, step 1 (204 mg, 0.459 mmol) and sodium azide (119 mg, 1.834 mmol) in anhydrous dimethyl sulfoxide (8 mL) was heated at 70° C. under nitrogen for 19 hours. The cooled reaction mixture was quenched by the addition of water (30 mL) and the resulting suspension stirred vigorously for 5 minutes. The mixture was then partitioned between ethyl acetate (100 mL) and water (100 mL), the organic phase separated, washed with water (100 mL) and saturated brine (100 mL), dried over magnesium sulfate, filtered and concentrated under reduced pressure to afford 120 mg (67%) of 2-azidomethyl-8-(2-chloro-phenyl)-2H-chromene as a yellow syrup that was used without further purification.

Step 2: To a solution of 2-azidomethyl-8-(2-chloro-phenyl)-2H-chromene (150 mg, 0.459 mmol) in tetrahydrofuran (5 mL) and water (0.5 mL) was added polymer-bound triphenylphosphine (~3 mmol/g, 0.459 g, 1.377 mmol) and the reaction mixture stirred at room temperature for 3 days. The brown suspension was then filtered through celite, the filter cake washed with ethyl acetate (50 mL) and the combined filtrates concentrated under reduced pressure to afford a yellow syrup. The product was dissolved in 2-propanol (1 mL) and diethyl ether (2 mL), a solution of hydrogen chloride (1.0 M in diethyl ether, 0.46 mL, 0.46 mmol) was added followed hexane (3 mL). The resulting precipitate was filtered to afford 81 mg (52%) of {[8-(2-chlorophenyl)-6-fluoro-2H-chromen-2-yl]methyl}amine hydrochloride as a grey solid. HRMS: calcd for $C_{16}H_{13}ClFNO+H+$, 290.07425. found (ESI, [M+H]$^+$), 290.0746.

Example 63

{[(2R)-8-(2,5-dichlorophenyl)-6-fluoro-2H-chromen-2-yl]methyl}amine hydrochloride Step 1: To a solution of [(R)-8-bromo-6-fluoro-3,4-dihydro-2H-chromen-2-yl)methyl 4-methylbenzenesulfonate, prepared in Example 38, step 2 (0.40 g, 0.97 mmol) and 2,5-dichlorophenylboronic acid (0.56 g, 2.9 mmol) in dioxane (10 ml) was added a solution of potassium carbonate (0.34 g, 2.4 mmol) in water (2 mL) and the mixture purged with nitrogen for 20 minutes. Dichlorobis(tri-o-tolylphosphine)palladium (II) (20 mg, 0.029 mmol) was added and the reaction mixture heated to reflux for 1 hour. The cooled reaction mixture was then partitioned between ethyl acetate (100 mL) and 2.0 M aqueous sodium hydroxide (100 mL). The organic layer was separated, washed with water (100 mL) and saturated brine (100 mL), dried over anhydrous sodium sulfate, filtered and concentrated under reduced pressure to afford a yellow syrup. Purification by flash chromatography using a solvent gradient of 5 to 20% ethyl acetate in hexane gave 0.41 g (88%) of ((R)-8-(2,5-dichlorophenyl)-6-fluoro-2H-chromen-2-yl)methyl 4-methylbenzenesulfonate as a colorless oil. MS (ES) m/z 496.0 ([M+NH$_4$]$^+$).

Step 2: A solution ((R)-8-(2,5-dichlorophenyl)-6-fluoro-2H-chromen-2-yl)methyl 4-methylbenzenesulfonate (410 mg, 0.85 mmol) and sodium azide (280 mg, 4.3 mmol) in anhydrous DMF (20 mL) was heated to 90° C. under nitrogen for 20 hours. The cooled reaction mixture was quenched by the addition of water (30 mL) and the resulting suspension stirred vigorously for 10 minutes. The mixture was then partitioned between ethyl acetate (100 mL) and water (100 mL), the organic phase separated, washed with water (100 mL) and saturated brine (100 mL), dried over anhydrous sodium sulfate, filtered and concentrated under reduced pressure. Chromatography with 0–30% ethyl acetate in hexanes afforded 240 mg (83%) of (2R)-2-azidomethyl-8-(2,5-dichloro-phenyl)-6-fluoro-chroman as a colorless oil. MS (APPI) m/z 322 ([M−N2+H]$^+$).

Step 3: To a solution of (R)-2-azidomethyl-8-(2,5-dichloro-phenyl)-6-fluoro-chroman (240 mg, 0.68 mmol) in tetrahydrofuran (10 mL) and water (0.5 mL) was added triphenylphosphine (0.27 g, 10.2 mmol) and the reaction mixture stirred at room temperature for 24 hours. The solvent was removed under vacuum to form a colorless oil. Chromatography with 0–5% methanol in methylene chloride plus 1% NH$_4$OH afforded {[(R-8-(2.5-dichlorophenyl)-6-fluoro-2H-chromen-2-yl]methyl}amine as a colorless oil. The oil was dissolved in ethyl acetate and made into its hydrochloride salt (121 mg, 45%) using excess ethereal hydrochloric acid to give a white solid, mp 217–219° C.; MS (ES) m/z 324.0 ([M+H]$^+$); [α]$_D^{25}$=+191.22° (c=5.1 mg/0.7 mL MeOH).

Elemental analysis for C$_{16}$H$_{12}$Cl$_2$FNO.HCl: Theory: C, 53.29; H, 3.63; N, 3.88. Found: C, 53.14; H, 3.35; N, 3.73.

Example 64

{[(2R)-8-(2-chlorophenyl)-6-fluoro-2H-chromen-2-yl]methyl}amine hydrochloride

Step 1: To a solution of (R)-8-bromo-6-fluoro-3,4-dihydro-2H-chromen-2-yl)methyl 4-methylbenzenesulfonate, prepared in Example 38, step 2 (0.40 g, 0.97 mmol) and 2-chlorophenylboronic acid (0.45 g, 2.9 mmol) in dioxane (10 ml) was added a solution of potassium carbonate (0.34 g, 2.4 mmol) in water (2 mL) and the mixture purged with nitrogen for 20 minutes. Dichlorobis(tri-o-tolylphosphine)palladium (II) (20 mg, 0.029 mmol) was added and the reaction mixture heated to reflux for 1 hour. The cooled reaction mixture was then partitioned between ethyl acetate (100 mL) and 2.0 M aqueous sodium hydroxide (100 mL). The organic layer was separated, washed with water (100 mL) and saturated brine (100 mL), dried over anhydrous sodium sulfate, filtered and concentrated under reduced pressure to afford a yellow syrup. Purification by flash chromatography using a solvent gradient of 5 to 20% ethyl acetate in hexane gave 0.40 g (93%) of ((R)-8-(2-chlorophenyl)-6-fluoro-2H-chromen-2-yl)methyl 4-methylbenzenesulfonate as a colorless oil. MS (ES) m/z 462.0 ([M+NH$_4$]$^+$).

Step 2: A solution ((R)-8-(2-chlorophenyl)-6-fluoro-2H-chromen-2-yl)methyl 4-methylbenzenesulfonate (400 mg, 0.90 mmol) and sodium azide (0.29 g, 4.5 mmol) in anhydrous DMF (20 mL) was heated to 90° C. under nitrogen for 20 hours. The cooled reaction mixture was quenched by the addition of water (30 mL) and the resulting suspension stirred vigorously for 10 minutes. The mixture was then partitioned between ethyl acetate (100 mL) and water (100 mL), the organic phase separated, washed with water (100 mL) and saturated brine (100 mL), dried over anhydrous sodium sulfate, filtered and concentrated under reduced pressure. Chromatography with 0–30% ethyl acetate in hexanes afforded 240 mg (88%) of (R)-2-azidomethyl-8-(2-chloro-phenyl)-6-fluoro-chroman as a colorless oil. MS (APPI) m/z 288 ([M−N2+H]$^+$).

Step 3: To a solution of (R)-2-azidomethyl-8-(2-chlorophenyl)-6-fluoro-chroman (210 mg, 0.67 mmol) in tetrahydrofuran (10 mL) and water (0.5 mL) was added triphenylphosphine (0.26 g, 10 mmol) and the reaction mixture stirred at room temperature for 24 hours. The solvent was removed under vacuum to form a colorless oil. Chromatography with 0–5% methanol in methylene chloride plus 1% NH$_4$OH afforded {[(R)-8-(2-chlorophenyl)-6-fluoro-2H-chromen-2-yl]methyl}amine as a colorless oil. The colorless oil was dissolved in ethyl acetate and made into its hydrochloride salt (56 mg, 25%) as a beige solid using excess ethereal hydrochloric acid, mp 145–147° C.; [α]$_D^{25}$=+256.01° (c=5.3 mg/0.7 mL MeOH).

Elemental analysis for C$_{16}$H$_{13}$ClFNO.HCl.0.75 H$_2$O: Theory: C, 56.57; H, 4.60; N, 4.12. Found: C, 56.87; H, 4.41; N, 3.98.

Example 65

{[(2R)-6-fluoro-8-(2-methoxyphenyl)-2H-chromen-2-yl]methyl}amine hydrochloride

Step 1: To a solution of (R)-8-bromo-6-fluoro-3,4-dihydro-2H-chromen-2-yl)methyl 4-methylbenzenesulfonate, prepared in Example 38, step 2 (0.30 g, 0.73 mmol) and 2-methoxyphenylboronic acid (0.22 g, 1.5 mmol) in dioxane (10 ml) was added a solution of potassium carbonate (0.25 g, 1.8 mmol) in water (2 mL) and the mixture purged with nitrogen for 20 minutes. Dichlorobis(tri-o-tolylphosphine) palladium (II) (17 mg, 0.022 mmol) was added and the reaction mixture heated to reflux for 1 hour. The cooled reaction mixture was then partitioned between ethyl acetate (100 mL) and 2.0 M aqueous sodium hydroxide (100 mL). The organic layer was separated, washed with water (100 mL) and saturated brine (100 mL), dried over anhydrous sodium sulfate, filtered and concentrated under reduced pressure to afford a yellow syrup. Purification by flash chromatography using a solvent gradient of 5 to 20% ethyl acetate in hexane gave 0.30 g (94%) of ((R)-8-(2-methoxyphenyl)-6-fluoro-2H-chromen-2-yl)methyl 4-methylbenzenesulfonate as a colorless oil. MS (ES) m/z 458.1 ([M+NH$_4$]$^+$).

Step 2: A solution ((R)-8-(2-methoxyphenyl)-6-fluoro-2H-chromen-2-yl)methyl 4-methylbenzenesulfonate (300 mg, 0.67 mmol) and sodium azide (0.22 g, 3.4 mmol) in anhydrous DMF (20 mL) was heated to 90° C. under nitrogen for 20 hours. The cooled reaction mixture was quenched by the addition of water (30 mL) and the resulting suspension stirred vigorously for 10 minutes. The mixture was then partitioned between ethyl acetate (100 mL) and water (100 mL), the organic phase separated, washed with water (100 mL) and saturated brine (100 mL), dried over anhydrous sodium sulfate, filtered and concentrated under reduced pressure. Chromatography with 0–30% ethyl acetate in hexanes afforded 190 mg (90%) of (2R)-2-azidomethyl-8-(2-methoxy-phenyl)-6-fluoro-chroman as a colorless oil.

MS (APPI) m/z 284 ([M–N2+H]$^+$).

Step 3: To a solution of (R)-2-azidomethyl-8-(2-methoxyphenyl)-6-fluoro-chroman (190 mg, 0.32 mmol) in tetrahydrofuran (10 mL) and water (0.5 mL) was added triphenylphosphine (0.26 g, 10 mmol) and the reaction mixture stirred at room temperature for 24 hours. The solvent was removed under vacuum to form a colorless oil. Chromatography with 0–5% methanol in methylene chloride plus 1% NH$_4$OH afforded {[(R)-8-(2-methoxyphenyl)-6-fluoro-2H-chromen-2-yl]methyl}amine as a colorless oil. The colorless oil was dissolved in ethyl acetate and made into its hydrochloride salt (119 mg, 61%) as an off-white crystalline solid, mp 198–200° C.; [α]$_D^{25}$=+173.89° (c=5.2 mg/0.7mL MeOH).

Elemental analysis for C$_{17}$H$_{16}$FNO$_2$.HCl: Theory: C, 63.46; H, 5.33; N, 4.35. Found: C, 63.26; H, 5.36; N, 4.22.

Example 66

{[(2R)-8-(2,6-dichlorophenyl)-6-fluoro-2H-chromen-2-yl]methyl}amine hydrochloride Step 1: A solution of (R)-(8-(2,6-dichlorophenyl)-6-fluoro-2H-chromen-2-yl]methyl 4-methylbenzenesulfonate prepared in Example 57, step 7 (500 mg, 1.0 mmol) and sodium azide (340 mg, 5.2 mmol) in anhydrous DMF (20 mL) was heated at 90° C. under nitrogen for 20 hours. The cooled reaction mixture was quenched by the addition of water (20 mL) and the resulting suspension stirred vigorously for 5 minutes. The mixture was then partitioned between ethyl acetate (100 mL) and water (100 mL), the organic phase separated, washed with water (100 mL) and saturated brine (100 mL), dried over anhydrous sodium sulfate, filtered and concentrated under reduced pressure. Column chromatography on silica gel with 10–25% ethyl acetate in hexanes afforded 310 mg (85%) of (R)-2-azidomethyl-8-(2,6-dichloro-phenyl)-6-fluoro-2H-chromene as a yellow oil. [α]$_D^{25}$=+282.1° (c=2.7 mg/0.7 MeOH); MS (EI) m/z 349. (M$^+$).

Step 2: To a solution of ((R)-2-azidomethyl-8-(2,6-dichloro-phenyl)-6-fluoro-2H-chromene (300 mg, 0.85 mmol) in tetrahydrofuran (10 mL) and water (0.5 mL) was added polymer-bound triphenylphosphine (~3 mmol/g, 0.85 g, 2.6 mmol) and the reaction mixture stirred at room temperature for 43 hours. The brown suspension was then filtered through celite, the filter cake washed with ethyl acetate (50 mL) and the combined filtrates concentrated under vacuum. Chromatography with 0–10% methanol in methylene chloride plus 1% NH$_4$OH afforded {[(2R)-8-(2,6-dichlorophenyl)-6-fluoro-2H-chromen-2-yl]methyl}amine as a colorless oil. The oil was dissolved in ethyl acetate and made into its hydrochlorde salt (83 mg, 27%) as a white crystalline solid using excess ethereal hydrochloric acid, mp 153–155° C.; [α]$_D^{25}$=+220.67° (c 1% solution in MeOH); MS (ES) m/z 324.0 ([M+H]$^+$).

Elemental Analysis for C$_{16}$H$_{12}$Cl$_2$NFO.HCl Theory: C, 53.29; H, 3.63; N, 3.88. Found: C, 53.13; H, 3.80; N, 3.65.

Example 67

{[(2R)-9-(2,6-dichlorophenyl)-2,3,4,5-tetrahydro-1-benzoxepin-2-yl]methyl}amine hydrochloride Step 1: To a solution of 3-allyl-2',6'-dichloro-1,1'-biphenyl-2-ol, prepared in Example 35, step 4 (0.5 g, 1.791 mmol), (S)-2-hydroxy-3-buten-1-yl p-tosylate (608 mg, 2.507 mmol) and triphenylphosphine (0.658 g, 2.507 mmol) in anhydrous toluene (20 mL) was added dropwise diethylazodicarboxylate (0.395 mL, 2.507 mmol) and the reaction mixture stirred at room temperature under nitrogen for 19 hours. The reaction was quenched by the addition of water (10 mL) and the biphasic mixture stirred vigorously for 1 hour. The mixture was then partitioned between diethyl ether (100 mL) and water (100 mL), the organic phase separated, washed with water (100 mL) and saturated brine (100 mL), dried over magnesium sulfate, filtered and concentrated under reduced pressure to afford a yellow syrup. Purification by flash chromatography using a solvent gradient of 3 to 10% ethyl acetate in hexane afforded 0.784 g (87%) of (2R)-2-[(3-allyl-2',6'-dichlorobiphenyl-2-yl)oxy]but-3-en-1-yl 4-methylbenzene sulfonate as a white solid. MS (ESI) m/z 520 9[M+NH$_4$]$^+$).

Step 2: To a solution of (2R)-2-[(3-allyl-2',6'-dichlorobiphenyl-2-yl)oxy]but-3-en-1-yl 4-methylbenzenesulfonate (702 mg, 1.394 mmol) in anhydrous dichloromethane (35 mL) at room temperature under nitrogen was added benzylidene-bis(tricyclohexylphosphine)dichlororuthenium (114 mg, 0.1394 mmol) and the reaction mixture stirred at room temperature for 5 hours. The reaction mixture was then concentrated under reduced pressure to afford a brown syrup. The crude product was dissolved in ethyl acetate (7 mL) and the solution added to a suspension of platinum (IV) oxide (32 mg, 0.139 mmol) in absolute ethanol (21 mL). The mixture was then hydrogenated at 12 psi of hydrogen for 1 hour. The reaction mixture was filtered through celite and the filtrate concentrated under reduced pressure to afford a brown syrup. Purification by flash chromatography using a solvent gradient of 3 to 10% ethyl acetate in hexane afforded 0.615 g (92%) of [(2R)-9-(2,6-dichlorophenyl)-2,3,4,5-tetrahydro-1-benzoxepin-2-yl]methyl 4-methylbenzenesulfonate as a yellow solid. MS (ESI) m/z 477 ([M+H]$^+$).

Step 3: A solution of [(2R)-9-(2,6-dichlorophenyl)-2,3,4,5-tetrahydro-1-benzoxepin-2-yl]methyl 4-methylbenzenesulfonate (381 mg, 0.798 mmol) and sodium azide (208 mg, 3.192 mmol) in anhydrous dimethyl sulfoxide (10 mL) was heated at 70° C. under nitrogen for 19 hours. The cooled reaction mixture was quenched by the addition of water (30 mL) and the resulting suspension stirred vigorously for 5 minutes. The mixture was then partitioned between ethyl acetate (100 mL) and water (100 mL), the organic phase separated, washed with water (100 mL) and saturated brine (100 mL), dried over magnesium sulfate, filtered and concentrated under reduced pressure to afford a colorless syrup. Purification by flash chromatography using 3% ethyl acetate in hexane as eluant gave 240 mg (86%) of (2R)-2-azidomethyl-9-(2,6-dichloro-phenyl)-2,3,4,5-tetrahydro-benzo[b]oxepine as a colorless syrup.

Step 4: To a solution of (2R)-2-azidomethyl-9-(2,6-dichloro-phenyl)-2,3,4,5-tetrahydro-benzo[b]oxepine (0.24 g, 0.689 mmol) in tetrahydrofuran (10 mL) and water (1 mL) was added polymer-bound triphenylphosphine (~3 mmol/g, 0.69 g, 2.068 mmol) and the reaction mixture stirred at room temperature for 20 hours. The brown suspension was then filtered through celite, the filter cake washed with ethyl acetate (50 mL) and the combined filtrates concentrated under reduced pressure to afford a yellow syrup. Purification by flash chromatography using a solvent gradient of 0 to 5% ammonia saturated methanol solution in dichloromethane gave 179 mg (80%) of {[(2R)-9-(2,6-dichlorophenyl)-2,3,4,5-tetrahydro-1-benzoxepin-2-yl]methyl}amine as a colorless syrup. The product was dissolved in 2-propanol (1 mL) and diethyl ether (3 mL), a solution of hydrogen chloride (1.0 M in diethyl ether, 0.55 mL, 0.55 mmol) was added followed by hexane (4 mL). The resulting white precipitate was filtered to afford 182 mg (73%) of {[(2R)-9-(2.6-dichlorophenyl)-2,3,4,5-tetrahydro-1-benzoxepin-2-yl]methyl}amine hydrochloride as a white solid. MS (ESI) m/z 322 ([M+H]$^+$).

Example 68

{[(2R)-9-(2,6-dichlorophenyl)-7-fluoro-2,3,4,5-tetrahydro-1-benzoxepin-2-yl]methyl}amine hydrochloride Step 1: A solution of 3-allyl-2',6'-dichloro-5-fluorobiphenyl-2-ol (3.26 g, 11.0 mmol) and (S)-2-hydroxy-3-buten-1-yl p-tosylate (4.0 g, 16.4 mmol) and triphenylphosphine (5.76 g, 21.9 mmol) in anhydrous tetrahydrofuran (60 mL) was added dropwise diethylazodicarboxylate (4.3 mL, 21.9 mmol) and the reaction mixture stirred at room temperature for 16 hours. The mixture was extracted with methylene chloride and washed with water. The solvent was removed under vacuum. Chromatography with 0–30% ethyl acetate in hexanes afforded 4.41 g (77%) of (R)-2-(3-allyl-2',6'-dichloro-5-fluorobiphenyl-2-yloxy)but-3-enyl 4-methyl benzenesulfonate as a yellow oil. $[\alpha]_D^{25}$=−15.92° (c=5.8 mg/0.7 mL MeOH); MS (ES) m/z 538.1 ([M+NH$^4$]$^+$).

Step 2: To a solution of (R)-2-(3-allyl-2',6'-dichloro-5-fluorobiphenyl-2-yloxy)but-3-enyl 4-methyl benzenesulfonate (1.06 g, 20.0 mmol) in anhydrous dichloroethane (50 mL) at room temperature under nitrogen was added benzylidene-bis(tricyclohexylphosphine)-dichlororuthenium (0.33 g, 0.4 mmol) and the reaction mixture stirred at room temperature overnight. The cooled reaction mixture was concentrated to a small volume under reduced pressure. Chromatography with 0–15% ethyl acetate in hexanes afforded 0.70 g (70%) of (R)-(9-(2,6-dichlorophenyl)-7-fluoro-2,5-dihydrobenzo[b]oxepin-2-yl)methyl 4-methyl-benzene-sulfonate as a brown foam. $[\alpha]^D{}_{25}$=+59.94° (c=5.4 mg/0.7 mL MeOH);
MS (ESI) m/z 510.1 ([M+NH$_4$]$^+$).

Step 3: A solution (R)-(9-(2,6-dichlorophenyl)-7-fluoro-2,5-dihydrobenzo[b]oxepin-2-yl)methyl 4-methylbenzenesulfonate (0.7 g, 1.4 mmol) in ethyl acetate/ethanol (10/10 mL) was added platinum (IV) oxide (0.2 g) and the mixture hydrogenated at 45 psi of hydrogen for 14 hours. The reaction mixture was then filtered through celite and the filtrate concentrated under reduced pressure. Chromatography with 10–30% ethyl acetate in hexanes afforded 0.60 g (85%) of (R)-(9-(2,6-dichlorophenyl)-7-fluoro-2,3,4,5-tetrahydrobenzo[b]oxepin-2-yl)methyl 4-methylbenzene-sulfonate as a colorless oil. $[\alpha]^D{}_{25}$=+24.81° (c=6.6 mg/0.7 mL MeOH); MS (ES) m/z 512.1 ([M+NH$_4$]$^+$).

Step 4: A solution of (R)-(9-(2,6-dichlorophenyl)-7-fluoro-2,3,4,5-tetrahydrobenzo[b]oxepin-2-yl)methyl 4-methylbenzene-sulfonate (230 mg, 0.46 mmol) and sodium azide (0.15 g, 2.3 mmol) in anhydrous DMF (20 mL) was heated to 90° C. under nitrogen overnight. The cooled reaction mixture was quenched by the addition of water (20 mL). The mixture was then partitioned between ethyl acetate (100 mL) and water (100 mL), the organic phase separated, washed with water (100 mL) and saturated brine (100 mL), dried over anhydrous sodium sulfate, filtered and concentrated under reduced pressure to afford a cream solid. Chromatography with 0–15% ethyl acetate in hexanes gave 270 mg (83%) of (R)-2-(azidomethals-9-(2,6-dichlorophenyl)-7-fluoro-2, 5-tetrahydrobenzo[b]oxepne as a light yellow oil. MS (EI) m/z 365 (M$^+$).

Step 5: To a solution of (R)-2-(azidomethyl)-9-(2,6-dichlorophenyl)-7-fluoro-2,3,4,5-tetrahydrobenzo[b]oxepine (0.17 g, 0.46 mmol) in tetrahydrofuran (10 mL) and water (1 mL) was added polymer-bound triphenylphosphine (~3 mmol/g, 0.46 g, 1.4 mmol) and the reaction mixture stirred at room temperature for 2 days. The brown suspension was then filtered through celite, the filter cake washed with ethyl acetate (50 mL) and the combined filtrates concentrated under vacuum. The solvent was removed under vacuum. Chromatography with 0–10% methanol in methylene chloride plus 1% NH$_4$OH afforded {[(R)-8-(2,6-dichlorophenyl)-6-fluoro-3,4-dihydro-2H-chromen-2-yl]methyl}amine as a colorless oil. The colorless oil was dissolved in ethyl acetate and made into its hydrochloride salt (0.13 g, 71%) as a white foam using excess ethereal hydrochloric acid, $[\alpha]_D{}^{25}$=+38.22° (c 1% solution in MeOH); MS (ES) m/z 340.0 ([M+H]$^+$).
Elemental Anal. for C$_{17}$H$_{16}$Cl$_2$NFO.HCl.H$_2$O Theory: C, 51.73; H, 4.85; N, 3.55. Found: C, 51.93; H, 3.80; N, 3.65

Example 69

((2R)-7-Chloro-8-o-tolylchroman-2-yl)methanamine hydrochloride

Step 1: To a solution of 2-bromotoluene (13.8 g, 80.6 mmol) and sodium carbonate (9.0 g, 84.9 mmol) in DME-water (5:1, 250 mL) was added 2-chloro-6-methoxybenzene boronic acid (5.0 g, 26.8 mmol) at 82° C., followed by tetrakis(triphenylphosphine)-palladium (0) (1.5 g, 1.4 mmol). The reaction mixture was heated at 82° C. overnight and cooled to room temperature. The resulting mixture was extracted with ethyl acetate, washed with water and saturated sodium chloride, dried (Na$_2$SO$_4$) and concentrated under reduced pressure. Purification by ISCO using a solvent gradient of 0 to 5% ethyl acetate in hexanes provided 3.9 g (62%) of 2-chloro-6-methoxy-2'-methylbiphenyl as a colorless oil.

Step 2: 2-Chloro-6-methoxy-2'-methylbiphenyl (15.0 g, 64.5 mmol) was heated in hydrogen bromide (33% in acetic acid, 60 mL) at 65° C. overnight. The resulting mixture was cooled to room temperature, poured in water and extracted with ethyl acetate. The organic layer was washed with water and saturated sodium chloride, dried over anhydrous sodium sulfate, filtered and concentrated under reduced pressure. The residue oil was further treated with potassium carbonate (10.5 g, 75.6 mmol) in methanol (100 mL) at room temperature for 2 h. The solvent was removed under reduced pressure. The residue was extracted with ethyl acetate and the organic layer was washed with water and saturated sodium chloride, dried over anhydrous sodium sulfate, filtered and concentrated under reduced pressure. Purification by ISCO using a solvent gradient of 10 to 40% ethyl acetate in hexanes produced 10.9 g (77%) of 6-chloro-2'-methyl-biphenyl-2-ol as a colorless oil.

Step 3: To a solution of 6-chloro-2'-methyl-biphenyl-2-ol (4.75 g, 21.7 mmol) in DMF (30 mL) was added potassium carbonate (4.5 g, 32.6 mmol) and allyl bromide (3.0 mL, 32.6 mmol) at room temperature. The resulting mixture was stirred at room temperature for 4 h. The mixture was extracted with ethyl acetate, washed with water and saturated sodium chloride, dried over anhydrous sodium sulfate, filtered and concentrated under reduced pressure. Purification by ISCO using a solvent gradient of O to 30% ethyl acetate in hexanes provided 5.6 g (100%) of 2-allyloxy-6-chloro-2'-methylbiphenyl as a light yellow oil.

Step 4: A solution of 2-allyloxy-6-chloro-2'-methylbiphenyl (4.0 g, 15.4 mmol) in mesitylene (100 mL) was refluxed for 24 h. The solvent was removed under reduced pressure. Purification by ISCO using a solvent gradient of 0 to 20% ethyl acetate in hexanes provided 3.0 g (75%) of 3-allyl-6-chloro-2'-methylbiphenyl-2-ol as a light yellow oil.

Step 5: To a solution of 3-allyl-6-chloro-2'-methylbiphenyl-2-ol (2.0 g, 7.7 mmol) in methylene chloride (70 mL) was added dichlorobis(acetonitrile)palladium (II) (0.22 g, 0.84 mmol). The resulting mixture was refluxed overnight. The solvent was removed under reduced pressure. Purification by ISCO using a solvent gradient of 5 to 20% ethyl acetate in hexanes provided 1.0 g (50%) of 6-chloro-2'-methyl-3-(prop-1-enyl)biphenyl-2-ol as a colorless oil.

Step 6: To a solution of 6-chloro-2'-methyl-3-(prop-1-enyl)biphenyl-2-ol (1.0 g, 3.86 mmol) in toluene (30 mL) was added triphenylphosphine (1.5 g, 5.79 mmol) and diethyl azodicarboxylate (0.9 mL, 5.79 mmol) followed by (S)-2-hydroxy-3-buten-1-yl p-tosylate (1.4 g, 5.79 mmol) at room temperature. The resulting mixture was stirred at room temperature overnight. The solvent was removed under reduced pressure. Purification by ISCO using a solvent gradient of 0 to 10% ethyl acetate in hexanes provided 1.4 g (75%) of (2R)-2-(6-chloro-2'-methyl-3-(prop-1-enyl)biphenyl-2-yloxy)but-3-enyl 4-methylbenzenesulfonate as a colorless oil.

Step 7: To a solution of (2R)-2-(6-chloro-2'-methyl-3-(prop-1-enyl)biphenyl-2-yloxy)but-3-enyl 4-methylbenzenesulfonate (1.4 g, 2.9 mmol) in 1,2-dichloroethane (30 mL) was added benzylidene-bis(tricyclohexylphosphine)dichlororuthenium (0.57 g, 0.69 mmol) and the resulting mixture was stirred at room temperature overnight. The solvent was removed under reduced pressure. Purification by ISCO using a solvent gradient of 0 to 20% ethyl acetate in hexanes provided 0.8 g (63%) of ((2R)-7-chloro-8-o-tolyl-2H-chromen-2-yl)methyl 4-methylbenzenesulfonate as a thick dark oil.

Step 8: A solution of ((2R)-7-chloro-8-o-tolyl-2H-chromen-2-yl)methyl 4-methylbenzenesulfonate (0.8 g, 1.8 mmol) in ethanol (40 mL) and ethyl acetate (10 mL) was prepared in a hydrogenation bottle and purged with nitrogen. Platinum (IV) oxide (84% Pt, 0.23 g) was added and the reaction mixture was shaken under a hydrogen atmosphere (40 psi) for 3.5 h. The resulting mixture was filtered through a pad of Celite and the solvent was removed under reduced pressure. Purification by ISCO using a solvent gradient of 0 to 20% ethyl acetate in hexanes provided 0.8 g (100%) of ((2R)-7-chloro-8-o-tolylchroman-2-yl)methyl 4-methylbenzenesulfonate as a thick dark oil.

Step 9: To a solution of ((2R)-7-chloro-8-o-tolylchroman-2-yl)methyl 4-methylbenzenesulfonate (0.8 g, 1.8 mmol) in DMSO (50 mL) was added sodium azide (1.2 g, 18.4 mmol) and the resulting mixture was heated at 60° C. overnight. The mixture was extracted with ethyl acetate, washed with water and saturated sodium chloride, dried with anhydrous sodium sulfate and concentrated under reduced pressure. Purification by ISCO using a solvent gradient of 0 to 20% ethyl acetate in hexanes provided 0.5 g (88%) of (2R)-2-(azidomethyl)-7-chloro-8-o-tolylchroman as a colorless oil.

Step 10: To a solution of (2R)-2-(azidomethyl)-7-chloro-8-o-tolylchroman (0.5 g, 1.6 mmol) in THF (15 mL) and water (0.5 mL) was added polymer-bound triphenylphosphine (3 mmol/g, 0.8 g, 2.4 mmol) and the resulting mixture was stirred at room temperature overnight. The mixture was filtered through a pad of Celite and concentrated under reduced pressure. Purification by ISCO using a solvent gradient of 0 to 10% methanol in methylene chloride provided 0.15 g of the title compound as a colorless oil. The oil was dissolved in ethyl acetate (5 mL) and to which hydrogen chloride (1.0 M in ethyl ether, 1.5 mL, 1.5 mmol) was added, solvent was removed and the solid was washed with ethyl ether (3×5 mL) to provide 0.13 g of ((2R)-7-chloro-8-o-tolylchroman-2-yl)methanamine hydrochloride as a white solid salt, mp 155° C.; MS (APPI) m/z 288 ([M+H]$^+$); $[\alpha]_D^{25}$=−55° (c=1% SOLN, MeOH).

Elemental analysis for $C_{17}H_{18}ClNO.HCl$: Theory: C, 62.97; H, 5.91; N, 4.32. Found: C, 61.71; H, 6.09; N, 4.00.

Example 70

((2R)-7-chloro-8-(2-chlorophenyl)chroman-2-yl)methanamine hydrochloride

Step 1: Treatment of 2-bromochlorobenzene (15.5 g, 80.6 mmol) with 2-chloro-6-methoxybenzene boronic acid (5.0 g, 26.8 mmol) in DME-water (5:1, 250 mL) according to the procedure described for Example 69, Step 1 provided 5.0 g (74%) of 2.2'-dichloro-6-methoxybiphenyl as a colorless oil.

Step 2: Treatment of 2,2'-dichloro-6-methoxybiphenyl (5.0 g, 20.9 mmol) with hydrogen bromide (33% in acetic acid, 60 mL) according to the procedure described for Example 69, Step 2 provided 4.2 g (89%) of 2',6-dichloro-biphenyl-2-ol as a colorless oil.

Step 3: To a solution of 2',6-dichloro-biphenyl-2-ol (10.0 g, 41.8 mmol) in DMF was added sodium hydride (60% in mineral oil, 2.5 g, 62.7 mmol) and allyl bromide (5.4 mL, 62.7 mmol) at room temperature. The resulting mixture was stirred at room temperature overnight. The mixture was extracted with ethyl acetate, washed with water and saturated sodium chloride, dried over anhydrous sodium sulfate, filtered and concentrated under reduced pressure. Purification by ISCO using a solvent gradient of 0 to 30% ethyl acetate in hexanes provided 11.6 g (100%) of 2-allyloxy-2', 6-dichlorobiphenyl as a light yellow oil Step 4: A solution of 2-allyloxy-2',6-dichlorobiphenyl (11.6 g, 41.8 mmol) in mesitylene (100 mL) was refluxed for 24 h. The solvent was removed under reduced pressure. Purification by ISCO using a solvent gradient of 0 to 20% ethyl acetate in hexanes provided 9.0 g (77%) of 3-allyl-2', 6-dichlorobiphenyl-2-ol as a light yellow oil.

Step 5: Treatment of 3-allyl-2',6-dichloro-biphenyl-2-ol (6.2 g, 22.2 mmol) in methylene chloride (200 mL) with dichlorobis(acetonitrile)palladium (II) (0.86 g, 3.3 mmol) according to the procedure described for Example 69, Step 5 provided 3.0 g (48%) of 2',6-dichloro-3-(prop-1-enyl) biphenyl-2-ol as a light yellow oil.

Step 6: Treatment of 2',6-dichloro-3-(prop-1-enyl)biphenyl-2-ol (3.0 g, 10.7 mmol) in toluene (100 mL) with triphenylphosphine (4.22 g, 16.1 mmol), diethyl azodicarboxylate (2.5 mL, 16.1 mmol) and (S)-2-hydroxy-3-buten-1-yl p-tosylate (2.4 g, 10.0 mmol) according to the procedure described for Example 69, Step 6 provided 3.0 g (60%) of (2R)-2-(2',6-dichloro-3-(prop-1-enyl)biphenyl-2-yloxy)but-3-enyl 4-methylbenzenesulfonate as a pale yellow oil.

Step 7: To a solution of (2R)-2-(2',6-dichloro-3-(prop-1-enyl)biphenyl-2-yloxy)but-3-enyl 4-methylbenzenesulfonate (3.0 g, 5.96 mmol) in 1,2-dichloroethane (60 mL) was added benzylidene-bis(tricyclohexylphosphine)dichlororuthenium (1.5 g, 1.82 mmol) and the resulting mixture was stirred at room temperature overnight. The solvent was removed under reduced pressure. Purification by ISCO using a solvent gradient of 0 to 20% ethyl acetate in hexanes provided 2.15 g (78%) of ((2R)-7-chloro-8-(2-chlorophenyl)-2H-chromen-2-yl)methyl 4-methylbenzenesulfonate as an off-white solid. MS (ESI) m/z 460.9 ([M+H]$^+$); m/z 477.9 ([M+NH$_4$]$^+$).

Step 8: Treatment of ((2R)-7-chloro-8-(2-chlorophenyl)-2H-chromen-2-yl)methyl 4-methylbenzenesulfonate (2.13 g, 4.62 mmol) in ethanol (100 mL) and ethyl acetate (15 mL) with platinum (IV) oxide (84% Pt, 0.50 g) according to the procedure described for Example 69, Step 8 provided 2.10 g (96%) of ((2R)-7-chloro-8-(2-chlorophenyl)chroman-2-yl)methyl 4-methylbenzenesulfonate as a pale yellow solid.

Step 9: Treatment of ((2R)-7-chloro-8-(2-chlorophenyl)chroman-2-yl)methyl 4-methylbenzenesulfonate (2.10 g, 4.53 mmol) with sodium azide (1.77 g, 27.20 mmol) in DMSO (50 mL) according to the procedure described for Example 69, Step 9 provided 1.5 g (99%) of (2R)-2-(azidomethyl)-7-chloro-8-(2-chlorophenyl)chroman as a white solid. MS (EI) m/z 333.0 [M]$^+$.

Step 10: Treatment of (2R)-2-(azidomethyl)-7-chloro-8-(2-chlorophenyl)chroman (1.5 g, 4.48 mmol) with polymer-bound triphenylphosphine (3 mmol/g, 1.94 g, 5.82 mmol) according to the procedure described for Example 69, Step 10 provided 0.70 g (45%) of ((2R)-7-chloro-8-(2-chlorophenyl)chroman-2-yl)methanamine hydrochloride as a white solid salt, mp 220–222° C.; MS (ESI) m/z 308.1 ([M+H]$^+$); $[\alpha]_D^{25}$=−26.4° (c=1% SOLN, MeOH).

Elemental analysis for C$_{16}$H$_{15}$Cl$_2$NO.HCl: Theory: C, 55.76; H, 4.68; N, 4.06. Found: C, 55.88; H, 4.36; N, 3.94.

Example 71

((2R)-8-(2-chlorophenyl)-7-fluorochroman-2-yl)methanamine hydrochloride

Step 1: Treatment of 2-bromochlorobenzene (9 mL, 77.6 mmol) with 2-fluoro-6-methoxybenzene boronic acid (10.0 g, 58.8 mmol) in DME-water (5:1, 250 mL) according to the procedure described for Example 69, Step 1 provided 17.0 g of 2'-chloro-2-fluoro-6-methoxybiphenyl as a colorless oil.

Step 2: Treatment of 2'-chloro-2-fluoro-6-methoxybiphenyl (17.0 g) with hydrogen bromide (33% in acetic acid, 60 mL) according to the procedure described for Example 69, Step 2 provided 7.5 g (57%) of 2'-chloro-6-fluorobiphenyl-2-ol as a colorless oil.

Step 3: Treatment of 2'-chloro-6-fluoro-biphenyl-2-ol (5.0 g, 22.5 mmol) with potassium carbonate (4.6 g, 33.7 mmol) and allyl bromide (2.9 mL, 33.7 mmol) in DMSO (100 mL) according to the procedure described for Example 69, Step 3 provided 4.5 g (76%) of 2-allyloxy-2'-chloro-6-fluorobighenyl as a pale yellow oil.

Step 4: A solution of 2-allyloxy-2'-chloro-6-fluorobiphenyl (9.0 g, 33.7 mmol) in mesitylene (100 mL) was refluxed for 24 h. The solvent was removed under reduced pressure. Purification by ISCO using a solvent gradient of 0 to 20% ethyl acetate in hexanes provided 7.0 g (81%) of 3-allyl-2'-chloro-6-fluorobiphenyl-2-ol as a colorless oil.

Step 5: Treatment of 3-allyl-2'-chloro-6-fluoro-biphenyl-2-ol (3.8 g, 14.5 mmol) in methylene chloride (150 mL) with dichlorobis(acetonitrile)palladium (II) (0.56 g, 2.2 mmol) according to the procedure described for Example 69, Step 5 provided 1.5 g (39%) of 2'-chloro-6-fluoro-3-(prop-1-enyl)biphenyl-2-ol as a light yellow oil.

Step 6: Treatment of 2'-chloro-6-fluoro-3-(prop-1-enyl)biphenyl-2-ol (2.0 g, 7.61 mmol) in toluene (60 mL) with triphenylphosphine (3.0 g, 11.45 mmol), diethyl azodicarboxylate (1.78 mL, 11.45 mmol) and (S)-2-hydroxy-3-buten-1-yl p-tosylate (3.0 g, 12.38 mmol) according to the procedure described for Example 69, Step 6 provided 1.5 g (40%) of (2R)-2-(2'-chloro-6-fluoro-3-(prop-1-enyl)biphenyl-2-yloxy)but-3-enyl 4-methylbenzenesulfonate as a pale yellow oil.

Step 7: Treatment of (2R)-2-(2'-chloro-6-fluoro-3-(prop-1-enyl)biphenyl-2-yloxy)but-3-enyl 4-methylbenzenesulfonate (1.5 g, 3.08 mmol) with benzylidene-bis(tricyclohexylphosphine)-dichlororuthenium (0.50 g, 0.61 mmol) in 1,2-dichloroethane (30 mL) according to the procedure described for Example 69, Step 7 provided 0.7 g (51%) of ((2R)-8-(2-chlorophenyl)-7-fluoro-2H-chromen-2-yl)methyl 4-methylbenzene-sulfonate as a thick dark oil.

Step 8: Treatment of ((2R)-8-(2-chlorophenyl)-7-fluoro-2H-chromen-2-yl)methyl 4-methylbenzenesulfonate (0.7 g, 1.57 mmol) in ethanol (40 mL) and ethyl acetate (10 mL) with platinum (IV) oxide (84% Pt, 0.21 g) according to the procedure described for Example 69, Step 8 provided 0.7 g (100%) of ((2R)-8-(2-chlorophenyl)-7-fluorochroman-2-yl)methyl 4-methylbenzenesulfonate as a pale yellow oil.

Step 9: Treatment of ((2R)-8-(2-chlorophenyl)-7-fluorochroman-2-yl)methyl 4-methylbenzenesulfonate (0.7 g, 1.56 mmol) with sodium azide (0.61 g, 9.40 mmol) in DMSO (20 mL) according to the procedure described for Example 69, Step 9 provided 0.33 g (67%) of (2R)-2-(azidomethyl)-8-(2-chlorophenyl)-7-fluorochroman as a pale yellow oil.

Step 10: Treatment of (2R)-2-(azidomethyl)-8-(2-chlorophenyl)-7-fluorochroman (0.33 g, 1.04 mmol) with polymer-bound triphenylphosphine (3 mmol/g, 0.5 g, 1.50 mmol) in THF (10 mL) and water (0.5 mL) according to the procedure described for Example 69, Step 10 provided 0.23 g (70%) of ((2R)-8-(2-chlorophenyl)-7-fluorochroman-2-yl)methanamine hydrochloride as a white salt, mp 223–225° C.; MS (APPI) m/z 292 ([M+H]$^+$); $[\alpha]_D^{25}$=−40.00° (c=1% SOLN, MeOH).

Elemental analysis for C$_{16}$H$_{15}$ClFNO.HCl: Theory: C, 58.55; H, 4.91; N, 4.27. Found: C, 58.52; H, 4.68; N, 4.11.

Example 72

((2R)-8-(4-Chloro-2-methylphenyl)-7-fluorochroman-2-yl)methanamine hydrochloride Step 1: Treatment of 2-bromo-4-chlorotoluene (20 mL, 0.15 mol) with 2-fluoro-6-methoxybenzene boronic acid (10.0 g, 58.8 mmol) in DME-water (5:1, 300 mL) according to the procedure described for Example 69, Step 1 provided 21.0 g of 4-chloro-2'-fluoro-6'-methoxy-2-methylbiphenyl as a colorless oil.

Step 2: Treatment of 4-chloro-2'-fluoro-6'-methoxy-2-methylbiphenyl (2.7 g, 10.8 mmol) with hydrogen bromide (33% in acetic acid, 50 mL) according to the procedure described for Example 69, Step 2 provided 2.2 g (86%) of 4'-chloro-6-fluoro-2'-methylbiphenyl-2-ol as a colorless oil.

Step 3: Treatment of 4'-chloro-6-fluoro-2'-methylbiphenyl-2-ol (2.7 g, 11.4 mmol) with potassium carbonate (2.4 g, 17.1 mmol) and allyl bromide (1.5 mL, 17.1 mmol) in DMSO (100 mL) according to the procedure described for Example 69, Step 3 provided 2.1 g (66%) of 2'-allyloxy-4-chloro-6'-fluoro-2-methylbiphenyl as a colorless oil.

Step 4: A solution of 2'-allyloxy-4-chloro-6'-fluoro-2-methylbiphenyl (2.1 g, 7.6 mmol) in mesitylene (70 mL) was refluxed for 24 h. The solvent was removed under reduced pressure. Purification by ISCO using a solvent gradient of 0 to 20% ethyl acetate in hexanes provided 2.0 g (95%) of 3-allyl-4'-chloro-6-fluoro-2'-methylbiphenyl-2-ol as a pale yellow oil.

Step 5: Treatment of 3-allyl-4'-chloro-6-fluoro-2'-methylbiphenyl-2-ol (2.0 g, 7.22 mmol) in methylene chloride (70 mL) with dichlorobis(acetonitrile)palladium (II) (0.25 g, 1.0 mmol) according to the procedure described for Example 69, Step 5 provided 1.6 g (80%) of 4'-chloro-6-fluoro-2'-methyl-3-(prop-1-enyl)biphenyl-2-ol as a colorless oil, MS (ESI) m/z 275.00 [M−H]−.

Step 6: Treatment of 4'-chloro-6-fluoro-2'-methyl-3-(prop-1-enyl)biphenyl-2-ol (1.6 g, 5.78 mmol) in toluene (60 mL) with triphenylphosphine (2.27 g, 8.67 mmol), diethyl azodicarboxylate (1.51 g, 8.67 mmol) and (S)-2-hydroxy-3-buten-1-yl p-tosylate (2.10 g, 8.67 mmol) according to the procedure described for Example 69, Step 6 provided 1.35 g (47%) of (2R)-2-(4'-chloro-6-fluoro-2'-methyl-3-(prop-1-enyl)biphenyl-2-yloxy)but-3-enyl 4-methylbenzenesulfonate as a light yellow oil.

Step 7: Treatment of (2R)-2-(4'-chloro-6-fluoro-2'-methyl-3-(prop-1-enyl)biphenyl-2-yloxy)but-3-enyl 4-methylbenzenesulfonate (1.35 g, 2.69 mmol) with benzylidene-bis(tricyclohexylphosphine)dichlororuthenium (0.70 g, 0.85 mmol) in methylene chloride (30 mL) according to the procedure described for Example 69, Step 7 provided 0.5 g (41%) of ((2R)-8-(4-chloro-2-methylphenyl)-7-fluoro-2H-chromen-2-yl)methyl 4-methylbenzenesulfonate as a brown oil.

Step 8: Treatment of ((2R)-8-(4-chloro-2-methylphenyl)-7-fluoro-2H-chromen-2-yl)methyl 4-methylbenzenesulfonate (0.5 g, 1.09 mmol) with platinum (IV) oxide (84% Pt, 0.21 g) in ethanol (25 mL) and ethyl acetate (5 mL) according to the procedure described for Example 69, Step 8 provided 0.5 g (100%) of ((2R)-8-(4-chloro-2-methylphenyl)-7-fluorochroman-2-yl)methyl 4-methylbenzenesulfonate as a light brown oil.

Step 9: Treatment of ((2R)-8-(4-chloro-2-methylphenyl)-7-fluorochroman-2-yl)methyl 4-methylbenzenesulfonate (0.5 g, 1.09 mmol) with sodium azide (0.43 g, 6.54 mmol) in DMSO (15 mL) according to the procedure described for Example 69, Step 9 provided 0.30 g (83%) of (2R)-2-(azidomethyl)-8-(4-chloro-2-methylphenyl)-7-fluorochroman as a colorless oil.

Step 10: Treatment of (2R)-2-(azidomethyl)-8-(4-chloro-2-methylphenyl)-7-fluorochroman (0.30 g, 0.90 mmol) with polymer-bound triphenylphosphine (3 mmol/g, 0.5 g, 1.50 mmol) in THF (10 mL) and water (0.5 mL) according to the procedure described for Example 69, Step 10 provided 0.21 g (69%) of ((2R)-8-(4-chloro-2-methylphenyl)-7-fluorochroman-2-yl)methanamine hydrochloride as a white solid salt, mp 100–102° C.; MS (ESI) m/z 306.1 ([M+H]+).

Elemental analysis for $C_{17}H_{17}ClFNO·HCl·0.3H_2O·0.4 C_4H_8O_2$: Theory: C, 58.35; H, 5.74; N, 3.66. Found: C, 58.44; H, 5.93; N, 3.31.

Example 73

((2R)-8-(2,4-dichlorophenyl)-7-fluorochroman-2-yl)methanamine hydrochloride

Step 1: Treatment of 2,4-dichlorobromobenzene (13.8 g, 61.2 mmol) with 2-fluoro-6-methoxybenzene boronic acid (5.0 g, 29.4 mmol) in DME-water (5:1, 150 mL) according to the procedure described for Example 69, Step 1 provided 5.0 g (63%) of 2,4-dichloro-2'-fluoro-6'-methoxybiphenyl as a colorless oil.

Step 2: Treatment of 2,4-dichloro-2'-fluoro-6'-methoxybiphenyl (5.0 g, 18.4 mmol) with hydrogen bromide (33% in acetic acid, 100 mL) according to the procedure described for Example 69, Step 2 provided 4.2 g (89%) of 2',4'-dichloro-6-fluorobiphenyl-2-ol as a light brown oil.

Step 3: Treatment of 2',4'-dichloro-6-fluorobiphenyl-2-ol (1.6 g, 6.2 mmol) with potassium carbonate (1.3 g, 9.3 mmol) and allyl bromide (0.79 mL, 9.3 mmol) in DMSO (50 mL) according to the procedure described for Example 69, Step 3 provided 1.7 g (92%) of 2'-allyloxy-2,4-dichloro-6'-fluorobiphenyl as a pale yellow oil.

Step 4: A solution of 2'-allyloxy-2,4-dichloro-6'-fluorobiphenyl (1.7 g, 5.7 mmol) in mesitylene (50 mL) was refluxed for 48 h. The solvent was removed under reduced pressure. Purification by ISCO using a solvent gradient of 0 to 20% ethyl acetate in hexanes provided 1.1 g (65%) of 3-allyl-2',4'-dichloro-6-fluorobiphenyl-2-ol as a pale yellow oil.

Step 5: Treatment of 3-allyl-2',4'-dichloro-6-fluorobiphenyl-2-ol (1.1 g, 3.70 mmol) with dichlorobis(acetonitrile)palladium (II) (0.15 g, 0.58 mmol) in methylene chloride (50 mL) according to the procedure described for Example 69, Step 5 provided 0.8 g (73%) of 2',4'-dichloro-6-fluoro-3-(prop-1-enyl)biphenyl-2-ol as a pale yellow oil.

Step 6: Treatment of 2',4'-dichloro-6-fluoro-3-(prop-1-enyl)biphenyl-2-ol (0.8 g, 2.69 mmol) in toluene (25 mL) with triphenylphosphine (1.06 g, 4.03 mmol), diethyl azodicarboxylate (0.70 g, 4.03 mmol) and (S)-2-hydroxy-3-buten-1-yl p-tosylate (0.97 g, 4.03 mmol) according to the procedure described for Example 69, Step 6 provided 0.6 g (43%) of (2R)-2-(2',4'-dichloro-6-fluoro-3-(prop-1-enyl)biphenyl-2-yloxy)but-3-enyl 4-methylbenzenesulfonate as a light yellow oil.

Step 7: Treatment of (2R)-2-(2',4'-dichloro-6-fluoro-3-(prop-1-enyl)biphenyl-2-yloxy)but-3-enyl 4-methylbenzenesulfonate (0.6 g, 1.15 mmol) with benzylidene-bis(tricyclohexylphosphine)dichlororuthenium (0.30 g, 0.36 mmol) in 1,2-dichloroethane (30 mL) according to the procedure described for Example 69, Step 7 provided 0.35 g (63%) of ((2R)-8-(2,4-dichlorophenyl)-7-fluoro-2H-chromen-2-yl)methyl 4-methylbenzenesulfonate as a brown oil.

Step 8: Treatment of ((2R)-8-(2,4-dichlorophenyl)-7-fluoro-2H-chromen-2-yl)methyl 4-methylbenzenesulfonate (0.35 g, 0.73 mmol) with platinum (IV) oxide (84% Pt, 0.14 g) in ethanol (20 mL) and ethyl acetate (5 mL) according to the procedure described for Example 69, Step 8 provided 0.35 g (100%) of ((2R)-8-(2,4-dichlorophenyl)-7-fluorochroman-2-yl)methyl 4-methylbenzenesulfonate as a light brown oil.

Step 9: Treatment of ((2R)-8-(2,4-dichlorophenyl)-7-fluorochroman-2-yl)methyl 4-methylbenzenesulfonate (0.35 g, 0.73 mmol) with sodium azide (0.28 g, 4.38 mmol) in DMSO (10 mL) according to the procedure described for Example 69, Step 9 provided 0.22 g (86%) of (2R)-2-(azidomethyl)-8-(2,4-dichlorophenyl)-7-fluorochroman as a colorless oil.

Step 10: Treatment of (2R)-2-(azidomethyl)-8-(2,4-dichlorophenyl)-7-fluorochroman (0.22 g, 0.62 mmol) with polymer-bound triphenylphosphine (3 mmol/g, 0.35 g, 1.05 mmol) in THF (10 mL) and water (0.5 mL) according to the procedure described for Example 69, Step 10 provided 97 mg (43%) of ((2R)-8-(2,4-dichlorophenyl)-7-fluorochroman-2-yl)methanamine hydrochloride as a white solid salt, mp 164–166° C.; MS (ESI) m/z 326.0 ([M+H]$^+$); $[\alpha]_D^{25}$=−26.00° (c=1% SOLN, MeOH).

Elemental analysis for $C_{16}H_{14}Cl_2FNO.HCl$: Theory: C, 52.99; H, 4.17; N, 3.86. Found: C, 53.24; H, 3.91; N, 3.59.

Example 74

((2R)-8-(Biphenyl-2-yl)-6-fluorochroman-2-yl) methanamine hydrochloride

Step 1: Treatment of 2-bromobiphenyl (6.85 g, 29.4 mmol) with 2-fluoro-6-methoxybenzene boronic acid (5.0 g, 29.4 mmol) in DME-water (5:1, 150 mL) according to the procedure described for Example 69, Step 1 provided 7.3 g (89%) of 5-fluoro-2-methoxy-2'-phenylbiphenyl as a colorless oil.

Step 2: To a solution of 5-fluoro-2-methoxy-2'-phenylbiphenyl (7.3 g, 26.2 mmol) in methylene chloride (100 mL) cooled to −78° C. was added through syringe boron tribromide (1.0 M in dichloromethane, 40.0 mL, 40.0 mmol). The reaction mixture was stirred and allowed to warm up to room temperature overnight. The resulting mixture was diluted with dichloromethane, washed with water and saturated sodium chloride, dried over anhydrous sodium sulfate and concentrated under reduced pressure. Purification by ISCO using a solvent gradient of 0 to 40% ethyl acetate in hexanes provided 6.8 g (98%) of 5-fluoro-2'-phenylbiphenyl-2-ol as a light brown oil.

Step 3: Treatment of 5-fluoro-2'-phenylbiphenyl-2-ol (6.8 g, 25.7 mmol) with potassium carbonate (5.3 g, 38.6 mmol) and allyl bromide (3.3 mL, 38.6 mmol) in DMSO (150 mL) according to the procedure described for Example 69, Step 3 provided 6.4 g (82%) of 2-allyloxy-5-fluoro-2'-phenylbiphenyl as a white solid. MS (EI) m/z 304.1264 ([M]$^+$); mp 48–49° C.

Step 4: A solution of 2-allyloxy-5-fluoro-2'-phenylbiphenyl (6.4 g, 21.0 mmol) in mesitylene (200 mL) was refluxed for 72 h. The solvent was removed under reduced pressure. Purification by ISCO using a solvent gradient of 0 to 20% ethyl acetate in hexanes afforded 6.2 g (96%) of 3-allyl-5-fluoro-2'-phenylbiphenyl-2-ol as a pale yellow oil.

Step 5: Treatment of 3-allyl-5-fluoro-2'-phenylbiphenyl-2-ol (3.0 g, 9.8 mmol) in methylene chloride (100 mL) with dichlorobis(acetonitrile)palladium (II) (0.50 g, 1.93 mmol) according to the procedure described for Example 69, Step 5 provided 2.78 g (93%) of 5-fluoro-2'-phenyl-3-(prop-1-enyl)biphenyl-2-ol as a pale yellow oil.

Step 6: Treatment of 5-fluoro-2'-phenyl-3-(prop-1-enyl) biphenyl-2-ol (2.78 g, 9.13 mmol) in toluene (100 mL) with triphenylphosphine (3.59 g, 13.69 mmol), diethyl azodicarboxylate (2.38 g, 13.69 mmol) and (S)-2-hydroxy-3-buten-1-yl p-tosylate (2.87 g, 11.87 mmol) according to the procedure described for Intermediate X6 provided 1.8 g (37%) of (2R)-2-(5-fluoro-2'-phenyl-3-(prop-1-enyl)biphenyl-2-yloxy)but-3-enyl 4-methylbenzenesulfonate as a light yellow solid. MS (ESI) m/z 546.1 [M+NH$_4$]$^+$.

Step 7: Treatment of (2R)-2-(5-fluoro-2'-phenyl-3-(prop-1-enyl)biphenyl-2-yloxy)but-3-enyl 4-methylbenzenesulfonate (1.8 g, 3.40 mmol) with benzylidene-bis(tricyclohexylphosphine)-dichlororuthenium (1.0 g, 1.22 mmol) in 1,2-dichloroethane (100 mL) according to the procedure described for Example 69, Step 7 provided 1.36 g (82%) of ((2R)-8-(biphenyl-2-yl)-6-fluoro-2H-chromen-2-yl)methyl 4-methylbenzenesulfonate as a brown solid. MS (ESI) m/z 504.1 ([M+NH$_4$]$^+$).

Step 8: Treatment of ((2R)-8-(biphenyl-2-yl)-6-fluoro-2H-chromen-2-yl)methyl 4-methylbenzenesulfonate (1.36 g, 2.79 mmol) with platinum (IV) oxide (84% Pt, 0.35 g) in ethanol (40 mL) and ethyl acetate (10 mL) according to the procedure described for Example 69, Step 8 provided 1.30 g (96%) of ((2R)-8-(biphenyl-2-yl)-6-fluorochroman-2-yl) methyl 4-methylbenzenesulfonate as an off-white solid. MS (ESI) m/z 489.2 ([M+H]$^+$); m/z 506.2 ([M+NH$_4$]$^+$).

Step 9: Treatment of ((2R)-8-(biphenyl-2-yl)-6-fluorochroman-2-yl)methyl 4-methylbenzenesulfonate (1.30 g, 2.66 mmol) with sodium azide (1.04 g, 15.96 mmol) in DMSO (30 mL) according to the procedure described for Example 69, Step 9 provided 0.85 g (89%) of (2R)-2-(azidomethyl)-8-(biphenyl-2-yl)-6-fluorochroman as a pale yellow oil.

Step 10: Treatment of (2R)-2-(azidomethyl)-8-(biphenyl-2-yl)-6-fluorochroman (0.85 g, 2.36 mmol) with polymer-bound triphenylphosphine (3 mmol/g, 1.02 g, 3.06 mmol) in THF (30 mL) and water (2 mL) according to the procedure described for Example Cl-Me provided 0.46 g (52%) of ((2R)-8-(biphenyl-2-yl)-6-fluorochroman-2-yl)methanamine hydrochloride as an off-white solid salt, mp 98° C.; MS (ESI) m/z 334.2 [M+H]$^+$; $[\alpha]_D^{25}$=−27.00° (c=1% SOLN, MeOH).

Elemental analysis for $C_{22}H_{20}FNO.HCl.C_4H_{10}O$ Theory: C, 70.53; H, 6.81; N, 3.26. Found: C, 70.57; H, 6.97; N, 3.22.

Biological Assays

A. Assessment of Effectiveness of Compounds as 5HT$_{2C}$ Agonists and Partial Agonists The ability of the compounds of this invention to act as 5HT$_{2C}$ agonists and partial agonists was established using several standard pharmacological test procedures; the procedures used and results obtained are provided below. In the test procedures, 5-HT stands for 5-hydroxytryptamine, mCPP stands for meta-chlorophenylpiperazine, and DOI stands for 1-(2,5-dimethoxy-4-iodophenyl)isopropylamine.

To evaluate the affinity of various compounds of formula I for activity at the 5-HT$_{2C}$ receptor, a CHO (Chinese Hamster Ovary) cell line transfected with the cDNA expressing the human 5-hydroxytryptamine-2C (h5-HT$_{2C}$) receptor was maintained in DMEM (Dulbecco's Modified Eagle Media) supplied with fetal calf serum, glutamine, and the markers: guaninephosphoribosyl transferase (GTP) and hypoxanthinethymidine (HT). The cells were allowed to grow to confluence in large culture dishes with intermediate changes of media and splitting. Upon reaching confluence, the cells were harvested by scraping. The harvested cells were suspended in half volume of fresh physiological phosphate buffered saline (PBS) solution and centrifuged at low speed (900×g). This operation was repeated once. The collected cells were then homogenized with a polytron at setting #7 for 15 sec in ten volumes of 50 mM Tris.HCl, pH 7.4 and 0.5 mM EDTA. The homogenate was centrifuged at 900×g for 15 min to remove nuclear particles and other cell debris. The pellet was discarded and the supernatant fluid recentrifuged at 40,000×g for 30 min. The resulting pellet was resuspended in a small volume of Tris.HCl buffer and the tissue protein content was determined in aliquots of 10–25 µL volumes. Bovine Serum Albumin (BSA) was used as the standard in the protein determination by the method of Lowry et al., (J. Biol. Chem., 193:265 (1951). The volume of the suspended cell membranes was adjusted with 50 mM Tris.HCl buffer containing: 0.1% ascorbic acid, 10 mM pargyline and 4 mM $CaCl_2$ to give a tissue protein concentration of 1–2 mg per ml of suspension. The preparation membrane suspension (many times concentrated) was aliquoted in 1 ml volumes and stored at −70 C until used in subsequent binding experiments.

Binding measurements were performed in a 96 well microtiter plate format, in a total volume of 200 µL. To each well was added: 60 µL of incubation buffer made in 50 mM Tris.HCl buffer, pH 7.4 and containing 4 mM $CaCl_2$; 20 µL of [$^{125}$I] DOI (S.A., 2200 Ci/mmol, NEN Life Science).

The dissociation constant, $K_D$ Of [$^{125}$I] DOI at the human serotonin 5-$HT_{2C}$ receptor was 0.4 nM by saturation binding with increasing concentrations of [$^{125}$I] DOI. The reaction was initiated by the final addition of 100 µL of tissue suspension containing 50 µg of receptor protein. Nonspecific binding is measured in the presence of 1 µM unlabeled DOI added in 20.0 µL volume. Test compounds were added in 20.0 µL. The mixture was incubated at room temperature for 60 min. The incubation was stopped by rapid filtration. The bound ligand-receptor complex was filtered off on a 96 well unifilter with a Packard ®Filtermate 196 Harvester. The bound complex caught on the filter disk was dried in a vacuum oven heated to 60° C. and the radioactivity measured by liquid scintillation with 40 µL Microscint-20 scintillant in a Packard TopCount® equipped with six (6) photomultiplier detectors.

Specific binding is defined as the total radioactivity bound less the amount bound in the presence of 1 µM unlabeled DOI. Binding in the presence of varying concentrations of test drugs is expressed as percent of specific binding in the absence of drug. These results are then plotted as log % bound vs log concentration of test drug. Non linear regression analysis of data points yields both the $IC_{50}$ and the $K_i$ values of test compounds with 95% confidence limits. Alternatively, a linear regression line of decline of data points is plotted, from which the $IC_{50}$ value can be read off the curve and the $K_i$ value determined by solving the following equation:

$$K_i = \frac{IC_{50}}{1 + L/K_D}$$

where L is the concentration of the radioactive ligand used and the $K_D$ is the dissociation constant of the ligand for the receptor, both expressed in nM.

The following $K_i$'s (95% confidence interval) are provided for various reference compounds in Table 2, below:

TABLE 2

$K_i$ Data for Reference Compounds

| Compound | $K_i$ |
|---|---|
| Ritanserin | 2.0 (1.3–3.1) nM |
| Ketanserin | 94.8 (70.7–127.0) nM |
| Mianserin | 2.7 (1.9–3.8) nM |
| Clozapine | 23.2 (16.0–34.0) nM |
| Methiothepin | 4.6 (4.0–6.0) nM |
| Methysergide | 6.3 (4.6–8.6) nM |
| Loxapine | 33.0 (24.0–47.0) nM |

TABLE 2-continued $K_i$ Data for Reference Compounds

| Compound | $K_i$ |
|---|---|
| mCPP | 6.5 (4.8–9.0) nM |
| DOI | 6.2 (4.9–8.0) nM |

The ability of the compounds of formula I to produce an agonist response at brain 5-$HT_{2C}$ was assessed by determining their effect on calcium mobilization using the following procedure: CHO cells stably expressing the human 5-$HT_{2C}$ receptor were cultured in Dulbecco's modified Eagle's medium (DMEM) supplemented with 10% fetal bovine serum and non-essential amino acids. Cells were plated at a density of 40K cells/well in 96-well clear-bottom black-wall plates 24 hours prior to the evaluation of 5-$HT_{2C}$ receptor-stimulated calcium mobilization. For calcium studies, cells were loaded with the calcium indicator dye Fluo-3-AM in Hank's buffered saline (HBS) for 60 minutes at 37° C. Cells were washed with HBS at room temperature and transferred to the fluorometric imaging plate reader (FLIPR, Molecular Devices, Sunnyvale, Calif.) for acquisition of calcium images. Excitation at 488 nm was achieved with an Argon ion laser and a 510–560 nm emission filter was used. Fluorescence images and relative intensities were captured at 1 second intervals and cells were stimulated by addition of agonist after 10 baseline measurements using the internal fluidics module of the FLIPR. An increase in fluorescence counts corresponds to an increase in intracellular calcium.

For the evaluation of agonist pharmacology the calcium changes in response to different concentrations of agonist were determined using a maximum minus minimum calculation of the raw fluorescence count data. Calcium changes were then expressed as a percentage of the response observed with a maximally effective concentration of 5-HT. $EC_{50}$ values were estimated by non-linear regression analysis of the log-concentration % maximum 5-HT response curves using the 4-parameter logistic function. In certain embodiments, compounds of the present invention provide an $EC_{50}$ of ≦about 1000 nM. In other embodiments, compounds of the present invention provide an $EC_{50}$ of ≦about 100 nM, in yet other embodiments ≦about 20 nM, in still other embodiments ≦about 5 nM, and certain embodiments ≦about 2 nM.

The following $EC_{50}$'s are provided for various reference compounds in Table 3, below

TABLE 3

$EC_{50}$ Data for Reference Compounds:

| Compound | $EC_{50}$ |
|---|---|
| 5-HT | 0.5 nM |
| DOI | 0.5 nM |
| mCPP | 5.4 nM |

Table 4 below shows the results of the activity of selected compounds of this invention in the assays described above. The compound numbers correspond to the compound numbers in Table 1, supra. Compounds having an activity designated as "A" provided a $K_i$ value of less than or equal to 10 nM; compounds having an activity designated as "B" provided a $K_i$ value between 10 nM and 50 nM; and compounds having an activity designated as "C" provided a $K_i$ value greater than 50 nM. Compounds having an activity designated as "D" provided an $EC_{50}$ value of less than or equal to 50 nM; compounds having an activity designated as "E" provided a an $EC_{50}$ value between 50 nM and 200 nM; and compounds having an activity designated as "F" provided a an $EC_{50}$ value greater than 200 nM. An activity designated as "–", for any compound listed in Table 4, below, means that the data was not provided for that compound.

TABLE 4

5-$HT_{2C}$ Activity of Selected Compounds

| Compound Number | 5-$HT_{2C}$ Binding $K_i$ avg (nM) | 5-$HT_{2C}$ Function $EC_{50}$ (nM) | EMax (%) |
|---|---|---|---|
| 1 | B | D | 80 |
| 2 | A | D | 80 |
| 3 | A | D | 90 |
| 4 | C | D | 80 |
| 5 | A | E | 90 |
| 6 | A | D | 90 |
| 7 | A | D | 90 |
| 8 | A | D | 100 |
| 9 | A | D | 100 |
| 10 | A | D | 100 |
| 11 | A | D | 100 |
| 12 | B | E | 90 |
| 13 | A | D | 100 |
| 14 | B | F | 80 |
| 15 | A | D | 90 |
| 16 | A | D | 100 |
| 17 | A | D | 80 |
| 18 | C | D | 90 |
| 19 | A | E | 80 |
| 20 | A | D | 90 |
| 21 | C | E | 80 |
| 22 | C | — | — |
| 23 | C | — | — |
| 24 | B | E | 100 |
| 25 | B | F | 90 |
| 26 | C | — | — |
| 27 | B | E | 80 |
| 28 | B | E | 100 |
| 29 | B | F | 80 |
| 30 | C | — | — |
| 31 | C | — | — |
| 32 | B | E | 90 |
| 33 | B | F | 80 |
| 34 | C | — | — |
| 35 | A | D | 90 |
| 36 | A | D | 80 |
| 37 | A | D | 100 |
| 38 | A | D | 80 |
| 39 | A | D | 100 |
| 40 | A | D | 90 |
| 41 | B | E | 90 |
| 42 | A | E | 90 |
| 43 | A | E | 90 |
| 44 | B | F | 80 |
| 45 | A | D | 90 |
| 46 | B | F | 90 |
| 47 | C | E | 90 |
| 48 | A | E | 90 |
| 49 | A | D | 90 |
| 50 | B | D | 90 |
| 51 | B | D | 80 |
| 52 | C | — | — |
| 53 | B | E | 70 |
| 54 | C | — | — |
| 55 | A | E | 70 |
| 56 | B | E | 80 |
| 57 | A | D | 80 |
| 58 | A | D | 60 |
| 59 | A | D | 90 |
| 60 | A | D | 100 |
| 61 | A | D | 90 |
| 62 | B | D | 100 |
| 63 | A | D | 90 |
| 64 | A | D | 90 |
| 65 | A | D | 80 |
| 66 | A | D | 90 |
| 67 | B | E | 80 |
| 68 | B | E | 80 |
| 69 | A | — | — |
| 70 | — | — | — |
| 71 | A | — | — |
| 72 | A | — | — |
| 73 | — | — | — |
| 74 | — | — | — |

The compounds of this invention thus have affinity for and agonist or partial agonist activity at brain serotonin 5-$HT_{2C}$ receptors. They are therefore of interest for the treatment of the central nervous system conditions described previously herein.

B. Assessment of Effectiveness of Compounds in Obesity Models

Obesity Model A

To evaluate acute in vivo efficacy of various compounds, 7 weeks-old male C57BL/6J mice are obtained from The Jackson Laboratory (Bar Harbor, Me.) and 6 weeks-old lean Zucker fa/? rats are purchased from Charles River Laboratories (Wilmington, Mass.). Mice and rats are single housed in a temperature-controlled (25° C.) facility with a 12-h light/dark cycle. Animals are allowed normal chow diet (Rodent chow #5001, PharmaServ, Framingham, Mass.) and water ad libitum. After one week acclimation, animals are randomized to vehicle (saline) or treatment groups. Animals are fasted overnight (16 hrs) and orally dosed with vehicle or compounds. Thirty minutes after compound administration, animals are given a weighed amount of food, and food intake was recorded 30 minutes, 1 h, 2 h, 4 h, 7 h and 24 h after refeeding.

Obesity Model B

To assess in vivo efficacy of various 5-$HT_{2C}$ compounds on weight loss, 5 weeks-old male C57BL/6J-DIO mice were fed a high-fat high-sucrose diet (58 kcal % fat, 16.4 kcal % protein, 25.5 kcal % carbohydrate) for 11 weeks. 6 weeks-old male Zucker fa/fa rats purchased from Charles River Laboratories were also used. Mice and rats were single housed in a temperature-controlled (25° C.) facility with a 12-h light/dark cycle. Animals were allowed food and water ad libitum. After one week acclimation, animals were randomized to vehicle (saline) or treatment groups. Animals were orally dosed once daily for 14 days. Body weight, food consumption, and/or body composition (NMR) were recorded. Epidydimal adipose tissue was collected at the end of the study. Results with respect to C57BL/6J-DIO mice are summarized in Table 5, below. Results with respect to Zucker rats are summarized in Table 6, below.

TABLE 5

| Compound # | Dose (mpk) | % Reduction food intake (vs vehicle) | | |
| --- | --- | --- | --- | --- |
| | | 0.5 hour | 2 hours | 4 hours |
| I-36 | 30 | 86 ± 11 | 72 ± 7 | 65 ± 8 |
| I-36 | 50 | 83 ± 6 | 77 ± 6 | 67 ± 9 |

TABLE 6

| Compound # | Dose (mpk) | % Reduction food intake (vs vehicle) | | |
| --- | --- | --- | --- | --- |
| | | 0.5 hour | 2 hours | 4 hours |
| I-36 | 30 | 0 ± 16 | 0 ± 8 | 0 ± 9 |
| I-36 | 50 | 58 ± 9 | 11 ± 17 | 0 ± 13 |

C. Assessment of Effectiveness in Treatment of Pain

Compounds of formula I may be evaluated in accordance with the present invention to establish the extent of their effectiveness to treat pain, and may optionally be compared with other pain treatments.

A variety of methods have been established in the art to evaluate the effectiveness of compounds for relieving pain. See e.g., Bennett et al, *Pain* 33: 87–107, 1988; Chaplan et al, *J. Neurosci. Methods* 53:55–63, 1994; and Mosconi et al, *Pain* 64:37–57, 1996. Below is a specific description of one strategy that may be employed.

Procedure: Individually housed Spraque-Dawley rats are given free access to rat chow and water. A 12-h light/12-h dark cycle is put in effect (lights on from 6:00 am to 6:00 pm). Animal maintenance and research are conducted in accordance with the guidelines provided by the National Institutes of Health Committee on Laboratory Animal Resources. These subjects are used in the tests as set forth below.

Test Method 1: Prostaglandin $E_2$-Induced Thermal Hypersensitivity.

The terminal 10 cm of the tail is placed into a thermos bottle containing water warmed to 38, 42, 46, 50, 54, or 58° C. The latency in seconds for the animal to remove the tail from the water is used as a measure of nociception. If the animal does not remove the tail within 20 sec, the experimenter removes the tail from the water and a maximum latency of 20 sec is recorded.

Following the assessment of baseline thermal sensitivity, thermal hypersensitivity is produced by a 50 μL injection of 0.1 mg prostaglandin $E_2$ ($PGE_2$) into the terminal 1 cm of the tail. Temperature-effect curves are generated before (baseline) and after (15, 30, 60, 90 and 120 min) the $PGE_2$ injection. Previous studies in other species (e.g., monkeys; Brandt et al., *J. Pharmacol. Exper. Ther.* 296:939, 2001) have demonstrated that $PGE_2$ produces a dose- and time-dependent thermal hypersensitivity that peaks 15 min after injection and dissipates after 2 hr.

Single compound studies. The ability of drugs to reverse $PGE_2$-induced thermal hypersensitivity is assessed using a single dose time-course procedure. Under this procedure, a single dose of the compound to be tested is administered intraperitoneally (IP), orally (PO) or intranasally (IN) 30 min before the injection of $PGE_2$. Tactile sensitivity is assessed 30 min after $PGE_2$ injection.

Combination compound studies. Combination studies with two or more potential pain treatment agents can be conducted. A minimally effective dose of a first agent, e.g., morphine is administered alone and in combination with ineffective doses of one or more compounds of formula I in the thermal warm-water tail withdrawal assay. Compounds are administered IP at the same time 30 min before testing.

Combination studies can also be conducted in the $PGE_2$-induced thermal hypersensitivity assay. For example, a dose of morphine that completely reverses thermal hypersensitivity (i.e., return to baseline) can be administered alone and in combination with doses of one or more compounds of formula I in the $PGE_2$-induced thermal warm-water tail withdrawal assay. Compounds are administered IP at the same time as $PGE_2$, which is administered 30 min before testing.

Test Method 1 Data Analysis The temperature that produced a half-maximal increase in the tail-withdrawal latency (i.e., $T_{10}$) is calculated from each temperature-effect curve. The $T_{10}$ is determined by interpolation from a line drawn between the point above and the point below 10 sec on the temperature-effect curve. For these studies, thermal hypersensitivity is defined as a leftward shift in the temperature-effect curve and a decrease in the $T_{10}$ value. Reversal of thermal hypersensitivity is defined as a return to baseline of the temperature-effect curve and the $T_{10}$ value and is calculated according to the following equation:

$$\% MPE = \frac{(T_{10}^{drug+PGE2}) - (T_{10}^{PGE2})}{(T_{10}^{baseline}) - (T_{10}^{PGE2})} \times 100$$

in which $T_{10}^{drug+PGE2}$ is the $T_{10}$ after a drug in combination with $PGE_2$, $T_{10}^{PGE2}$ is the $T_{10}$ after $PGE_2$ alone, and $T_{10}^{baseline}$ is the $T_{10}$ under control conditions. A % MPE value of 100 indicates a complete return to the baseline thermal sensitivity observed without the $PGE_2$ injection. A value of greater than 100% indicates that the compound tested reduced thermal sensitivity more than the baseline thermal sensitivity without the $PGE_2$ injection.

Test Method 2: Chronic Constriction Injury

Rats are anesthetized with 3.5% halothane in $O_2$ at 1 L/min and maintained with 1.5% halothane in $O_2$ during surgery. A modified chronic sciatic nerve constriction injury (Mosconi & Kruger, 1996; Bennett & Xie, 1988) is produced by a cutaneous incision and a blunt dissection through the biceps femoris to expose the sciatic nerve. A PE 90 Polyethylene tubing (Intramedic, Clay Adams; Becton Dickinson Co.) cuff (2 mm length) is placed around the sciatic nerve at the level of the mid-thigh. The wound is closed in layers using 4–0 silk suture and wound clips. Testing is conducted 6–10 days after surgery.

Animals are placed in elevated wire cages and allowed 45–60 minutes to acclimate to the testing room. Baseline tactile sensitivity is assessed using a series of calibrated von Frey monofilaments (Stoelting; Wood Dale, Ill.) 0–3 days before surgery. Von Frey monofilaments are applied to the mid-plantar hind paw in sequential ascending or descending order, as necessary, to hover as closely as possible to the threshold of responses. The threshold is indicated by the lowest force that evoked a brisk withdrawal response to the stimuli. Thus, a withdrawal response leads to the presentation of the next lighter stimulus and the lack of a withdrawal response leads to the presentation of the next stronger stimulus. Rats with baseline thresholds<4 g force are excluded from the study. Approximately one week following CCI surgery, tactile sensitivities are reassessed and animals that exhibit motor deficiency (i.e. paw dragging) or failure to exhibit subsequent tactile hypersensitivity (threshold≧10 g) are excluded from further testing. Under cumulative dosing conditions, compounds are administered IP every 30 minutes with the cumulative dose increasing in ½ log unit increments. Tactile hypersensitivity is assessed 20–30 minutes following each drug administration.

Test Method 2 Data Analysis. The 50% threshold values (in gm force) estimated by the Dixon non-parametric test (Chaplan et al, 1994) are calculated and fifteen-grams of force is used as the maximal force. Dose-effect curves are generated for each experimental condition for each rat. Individual tactile hypersensitivity threshold values are averaged to provide a mean (±1 SEM). Reversal of tactile hypersensitivity was defined as a return to baseline tactile sensitivity and was calculated according to the following equation:

$$\% \text{ Reversal} = \frac{(50\%^{drug+CCI}) - (50\%^{CCI})}{(50\%^{baseline}) - (50\%^{CCI})} \times 100$$

in which $50\%^{drug+CCI}$ is the 50% value after compound in animals approximately one week after CCI surgery, $50\%^{CCI}$ is the 50% value approximately one week after CCI surgery alone, and $50\%^{baseline}$ is the 50% value before CCI surgery. Maximal effect of 100% reversal represents a return to the mean pre-operative threshold value for subjects in that experimental condition.

Test Method 3: Scheduled-Controlled Responding.

Rats are trained under a multiple-cycle procedure during experimental sessions conducted five days each week. Each training cycle consists of a 10-min pretreatment period followed by a 10-min response period. During the pretreatment period, stimulus lights are not illuminated, and responding has no scheduled consequences. During the response period, the left or right stimulus lights are illuminated (counterbalanced among subjects), the response lever is extended and subjects can respond under a fixed ratio 30 schedule of food presentation. Training sessions consist of 3 consecutive cycles. Testing sessions are identical to training sessions except that a single dose of drug is administered at the start of the first cycle.

Test Method 3 Data analysis. Operant response rates from individual animals are averaged for the three cycles during test sessions and are converted to percent of control response rates using the average rate from the previous training day as the control value (i.e., average of three cycles). Data are presented as the mean (±1 SEM) response rate as a percent of control. Thus, for example, a test value of 100% would indicate the response rate after administration of the compound to be tested is the same as the control response rate and there is no adverse effect of the compound tested.

Test Method 4: Assessment of Effectiveness in Tactile Allodynia Model

Compound: Test compounds are dissolved in sterile saline and gabapentin is suspended in 2% Tween 80 in 0.5% methylcellulose and sterile water. All compounds are administered intraperitoneally (i.p.).

Subjects: Male Sprague-Dawley rats (125–150 g, Harlan; Indianapolis, Ind.) are individually housed on bedding. For all studies animals are maintained in climate-controlled rooms on a 12-hour light/dark cycle (lights on at 0630) with food and water available ad libitum.

Surgery: All surgical procedures are performed under 4% isoflurane/O$_2$ anesthesia, delivered via nose cone and maintained at 2.5% for the duration of the surgery.

L5 Spinal Nerve Ligation (SNL): Surgery is performed as previously described (Kim and Chung) with the exception that nerve injury is produced by tight ligation of the left L5 spinal nerve.

Assessment of Tactile Allodynia (Tactile Sensitivity): Tactile thresholds are assessed using a series of calibrated von Frey monofilaments (Stoelting; Wood Dale, Ill.). The threshold that produced a 50% likelihood of a withdrawal is determined using the up-down method, as previously described (Chaplan et al., 1994). Animals are placed in elevated wire cages and allowed 45–60 minutes to acclimate to the testing room. Von Frey monofilaments are applied to the mid-plantar left hind paw in sequential ascending or descending order, as necessary, to hover as closely as possible to the threshold of responses. The lowest force that evokes a brisk withdrawal response to the stimuli determined the pain threshold. Tactile thresholds are determined on the day prior to surgery and rats with baseline thresholds <10 g force are excluded from studies. Three weeks after SNL surgery tactile thresholds are reassessed and animals that fail to exhibit subsequent tactile allodynia (threshold ≧5 g) are excluded from further testing. Subjects are pseudo-randomly divided into test groups (n=8–10) so that average baseline and post-surgery sensitivities are similar among groups. Rats are administered a test compound (3, 10 or 17.8, i.p.), gabapentin (100 mg/kg, i.p., postivie control) or vehicle and tactile thresholds are assessed up to 60, 180 and 300 minutes after dosing.

Analysis of Results: Statistical analysis is done using a repeated measures analysis of variance (ANOVA) using a customized SAS-excel application (SAS Institute, Cary, N.C.). Significant main effects are analyzed further by subsequent least significant difference analysis. The criterion for significant differences is p<0.05. Reversal of tactile allodynia is calculated according to the following equation:

$$\% \text{ Reversal} = \frac{(50\% \text{ threshold}^{drug+post\,surgery}) - (50\% \text{ treshold}^{post\,surgery})}{(50\% \text{ threshold}^{pre\,surgery}) - (50\% \text{ threshold}^{post\,surgery})} \times 100$$

In which $50\% \text{ threshold}^{drug+post\,surgery}$ is the 50% threshold in g force after drug in nerve injured subjects, $50\% \text{ threshold}^{post\,surgery}$ is the 50% threshold in g force in nerve injured subjects, and $50\% \text{ threshold}^{pre\,surgery}$ is the 50% threshold in g force before nerve injury. Maximal effect of 100% reversal represents a return to the mean pre-operative threshold value for subjects in that experimental condition. See FIG. 1.

Test Method 5: Assessment of Effectiveness in Chronic Inflammatory Pain Compounds:

Test compounds are dissolved in sterile saline and administered intraperitoneally (i.p.). Celecoxib was used as a positive control and is suspended in 2% Tween 80 in 0.5% methylcellulose and administered orally (p.o.).

Subjects: Male Sprague-Dawley rats (125–150 g, Harlan; Indianapolis, Ind.) are housed 3/cage on bedding and. animals are maintained in climate-controlled rooms on a 12-hour light/dark cycle (lights on at 0630) with food and water available ad libitum.

Freund's complete adjuvant (FCA) of mechanical hyperalgesia: The hind paw withdrawal thresholds (PWTs) to a noxious mechanical stimulus are determined using an analgesimeter (model 7200; Ugo Basile). Cutoff was set at 250 g, and the endpoint taken is complete paw withdrawal. PWT is determined once for each rat at each time point (n=10/group). Baseline PWT is determined, and the rats were anesthetized with isofluorane (2% in oxygen) and received an intraplantar injection of 50% FCA (50 μl, diluted in saline) to the left hind paw. Twenty-four hours after FCA injection, pre-drug PWTs were measured, and the rats are administered vehicle or compound and assessed on PWTs 1, 3, 5, and 24 hours post-drug administration.

Analysis of Results: Statistical analysis is done using a one way analysis of variance (ANOVA) using a customized SAS-excel application (SAS Institute, Cary, N.C.). Significant main effects are analyzed further by subsequent least significant difference analysis. The criterion for significant differences is p<0.05 from vehicle-treated FCA rats. Data is presented as percent reversal according to the following equation: percent reversal=[(post-dose threshold)-pre-dose threshold))/(baseline threshold-pre-dose threshold)]×100.

D. Assessment of Effectiveness in Treatment of Depression

Effectiveness of compounds of the present invention may be determined by the tail suspension test. While not a direct model of depression, the tail suspension test is an assay that can evaluate antidepressant-like effects of drugs. Clinically effective drugs such as Prozac (fluoxetine) are effective in this assay. Specifically, they decrease the amount of time the mice spend immobile after being hung upside down by their tails during the test. It is impossible to determine if a mouse is indeed depressed. However, the fact that clinically effective antidepressants reduce immobility lends predictive validity to the model.

Male Swiss Webster mice (Charles River) weighing 25–35 g are housed in groups of five per cage in an AALAC-accredited facility that is maintained on a 12-h light dark cycle (lights on at 0600 h) and have free access to food and water. Experimental groups consist of 12 mice, randomly assigned to treatment groups. Experiments are performed between 9:00 AM and noon in accordance to the Guide for the Care and Use of Laboratory Animals as adopted and promulgated by the National Institutes of Health (Pub. 85–23, 1985).

Solutions of test compounds are dissolved in distilled water. Compounds are injected i.p. at a volume of 10 ml/kg body weight. Combination treatments are cotreated, 30 minutes prior to the test.

The procedure described herein is substantially similar to that described by Steru et al. (1985). 30 minutes following treatment, the mice are suspended upside down by the tail using adhesive laboratory tape (VWR International), to a flat metal bar connected to a strain gauge within a tail suspension chamber (Med Associates). The time spent immobile during a 6-minute test session is automatically recorded. 8 mice are simultaneously tested within separate chambers. Data collected are expressed as a mean of immobility time and statistical analysis is performed using a one-way ANOVA with least significant difference (LSD) post-hoc test.

The entire disclosure of each patent, patent application, and publication cited or described in this document is hereby incorporated by reference.

While we have presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

We claim:
1. A compound of formula I:

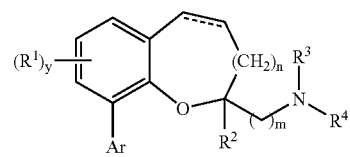

or a pharmaceutically acceptable salt thereof, wherein:
  m is 1 or 2;
  n is 0 or 1;
  ----- designates a single or double bond;
  Ar is thienyl, furyl, pyridyl, pyrimidinyl or phenyl wherein Ar is optionally substituted with one or more $R^x$ groups;
  each $R^x$ is independently halogen, -Ph, —CN, —R or —OR;
  each R is independently hydrogen, $C_{1-6}$ aliphatic or halo-substituted $C_{1-6}$ aliphatic;
  y is 0–3;
  each $R^1$ is independently —R, —CN, halogen or —OR;
  $R^2$ is hydrogen, $C_{1-3}$ alkyl, or —O($C_{1-3}$ alkyl); and
  each of $R^3$ and $R^4$ is independently hydrogen, $C_{1-6}$ aliphatic or fluoro-substituted $C_{1-6}$ aliphatic.

2. The compound according to claim 1, wherein said compound is of formula Ia:

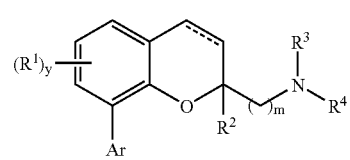

or a pharmaceutically acceptable salt thereof.

3. The compound according to claim 1, wherein said compound has the formula IIc or IId:

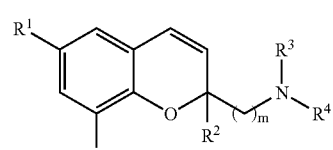

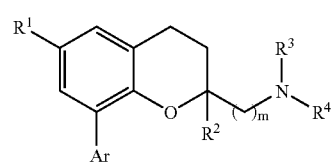

or a pharmaceutically acceptable salt thereof.

4. The compound according to claim 3, wherein Ar is thienyl, furyl, or pyridyl, or a pharmaceutically acceptable salt thereof.

5. The compound according to claim 3, wherein Ar is unsubstituted phenyl, or a pharmaceutically acceptable salt thereof.

6. The compound according to claim 3, wherein said compound is of formula IIIb or IIId:

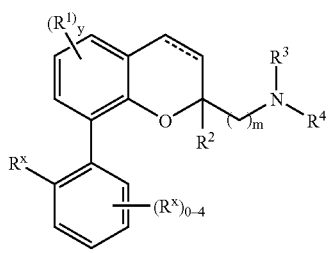

IIIb

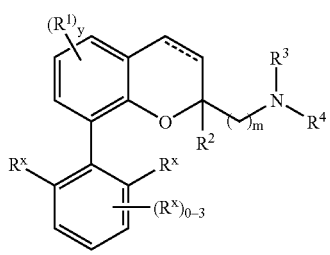

IIId or a pharmaceutically acceptable salt thereof.

7. The compound according to claim 6, wherein each $R^x$ is independently selected from —R, —CN, halogen or —OR, or a pharmaceutically acceptable salt thereof.

8. The compound according to claim 2, wherein:
each $R^1$ is independently —R, —CN, halogen or —OR;
$R^2$ is hydrogen, methyl, or methoxy;
Ar is pyridyl, pyrimidinyl, thienyl, furyl, or phenyl optionally substituted with one or more $R^x$ groups;
each $R^x$ is independently selected from —R, —CN, halogen or —OR; and
each of $R^3$ and $R^4$ is independently hydrogen, methyl, ethyl, cyclopropyl, 2-fluoroethyl, or 2,2-difluoroethyl, or a pharmaceutically acceptable salt thereof.

9. The compound according to claim 1, wherein said compound is of formula Ib:

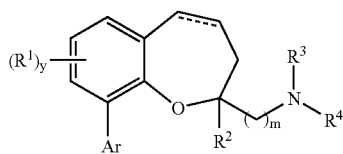

Ib or a pharmaceutically acceptable salt thereof.

10. The compound according to claim 9, wherein each $R^1$ is independently —R, —CN, halogen or —OR, or a pharmaceutically acceptable salt thereof.

11. The compound according to claim 10, wherein said compound is of formula IIa or IIb:

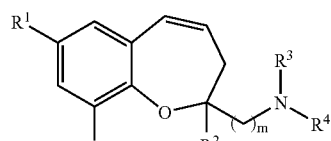

IIa

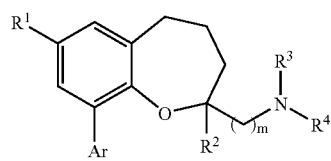

IIb or a pharmaceutically acceptable salt thereof.

12. The compound according to claim 11, wherein Ar is thienyl, furyl, or pyridyl, or a pharmaceutically acceptable salt thereof.

13. The compound according to claim 12, wherein Ar is unsubstituted phenyl, or a pharmaceutically acceptable salt thereof.

14. The compound according to claim 12, wherein said compound is of formula IIIa or IIIc:

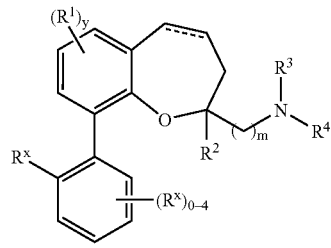

IIIa

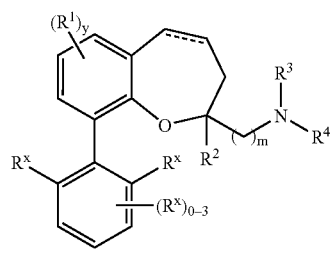

IIIc or a pharmaceutically acceptable salt thereof.

15. The compound according to claim 14, wherein each $R^x$ is independently selected from R, CN, halogen or OR, or a pharmaceutically acceptable salt thereof.

16. The compound according to claim 9, wherein:
each $R^1$ is independently —R, —CN, halogen or —OR;
$R^2$ is hydrogen, methyl, or methoxy;
Ar is pyridyl, pyrimidinyl, thienyl, furyl, or phenyl optionally substituted with one or more $R^x$ groups;
each $R^x$ is independently selected from —R, —CN, halogen or —OR; and
each of $R^3$ and $R^4$ is independently hydrogen, methyl, ethyl, cyclopropyl, 2-fluoroethyl, or 2,2-difluoroethyl, or a pharmaceutically acceptable salt thereof.

17. The compound according to claim 1, wherein Ar is selected from:
i
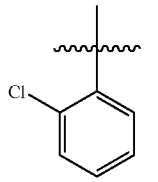
ii
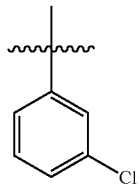
iii
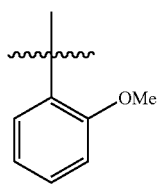
iv
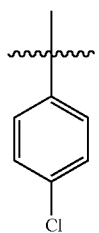
v
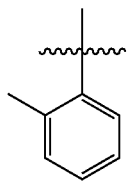
vi
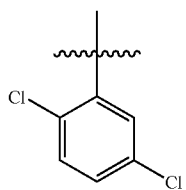
vii
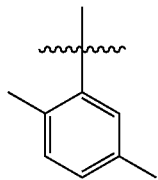
viii
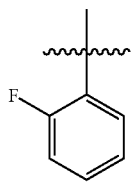
-continued
ix
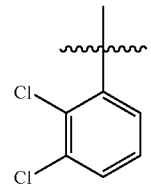
x
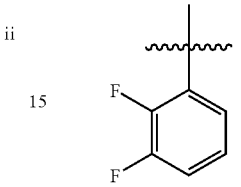
xi
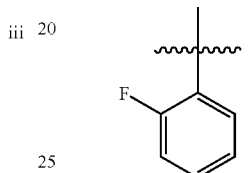
xii
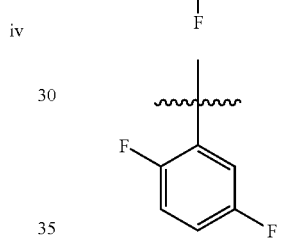
xiii
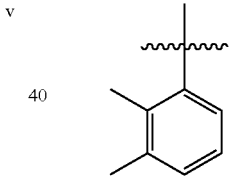
xiv
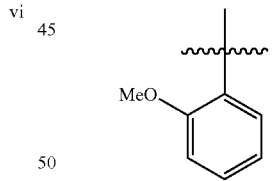
xv
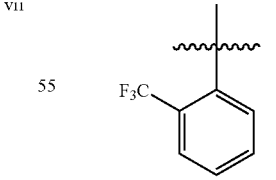
xvi
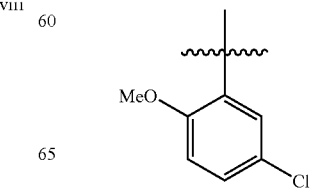

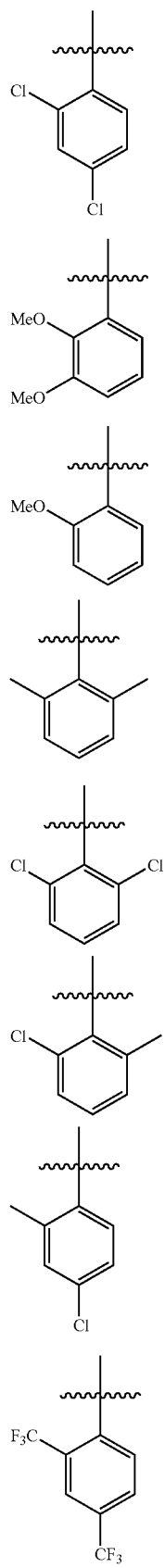
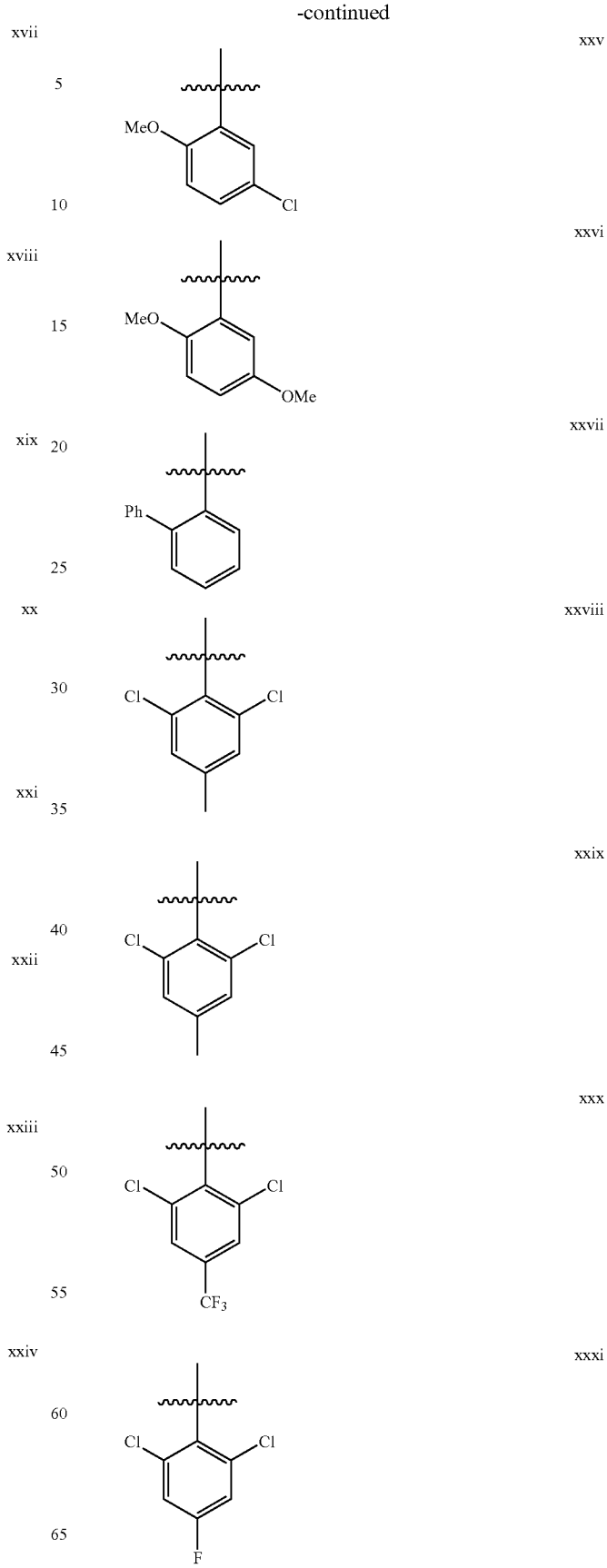

-continued
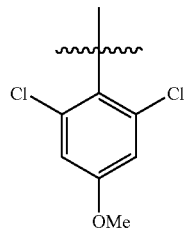 xxxii
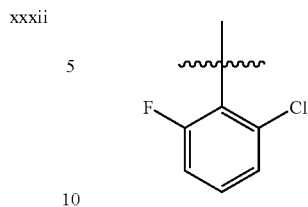 xxxix
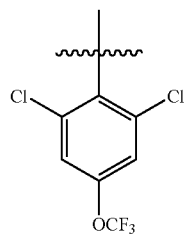 xxxiii
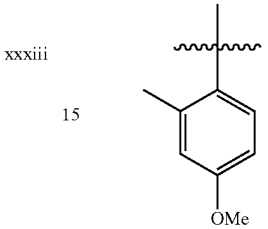 xl
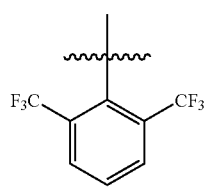 xxxiv
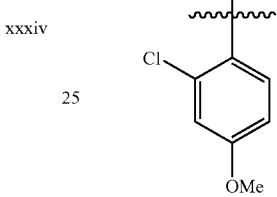 xli
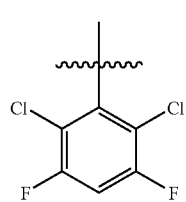 xxxv
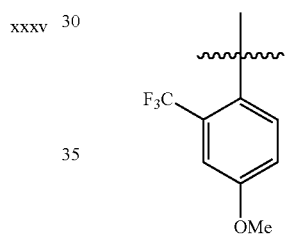 xlii
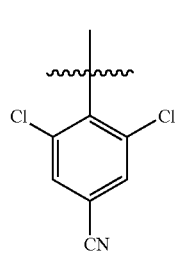 xxxvi
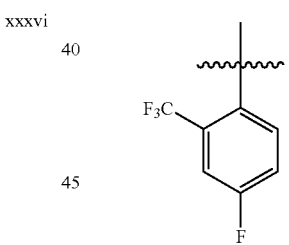 xliii
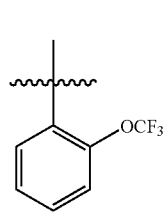 xxxvii
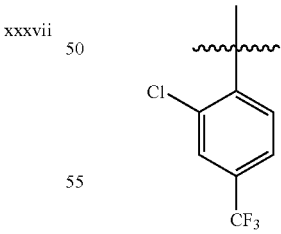 xliv
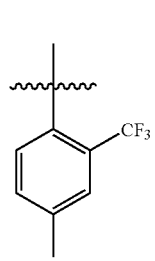 xxxviii
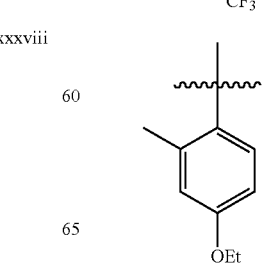 xlv

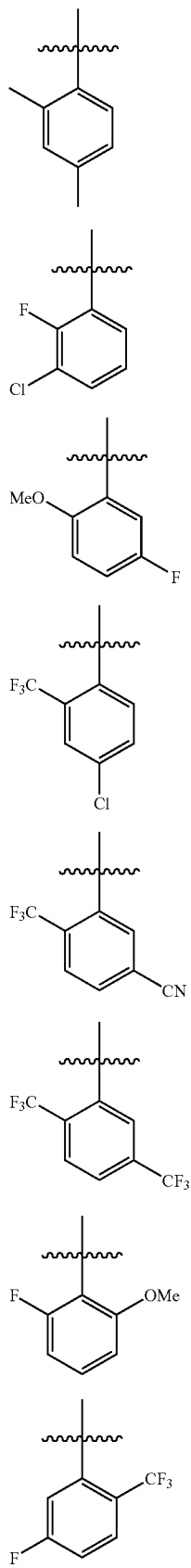
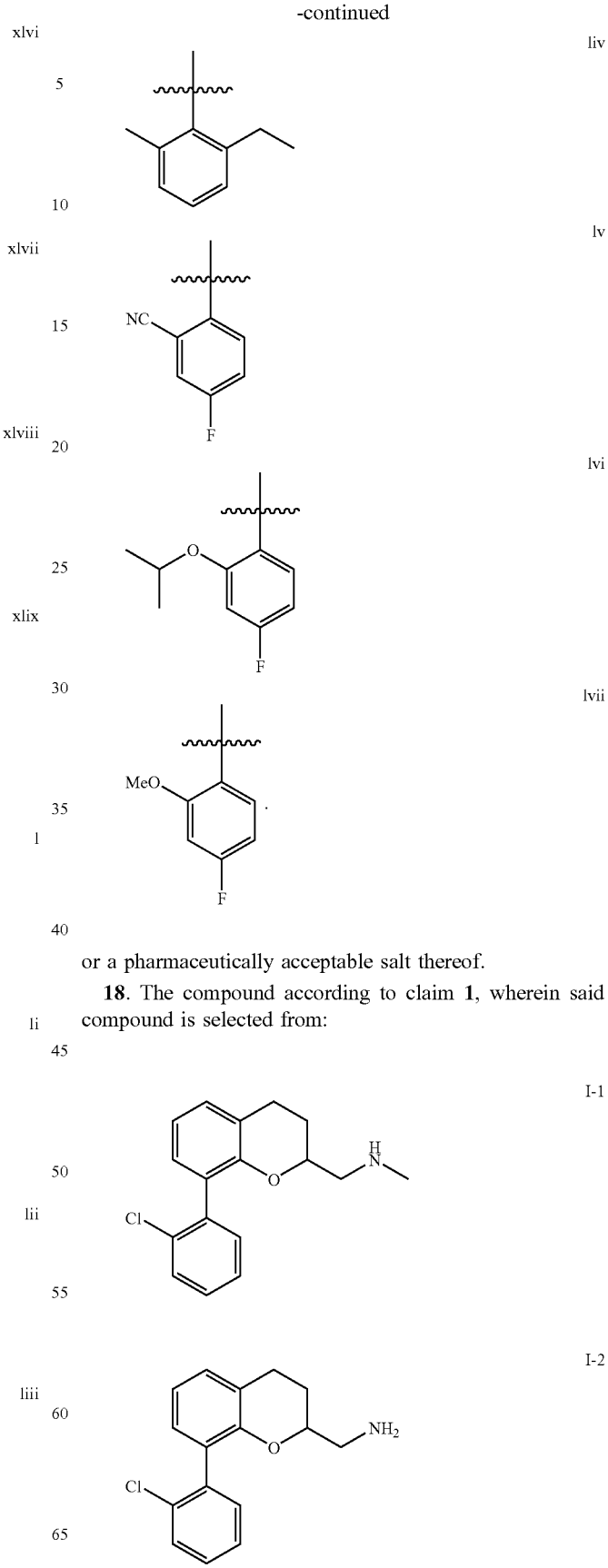
or a pharmaceutically acceptable salt thereof.
18. The compound according to claim 1, wherein said compound is selected from:

-continued
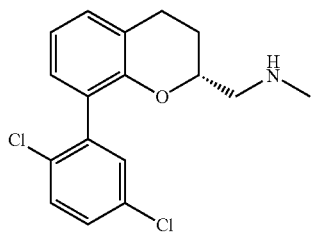
I-3
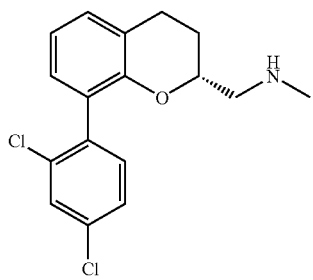
I-4
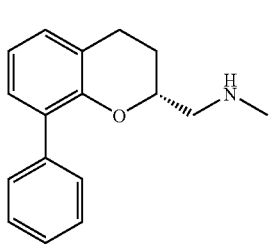
I-5
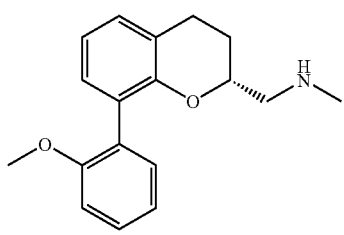
I-6
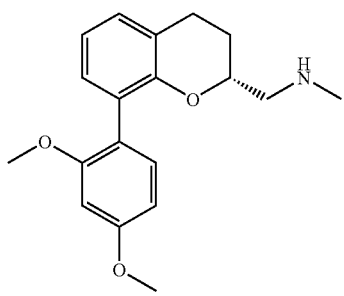
I-7
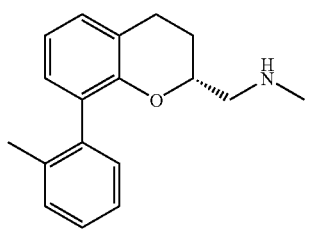
I-8
-continued
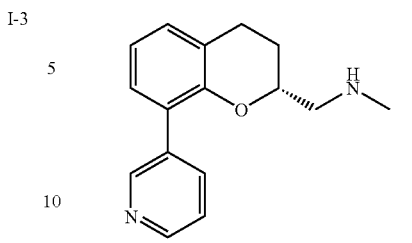
I-9
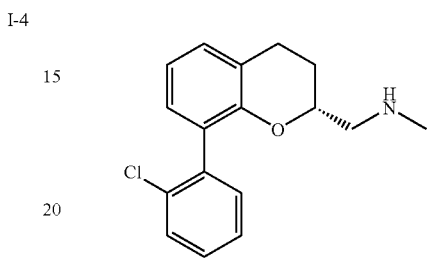
I-10
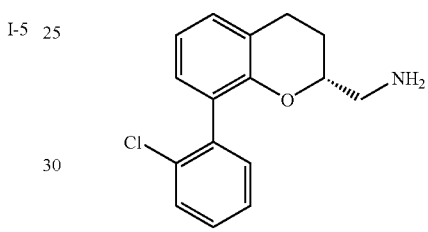
I-11
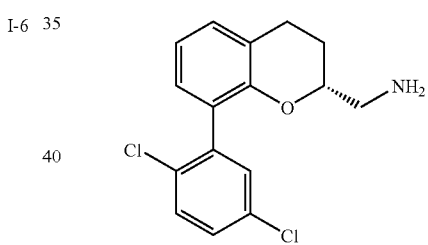
I-12
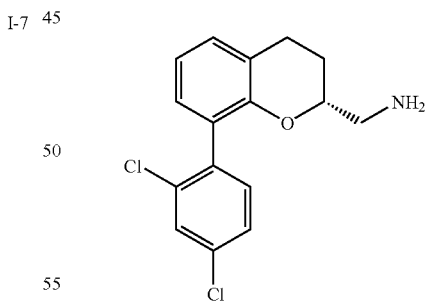
I-13
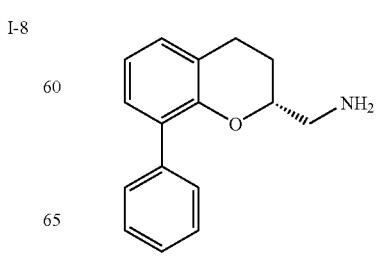
I-14

-continued
I-15 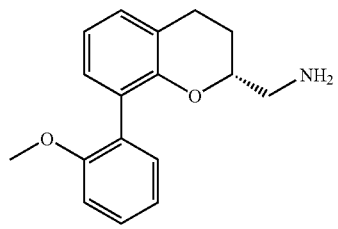
I-16 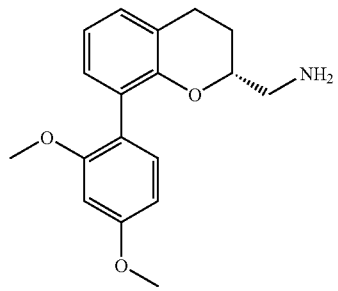
I-17 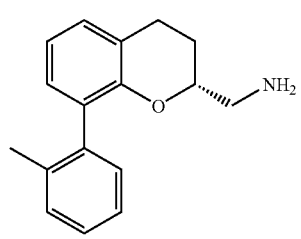
I-18 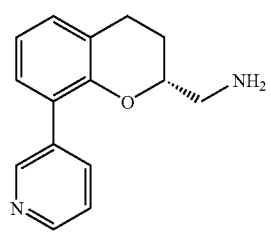
I-19 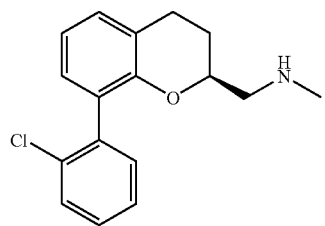
I-20 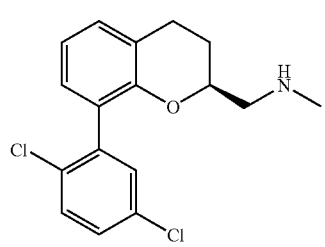
-continued
I-21 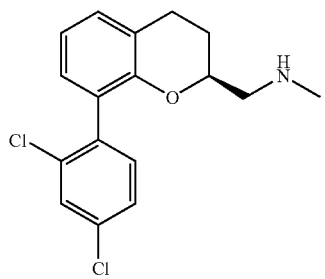
I-22 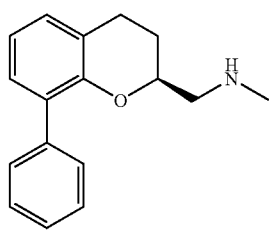
I-23 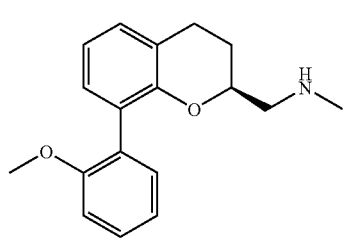
I-24 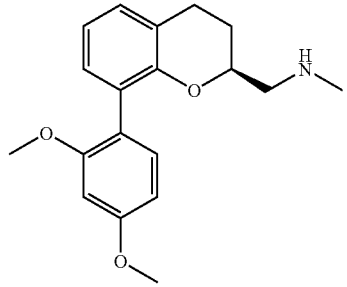
I-25 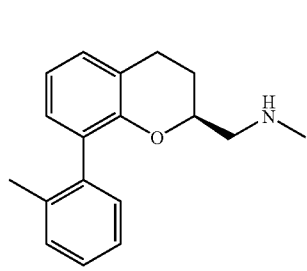
I-26 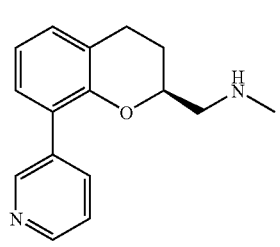

I-27
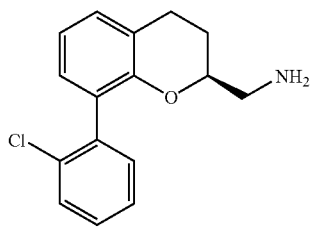
I-28
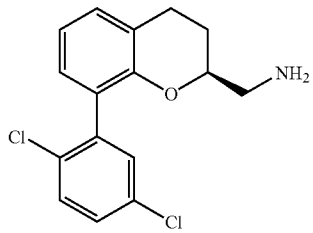
I-29
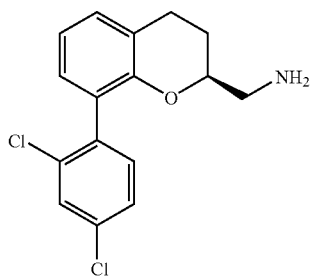
I-30
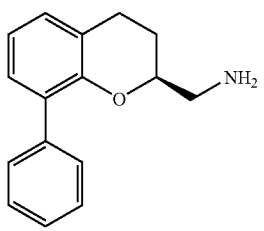
I-31
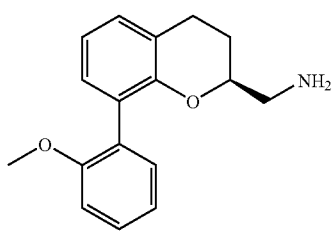
I-32
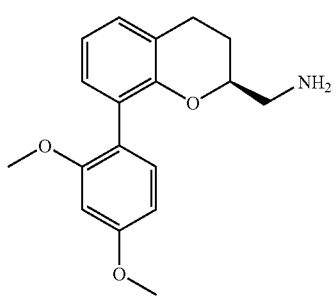
I-33
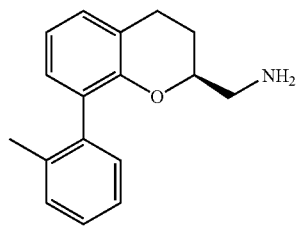
I-34
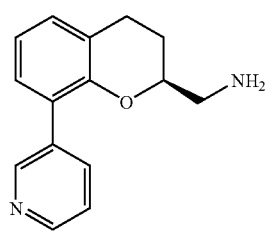
I-35
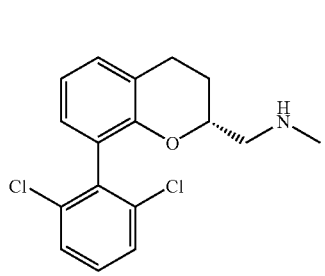
I-36
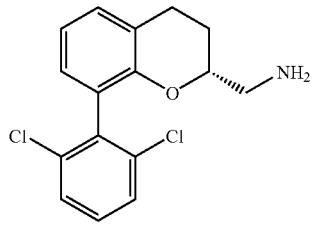
I-37
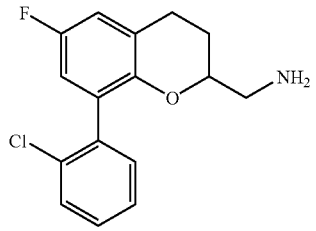
I-38
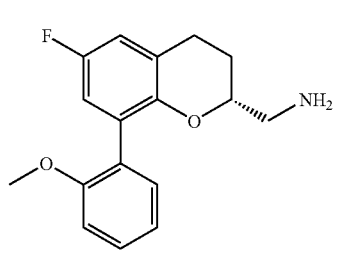

-continued
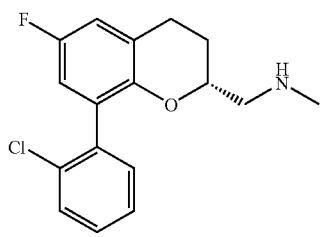
I-39
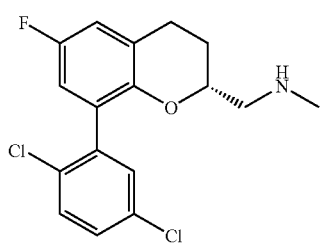
I-40
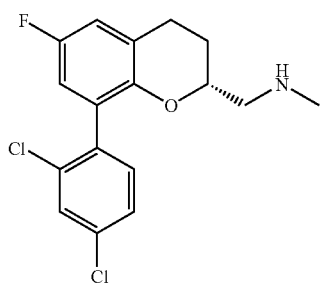
I-41
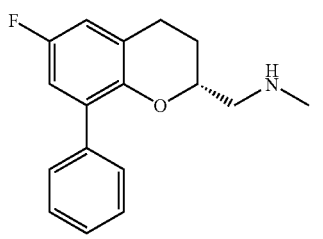
I-42
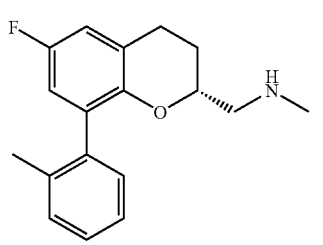
I-43
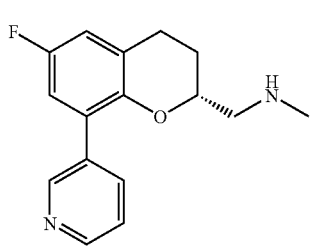
I-44
-continued
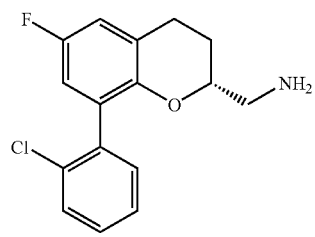
I-45
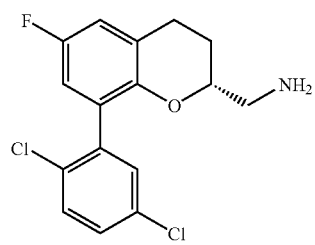
I-46
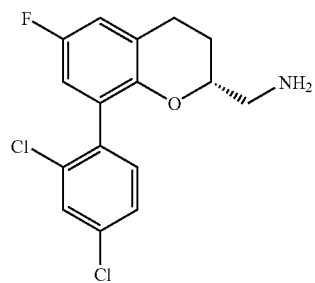
I-47
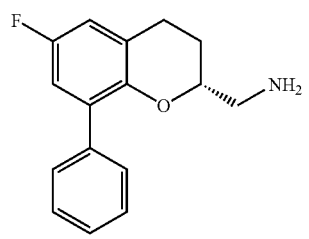
I-48
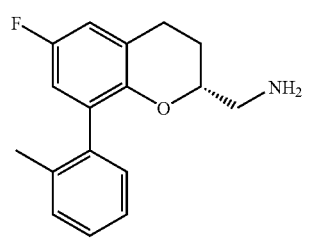
I-49
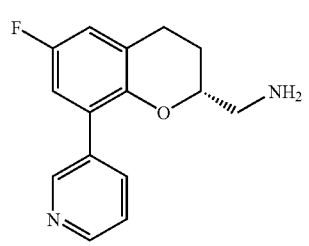
I-50

-continued
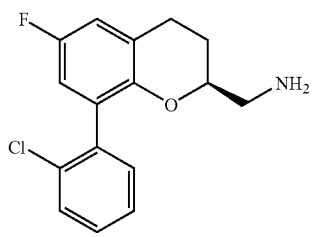
I-51
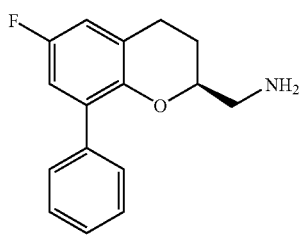
I-52
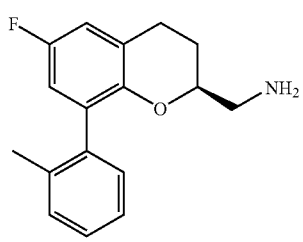
I-53
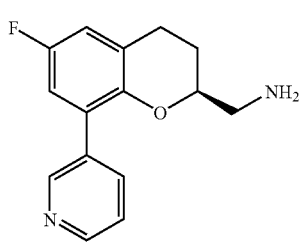
I-54
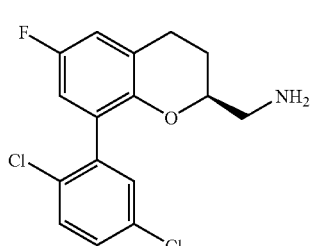
I-55
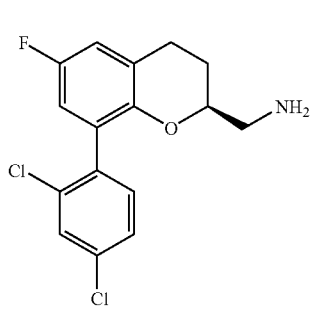
I-56
-continued
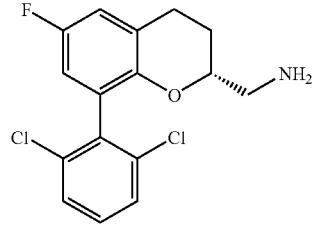
I-57
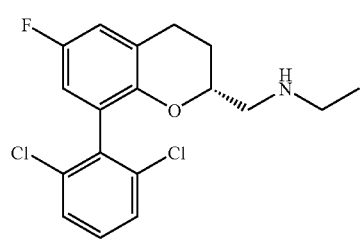
I-58
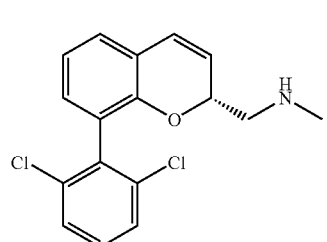
I-59
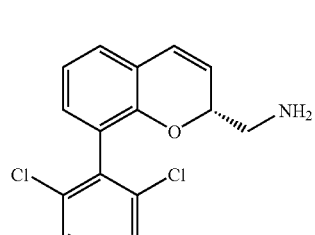
I-60
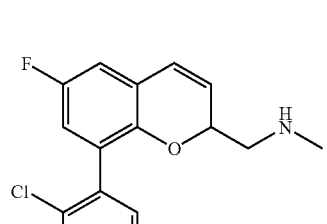
I-61
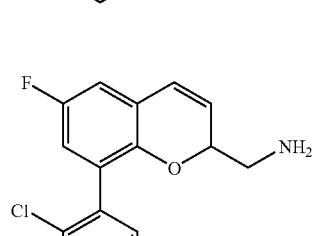
I-62

-continued
I-63 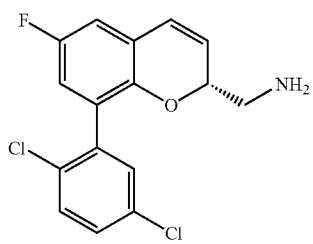
I-64 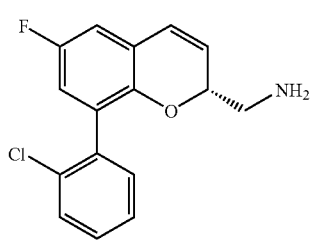
I-65 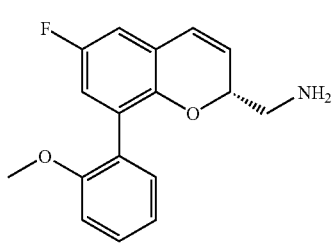
I-66 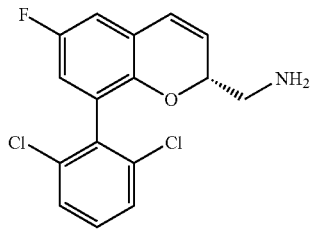
I-67 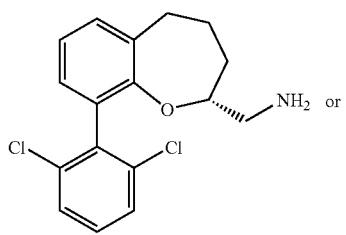 or
I-68 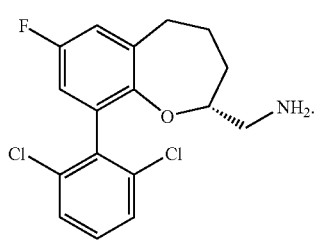.
-continued
I-69 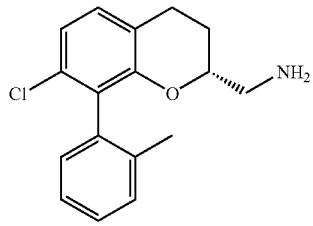
I-70 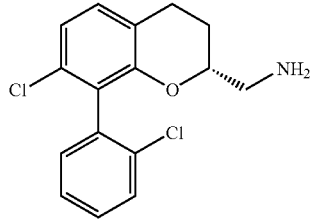
I-71 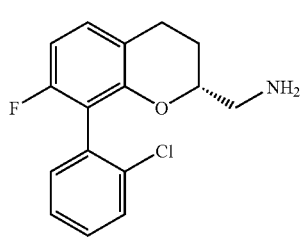
I-72 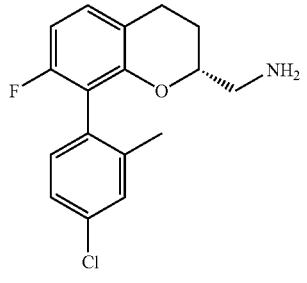
I-73 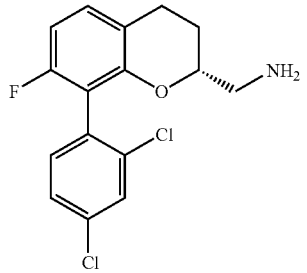
I-74 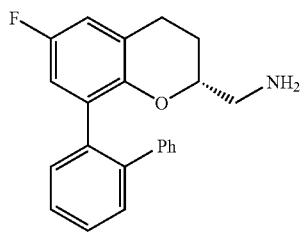

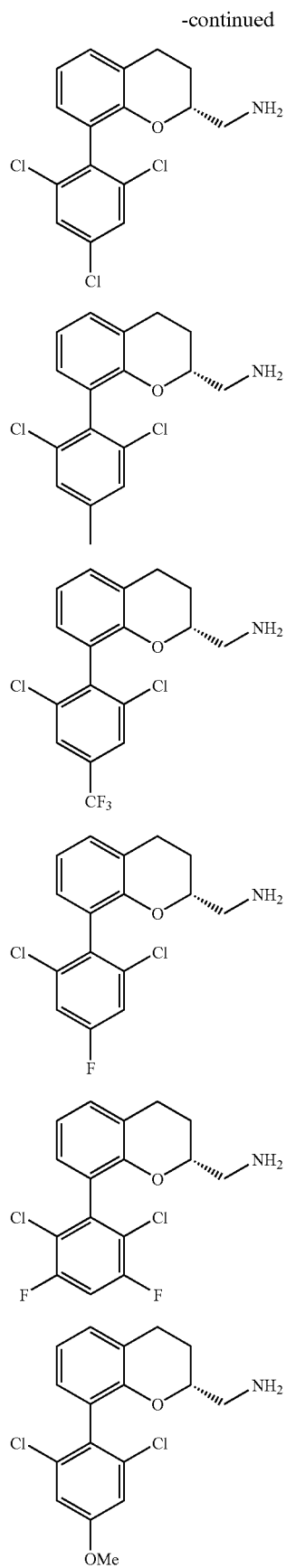
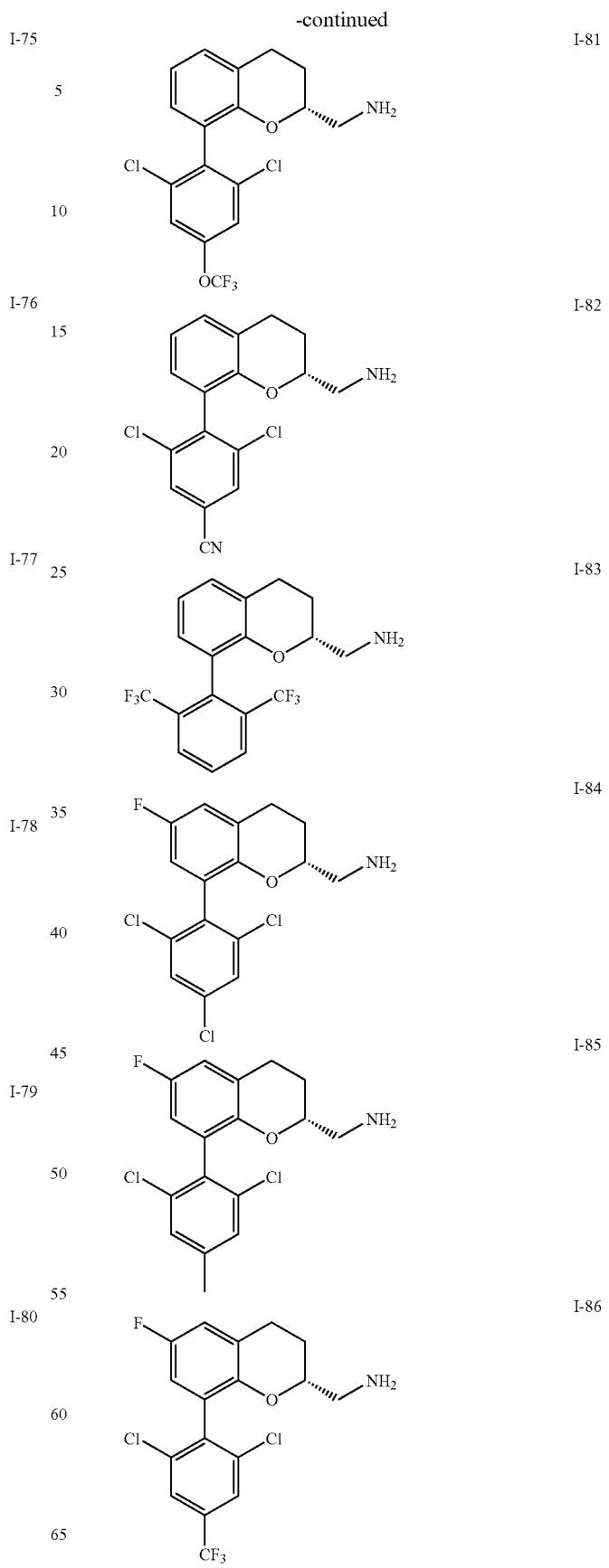

-continued
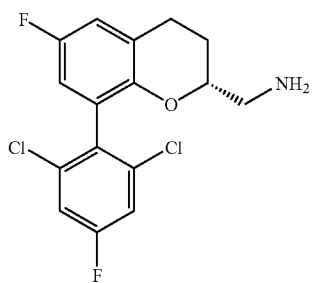
I-87
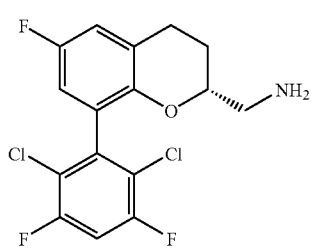
I-88
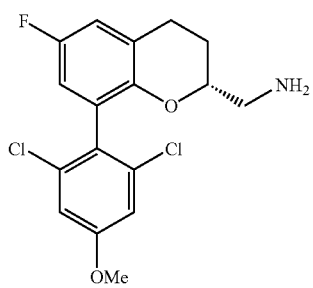
I-89
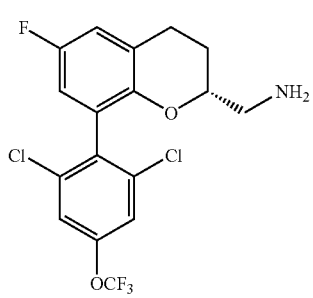
I-90
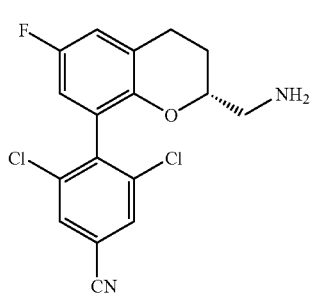
I-91
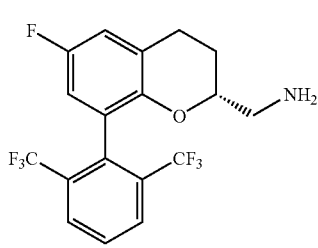
I-92
-continued
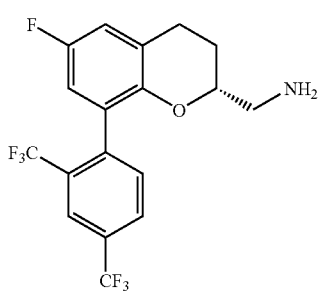
I-93
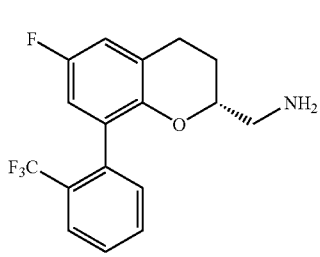
I-94
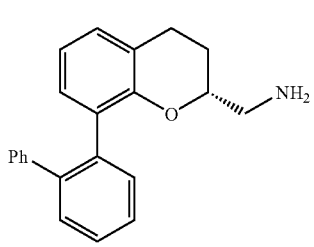
I-95
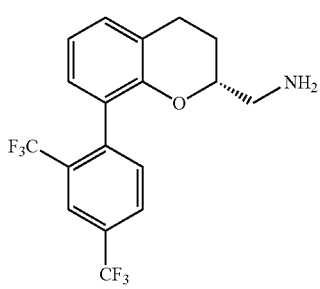
I-96
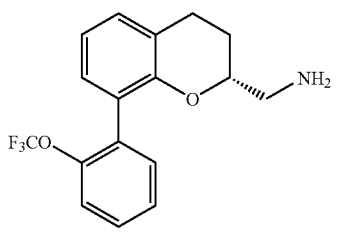
I-97
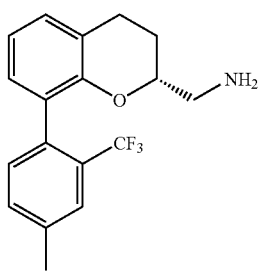
I-98

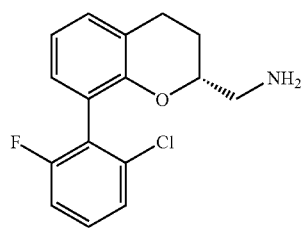
I-99
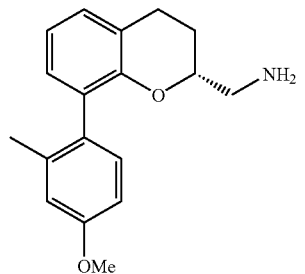
I-100
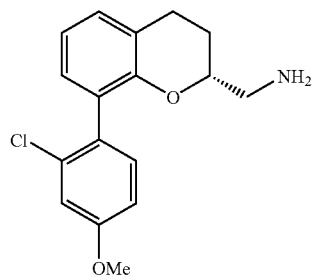
I-101
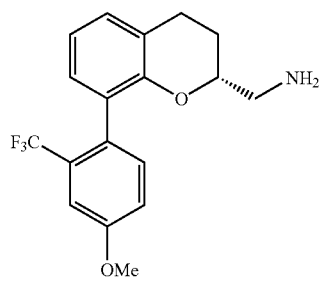
I-102
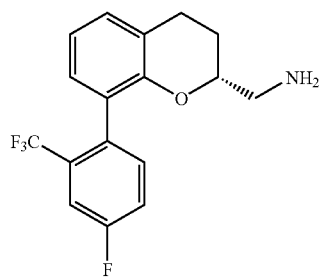
I-103
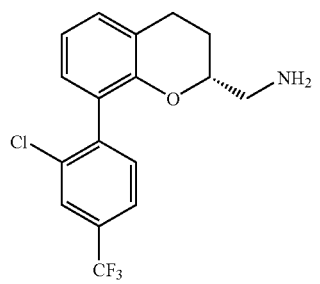
I-104
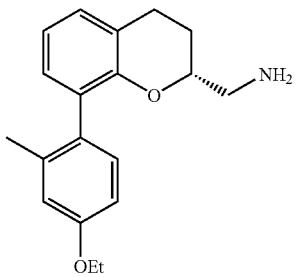
I-105
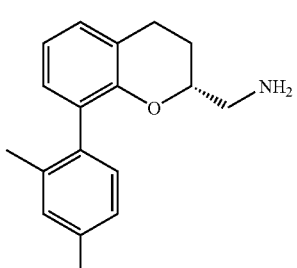
I-106
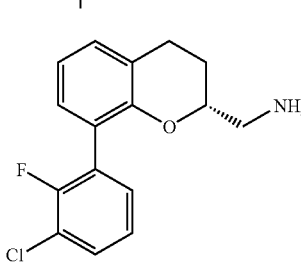
I-107
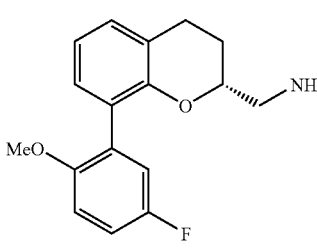
I-108
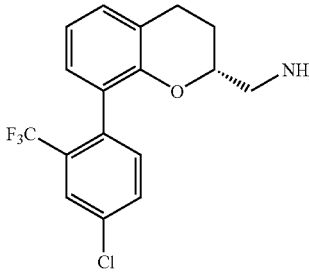
I-109
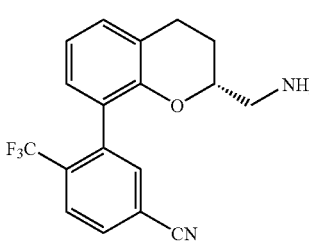
I-110

-continued
I-111 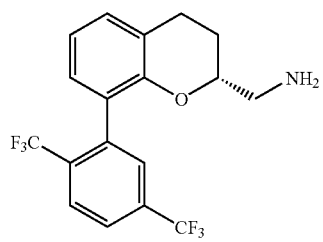
I-112 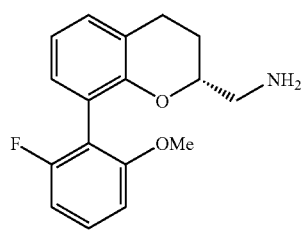
I-113 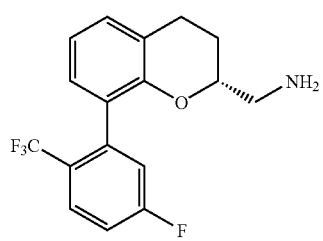
I-114 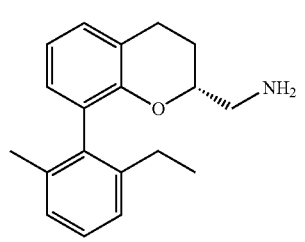
I-115 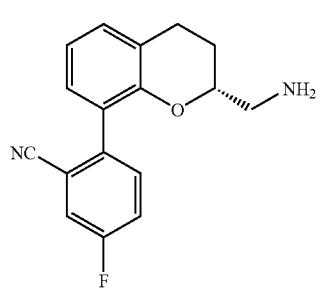
I-116 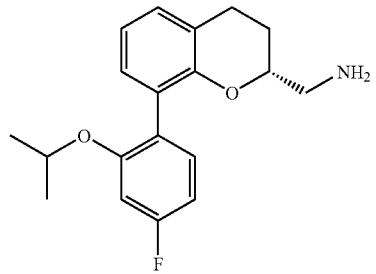
-continued
I-117 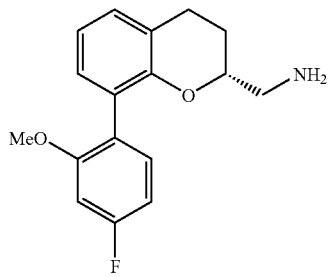
I-118 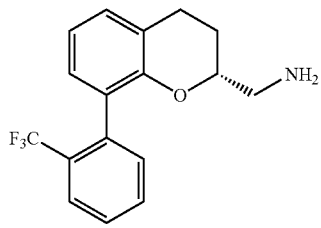
I-119 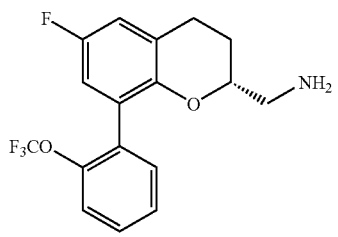
I-120 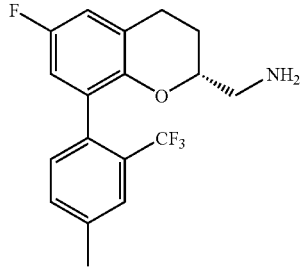
I-121 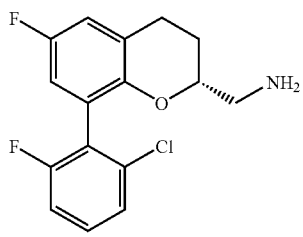
I-122 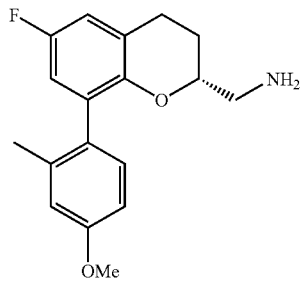

-continued
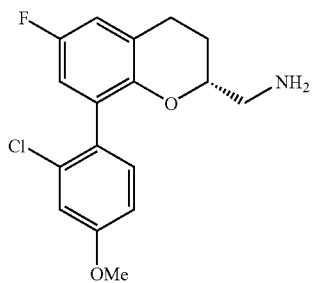
I-123
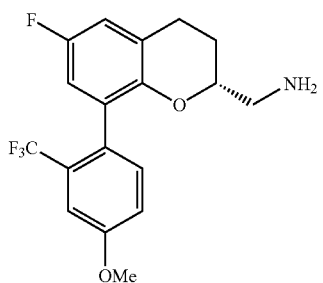
I-124
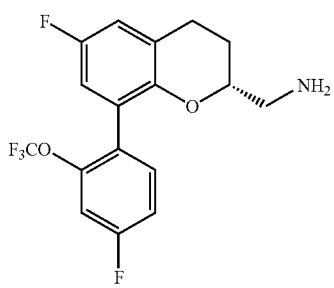
I-125
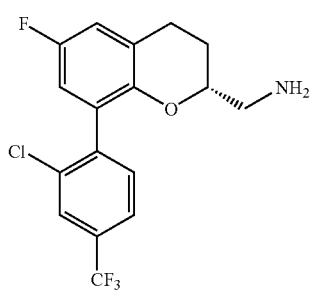
I-126
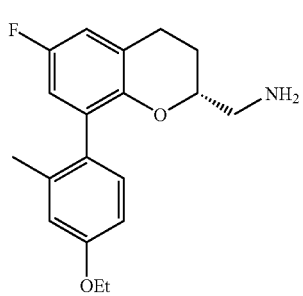
I-127
-continued
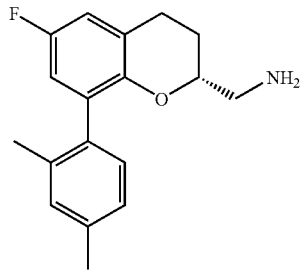
I-128
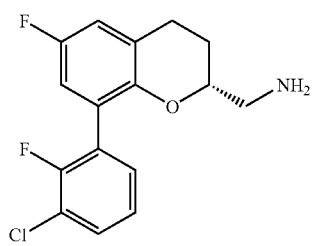
I-129
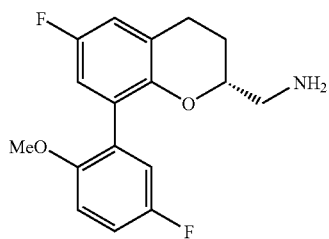
I-130
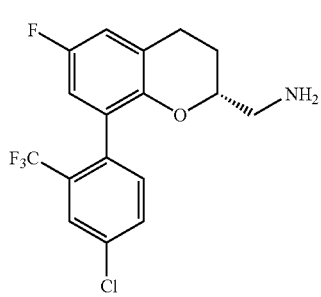
I-131
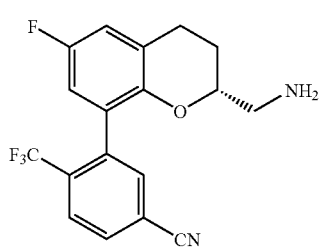
I-132

-continued
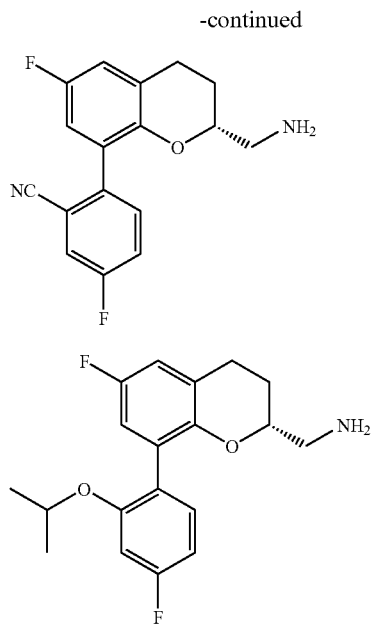
I-133
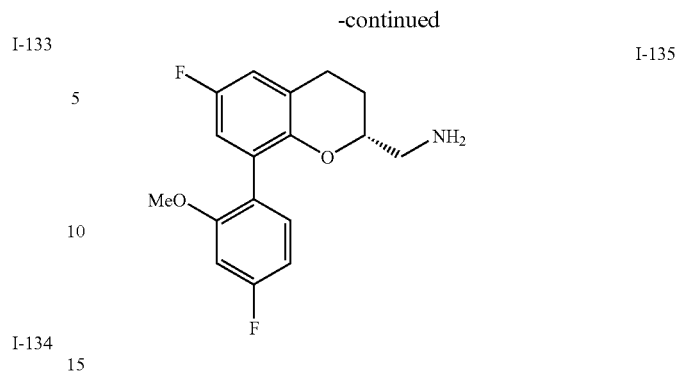
I-134
I-135
an enantiomer or racemate thereof, or a pharmaceutically acceptable salt thereof.
19. A composition comprising a compound according to claim 1, or a pharmaceutically acceptable salt thereof, and one or more pharmaceutically acceptable carriers, diluents, or excipients.
* * * * *